(12) United States Patent
Lavis et al.

(10) Patent No.: US 10,495,632 B2
(45) Date of Patent: *Dec. 3, 2019

(54) AZETIDINE-SUBSTITUTED FLUORESCENT COMPOUNDS

(71) Applicant: HOWARD HUGHES MEDICAL INSTITUTE, Chevy Chase, MD (US)

(72) Inventors: Luke D. Lavis, Leesburg, VA (US); Jonathan B. Grimm, Ashburn, VA (US); Jiji Chen, Ellicott, MD (US); Timothee Lionnet, Sterling, VA (US); Zhengjian Zhang, San Mateo, CA (US); Andrey Revyakin, Leicester (GB); Joel Slaughter, Medford, OR (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,388

(22) Filed: Dec. 6, 2018

(65) Prior Publication Data

US 2019/0107534 A1 Apr. 11, 2019

Related U.S. Application Data

(63) Continuation of application No. 16/000,614, filed on Jun. 5, 2018, now Pat. No. 10,161,932, which is a continuation of application No. 15/897,571, filed on Feb. 15, 2018, now Pat. No. 10,018,624, which is a continuation of application No. 15/301,270, filed as application No. PCT/US2015/023953 on Apr. 1, 2015, now Pat. No. 9,933,417.

(60) Provisional application No. 61/991,109, filed on May 9, 2014, provisional application No. 61/973,795, filed on Apr. 1, 2014.

(51) Int. Cl.
| | |
|---|---|
| *C07D 401/14* | (2006.01) |
| *C07D 405/14* | (2006.01) |
| *C07D 413/14* | (2006.01) |
| *C07D 403/14* | (2006.01) |
| *C07D 405/04* | (2006.01) |
| *C07D 473/18* | (2006.01) |
| *C07D 205/06* | (2006.01) |
| *C07D 493/10* | (2006.01) |
| *C07D 519/00* | (2006.01) |
| *A61K 31/397* | (2006.01) |
| *A61K 31/438* | (2006.01) |
| *A61K 31/473* | (2006.01) |
| *A61K 31/536* | (2006.01) |
| *A61K 31/498* | (2006.01) |
| *A61K 31/095* | (2006.01) |
| *G01N 33/52* | (2006.01) |
| *C09B 57/02* | (2006.01) |
| *C07F 7/08* | (2006.01) |
| *C09B 1/16* | (2006.01) |
| *C09B 11/02* | (2006.01) |
| *C09B 11/28* | (2006.01) |
| *C09B 15/00* | (2006.01) |
| *C09B 19/00* | (2006.01) |
| *C09B 69/00* | (2006.01) |
| *C09K 11/06* | (2006.01) |
| *G01N 33/58* | (2006.01) |
| *C09B 11/24* | (2006.01) |
| *C09B 21/00* | (2006.01) |

(52) U.S. Cl.
CPC ........... *G01N 33/52* (2013.01); *C07D 205/06* (2013.01); *C07D 401/14* (2013.01); *C07D 403/14* (2013.01); *C07D 405/04* (2013.01); *C07D 405/14* (2013.01); *C07D 413/14* (2013.01); *C07D 473/18* (2013.01); *C07D 493/10* (2013.01); *C07D 519/00* (2013.01); *C07F 7/0812* (2013.01); *C09B 1/16* (2013.01); *C09B 11/02* (2013.01); *C09B 11/24* (2013.01); *C09B 11/28* (2013.01); *C09B 15/00* (2013.01); *C09B 19/00* (2013.01); *C09B 21/00* (2013.01); *C09B 57/02* (2013.01); *C09B 69/008* (2013.01); *C09K 11/06* (2013.01); *G01N 33/582* (2013.01); *C09K 2211/1029* (2013.01); *C09K 2211/1044* (2013.01); *C09K 2211/1096* (2013.01)

(58) Field of Classification Search
None
See application file for complete search history.

(56) References Cited

U.S. PATENT DOCUMENTS

| | | | | |
|---|---|---|---|---|
| 9,933,417 B2 * | 4/2018 | Lavis | ................... | C07F 7/0812 |
| 10,018,624 B1 * | 7/2018 | Lavis | ................... | C07F 7/0812 |
| 10,161,932 B2 * | 12/2018 | Lavis | ................... | C07F 7/0812 |

FOREIGN PATENT DOCUMENTS

| | | |
|---|---|---|
| WO | 2004087687 A1 | 10/2004 |
| WO | WO-2012125983 A1 * | 9/2012 ........... C07D 279/18 |

OTHER PUBLICATIONS

European Patent Office, Examination Report issued in corresponding Application No. 15774408.7, dated Mar. 4, 2019.

(Continued)

*Primary Examiner* — Michael Barker
(74) *Attorney, Agent, or Firm* — Stites & Harbison, PLLC; Mandy Wilson Decker

(57) ABSTRACT

The presently-disclosed subject matter includes azetidine-substituted fluorescent compounds, where the compounds may be used as probes, dyes, tags, and the like. The presently-disclosed subject matter also includes kits comprising the same as well as methods for using the same to detect a target substance.

24 Claims, 17 Drawing Sheets

(56) References Cited

OTHER PUBLICATIONS

Japan Patent Office, Office Action (Notice of Reasons for Refusal) issued in corresponding Application No. 2016-560446, dated Apr. 9, 2019. (A partial translation is attached.).
The State Intellectual Property Office of China, Second Office Action issued in corresponding Application No. 201580029319.X, dated Jan. 24, 2019.

* cited by examiner

AZETIDINE-SUBSTITUTED FLUORESCENT COMPOUNDS

RELATED APPLICATIONS

This applications claims the benefit of U.S. Provisional Patent Application No. 61/973,795, filed Apr. 1, 2014, U.S. Provisional Patent Application No. 61/991,109, filed May 9, 2014, International Patent Application No. PCT/US15/23953, filed Apr. 1, 2015, U.S. Pat. No. 9,933,417 filed Sep. 30, 2016, U.S. Pat. No. 10,018,624 filed on Feb. 15, 2018, and U.S. patent application Ser. No. 16/000,614 filed on Jun. 5, 2018, the entire disclosures of which are hereby incorporated by reference.

TECHNICAL FIELD

The presently-disclosed subject matter relates to fluorescent compounds. In particular, the presently-disclosed subject matter relates to azetidine-substituted polycyclic chemical fluorophores as well as method for making and using the same.

INTRODUCTION

Fluorescence microscopy enables the imaging of specific molecules inside living cells. This technique relies on the precise labeling of biomolecules with bright, photostable fluorescent dyes. Genetically encoded fluorophores, such as green fluorescent protein (GFP), are the mainstay of fluorescence imaging, allowing labeling with genetic specificity. However, these proteinous dyes lack the requisite photostability for many applications such as single-molecule imaging experiments. Over the past two decades, a number of alternative labeling strategies have been developed that combine the genetic specificity of fluorescent proteins with the favorable photophysics of small molecule fluorophores. Attractive alternatives include FlAsH, enzyme-based self-labeling tags (e.g., SnapTag and HaloTag), electrophilic ligand-receptor pairs (e.g., TMPTag and coumarin-PYP), and lipoic acid ligase variants. Self-labeling tags allow the labeling of a specific protein fusion with diverse synthetic fluorophores. Self-labeling tags have enabled numerous imaging experiments inside living cells.

Although the general collection of chemical dyes is extensive, relatively few exhibit the cell permeability needed for intracellular labeling. Thus, the available palette of intracellular self-labeling tag ligands has been limited to classic, net neutral fluorophores based on coumarin and rhodamine scaffolds, which exhibit membrane permeability and rapid labeling kinetics, but suboptimal brightness and photostability. Previous campaigns to improve dye performance (e.g., Cy, Alexa Fluor) involved substantial modifications such as structural rigidification and addition of sulfonate groups. These efforts resulted in highly polar, cell-impermeant dyes, useful in vitro or on the cell exterior, but incompatible with live-cell intracellular applications.

Despite the compatibility of self-labeling tags and rhodamine dyes, little work has been done to optimize this fluorophore class for live-cell labeling experiments. Previous efforts have focused on increasing water solubility along with fluorescence brightness and photostability, often through significant structural modifications. Such dyes function for in vitro and extracellular applications, but are too polar to passively enter cells.

Accordingly, there remains a need for compounds that are easy to synthesize, display improved brightness, and exhibit appropriate cell permeability. There remains a need for compounds that can function as self-labeling tags in vivo.

SUMMARY

The presently-disclosed subject matter, as embodied and broadly described herein, in one aspect, relates to compounds useful as fluorescent tags, methods of making same, methods of using the compounds to image one or more target substances, possibly in live cells, and kits for using the compounds. In some embodiments the present compounds are azetidine-substituted derivatives of known fluorescent tags. In some embodiments the present azetidine-substituted compounds can exhibit greater quantum yields relative to their original parent compounds.

Embodiments of the presently-disclosed compounds include the formula:

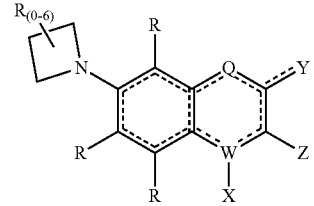

wherein:
  each R is independently selected from halogen, H, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, $SO_3H$, and alkyl, alkyl being optionally substituted with one or more heteroatoms independently selected from N, O, and S, halogen, OH, O(alkyl), O(aryl), C(O)$NR_2$, SH, S(alkyl), S(aryl), amine, $NO_2$, CHO, COO, COOH, COO(alkyl), COO(aryl), $PO_3H_2$, and/or $SO_3H$;

Q is selected from $CR_{(2)}$, NR, O, S, $SiR_{(2)}$, and Se;

W is selected from C and N;

X is selected from a lone pair of electrons, H, alkyl, aryl, halogen, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, and $SO_3H$, X being optionally substituted with one or more heteroatoms independently selected from N, O, and S, halogen, OH, O(alkyl), O(aryl), SH, S(alkyl), S(aryl), amine, $NO_2$, CHO, COO, COOH, C(O)$NR_2$, COO(alkyl), COO(aryl), $PO_3H_2$, and/or $SO_3H$;

Y is selected from H, $CR_{(2)}$, C(O)$NR_2$, NR, O, and S; and

Z is selected from H, halogen, CN, OH, O(alkyl), O(aryl), SH, S(alkyl), S(aryl), amine, $NO_2$, CHO, COOH, COO(alkyl), COO(aryl), C(O)$NR_2$, $PO_3H_2$, $SO_3H$, aryl, and alkyl, alkyl and aryl being optionally substituted with one or more heteroatoms independently selected from N, O, and S, halogen, OH, O(alkyl), O(aryl), SH, S(alkyl), S(aryl), amine, $NO_2$, CHO, COOH, C(O)$NR_2$, COO(alkyl), COO(aryl), $PO_3H_2$, and $SO_3H$, or wherein Z and Y, taken together with the atoms to which they are bonded, can form a substituted or unsubstituted 5-7 membered ring.

Embodiments of the presently-disclosed further include compounds of the formula:

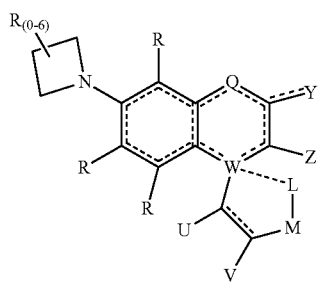

wherein:
  each R is independently selected from halogen, H, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, and alkyl, alkyl being optionally substituted with one or more heteroatoms independently selected from N, O, and S, halogen, OH, O(alkyl), O(aryl), $C(O)NR_2$, SH, S(alkyl), S(aryl), amine, $NO_2$, CHO, COO, COOH, COO(alkyl), COO(aryl), $PO_3H_2$, and/or $SO_3H$;
  Q is selected from $CR_{(2)}$, NR, O, S, $SiR_{(2)}$, and Se;
  W is selected from C and N;
  M is selected from $CR_{(2)}$, C(O), $SO_2$, and $PO_2$;
  L is selected from O, S, NR, and $CN_2$, wherein optionally L and W, taken together with the atoms to which they are bonded, can form a substituted or unsubstituted 5-7 membered ring;
  U and V are independently selected from H, alkyl, halogen, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, and $SO_3H$, alkyl being optionally substituted with one or more heteroatoms independently selected from N, O, and S, halogen, OH, O(alkyl), O(aryl), SH, S(alkyl), S(aryl), amine, $NO_2$, CHO, COO, COOH, $C(O)NR_2$, COO(alkyl), COO(aryl), $PO_3H_2$, and/or $SO_3H$, or wherein U and V, taken together with the atoms to which they are bonded, can form a substituted or unsubstituted 5-7 membered ring;
  Y is selected from H, $CR_{(2)}$, $C(O)NR_2$, NR, O, and S; and
  Z is selected from H, halogen, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, aryl, and alkyl, alkyl and aryl being optionally substituted with one or more heteroatoms independently selected from N, O, and S, halogen, OH, O(alkyl), O(aryl), SH, S(alkyl), S(aryl), amine, $NO_2$, CHO, COOH, $C(O)NR_2$, COO(alkyl), COO(aryl), $PO_3H_2$, and $SO_3H$, or wherein Z and Y, taken together with the atoms to which they are bonded, can form a substituted or unsubstituted 5-7 membered ring.

Embodiments of the presently-disclosed subject matter also include a kit. The kit can include any of the compounds described herein and a binding element that binds the compounds reversibly or irreversibly. In some embodiments the binding element includes a protein. In some embodiments the kit includes a compound having the formula:

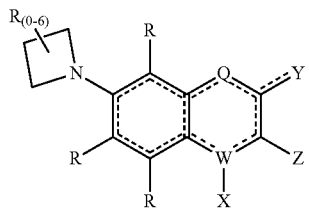

wherein:
  each R is independently selected from halogen, H, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, and alkyl, alkyl being optionally substituted with one or more heteroatoms independently selected from N, O, and S, halogen, OH, O(alkyl), O(aryl), $C(O)NR_2$, SH, S(alkyl), S(aryl), amine, $NO_2$, CHO, COO, COOH, COO(alkyl), COO(aryl), $PO_3H_2$, and/or $SO_3H$;
  Q is selected from $CR_{(2)}$, NR, O, S, $SiR_{(2)}$, and Se;
  W is selected from C and N;
  X is selected from a lone pair of electrons, H, alkyl, aryl, halogen, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, and $SO_3H$, X being optionally substituted with one or more heteroatoms independently selected from N, O, and S, halogen, OH, O(alkyl), O(aryl), SH, S(alkyl), S(aryl), amine, $NO_2$, CHO, COO, COOH, $C(O)NR_2$, COO(alkyl), COO(aryl), $PO_3H_2$, and/or $SO_3H$;
  Y is selected from H, $CR_{(2)}$, $C(O)NR_2$, NR, O, and S; and
  Z is selected from H, halogen, CN, OH, O(alkyl), O(aryl), SH, S(alkyl), S(aryl), amine, $NO_2$, CHO, COOH, COO(alkyl), COO(aryl), $C(O)NR_2$, $PO_3H_2$, $SO_3H$, aryl, and alkyl, alkyl and aryl being optionally substituted with one or more heteroatoms independently selected from N, O, and S, halogen, OH, O(alkyl), O(aryl), SH, S(alkyl), S(aryl), amine, $NO_2$, CHO, COOH, $C(O)NR_2$, COO(alkyl), COO(aryl), $PO_3H_2$, and $SO_3H$, or wherein Z and Y, taken together with the atoms to which they are bonded, can form a substituted or unsubstituted 5-7 membered ring; and
  further comprising a binding element that binds the compound, optionally reversibly or irreversibly.

In some embodiments of kits, the kits include a compound of the formula:

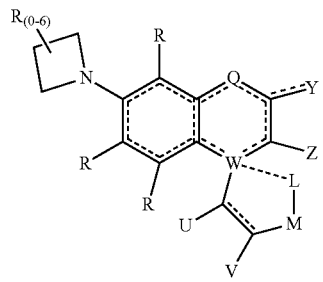

wherein:
  each R is independently selected from halogen, H, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, and alkyl, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO(alkyl), COO(aryl), PO$_3$H$_2$, and/or SO$_3$H;

Q is selected from CR$_{(2)}$, NR, O, S, SiR$_{(2)}$, and Se;

W is selected from C and N;

M is selected from CR$_{(2)}$, C(O), SO$_2$, and PO$_2$;

L is selected from O, S, NR, and CN$_2$, wherein optionally L and W, taken together with the atoms to which they are bonded, can form a substituted or unsubstituted 5-7 membered ring;

U and V are independently selected from H, alkyl, halogen, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, alkyl being optionally substituted with one or more heteroatoms independently selected from N, O, and S, halogen, OH, O(alkyl), O(aryl), SH, S(alkyl), S(aryl), amine, NO$_2$, CHO, COO, COOH, C(O)NR$_2$, COO(alkyl), COO(aryl), PO$_3$H$_2$, and/or SO$_3$H, or wherein U and V, taken together with the atoms to which they are bonded, can form a substituted or unsubstituted 5-7 membered ring;

Y is selected from H, CR$_{(2)}$, C(O)NR$_2$, NR, O, and S; and

Z is selected from H, halogen, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, SO$_3$H, aryl, and alkyl, alkyl and aryl being optionally substituted with one or more heteroatoms independently selected from N, O, and S, halogen, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, or wherein Z and Y, taken together with the atoms to which they are bonded, can form a substituted or unsubstituted 5-7 membered ring; and further comprising a binding element that binds the compound, optionally reversibly or irreversibly.

Embodiments of the presently-disclosed subject matter also include a methods for imaging, measuring, and/or detecting a target substance. In some embodiments the method can include contacting a sample, which is suspected or known as having the target substance, with any of the compounds described herein, and then detecting an emission light from the compound, the emission light indicating the presence of the target substance.

In some embodiments, the method includes contacting a sample with a compound that selectively binds a target substance, the compound being of the formula:

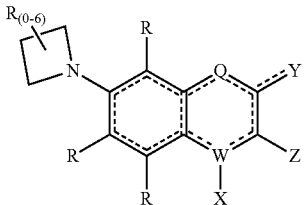

wherein:
each R is independently selected from halogen, H, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, SO$_3$H, and alkyl, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO(alkyl), COO(aryl), PO$_3$H$_2$, and/or SO$_3$H;

Q is selected from CR$_{(2)}$, NR, O, S, SiR$_{(2)}$, and Se;

W is selected from C and N;

X is selected from a lone pair of electrons, H, alkyl, aryl, halogen, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, X being optionally substituted with one or more heteroatoms independently selected from N, O, and S, halogen, OH, O(alkyl), O(aryl), SH, S(alkyl), S(aryl), amine, NO$_2$, CHO, COO, COOH, C(O)NR$_2$, COO(alkyl), COO(aryl), PO$_3$H$_2$, and/or SO$_3$H;

Y is selected from H, CR$_{(2)}$, C(O)NR$_2$, NR, O, and S; and

Z is selected from H, halogen, CN, OH, O(alkyl), O(aryl), SH, S(alkyl), S(aryl), amine, NO$_2$, CHO, COOH, COO(alkyl), COO(aryl), C(O)NR$_2$, PO$_3$H$_2$, SO$_3$H, aryl, and alkyl, alkyl and aryl being optionally substituted with one or more heteroatoms independently selected from N, O, and S, halogen, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, or wherein Z and Y, taken together with the atoms to which they are bonded, can form a substituted or unsubstituted 5-7 membered ring; and detecting an emission light from the compound, the emission light indicating the presence of the target substance.

In some embodiments the methods include contacting a sample with a compound of the formula:

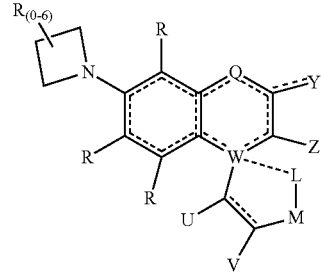

wherein:
each R is independently selected from halogen, H, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, SO$_3$H, and alkyl, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO(alkyl), COO(aryl), PO$_3$H$_2$, and/or SO$_3$H;

Q is selected from CR$_{(2)}$, NR, O, S, SiR$_{(2)}$, and Se;

W is selected from C and N;

M is selected from CR$_{(2)}$, C(O), SO$_2$, and PO$_2$;

L is selected from O, S, NR, and CN$_2$, wherein optionally L and W, taken together with the atoms to which they are bonded, can form a substituted or unsubstituted 5-7 membered ring;

U and V are independently selected from H, alkyl, halogen, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, alkyl being optionally substituted with one or more heteroatoms independently selected from N, O, and S, halogen, OH, O(alkyl), O(aryl), SH, S(alkyl), S(aryl), amine, $NO_2$, CHO, COO, COOH, $C(O)NR_2$, COO(alkyl), COO (aryl), $PO_3H_2$, and/or $SO_3H$, or wherein U and V, taken together with the atoms to which they are bonded, can form a substituted or unsubstituted 5-7 membered ring;

Y is selected from H, $CR_{(2)}$, $C(O)NR_2$, NR, O, and S; and

Z is selected from H, halogen, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, aryl, and alkyl, alkyl and aryl being optionally substituted with one or more heteroatoms independently selected from N, O, and S, halogen, OH, O(alkyl), O(aryl), SH, S(alkyl), S(aryl), amine, $NO_2$, CHO, COOH, $C(O)NR_2$, COO(alkyl), COO(aryl), $PO_3H_2$, and $SO_3H$, or wherein Z and Y, taken together with the atoms to which they are bonded, can form a substituted or unsubstituted 5-7 membered ring; and detecting an emission light from the compound, the emission light indicating the presence of the target substance.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The novel features of the subject matter of the present disclosure are set forth with particularity in the appended claims. A better understanding of the features and advantages of the presently disclosed subject matter will be obtained by reference to the following detailed description that sets forth illustrative embodiments, in which the principles of the present disclosure are used, and the accompanying drawings of which:

DESCRIPTION OF EXEMPLARY EMBODIMENTS

Figure 1:
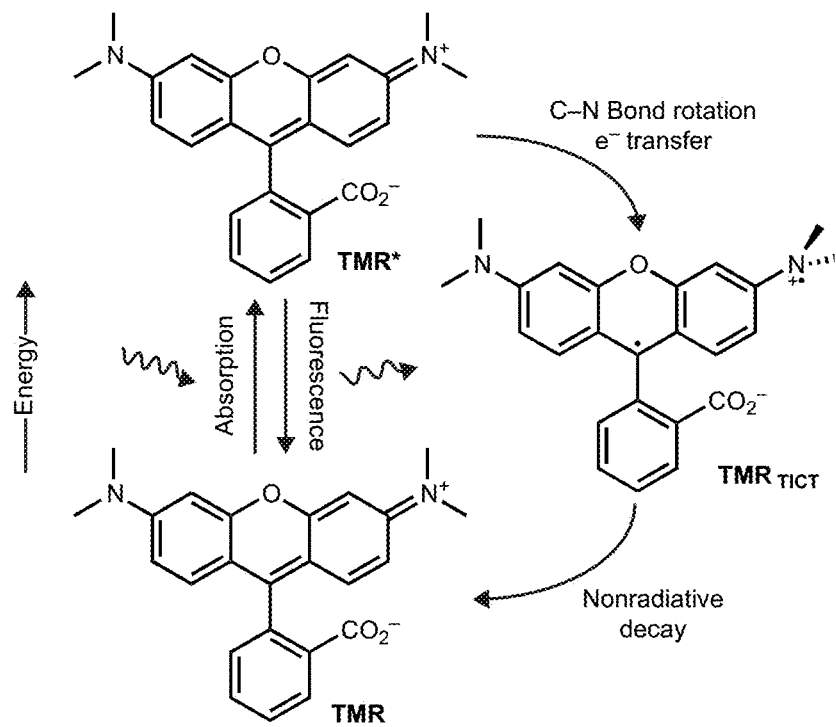
FIG. 1 includes a Jabloński diagram showing the process of twisted internal charge transfer (TICT).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds that have utility as fluorophores (e.g., fluorescent dyes). The present compounds can be utilized as fluorescent probes to observe and characterize the location and/or concentration of particular substances. In this regard, the terms "probe," "dyes," "tags," and the like are used interchangeably herein to refer to compounds comprising a fluorophore moiety which is selective for and/or is bonded to a binding element that is selective for a target substance. The probes can emit an emission light, which can be used to determine the presence of and/or measure the quantity of the target substance. In this respect, the presently-disclosed subject matter also includes methods for using the present compounds and their intermediates, as well as methods for preparing such compounds and the their intermediates.

Definitions

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a compound" includes a plurality of such compounds, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "absorption wavelength" as used herein refers to the wavelength of light capable of being absorbed by a compound in order to excite the compound to emit a light. The light emitted from a compound that has been excited with an absorption light will have an "emission wavelength."

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "protein" means any polymer comprising any of the 20 protein amino acids, regardless of its size. Although "polypeptide" is often used in reference to relatively large proteins, and "peptide" is often used in reference to small proteins, usage of these terms in the art overlaps and varies. The term "protein" as used herein refers to peptides, polypeptides and proteins, unless otherwise noted.

The term "selectively bind" is used herein to refer to the property of an atom, moiety, and/or molecule preferentially being drawn to or binding a particular compound. In some instances the atom, moiety, and/or molecule selectively binds to a particular site on a compound, such as an active site on a protein molecule.

The term "detect" is used herein to refer to the act of viewing, imagining, indicating the presence of, measuring, and the like a target substance based on the light emitted from the present compounds. More specifically, in some instances the present compounds can be bound to a target substance, and, upon being exposed to an absorption light, will emit an emission light. The presence of an emission light can indicate the presence of a target substance, whereas the quantification of the light intensity can be used to measure the concentration of a target substance.

The term "target substance" refers to a substance that is selectively bound directly by the presently-disclosed compounds and/or indirectly by a molecule that is bound to the present compound. A target substances can include, but is not limited to, a protein, carbohydrates, polysaccharide, glycoprotein, hormone, receptor, antigen, antibody, virus, substrate, metabolite, inhibitor, drug, nutrient, growth factor, and the like. In some embodiments the target substance refers to an entire molecule, and in other embodiments the target substances refers to a site on a molecule, such as a binding site on a particular protein.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless stated otherwise, all chemical groups described herein include both unsubstituted and substituted varieties.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

Where substituent groups are specified by their conventional chemical formula written from left to right, they equally encompass the chemically identical substituents that would result from writing the structure from right to left. For instance, —$CH_2O$— also encompasses recite —$OCH_2$—.

It should be understood that the bond types and locations in the chemical structures provided herein may adapt depending on the substituents in the compound, even if not specifically recited. For instance, —X— where X can be either C or N can refer to, respectively, —$CH_2$— or —NH—, where the lone pair of electrons on N is not illustrated. Thus, even if not specifically illustrated, the chemical compounds described herein include any hydrogen atoms, lone pair of electrons, and the like necessary for completing a chemical structure.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also refer to both substituted or unsubstituted alkyls. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, haide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "ring" as used herein refers to a substituted or unsubstituted cycloalkyl, substituted or unsubstituted heterocycloalkyl, substituted or unsubstituted aryl, or substituted or unsubstituted heteroaryl. A ring includes fused ring moieties, referred to as a fused ring system wherein a ring may be fused to one or more rings selected from a substituted or unsubstituted cycloalkyl, substituted or unsubstituted heterocycloalkyl, substituted or unsubstituted aryl, and substituted or unsubstituted heteroaryl in any combination. The number of atoms in a ring is typically defined by the number of members in the ring. For example, a "5- to 8-membered ring" means there are 5 to 8 atoms in the encircling arrangement. A ring can optionally include a heteroatom. The term "ring" further includes a ring system comprising more than one "ring", wherein each "ring" is independently defined as above.

Some of the unsaturated structures described herein, such as ring structures including cycloalkyl and aryl, are illustrated with dashed bonds to signify the potential existence of a resonance structure. Structures having dashed bonds are intended to reflect every possible configuration of the structure, but does not necessarily imply that all possible structures are in existence. It should be understood that the types of bonds (e.g., single bond, double bond) in such structures will vary depending on the atoms in the structure as well as whether the structures are substituted with one or more additional atoms or moieties.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), N(alkyl)$_2$, and N(aryl)$_2$.

The term "carboxylic acid" as used herein is represented by a formula —C(O)OH.

The term "ester" as used herein is represented by a formula —$OC(O)A^1$ or $C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -($A^1$O(O)C-$A^2$—C(O)O)$_a$— or ($A^1$O(O)C-$A^2$—O—OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "halide" or "halogen" refers to at least one of the halogens selected from fluorine, chlorine, bromine, and iodine.

The term "thiol" as used herein is represented by a formula SH.

Compounds

The presently-disclosed subject matter includes compounds that are azetidine-substituted. In certain embodiments the azetidine-substituted compounds are modified forms of compounds comprising an electron-donating N,N-dialkylamino motif for fluorescence. In such embodiments the N,N-dialkyl group of the original parent compound is replaced with azetidine. Some unmodified fluorophores comprising the N,N-dialkylamino motif are prone to a nonradiative decay mechanism and/or exhibit modest quantum yield. However, embodiments of the present compounds that include a substitution of the dimethylamino group for an azetidine moiety can reduce or eliminate this nonradiative decay pathway and increase the quantum yield values of the fluorophores relative to corresponding non-azetidine-substituted compounds.

By virtue of having increased quantum yields, some embodiments of the present compounds also exhibit brightness and photostability that is comparable or superior to corresponding non-azetidine-substituted compounds. In some embodiments compounds with improved quantum yield require lower illumination powers for biological imaging experiments, and are less likely to undergo destructive relaxation pathways, resulting in higher photostability.

The properties of certain embodiments of the present compounds are superior and unexpected. A planar structure can be beneficial for fluorescent emissions to occur in xanthenium dyes and other similar structures. It had previously been thought that substitution with lower rings, such as those having about 3 or 4 carbons, would compromise the planar structure of the compounds. Specifically, modification with a four-membered azetidine ring system is highly strained (26 kcal mol$^{-1}$) and intuitively was not believed not to be compatible with the planar delocalized structures found in many fluorescent molecules.

The present inventors found that the novel azetidine-substitution described herein surprisingly and unexpectedly retain and can even enhance the fluorescent characteristics of the corresponding non-azetidine-substituted compounds.

Embodiments of the present azetidine-substituted compounds also comprise a structure that can be less susceptible to undergo a twisted internal charge transfer (TICT). This surprising and unexpected characteristic provides certain embodied compounds with a high quantum yield, and in some instances a quantum yield that is higher than that of the base non-azetidine-substituted compound.

It should be understood that the presently-disclosed azetidine-substitutions can be performed on a wide variety of fluorophores, including known fluorophores. In some instances the azetidine-substitution permit the base fluorophores to retain and/or enhance their beneficial properties. For example, embodiment embodiments of the present compounds include azetidine-substituted rhodamine compounds that retain or enhance the brightness, photostability, and/or insensitivity to light of non-azetidine-substituted rhodamine compounds.

Of the extant collection of chemical fluorophores, the rhodamine dyes are a useful class for live-cell imaging with genetically encoded self-labeling tags. This utility stems from the brightness, photostability, insensitivity to pH, and modifiable structure of rhodamine dyes. The spectral characteristics of rhodamines can be controlled to allow access to dyes with absorption maxima ranging from blue to the infrared. In addition, rhodamine dyes exist in equilibrium between an "open," zwitterionic, quinoid form and a "closed," lipophilic, lactone form. This dynamic amphipathicity makes rhodamine dyes excellent ligands for live-cell labeling technologies; the dye efficiently traverses the cellular membrane without detergents or chemical masking groups and excess ligand can be rapidly washed away.

In some embodiments of the presently-disclosed subject matter, a compound of the following formula is provided:

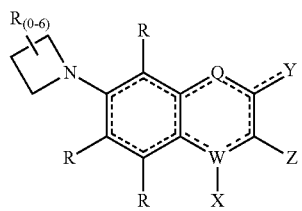

wherein each R is independently selected from halogen, H, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, SO$_3$H, and alkyl, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO(alkyl), COO(aryl), PO$_3$H$_2$, and/or SO$_3$H; Q is selected from CR$_{(2)}$, C(O)NR$_2$, NR, O, S, SiR$_{(2)}$, and Se; W is selected from C and N; X is selected from a lone pair of electrons, H, alkyl, aryl, halogen, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, X being optionally substituted with one or more heteroatoms independently selected from N, O, and S, halogen, OH, O(alkyl), O(aryl), SH, S(alkyl), S(aryl), amine, NO$_2$, CHO, COO, COOH, C(O)NR$_2$, COO(alkyl), COO(aryl), PO$_3$H$_2$, and/or SO$_3$H; Y is selected from H, CR$_{(2)}$, C(O)NR$_2$, NR, O, and S; and Z is selected from H, halogen, CN, OH, O(alkyl), O(aryl), SH, S(alkyl), S(aryl), amine, NO$_2$, CHO, COOH, COO(alkyl), COO(aryl), C(O)NR$_2$, PO$_3$H$_2$, SO$_3$H, aryl, and alkyl, alkyl and aryl being optionally substituted with one or more heteroatoms independently selected from N, O, and S, halogen, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, or wherein Z and Y, taken together with the atoms to which they are bonded, can form a substituted or unsubstituted 5-7 membered ring.

In some embodiments wherein Y and Z, taken together with the atoms to which they are bonded, form the 5-7 membered ring being substituted with one or more additional heteroatoms selected from N, O and S or/and one or more substituents selected from halogen, CN, OH, O(alkyl), O(aryl), SH, S(alkyl), S(aryl), amine, NO$_2$, CHO, COOH, COO(alkyl), COO(aryl), PO$_3$H$_2$, SO$_3$H, and alkyl. In specific embodiments wherein Y and Z, taken together with the atoms to which they are bonded, form the 5-7 membered ring that is substituted with an unsubstituted or substituted azetidine group.

In some embodiments of the presently-disclosed subject matter, a compound can be of the following formula:

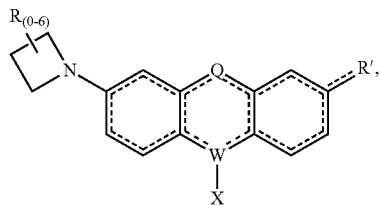

wherein R' is selected from halogen, H, CN, OH, O(alkyl), O(aryl), SH, S(alkyl), S(aryl), amine, $NO_2$, CHO, COOH, COO(alkyl), COO(aryl), C(O)$NR_2$, $PO_3H_2$, $SO_3H$, and alkyl, alkyl being optionally substituted with one or more heteroatoms independently selected from N, O, and S, halogen, OH, O(alkyl), O(aryl), SH, S(alkyl), S(aryl), C(O)$NR_2$, amine, $NO_2$, CHO, COO, COOH, COO(alkyl), COO(aryl), $PO_3H_2$, and/or $SO_3H$. In other embodiments R' is selected from an azetidine moiety (group) that is unsubstituted or is substituted with one or more of halogen, H, CN, OH, O(alkyl), O(aryl), SH, S(alkyl), S(aryl), amine, $NO_2$, CHO, COOH, COO(alkyl), C(O)$NR_2$, COO(aryl), $PO_3H_2$, $SO_3H$, and alkyl.

In some embodiments of the presently-disclosed subject matter, a compound can be of the following formula:

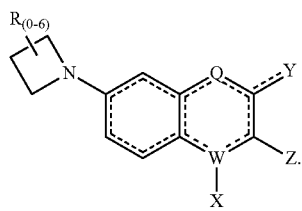

In some embodiments of the presently-disclosed subject matter, a compound can be of the following formula:

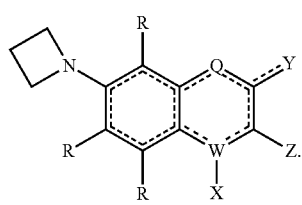

In some embodiments of the presently-disclosed subject matter, a compound can be of the following formula:

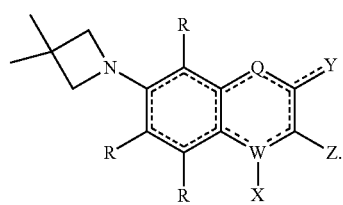

In some embodiments of the presently-disclosed subject matter, a compound can be of the following formula:

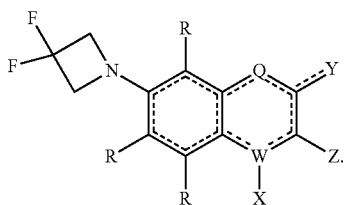

In some embodiments of the presently-disclosed subject matter, a compound can be of the following formula:

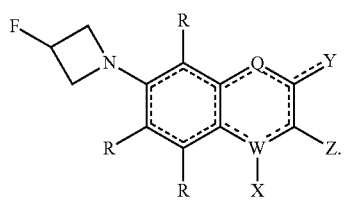

In some embodiments of the presently-disclosed subject matter, a compound can be of the following formula:

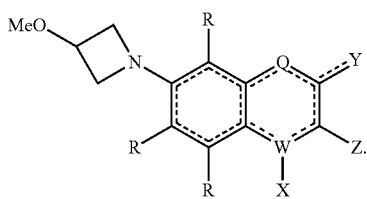

In some embodiments of the presently-disclosed subject matter, a compound can be of the following formula:

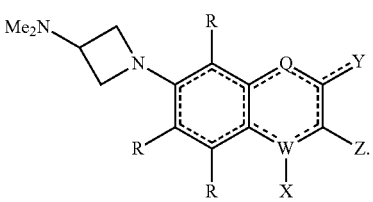

In some embodiments of the presently-disclosed subject matter, a compound can be of the following formula:

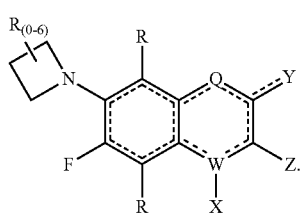

In some embodiments of the presently-disclosed subject matter, X is a substituted aryl.

In other embodiments, X can also be selected from, but is not limited to, H, C,

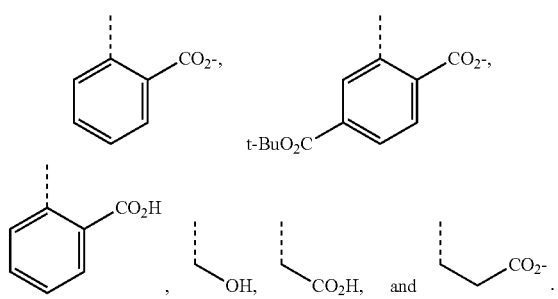

In some embodiments, W is N and X is a lone pair of electrons. In some embodiments X can partially or wholly comprise a linker that is capable of binding the present compounds to a binding element, as described herein. In other embodiments X can partially or wholly comprise a binding element. The structures of X illustrated herein are provided for illustrative purposes only, as X in some embodiments is dependent on the linker that may be used in conjunction with a compound, the binding element that may be used in conjunction with a compound, and/or the target substance to be detected by a compound.

In some embodiments of the presently-disclosed subject matter, a compound can be selected according to at least one of the following formula:

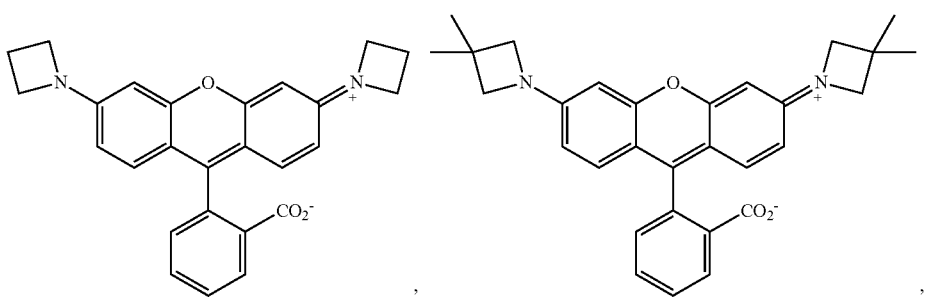

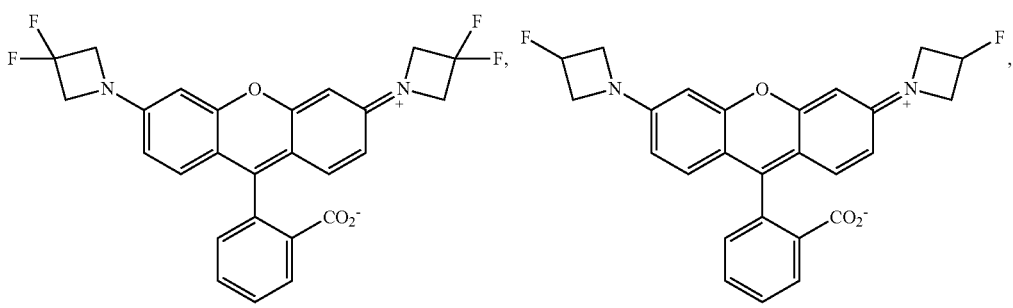

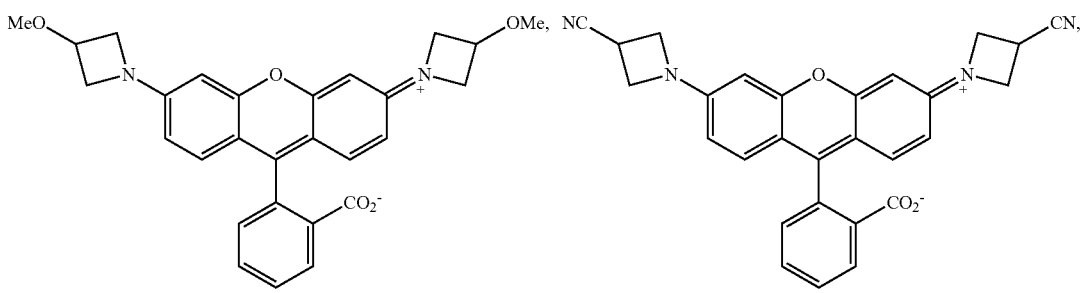

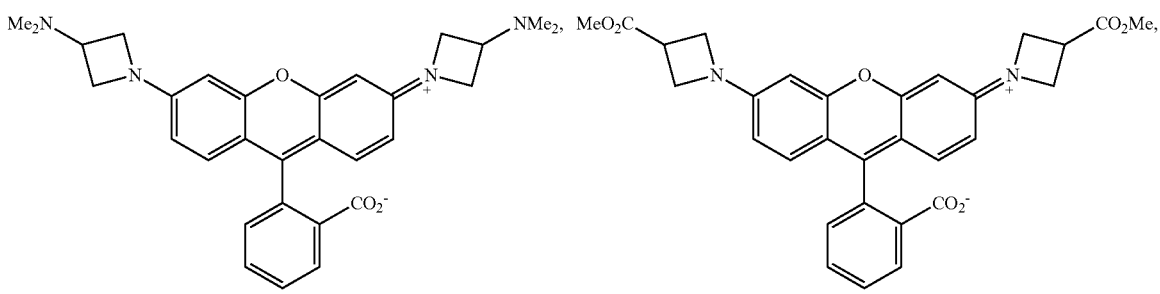

-continued
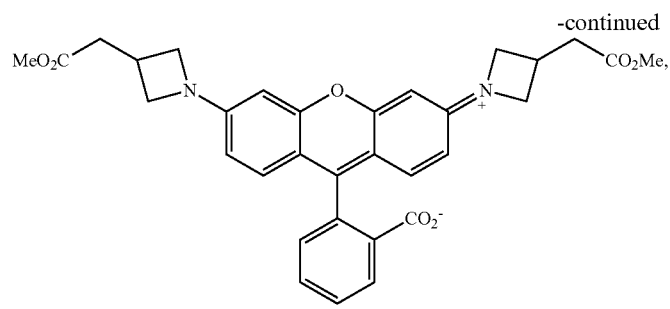
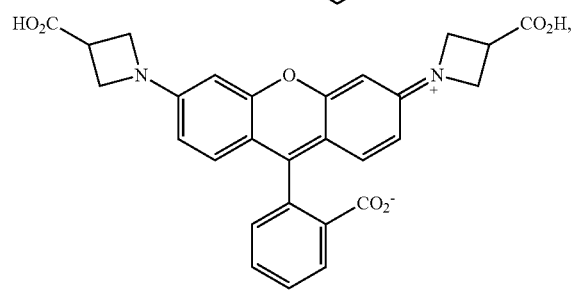
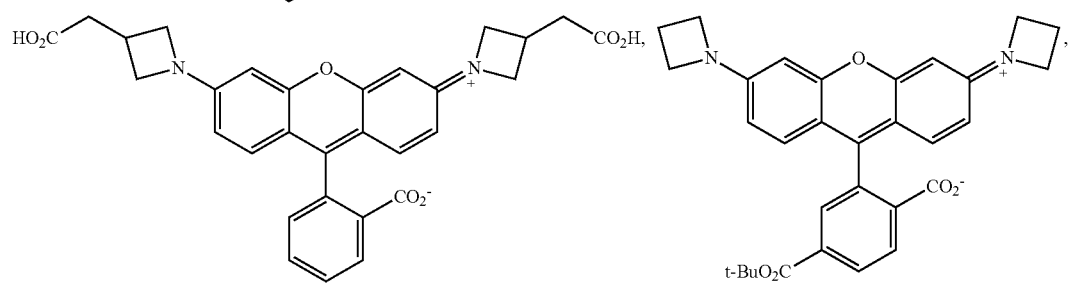
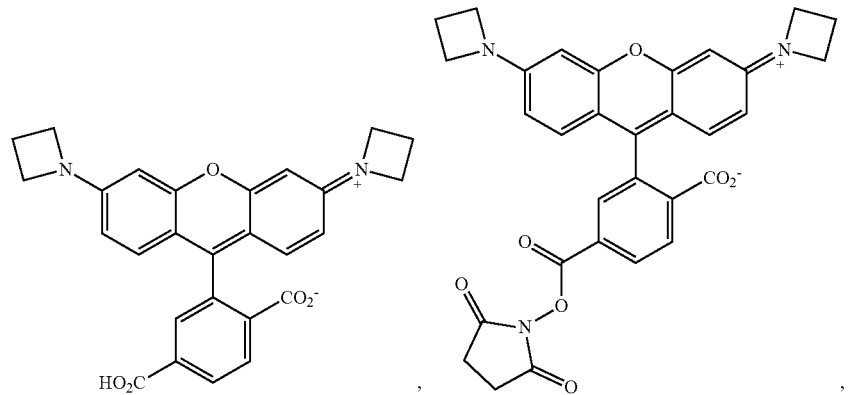
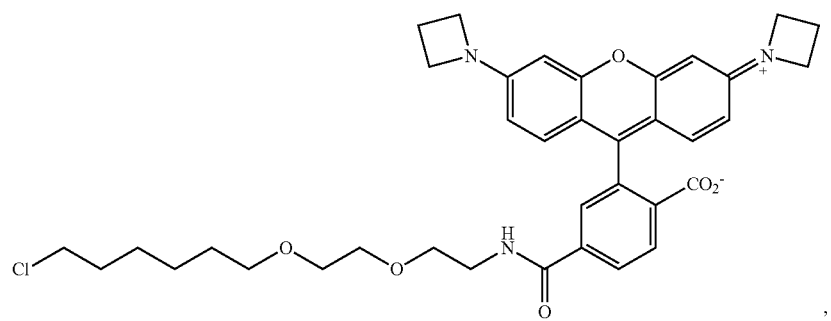

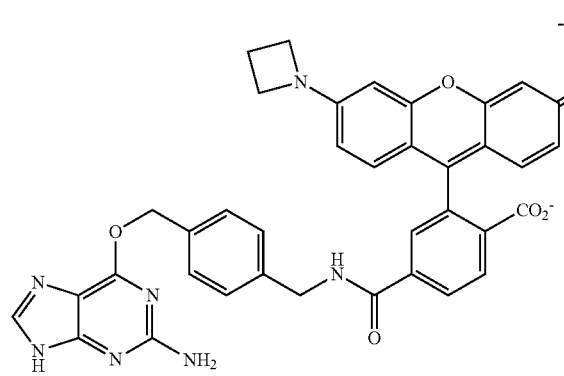
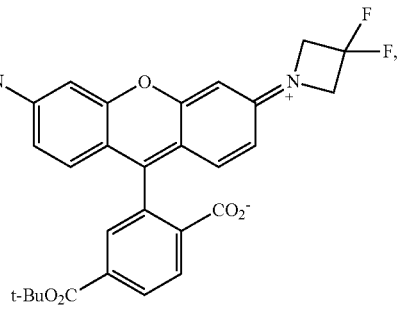
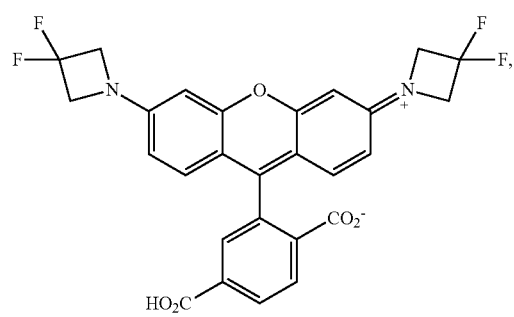
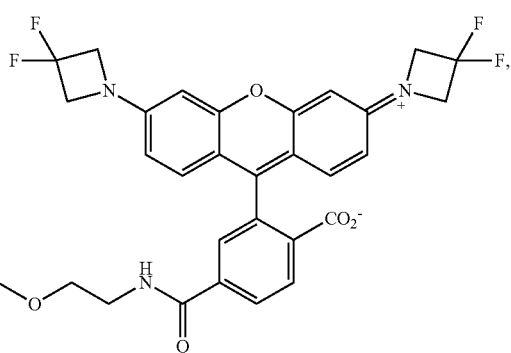
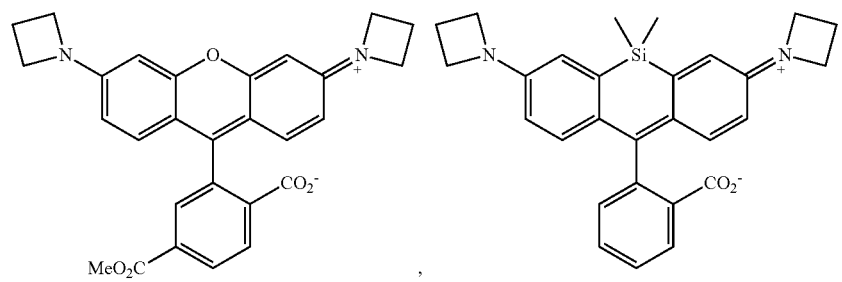
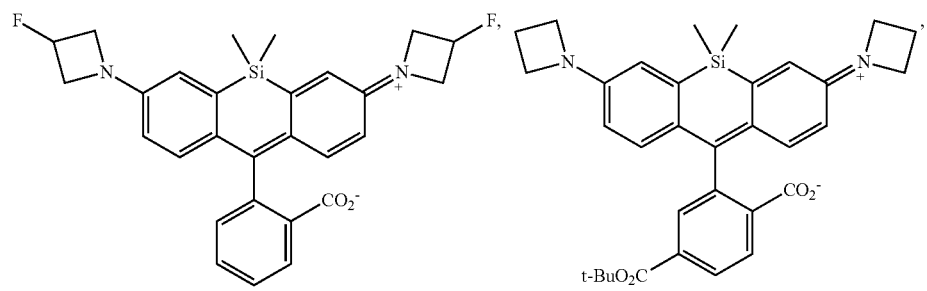

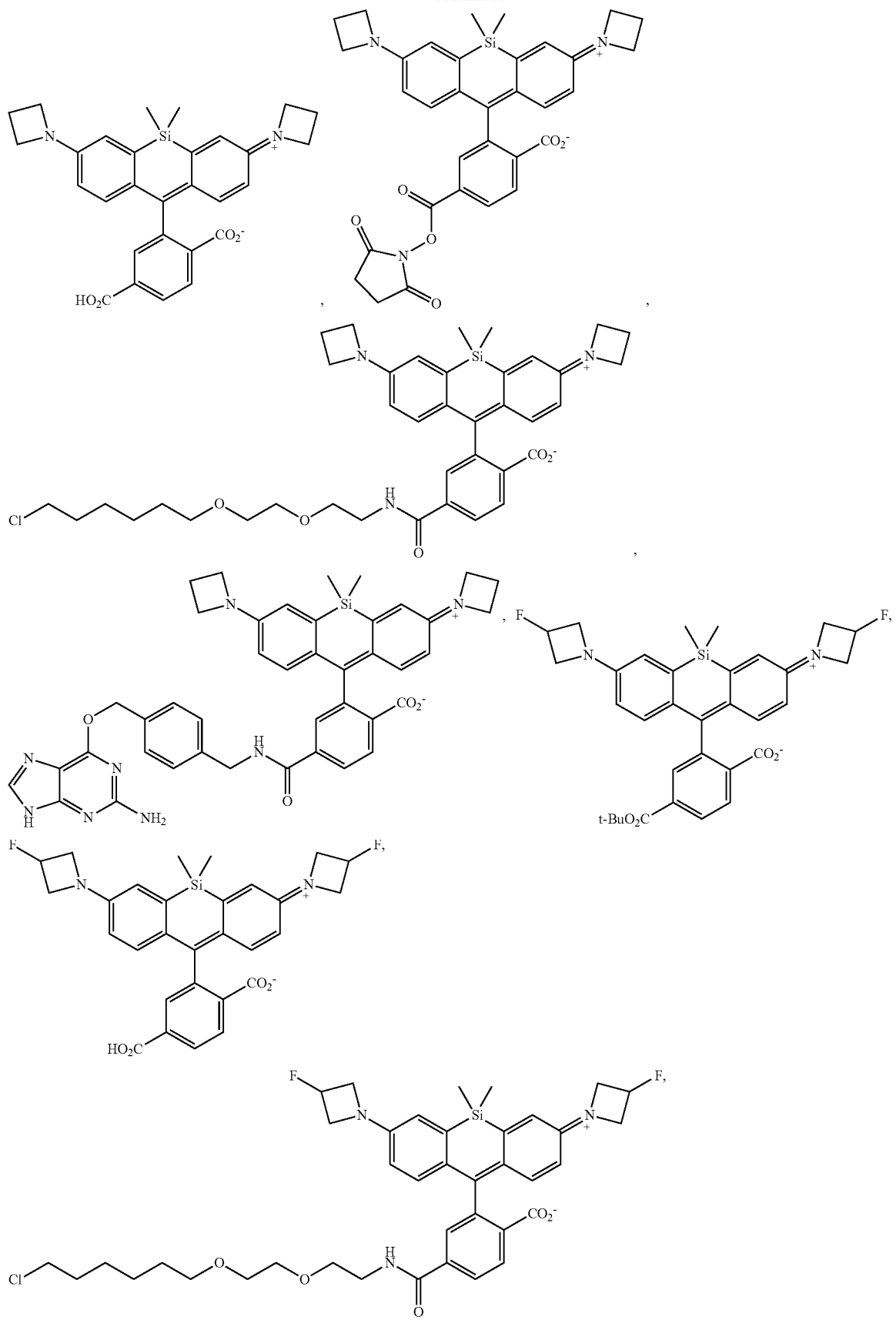

-continued
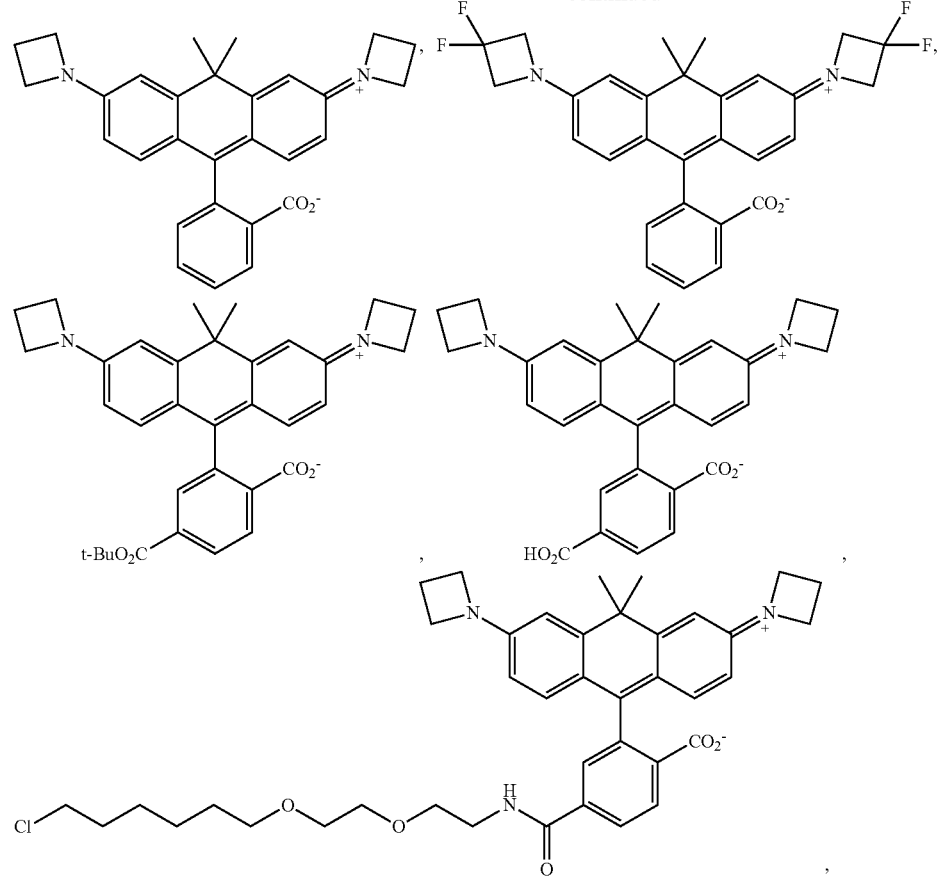
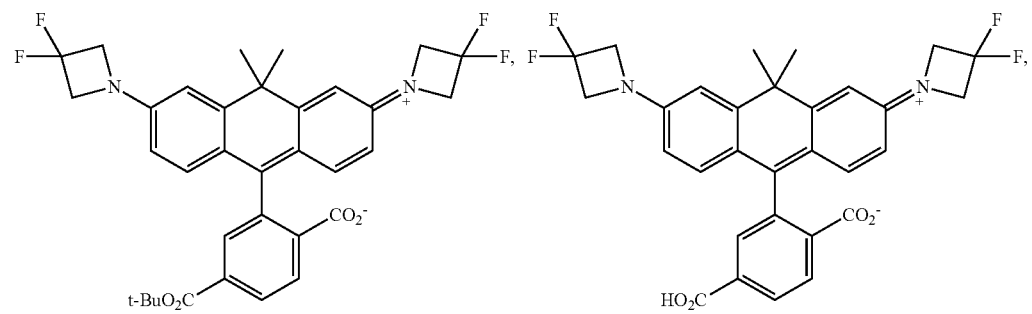
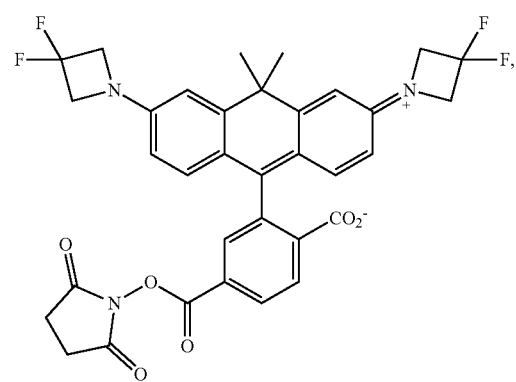

-continued

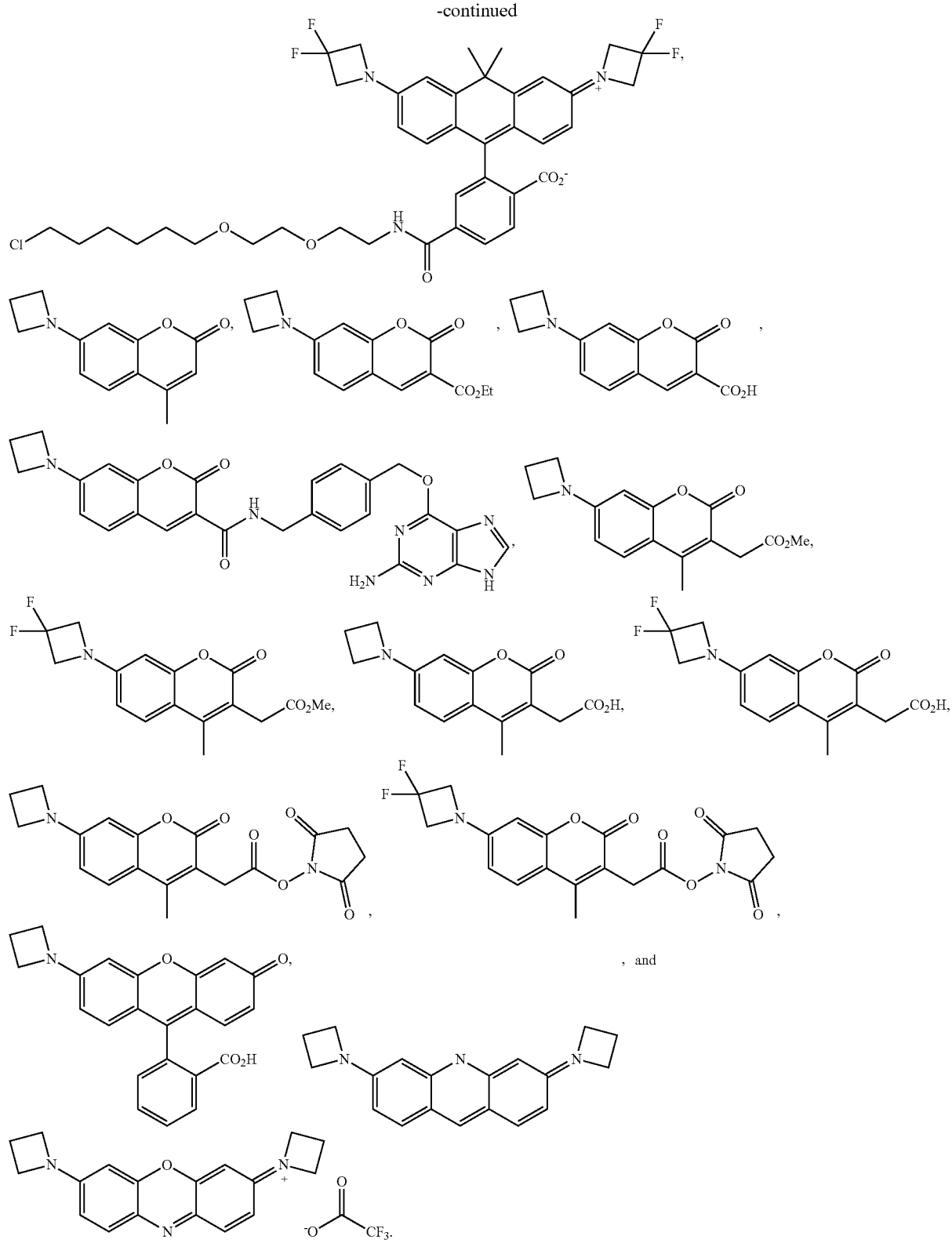

The presently-disclosed subject matter also includes derivatives of any of the compounds described herein.

The compounds described herein can contain one or more double bonds and, thus, potentially can give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

As discussed herein, it should be understood that the presently-disclosed azetidine-substitutions are generalizable and can be applied to a wide variety of compounds. Exemplary compounds include azetidine-substituted rhodamine derivatives, azetidine-substituted coumarin derivatives, azetidine-substituted rhodol derivatives, azetidine-substituted acridine derivatives, azetidine-substituted oxazine derivatives, azetidine-substituted naphthalimide derivatives, azetidine-substituted carborhodamine derivatives, azetidine-substituted silarhodamine derivatives, and the like. Those of ordinary skill will recognize other compounds capable of the presently-disclosed azetidine-substitutions. As described above, these and other derivatives of the presently-disclosed subject matter can retain and/or enhance the beneficial characteristics of the corresponding non-azetidine-substituted compounds. For example, embodiments of azetidine-substituted compounds with minimal structural changes can preserve the cell permeability and efficiency of intracellular labeling of the original non-azetidine-substituted compound.

Furthermore, as described herein, the azetidine moieties can be substituted or unsubstituted. Table 1 below describes embodiments of azetidinyl-rhodamines, azetidinyl-carborhodamines, and azetidinyl-sila-rhodamines bearing substituents on the azetidine rings. It should be understood that the azetidine moieties described in Table 1 can be incorporated into any of the compounds described herein.

TABLE 1

Spectroscopic data for embodiments of azetidinyl-rhodamines, azetidinyl-carborhodamines, and azetidinyl-sila-rhodamines.

| $NR_2$ | X | $\lambda_{max}$ (nm) | $\varepsilon$ ($M^{-1}\,cm^{-1}$) | $\lambda_{em}$ (nm) | $\phi$ |
|---|---|---|---|---|---|
| azetidinyl | O | 549 | 101,000 | 571 | 0.88 |
| 3,3-dimethyl-azetidinyl | O | 550 | 110,000 | 572 | 0.83 |

TABLE 1-continued

Spectroscopic data for embodiments of azetidinyl-rhodamines, azetidinyl-carborhodamines, and azetidinyl-sila-rhodamines.

| $NR_2$ | X | $\lambda_{max}$ (nm) | $\varepsilon$ ($M^{-1}\,cm^{-1}$) | $\lambda_{em}$ (nm) | $\phi$ |
|---|---|---|---|---|---|
| 3-MeO-azetidinyl | O | 541 | 109,000 | 564 | 0.88 |
| 3-Me$_2$N-azetidinyl | O | 542 | 111,000 | 565 | 0.57 |
| 3-F-azetidinyl | O | 536 | 113,000 | 560 | 0.87 |
| 3,3-F$_2$-azetidinyl | O | 525 | 94,000 | 549 | 0.91 |
| 3-NC-azetidinyl | O | 533 | 108,000 | 557 | 0.89 |
| 3-HO$_2$C-azetidinyl | O | 545 | 108,000 | 568 | 0.87 |
| 3-(HO$_2$CCH$_2$)-azetidinyl | O | 549 | 111,000 | 572 | 0.87 |
| azetidinyl | CMe$_2$ | 608 | 99,000 | 631 | 0.67 |

TABLE 1-continued

Spectroscopic data for embodiments of azetidinyl-rhodamines, azetidinyl-carborhodamines, and azetidinyl-sila-rhodamines.

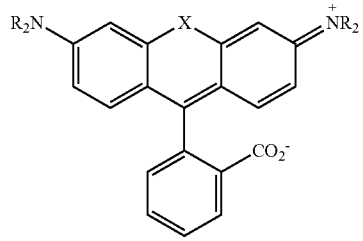

| NR$_2$ | X | $\lambda_{max}$ (nm) | $\varepsilon$ (M$^{-1}$ cm$^{-1}$) | $\lambda_{em}$ (nm) | $\phi$ |
|---|---|---|---|---|---|
| 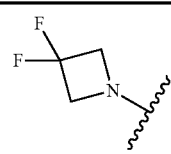 | CMe$_2$ | 585 | 156,000$^a$ | 609 | 0.78 |
| 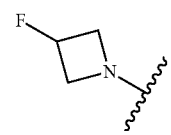 [SMILES: *N1CC(F)C1] | SiMe$_2$ | 646 | 152,000$^b$ | 664 | 0.54 |
| 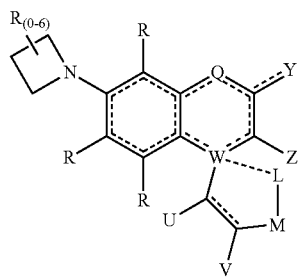 | SiMe$_2$ | 635 | 167,000$^a$ | 652 | 0.56 |

All measurements were taken in 10 mM HEPES pH 7.3 unless otherwise noted.
$^a$Extinction coefficient measured in trifluoroethanol containing 0.1% (v/v) trifluoroacetic acid.
$^b$Extinction coefficient measured in ethanol containing 0.1% (v/v) trifluoroacetic acid.

The present compounds can have a broad range of absorption and emission properties. Since the present azetidine-substitution can be performed on a variety of compounds, embodiments of the present azetidine-substituted compounds can include absorption wavelengths in the ultraviolet to the near-infrared spectrum. Specific embodiments of the present compounds can include absorption wavelengths selected of about 100 nm, 200 nm, 300 nm, 400 nm, 500 nm, 600 nm, 700 nm, 800 nm, 900 nm, 1000 nm, or any value therebetween. In some embodiments the compounds include an absorption wavelength of more than about 1000 nm. Once activated, the present compounds can emit a detectable emission light. The wavelength of the emission light can vary depending on the base compound its substitutions, and in some embodiments the emission wavelength is a wavelength of about 100 nm to about 1000 nm, including about 100 nm, 200 nm, 300 nm, 400 nm, 500 nm, 600 nm, 700 nm, 800 nm, 900 nm, 1000 nm, or any value therebetween.

Figure 33:
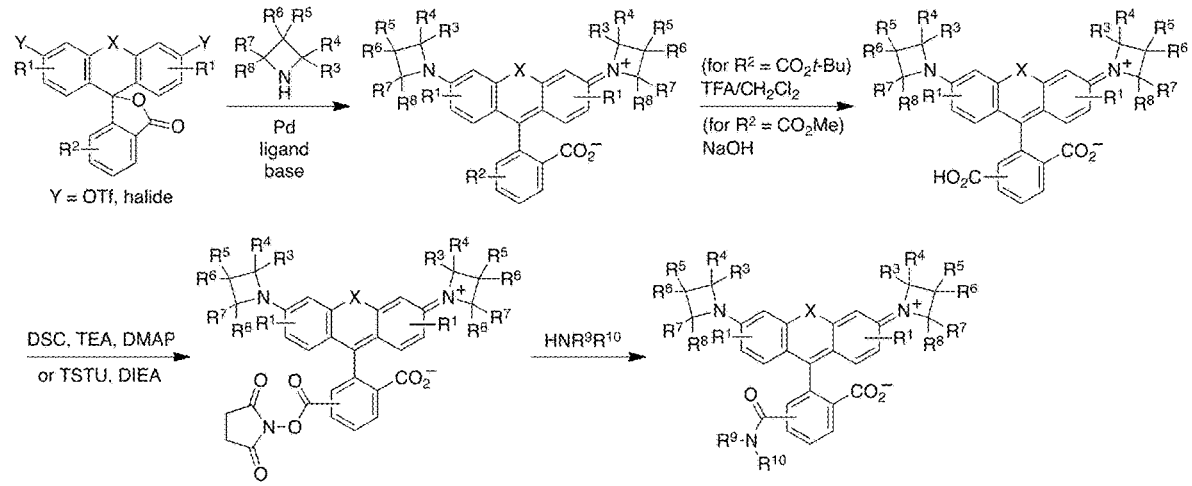
FIG. 33 includes an exemplary synthetic scheme for synthesizing a compound in accordance with an embodiment of the presently-disclosed subject matter.

Those of ordinary skill in the art will also appreciate that the present compounds comprise both open and closed (e.g. lactone) forms of the present fluorophores. In some instances the present azetidinyl fluorophores that possess ester substituents can be deprotected through acid- or base-mediated conditions to generate azetidinyl dyes with carboxylic acid handles. The scheme shown in FIG. 33 illustrates an exemplary fluorophore transitioning between a closed "lactone" form and an open form having a carboxylic acid handle. In other embodiments the compounds can transition from a closed form to an open form upon being exposed to an absorption light. Thus, in some embodiments, the present compounds can be photo or chemically activated in order to transition between closed and open forms. All of the compounds described herein include both the closed form and open form for each fluorophore.

In some embodiments, both open and closed forms of embodiments of the presently-disclosed compounds can be represented by the following formula:

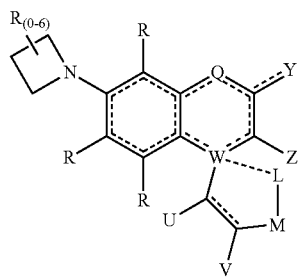

wherein each R is independently selected from halogen, H, CN, OH, O(alkyl), O(aryl), SH, S(alkyl), S(aryl), amine, NO$_2$, CHO, COOH, C(O)NR$_2$, COO(alkyl), COO(aryl), PO$_3$H$_2$, SO$_3$H, and alkyl, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO (alkyl), COO(aryl), PO$_3$H$_2$, and/or SO$_3$H; Q is selected from CR$_{(2)}$, C(O)NR$_2$, NR, O, S, SiR$_{(2)}$, and Se; W is selected from C and N; M is selected from CR$_{(2)}$, C(O)NR$_2$, C(O), SO$_2$, and PO$_2$; L is selected from O, S, NR, CN$_2$, and C(O)NR$_2$, wherein optionally L and W, taken together with the atoms to which they are bonded, can form a substituted or unsubstituted 5-7 membered ring; U and V are independently selected from H, alkyl, halogen, CN, OH, O(alkyl), O(aryl), SH, S(alkyl), C(O)NR$_2$, S(aryl), amine, NO$_2$, CHO, COOH, COO(alkyl), COO(aryl), PO$_3$H$_2$, and SO$_3$H, alkyl being optionally substituted with one or more heteroatoms independently selected from N, O, and S, halogen, OH, O(alkyl), O(aryl), C(O)NR$_2$, SH, S(alkyl), S(aryl), amine, NO$_2$, CHO, COO, COOH, COO(alkyl), COO(aryl), PO$_3$H$_2$, and/or SO$_3$H, or wherein U and V, taken together with the atoms to which they are bonded, can form a substituted or unsubstituted 5-7 membered ring; Y is selected from H, CR$_{(2)}$, C(O)NR$_2$, NR, O, and S; and Z is selected from H, halogen, CN, OH, O(alkyl), O(aryl), SH, S(alkyl), S(aryl), amine, NO$_2$, CHO, COOH, COO(alkyl), COO(aryl), C(O) NR$_2$, PO$_3$H$_2$, SO$_3$H, aryl, and alkyl, alkyl and aryl being optionally substituted with one or more heteroatoms independently selected from N, O, and S, halogen, OH, O(alkyl), O(aryl), SH, S(alkyl), S(aryl), amine, NO$_2$, CHO, COOH, C(O)NR$_2$, COO(alkyl), COO(aryl), PO$_3$H$_2$, and SO$_3$H, or wherein Z and Y, taken together with the atoms to which they are bonded, can form a substituted or unsubstituted 5-7 membered ring.

In some embodiments of such compounds, the compounds have a structure represented by the following formula:

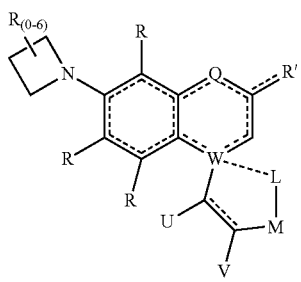

wherein R' is selected from halogen, H, CN, OH, O(alkyl), O(aryl), SH, S(alkyl), S(aryl), amine, $NO_2$, CHO, COOH, COO(alkyl), COO(aryl), $C(O)NR_2$, $PO_3H_2$, $SO_3H$, and alkyl, alkyl being optionally substituted with one or more heteroatoms independently selected from N, O, and S, halogen, OH, O(alkyl), O(aryl), SH, S(alkyl), S(aryl), amine, $NO_2$, CHO, COO, COOH, $C(O)NR_2$, COO(alkyl), COO(aryl), $PO_3H_2$, $SO_3H$, or an azetidine group that is unsubstituted or substituted with one or more of halogen, H, CN, OH, O(alkyl), O(aryl), SH, S(alkyl), S(aryl), amine, $NO_2$, CHO, $C(O)NR_2$, COOH, COO(alkyl), COO(aryl), $PO_3H_2$, $SO_3H$, and alkyl.

In this regard, exemplary open form compounds of the presently-disclosed subject matter have the following formula:

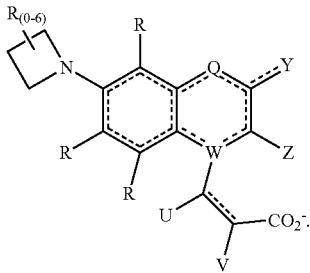

In some embodiments, the closed form of the presently-disclosed compounds include the following formula:

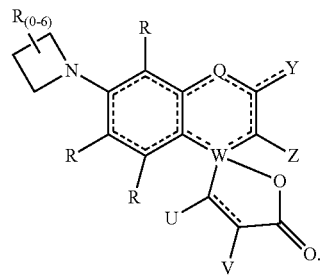

In other embodiments, the closed form of the presently-disclosed compounds include the following formula:

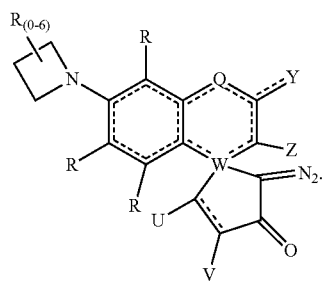

In some embodiments of U and V include a substituted aryl, and in some embodiments the compound can be represented by the following formula:

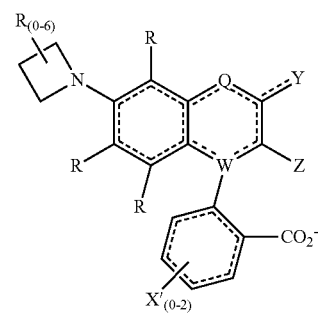

wherein X' is selected from H, OH, alkyl, aryl, halogen, CN, OH, O(alkyl), O(aryl), SH, S(alkyl), S(aryl), amine, $NO_2$, CHO, COOH, COO(alkyl), COO(aryl), $C(O)NR_2$, $PO_3H_2$, and $SO_3H$, In certain embodiments of closed form compounds, the compounds include a formula selected from:

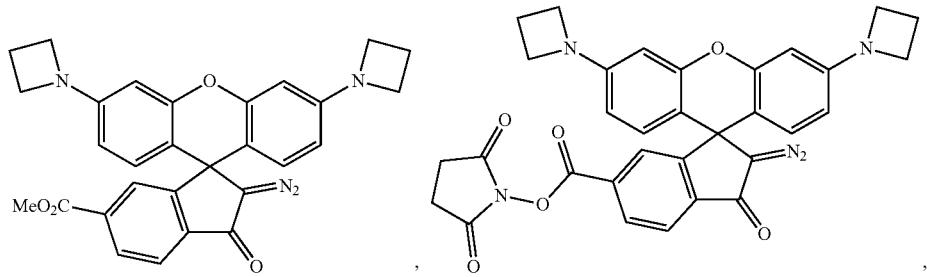

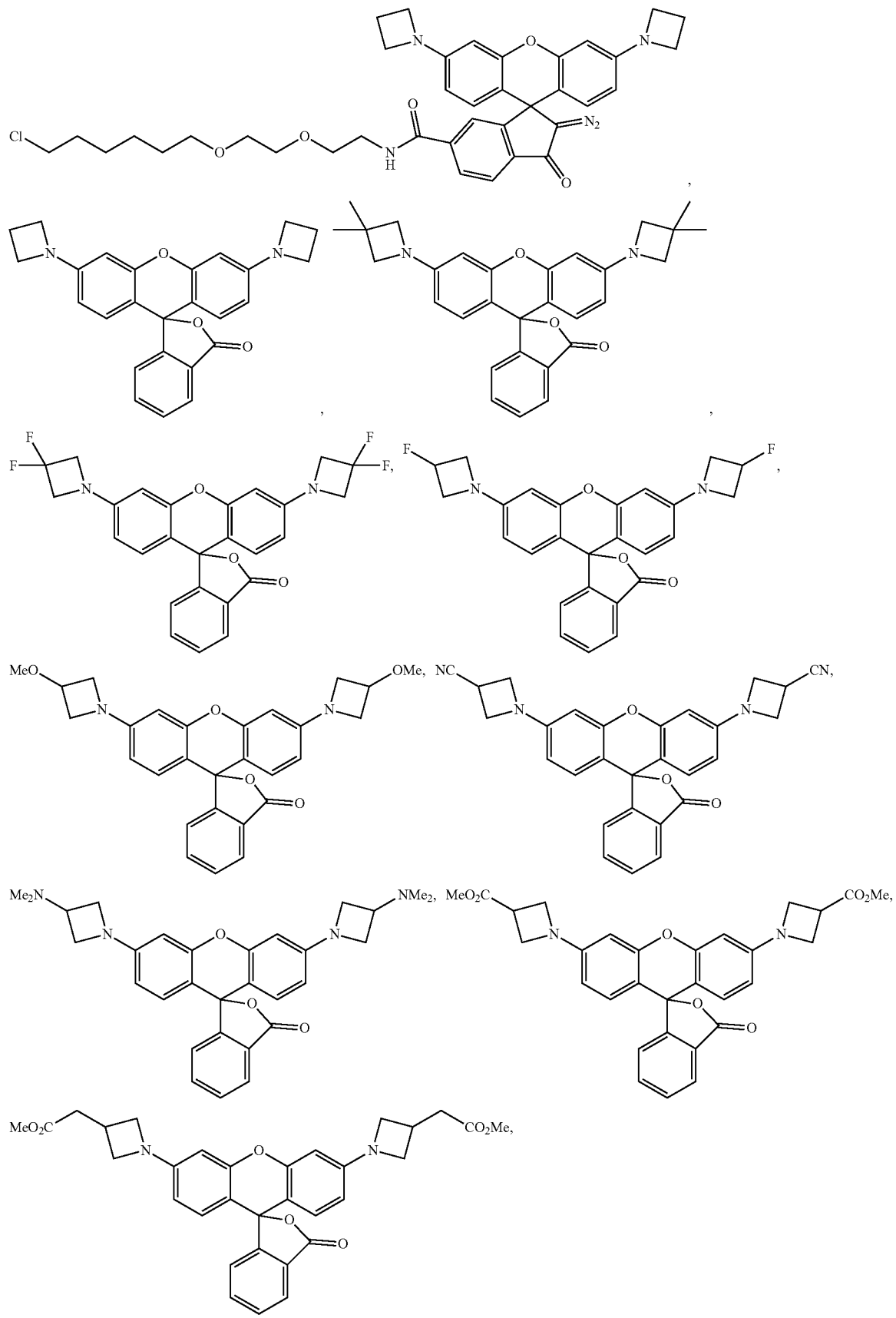

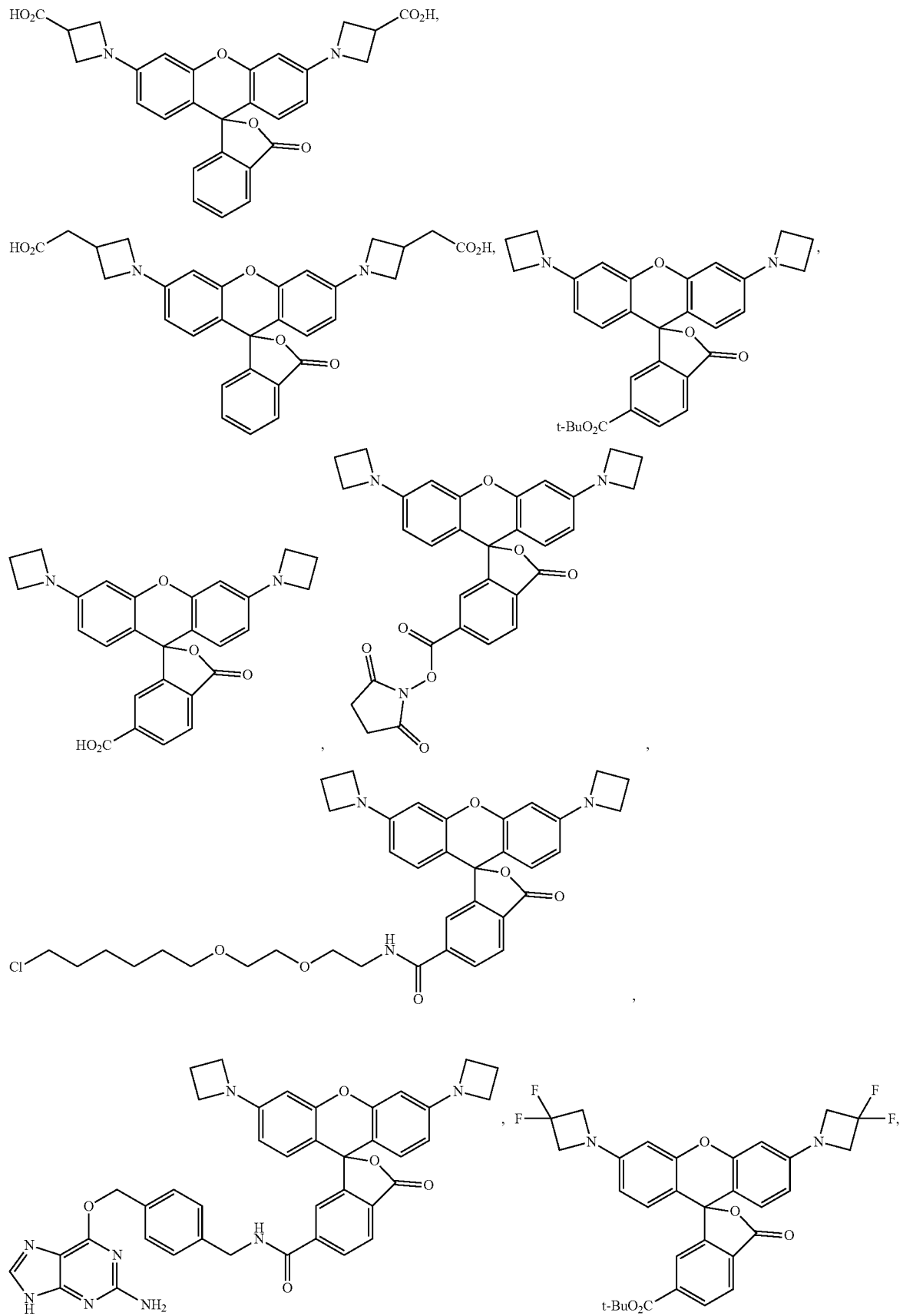

-continued
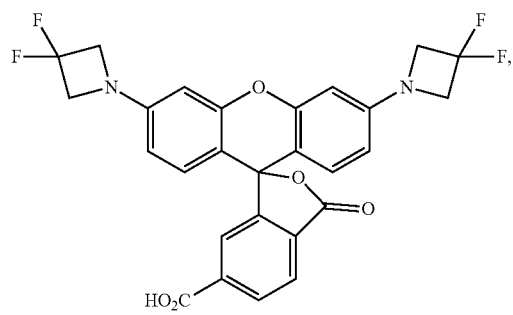
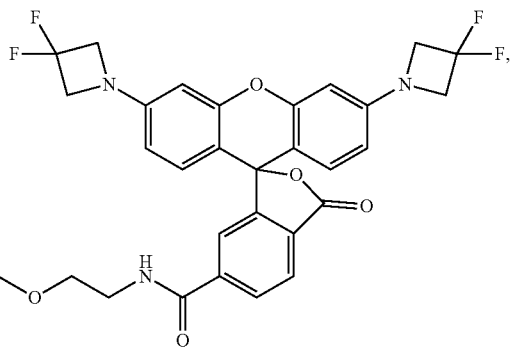
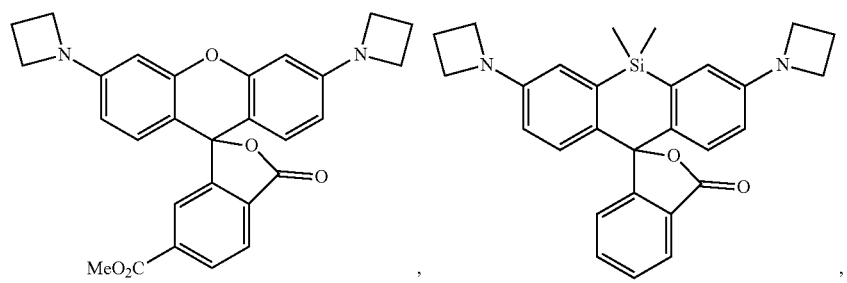
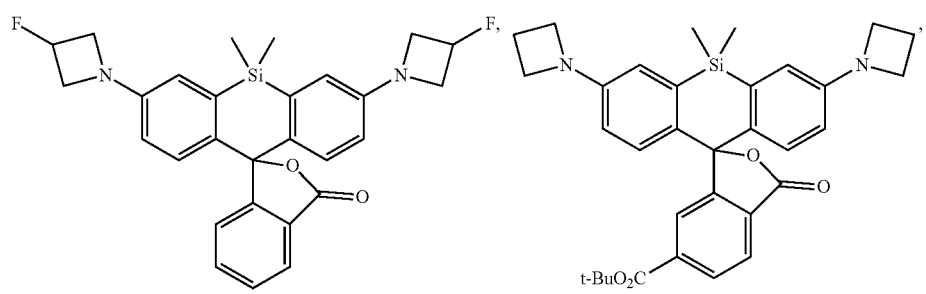
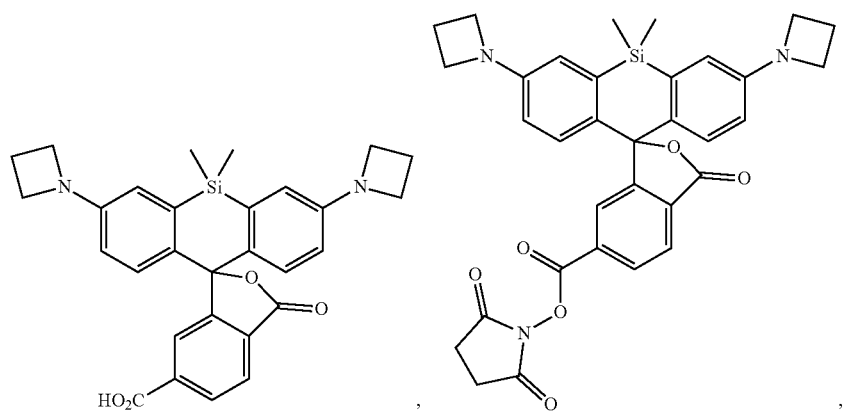

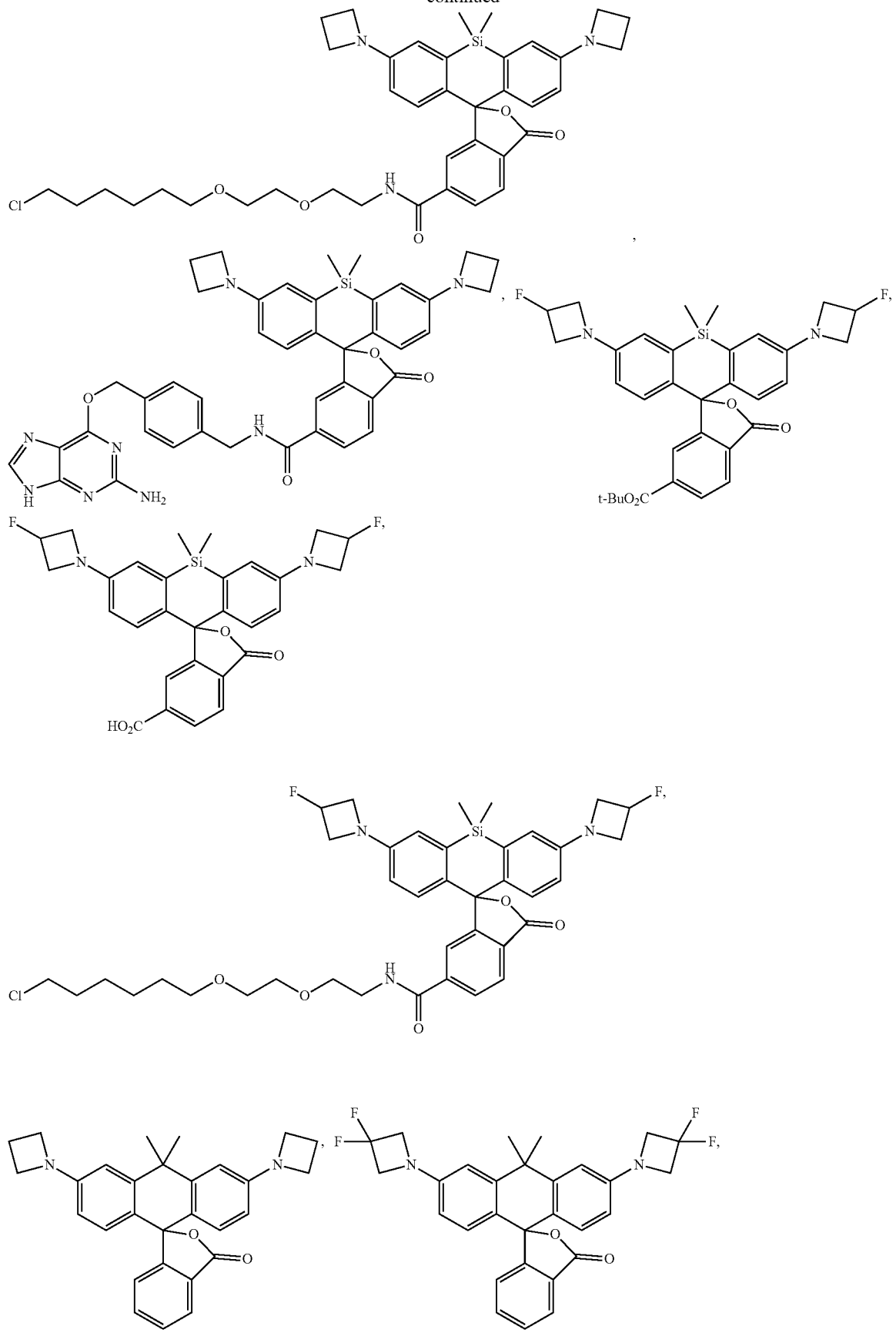

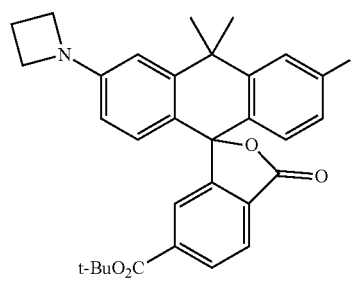
-continued
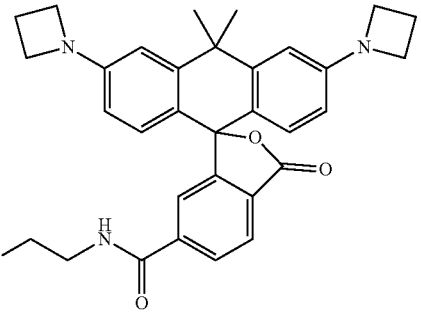
,
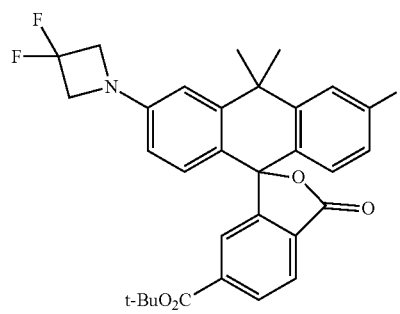
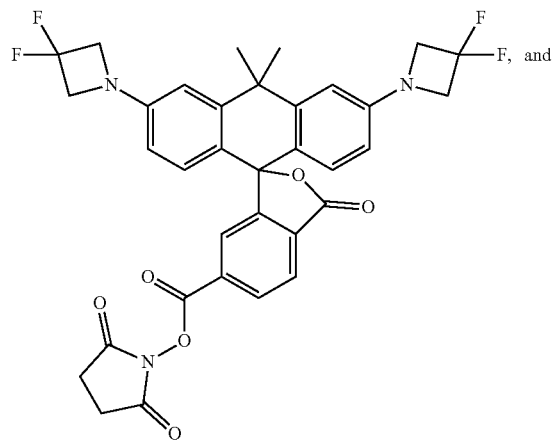
and
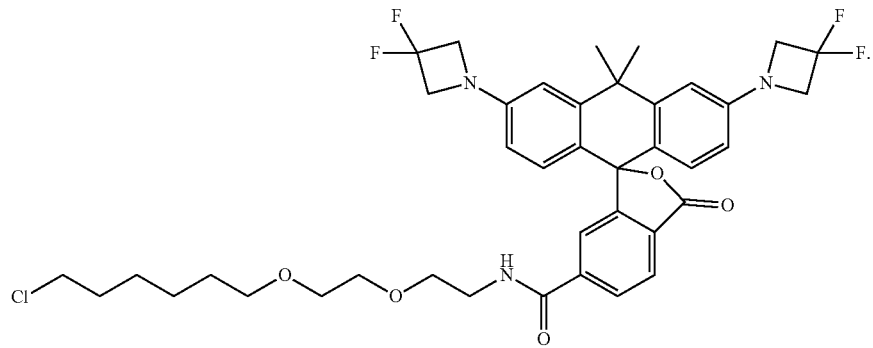

While the above structures are provided for illustrative purposes, those of ordinary skill in the art will appreciate all the open and closed forms of the compounds disclosed herein upon review of this paper.

Kits

The presently-disclosed subject matter includes kits comprising any of the compound(s) described herein, packaged together with an appropriate binding element. In some instances binding elements are referred to as ligands herein. The binding element can bind the compound reversibly and/or irreversibly. In some embodiments the binding element can be bound to the compound directly, and in other embodiments the binding element is bound to the compound indirectly. In some embodiments a compound can be bound to a binding element indirectly via a linker, wherein in some embodiments the linker includes unsubstituted or substituted alkyl or the like. Some embodiments of kits are further provided with a linker for attachment to the present compounds.

The binding element can generally selectively bind a molecule or substance of interest (i.e., target substance). Exemplary binding elements include, but are not limited to, amino acid(s), a protein, an antibody or fragment thereof, an antigen, a polysaccharide, a nucleoside, a nucleotide, an oligonucleotide, a nucleic acid, a drug, a hormone, a lipid, a synthetic polymer, a solid support, a polymeric microparticle, a cell, a virus, an enzymatic substrate, and the like. or a virus. Binding elements can be used to detect a molecule or substance to be observed and/or characterized, can indicate a particular event has occurred, and/or can indicate the presence of another molecule or substance (i.e., target substance).

In some embodiments there is provided a kit that comprises two or more different compounds in accordance with the presently-disclosed subject matter. Such embodiments may be further provided with one or more bind elements, wherein the compounds can by bound to the same or different binding elements. In some embodiments each of the compounds and/or binding elements may selectively bind different molecules, particles, substances, or the like. Additionally or alternatively, in some embodiments the kit comprises two or more different compounds in accordance with the presently-disclosed subject matter that have different absorption wavelengths and/or emission wavelengths, and therefore can be practiced during multiplex procedures.

Methods of Use

The presently-disclosed subject matter further includes a method of using the compounds described herein. In some embodiments the method comprises utilizing the compound as a reporter for enzyme activity, as a fluorescent tag, as a sensor for a target substance (an analyte), as an agent for imaging experiments, and/or as an imaging agent for super-resolution microscopy.

Some embodiments of the presently-disclosed subject matter include methods for detecting a target sample that comprise contacting a sample with a compound of the following formula:

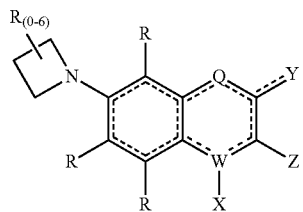

wherein each R is independently selected from halogen, H, CN, OH, O(alkyl), O(aryl), SH, S(alkyl), S(aryl), amine, NO₂, CHO, COOH, C(O)NR₂, COO(alkyl), COO(aryl), PO₃H₂, SO₃H, and alkyl, alkyl being optionally substituted with one or more heteroatoms independently selected from N, O, and S, halogen, OH, O(alkyl), O(aryl), C(O)NR₂, SH, S(alkyl), S(aryl), amine, NO₂, CHO, COO, COOH, COO (alkyl), COO(aryl), PO₃H₂, and/or SO₃H; Q is selected from CR₍₂₎, NR, O, S, SiR₍₂₎, and Se; W is selected from C and N; X is selected from a lone pair of electrons, H, alkyl, aryl, halogen, CN, OH, O(alkyl), O(aryl), SH, S(alkyl), S(aryl), amine, NO₂, CHO, COOH, C(O)NR₂, COO(alkyl), COO (aryl), PO₃H₂, and SO₃H, X being optionally substituted with one or more heteroatoms independently selected from N, O, and S, halogen, OH, O(alkyl), O(aryl), SH, S(alkyl), S(aryl), amine, NO₂, CHO, COO, COOH, C(O)NR₂, COO (alkyl), COO(aryl), PO₃H₂, and/or SO₃H; Y is selected from H, CR₍₂₎, C(O)NR₂, NR, O, and S; and Z is selected from H, halogen, CN, OH, O(alkyl), O(aryl), SH, S(alkyl), S(aryl), amine, NO₂, CHO, COOH, COO(alkyl), COO(aryl), C(O) NR₂, PO₃H₂, SO₃H, aryl, and alkyl, alkyl and aryl being optionally substituted with one or more heteroatoms independently selected from N, O, and S, halogen, OH, O(alkyl), O(aryl), SH, S(alkyl), S(aryl), amine, NO₂, CHO, COOH, C(O)NR₂, COO(alkyl), COO(aryl), PO₃H₂, and SO₃H, or wherein Z and Y, taken together with the atoms to which they are bonded, can form a substituted or unsubstituted 5-7 membered ring.

Alternatively or additionally, in some embodiments of methods for detecting a target sample, the method comprises a step of contacting a sample with a compound of the following formula:

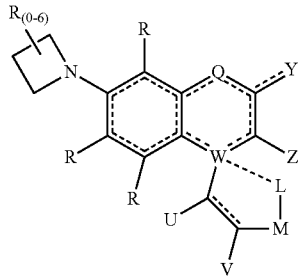

wherein each R is independently selected from halogen, H, CN, OH, O(alkyl), O(aryl), SH, S(alkyl), S(aryl), amine, NO₂, CHO, COOH, C(O)NR₂, COO(alkyl), COO(aryl), PO₃H₂, SO₃H, and alkyl, alkyl being optionally substituted with one or more heteroatoms independently selected from N, O, and S, halogen, OH, O(alkyl), O(aryl), C(O)NR₂, SH, S(alkyl), S(aryl), amine, NO₂, CHO, COO, COOH, COO (alkyl), COO(aryl), PO₃H₂, and/or SO₃H; Q is selected from CR₍₂₎, NR, O, S, SiR₍₂₎, and Se; W is selected from C and N; M is selected from CR₍₂₎, C(O), SO₂, and PO₂; L is selected from O, S, NR, and $CN_2$, wherein optionally L and W, taken together with the atoms to which they are bonded, can form a substituted or unsubstituted 5-7 membered ring; U and V are independently selected from H, alkyl, halogen, CN, OH, O(alkyl), O(aryl), SH, S(alkyl), C(O)$NR_2$, S(aryl), amine, $NO_2$, CHO, COOH, COO(alkyl), COO(aryl), $PO_3H_2$, and $SO_3H$, alkyl being optionally substituted with one or more heteroatoms independently selected from N, O, and S, halogen, OH, O(alkyl), O(aryl), C(O)$NR_2$, SH, S(alkyl), S(aryl), amine, $NO_2$, CHO, COO, COOH, COO(alkyl), COO(aryl), $PO_3H_2$, and/or $SO_3H$, or wherein U and V, taken together with the atoms to which they are bonded, can form a substituted or unsubstituted 5-7 membered ring; Y is selected from H, $CR_{(2)}$, C(O)$NR_2$, NR, O, and S; and Z is selected from H, halogen, CN, OH, O(alkyl), O(aryl), SH, S(alkyl), S(aryl), amine, $NO_2$, CHO, COOH, COO(alkyl), COO(aryl), C(O)$NR_2$, $PO_3H_2$, $SO_3H$, aryl, and alkyl, alkyl and aryl being optionally substituted with one or more heteroatoms independently selected from N, O, and S, halogen, OH, O(alkyl), O(aryl), SH, S(alkyl), S(aryl), amine, $NO_2$, CHO, COOH, C(O)$NR_2$, COO(alkyl), COO(aryl), $PO_3H_2$, and $SO_3H$, or wherein Z and Y, taken together with the atoms to which they are bonded, can form a substituted or unsubstituted 5-7 membered ring.

The presently-disclosed method for detecting a target substance can further comprise a detecting step that includes detecting an emission light from the compound, the emission light indicating the presence of the target substance.

In some embodiments the method for using the compounds further comprises exciting the compound by exposing the compound to an absorption light that includes an absorption wavelength. As described herein, the absorption light can include a of ultraviolet light to near infrared light. In specific embodiments the absorption wavelength can be in a range from about 100 nm to about 1000 nm, in a range of 200 nm to about 800 nm, and/or in a range of about 450 nm to about 650 nm. In some embodiments the absorption wavelength is about 100 nm, 200 nm, 300 nm, 400 nm, 500 nm, 600 nm, 700 nm, 800 nm, 900 nm, or 1,000 nm.

In some embodiments the detecting step is performed by use of fluorescence spectroscopy or by the naked eye. Thus, in some embodiments the detecting step is performed with a microscope. In some embodiments the presence of a target substance can indicate the occurrence or absence of a particular biological function, as will be appreciated by those of ordinary skill in the art. In some embodiments the method is performed in a live cell and/or subject.

Some embodiments of detection methods comprise contacting the sample with two or more embodiments of compounds that are selective for different target substances. Methods for detecting two or more target substances with two or more of the presently-disclosed compounds are referred to herein as "multiplex" detection methods.

In some of the present multiplex methods, two or more distinct target substances and/or two or more regions of one target substance are detected using two or more probes, wherein each of the probes is labeled with a different embodiment of the present compounds. The presently-disclosed compounds can be used in multiplex detection methods for a variety of target substances.

In this regard, multiplex methods can comprise contacting the sample with a first compound and a second compound in accordance with the presently-disclosed subject matter. The first compound can be selective for a first target substance and can be capable of emitting a first emission light, and the second compound can be selective for a second target substance and can be of emitting a second emission light.

The detecting step includes detecting the first emission light that indicates the presence of the first target substance and the second emission light that indicates the presence of the second target substance., and then detecting a second emission light from the compound. The second emission light can indicate the presence of a second target substance. In some embodiments the emission wavelength and the second emission wavelength are different form one another. This novel method thereby provides an efficient means for detecting a plurality of different target substances in one substance simultaneously.

Methods of Synthesis

The presently-disclosed subject matter further includes a method of producing a compound as described herein. Methods for synthesizing embodiments of the presently-disclosed compounds generally include one or more well-known synthesis steps. While certain embodiments of methods for synthesizing the present compounds are described herein, methods of synthesis should be not limited to the methods described herein, as methods for synthesis can include any methods that would be readily apparent to those of ordinary skill in the art.

In some embodiments the method comprises forming the C(aryl)-N (e.g., C(aryl)-azetidine) bonds of the compounds at a late stage in the synthesis method. In some embodiments Buchwald-Hartwig cross-coupling of nitrogen nucleophiles with fluorescein ditriflates is utilized. In some embodiments the method proceeds under Buchwald-Hartwig conditions using Pd(OAc)$_2$, BINAP, and Cs$_2$CO$_3$ in toluene at about 100° C. In other embodiments the method proceeds utilizing Pd$_2$dba$_3$ with the active biaryl ligand XPhos, with Cs$_2$CO$_3$ as a base and dioxane as a solvent at about 80° C. to about 100° C. Thus, Pd-catalyzed cross-coupling with disparate N-alkyl coupling partners represents an embodiment of a method for synthesizing the present compounds.

In some embodiments the synthesis of compounds, such as rhodamine dyes, by direct amination can be impractical. For at least these compounds, carbamates can be utilized in a method for synthesizing the compounds. Other exemplary methods for synthesizing the present compounds are described in Grimm et al., Synthesis of Rhodamines from Fluoresceins Using Pd-Catalyzed C—N Cross-Coupling, *Org. Lett.* 13, 6354-6357, (2011), which is incorporated herein by this reference.

Furthermore, a non-limiting list of methods for synthesizing embodiments of the presently-disclosed compounds are illustrated in the exemplary schemes shown in FIGS. 31 to 38.

Figure 31:
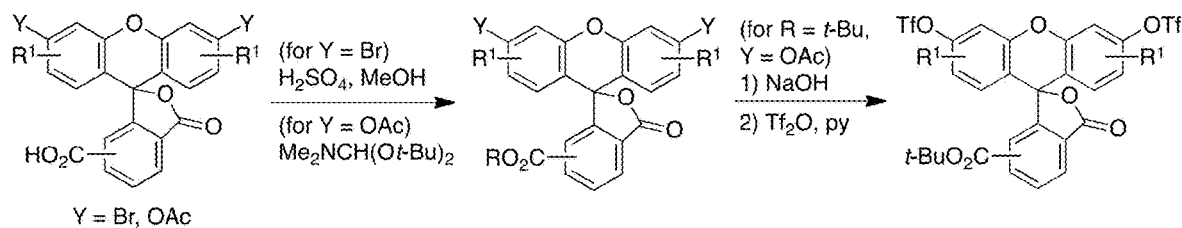
FIG. 31 includes an exemplary synthetic scheme for synthesizing a compound in accordance with an embodiment of the presently-disclosed subject matter.

FIG. 31 includes a general synthesis scheme for the preparation of exemplary dibromofluorans and fluorescein ditriflates. Dibromofluorans and fluorescein diacetates possessing carboxylic acid substituents can be protected as esters via acid-catalyzed Fischer esterification or through reaction with the di-tert-butyl acetal of DMF. The fluorescein diacetates can then be hydrolyzed with base; the resulting substituted fluoresceins can be converted to fluorescein ditriflates with trifluoromethanesulfonic anhydride.

Figure 32:
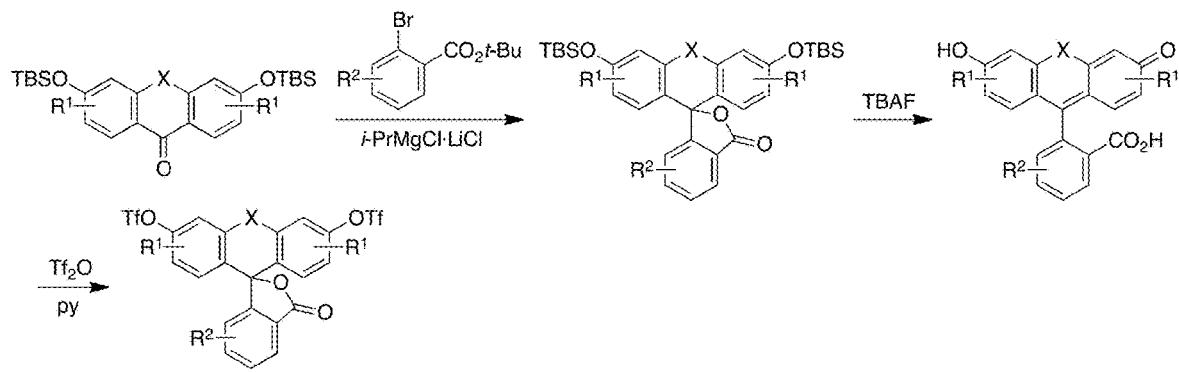
FIG. 32 includes an exemplary synthetic scheme for synthesizing a compound in accordance with an embodiment of the presently-disclosed subject matter.

FIG. 32 includes a general synthesis scheme for the preparation of exemplary carbo- and silafluorescein ditriflates. Reaction of TBS-protected anthrones and Si-anthrones with aryl Grignard reagents can allow access to TBS-protected carbofluoresceins and silafluoresceins. TBAF-mediated deprotection followed by reaction with trifluoromethanesulfonic anhydride can afford carbofluorescein ditriflates and silafluorescein ditriflates.

FIG. 33 includes a general synthesis scheme for the preparation of exemplary azetidinyl-rhodamines, -carborhodamines, and -sila-rhodamines. Buchwald-Hartwig palladium-catalyzed C—N cross-coupling of azetidines with dibromofluorans, fluorescein ditriflates, carbofluorescein ditriflates, or silafluorescein ditriflates can directly afford azetidinyl fluorophores. The azetidinyl fluorophores that possess ester substituents can be deprotected through acid- or base-mediated conditions to generate azetidinyl dyes with carboxylic acid handles. The acids can be further derivatized into N-hydroxysuccinimidyl (NHS) esters by reaction with DSC or TSTU and subsequently reacted with amines to generate analogs with pendant amide groups.

Figure 34:
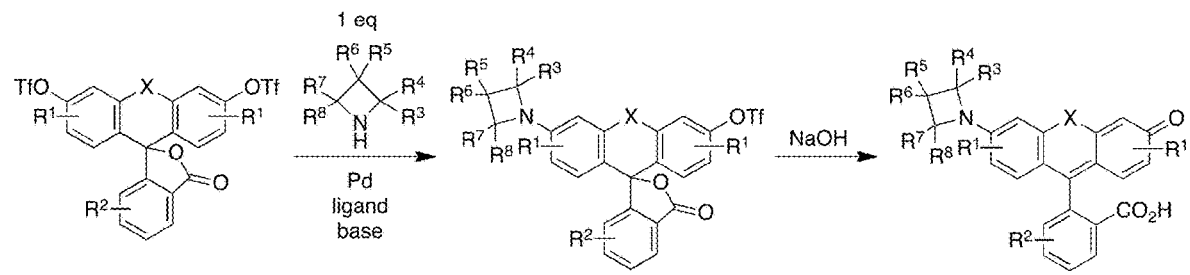
FIG. 34 includes an exemplary synthetic scheme for synthesizing a compound in accordance with an embodiment of the presently-disclosed subject matter.

FIG. 34 includes a general synthesis scheme for the preparation of exemplary azetidinyl-rhodols. Buchwald-Hartwig palladium-catalyzed C—N cross-coupling of azetidines (1 equivalent) with fluorescein ditriflates, carbofluorescein ditriflates, or silafluorescein ditriflates can provide, upon hydrolysis of the remaining triflate moiety, azetidinyl-rhodols.

Figure 35:
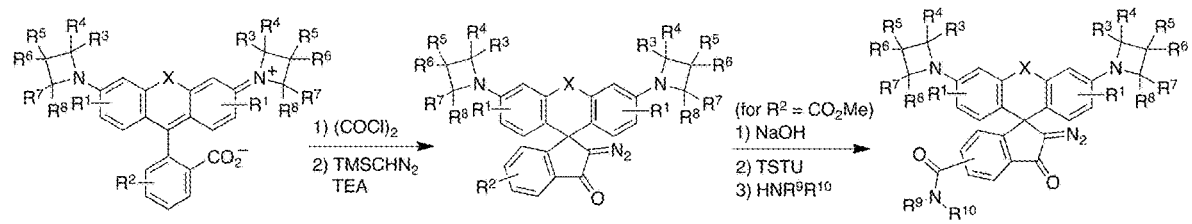
FIG. 35 includes an exemplary synthetic scheme for synthesizing a compound in accordance with an embodiment of the presently-disclosed subject matter.

FIG. 35 includes a general synthesis scheme for the preparation of exemplary fluorogenic 2-diazo-1-indanone dyes from azetidinyl-rhodamines, -carborhodamines, and -sila-rhodamines. Reaction of azetidinyl-rhodamines with oxalyl chloride followed by (trimethylsilyl)diazomethane can afford 2-diazo-1-indanones. Base-mediated hydrolysis of ester substituents can yield 2-diazo-1-indanones with acid moieties, which can be further derivatized into N-hydroxysuccinimidyl (NHS) esters by reaction with TSTU and reacted with amines to generate analogs with pendant amide groups.

Figure 36:
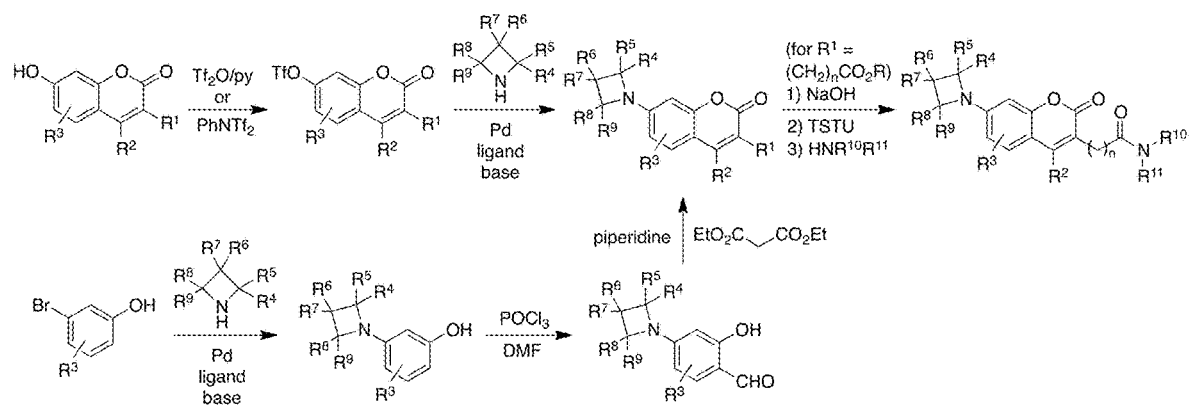
FIG. 36 includes an exemplary synthetic scheme for synthesizing a compound in accordance with an embodiment of the presently-disclosed subject matter.

FIG. 36 includes a general synthesis scheme for the preparation of exemplary azetidinyl-coumarins. Coumarin triflates can be synthesized by reaction of 7-hydroxycoumarins with trifluoromethanesulfonic anhydride or N-phenyl-bis(trifluoromethanesulfonimide). Buchwald Hartwig palladium-catalyzed C—N cross-coupling of azetidines with coumarin triflates can yield azetidinyl-coumarins. Alternatively, azetidinyl-phenols can be prepared by C—N cross-coupling of bromophenols with azetidines. Vilsmeier-Haack formylation of azetidinyl-phenols can then provide aldehydes that can be condensed with malonates to afford azetidinyl-coumarins. For examples possessing ester substituents, base-mediated hydrolysis can yield azetidinyl-coumarins with carboxylic acids. Such carboxylic acids can be further derivatized into N-hydroxysuccinimidyl (NHS) esters by reaction with TSTU and reacted with amines to generate analogs with pendant amide groups.

Figure 37:
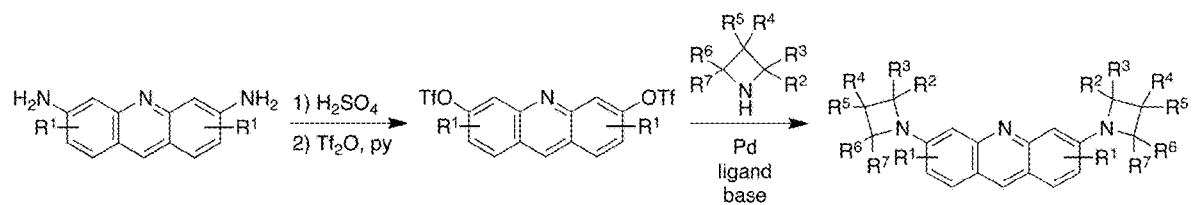
FIG. 37 includes an exemplary synthetic scheme for synthesizing a compound in accordance with an embodiment of the presently-disclosed subject matter.

FIG. 37 includes a general synthesis scheme for the preparation of exemplary azetidinyl-acridines. Reaction of diaminoacridines with acid at elevated temperature can provide dihydroxyacridines, which can then be reacted with trifluoromethanesulfonic anhydride to access acridine ditriflates. Acridine ditriflates can then be subjected to Buchwald-Hartwig palladium-catalyzed CN cross-coupling with azetidines to prepare azetidinyl-acridines.

Figure 38:
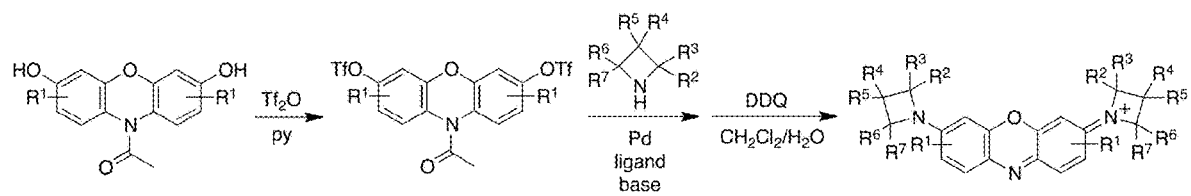
FIG. 38 includes an exemplary synthetic scheme for synthesizing a compound in accordance with an embodiment of the presently-disclosed subject matter.

FIG. 38 includes a general synthesis scheme for the preparation of exemplary azetidinyl-oxazines. The ditriflates of phenoxazines can be prepared by reaction of dihydroxyphenoxazines with trifluoromethanesulfonic anhydride. The ditriflates can be subjected to Buchwald-Hartwig palladium-catalyzed CN cross-coupling with azetidines and subsequently oxidized with DDQ to access azetidinyl-oxazines.

Those of ordinary skill will recognize that the methods and schemes described herein are provided for illustrative purposes only and are not intended to limit the scope of the reactions or reaction sequences useful for synthesizing embodiments of the presently-disclosed compounds.

EXAMPLES

The presently-disclosed subject matter is further illustrated by the following specific but non-limiting examples. The following examples may include compilations of data that are representative of data gathered at various times during the course of development and experimentation related to the present invention.

Example 1

This Example characterizes a structural modification to improve the brightness and photostability of rhodamine dyes, and specifically a novel azetidinyl auxochrome that elicited an increase in quantum efficiency relative to the parent dye. The facile synthesis of the azetidinyl rhodamine dye preserved the spectral properties, cell permeability, and utility of parent dye. Computational experiments were performed using the commercial software package Spartan'10 (version 1.1.0, Wavefunction).

The simplest known rhodamine fluorophore, rhodamine 110 (Table 2), exhibits an absorption maximum in the blue ($\lambda_{max}$=497 nm) with a high extinction coefficient ($\varepsilon$=7.6×10$^4$ M$^{-1}$cm$^{-1}$), emission in the green ($\lambda_{em}$=520 nm), and a high quantum yield ($\phi$=0.88). Alkylation of the rhodamine elicits a bathochromic shift in absorption and fluorescence emission wavelengths. For example, tetramethylrhodamine (TMR) shows $\lambda_{max}/\lambda_{em}$=548/572 nm and $\varepsilon$=7.8×10$_4$ m$^{-1}$cm$^{-1}$ (Table 2). This shift in spectral properties is accompanied by a significant decrease in quantum yield, with TMR showing $\phi$=0.41. Both of these dyes are used in commercial self-labeling tag substrates and can be used to label intracellular and extracellular proteins in living cells.

TABLE 2

Spectroscopic data for rhodamine 110, tetramethylrhodamine (TMR), and aza-cyclic rhodamines with ring sizes 3-7.

| NR$_2$ | $\lambda_{max}$ (nm) | $\varepsilon$ (M$^{-1}$ cm$^{-1}$) | $\lambda_{em}$ (nm) | $\phi$ | r (ns) |
|---|---|---|---|---|---|
| —NH$_2$ | 497 | 76,000 | 520 | 0.88 | 3.26 |
| —N(CH$_3$)$_2$ | 548 | 78,000 | 572 | 0.41 | 2.21 |
| —N(azetidinyl) | — | — | — | — | — |

TABLE 2-continued

Spectroscopic data for rhodamine 110, tetramethylrhodamine (TMR), and aza-cyclic rhodamines with ring sizes 3-7.

| $NR_2$ | $\lambda_{max}$ (nm) | $\epsilon$ ($M^{-1}$ $cm^{-1}$) | $\lambda_{em}$ (nm) | $\phi$ | $\tau$ (ns) |
|---|---|---|---|---|---|
| —N(azetidine) | 549 | 101,000 | 571 | 0.88 | 3.84 |
| —N(pyrrolidine) | 553 | 76,000 | 576 | 0.74 | 3.60 |
| —N(piperidine) | 550 | 80,000 | 586 | 0.10 | 0.59 |
| —N(azepane) | 550 | 106,000 | 583 | 0.25 | 1.62 |

All measurements were taken in 10 mM HEPES pH 7.3 unless otherwise noted.

The lower quantum efficiency of N,N,N',N'-tetraalkylrhodamines such as TMR can be explained by an energetically favorable twisted internal charge transfer (TICT) state (FIG. 1). After excitation, electron transfer from the nitrogen atom to the xanthene ring results in a pyramidyl nitrogen and a twisted $C_{aryl}$—N bond. This TICT state rapidly relaxes without emission of a photon and is a major path of nonradiative decay in rhodamine dyes. This diradical species may also undergo irreversible reactions leading to bleaching of the fluorophore. Thus, rhodamine derivatives where TICT is disfavored should exhibit increased quantum efficiency, longer fluorescence lifetimes, and higher photostability.

Using standard ab initio Hartree-Fock methods to estimate equilibrium geometry, and omitting the ortho-carboxyl group from the structures to prevent cyclization to the closed lactone form during energy minimization, the structures shown in Table 2 were analyzed for the length of the aryl carbon-nitrogen bond ($C_{aryl}$—N) and the minimum distance between hydrogen substituents ortho and alpha to the nitrogen. These values are parameters in the propensity of the molecule to undergo TICT. A shorter $C_{aryl}$—N value signifies increased double-bond character and lower tendency to adopt a twisted conformation. Likewise, a larger $H_o$-$H_\alpha$ value indicates less steric clash between substituents and lower predisposition for bond rotation.

The calculated structure of the aziridine derivative contained puckered aziridine rings with the nitrogens out of the plane of the xanthene system, consistent with the large ring strain (27 kcal $mol^{-1}$) present in the three-membered ring. The other rhodamines minimized to a largely planar structure encompassing the aniline nitrogens, suggesting these dyes prefer the extended conjugation found in fluorescent rhodamines. The projected structure of the azetidinyl-rhodamine ($JF_{549}$, Example 7) was surprising given the relatively large ring strain present in azetidine (estimated at 26 kcal $mol^{-1}$), which would be expected to favor pyramidal nitrogen atoms. $JF_{549}$ showed the shortest $C_{aryl}$—N bond length (1.349 Å) and longest $H_o$-$H_\alpha$ distance (2.56 Å) of the planar calculated structures. Additionally, N-arylazetidines exhibit higher IP values compared to N,N-dialkylanilines (1-phenylazetidine IP=7.61 eV; N,N-dimethylaniline IP=7.37 eV) suggesting a higher energetic penalty for the electron transfer from the aniline nitrogen to the xanthene ring system to form the TICT state. These results implied that $JF_{549}$ would be less prone to undergo TICT and thus exhibit superior fluorescent properties to the TMR fluorophore (2).

The compounds of Table 2 were then synthesized and evaluated for their fluorescence properties. A facile and efficient synthesis of rhodamines from fluorescein ditriflates using the Buchwald-Hartwig cross-coupling was used, and allowed the preparation of compounds from fluorescein. Relatively high catalyst loading (10%) was required to minimize triflate hydrolysis and ensure high yields. $JF_{549}$ and the larger ring structures were highly colored, polar compounds that were purified by normal-phase flash chromatography with a strong solvent system ($CH_2Cl_2$/$CH_3OH$/$NH_3$). In contrast, the aziridinyl-rhodamine was a colorless, nonpolar molecule and could be purified by normal-phase chromatography using weak solvent mixtures (EtOAc/hexanes).

The photophysical properties of the synthesized compounds the compounds were evaluated in aqueous solution, comparing them to known rhodamine 110 and tetramethylrhodamine. The data suggested the ring strain in the aziridine substituents forces the aziridinyl-rhodamine to adopt the closed lactone form. $JF_{549}$ (Example 7) and the larger ring structures showed $\lambda_{max}$ and $\mu_{em}$ values similar to TMR with increased ring size causing a slight bathochromic shift of up to 10 nm. Interestingly, $JF_{549}$ and the azepane derivative showed a ~30% higher extinction coefficient than the other dyes. The incorporation of aniline nitrogens into a simple cyclic system was proposed to control many of the structural parameters in the formation of the TICT state. The higher ring strain in smaller azacycles such as the aziridine and azetidine-containing structures was previously believed to preclude the planar configuration required for the fluorescent xanthenium structure.

The $\lambda_{max}$, $\lambda_{em}$, and $\epsilon$ of the different rhodamine dyes showed modest dependence on substituent ring size, but the fluorescence lifetime ($\tau$) and quantum yield ($\phi$) varied as ring size changed (Table 2). $JF_{549}$ exhibited a high quantum yield value ($\phi$=0.88) and long fluorescence lifetime ($\tau$=3.8 ns), larger than the values for TMR ($\phi$=0.41, $\tau$=2.2 ns), and similar to the parent rhodamine 110 (1; $\phi$=0.88, $\tau$=3.3 ns). $JF_{549}$ was also 60% brighter than the pyrrolidine derivative, which showed $\phi$=0.74 and $\tau$=3.6 ns. The piperidine derivative showed a sharp decrease in fluorescence with $\phi$=0.10 and $\tau$=0.6 ns; the lifetime values for the pyrrolidine and piperidine derivatives were consistent with those for similar fluorophores. The azepane derivative gave slightly higher values of $\phi$=0.25 and $\tau$=1.62 ns relative to the piperidine derivative.

Figure 2:
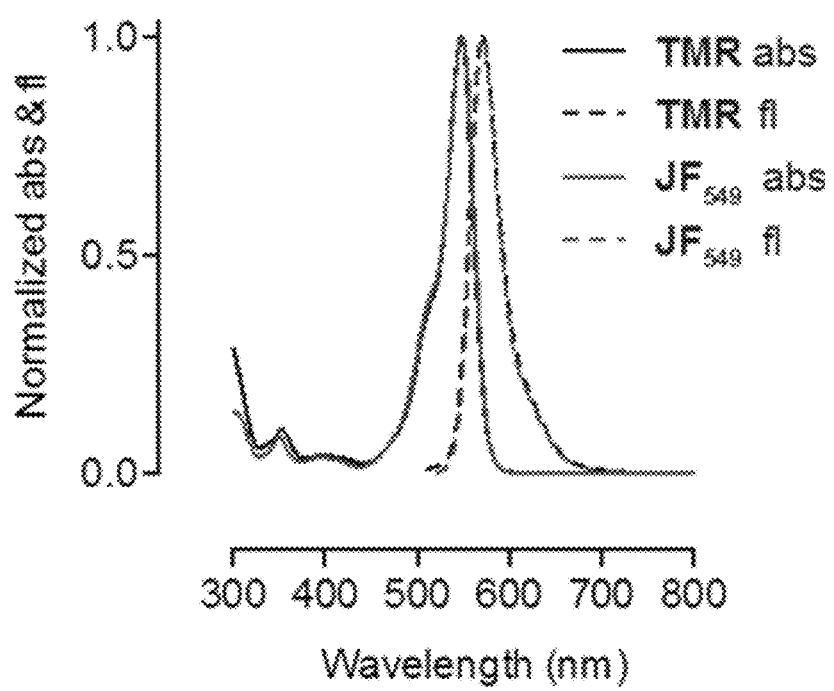
FIG. 2 includes a plot showing the normalized absorption (abs) and fluorescence emission (fl) spectra for tetramethylrhodamine and $JF_{549}$.
Figure 3:
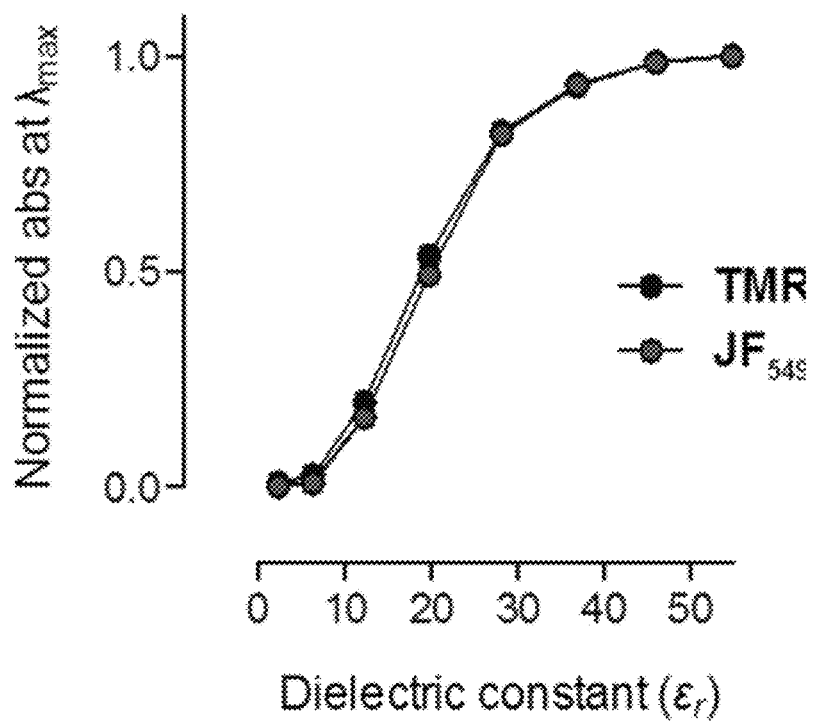
FIG. 3 includes a plot showing the normalized absorbance versus dielectric constant ($\varepsilon_r$) for tetramethylrhodamine and $JF_{549}$.

The improved brightness of $JF_{549}$ under one-photon excitation (Table 2) extended to two-photon excitation and was brought about by a structural change that preserved many of the desirable properties of TMR. For example, the absorption and emission spectra of TMR and JF$_{549}$ are superimposable (FIG. 2) and the dyes showed comparable sensitivity to solvent polarity (FIG. 3), suggesting similar cell permeability.

Example 2

This Example describes procedures performed to evaluate the performance of the dye JF$_{549}$ as a label in cellular imaging. JF$_{549}$-HaloTag ligand (Example 21) was synthesized starting from a 6-carboxyfluorescein derivative. The diacetate derivative of 6-carboxyfluorescein was first protected as a tert-butyl ester. The acetate groups were saponified with NaOH, and this intermediate was triflated to give 6-tert-carboxyfluorescein ditriflate in 69% yield over two steps. Cross-coupling with azetidine gave the rhodamine, which was deprotected to yield the carboxylic acid. Treatment of the carboxylic acid with DSC followed by reaction with HaloTag(O2)amine yielded JF$_{549}$-HaloTag ligand (Example 21). This molecule was a direct analog of the commercial TMR-based HaloTag ligand. Notably, rhodamine dyes exist in equilibrium between an "open," zwitterionic, quinoid form and a "closed," lipophilic, lactone form. This dynamic amphipathicity makes net neutral rhodamines such as rhodamine 110, TMR, and JF$_{549}$ useful ligands for live-cell labeling technologies, since the dyes efficiently traverse the cellular membrane without detergents or chemical masking groups and excess ligand can be rapidly washed away.

Figure 4:
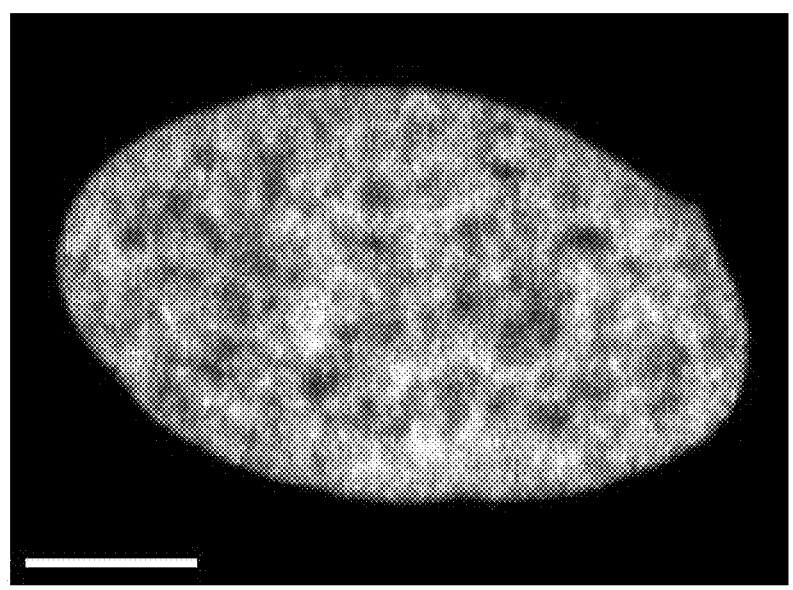
FIG. 4 includes a confocal maximum projection image of a nucleus from a live, washed HeLa cell expressing HaloTag-H2B and incubated with $JF_{549}$-HaloTag ligand; scale bar=5 μm.

The labeling kinetics of TMR and JF$_{549}$ HaloTag ligands were compared with a novel Cy3 HaloTag ligand while measuring the brightness and photon yield of the resulting conjugates. The JF$_{549}$ ligand showed comparable labeling kinetics to the TMR ligand and increased brightness relative to the other dyes in vitro. Incubation of live cells expressing a HaloTag-histone 2B (H2B) fusion with the JF$_{549}$ ligand resulted in bright nuclear labeling (FIG. 4) and low cytoplasmic background, demonstrating that the JF$_{549}$-HaloTag ligand efficiently crossed the membrane of live cells and selectively labeled the HaloTag protein.

Figure 5:
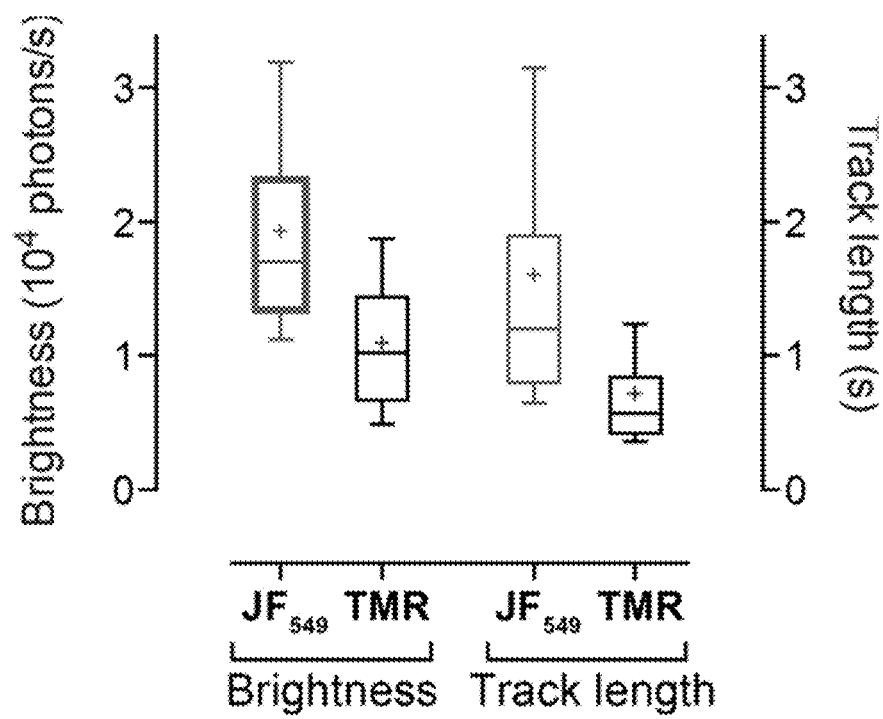
FIG. 5 includes a whisker plot showing a comparison of brightness (n>4,000) and track length (n>500) of HaloTag-H2B molecules labeled with $JF_{549}$-HaloTag ligand or tetramethylrhodamine-HaloTag ligand, where the cross indicates the mean and the whiskers span the 10-90 percentile.

Incubation of the JF$_{549}$ and TMR ligands using low amounts of ligand (<50 nM) allowed imaging of single molecules and evaluation of fluorophore brightness (photons/s) and photostability (i.e., tracklength, s) of individual molecules of labeled HaloTag-H2B. The JF$_{549}$ ligand demonstrated a large increase in both brightness and photostability compared to TMR ligand (FIG. 5). Proteins labeled with TMR ligand showed average photons/s=$1.1 \times 10^4$ and a mean track length of 0.72 s. Conjugates of JF$_{549}$ ligand emitted nearly twice the number of photons/s ($1.9 \times 10^4$) and lasted about twice as long (average track length=1.6 s). This improvement in single molecule brightness extended to direct stochastic optical reconstruction microscopy (dSTORM) experiments, where the use of a reducing environment enables the reversible photoswitching of synthetic fluorophores.

Figure 6:
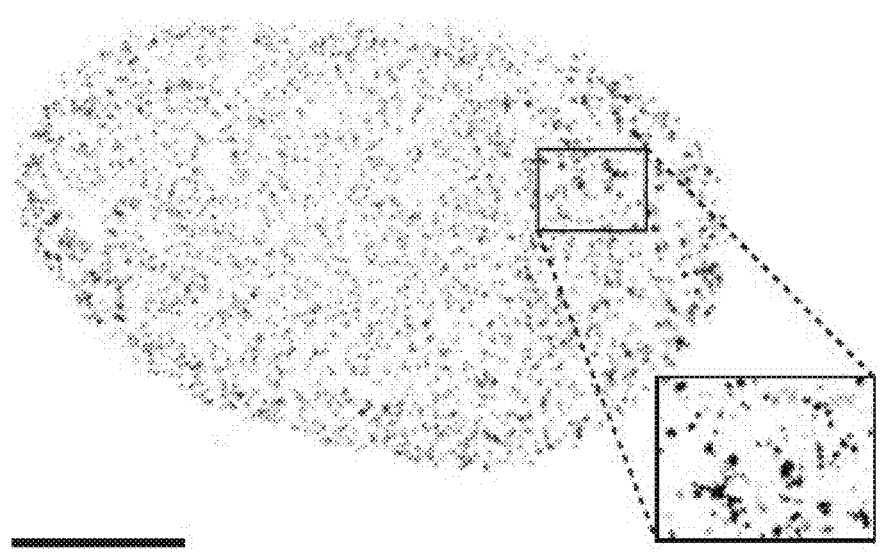
FIG. 6 includes a dSTORM fluorescence microscopy image of a fixed U2OS cell expressing HaloTag-H2B and labeled with $JF_{549}$-HaloTag ligand. The mean localization error was 17.2 nm, the median localization error was 14.1 nm; scale bar=5 μm.
Figure 7:
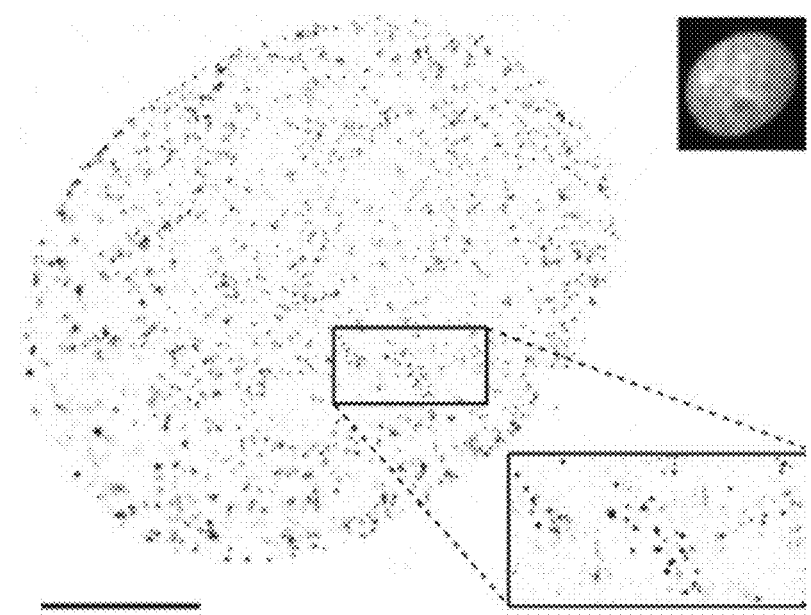
FIG. 7 includes dSTORM and wide-field (inset) fluorescence microscopy images of a fixed U2OS cell expressing HaloTag-H2B and labeled with TMR-HaloTag ligand. The mean localization error was 19.2 nm, the median localization error was 17.0 nm; scale bar=5 μm.
Figure 8:
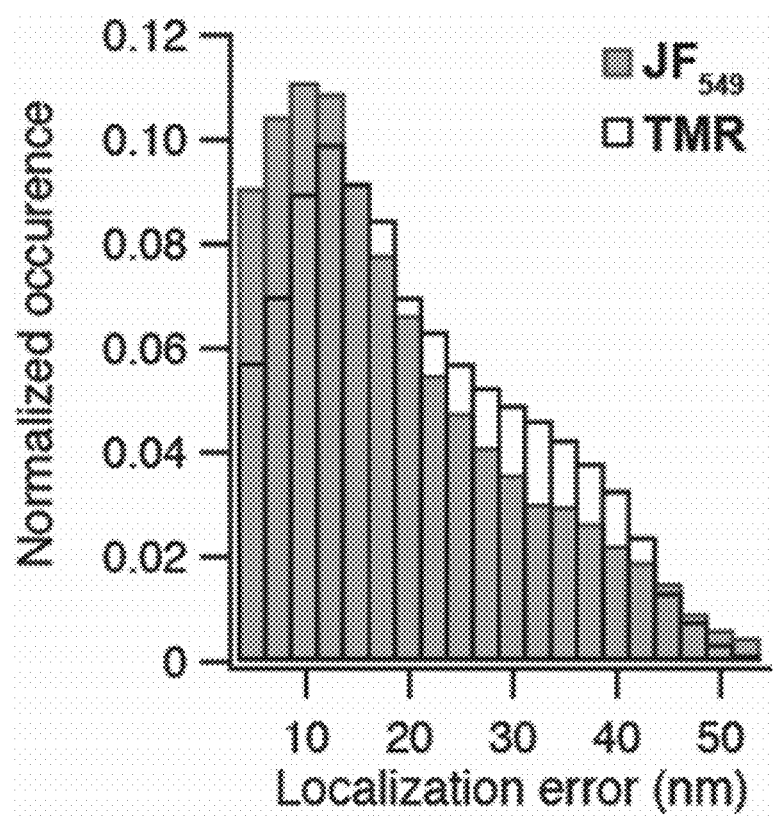
FIG. 8 includes a plot showing normalized distributions of the localization errors for imaging experiments using the $JF_{549}$-HaloTag ligand (FIG. 6) and the TMR-HaloTag ligand (FIG. 7).
Figure 9:
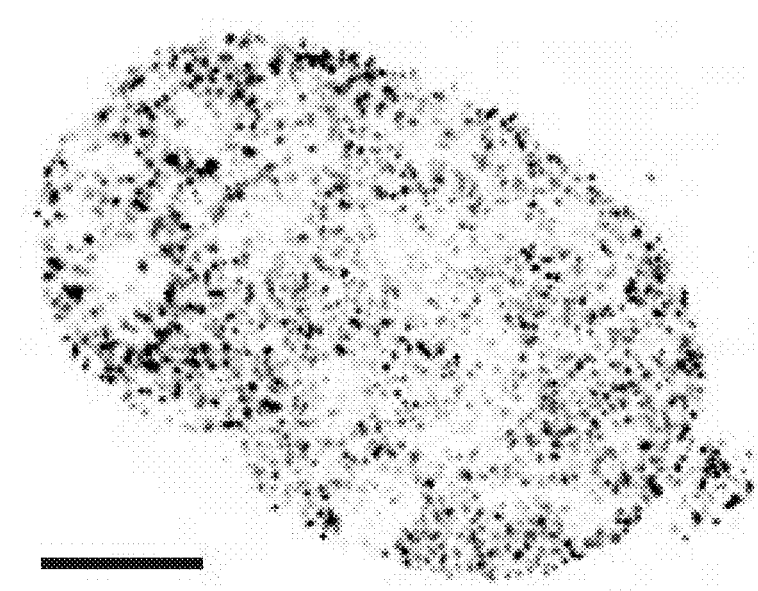
FIG. 9 includes a dSTORM fluorescence microscopy image of the nucleus of a live HeLa cell expressing HaloTag-H2B and labeled with $JF_{549}$-HaloTag ligand; scale bar=5 μm.

This resulted in a super-resolution image of H2B using the JF$_{549}$ ligand (FIG. 6) or TMR ligand (FIG. 7) with median localization errors ($\sigma$) of 14.1 nm and 17.0 nm, respectively (FIG. 8). dSTORM could be performed inside living cells using the cellular reducing environment to elicit photoswitching of the JF$_{549}$ label (FIG. 9). Thus, JF$_{549}$ performed in this spectral range for HaloTag conjugation in vitro, in fixed cells, and in live cells.

Example 3

This Example describes the extension of azetidinyl substitution to other dye scaffolds, including other red-shifted isologs of rhodamines containing carbon and silicon atoms. This Example demonstrates that the azetidinyl substitution is generalizable to different fluorophore scaffolds and can produce increases in brightness relative to the original parent fluorophore scaffolds.

The N,N-dialkyl motif is found in numerous classic fluorophore scaffolds (Table 3), including coumarins (e.g., Coumarin 461), acridines (e.g., Acridine Orange), rhodols, carborhodamines, oxazines (e.g., Oxazine 1), and silarhodamines. TICT has been proposed as a major contributor to nonradiative decay in these fluorescent systems, leading to modest quantum efficiencies. As with the rhodamines described in the previous examples, a Pd-catalyzed cross-coupling approach was used to install the azetidine motif in these fluorophores, starting from accessible aryl halides or aryl triflates.

TABLE 3

Spectroscopic data for embodiments of fluorophore scaffolds having the N,N-dialkyl (i.e., dimethylamino or diethylamino) moiety(ies) replaced with azetidine rings.

| Parent structure | Substitution | $\lambda_{max}$ (nm) | $\varepsilon$ (M$^{-1}$ cm$^{-1}$) | $\lambda_{em}$ (nm) | $\phi$ |
|---|---|---|---|---|---|
| [Coumarin structure with R$_2$N, O, CH$_3$] | R$_2$N = N(CH$_3$)$_2$ | 372 | 18,000 | 470 | 0.19 |
| | R$_2$N = azetidinyl | 354 | 15,000 | 467 | 0.96 |

TABLE 3-continued
Spectroscopic data for embodiments of fluorophore scaffolds having the
N,N-dialkyl (i.e., dimethylamino or diethylamino) moiety(ies) replaced with azetidine rings.
| Parent structure | Substitution | $\lambda_{max}$ (nm) | $\epsilon$ (M$^{-1}$ cm$^{-1}$) | $\lambda_{em}$ (nm) | $\phi$ |
|---|---|---|---|---|---|
| 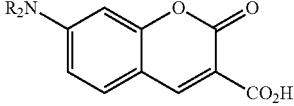 | R$_2$N = 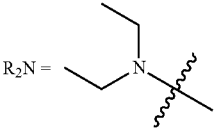 | 410 | 35,000 | 471 | 0.03 |
|  | R$_2$N = 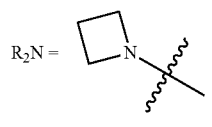 | 387 | 24,000 | 470 | 0.84 |
| 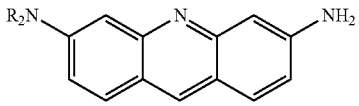 | R$_2$N = 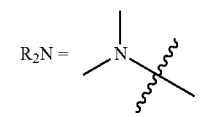 | 493 | 50,000 | 528 | 0.21 |
|  | R$_2$N = 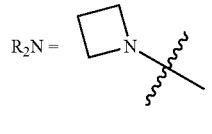 | 492 | 47,000 | 531 | 0.52 |
| 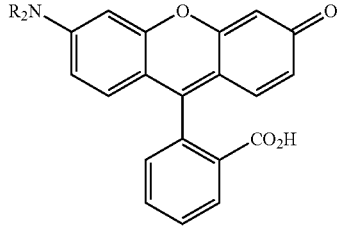 | R$_2$N = 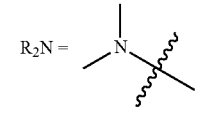 | 518 | 60,000 | 546 | 0.21 |
|  | R$_2$N = 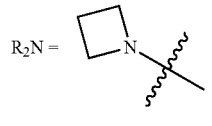 | 519 | 59,000 | 546 | 0.85 |
| 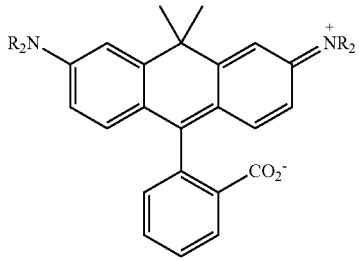 | R$_2$N = 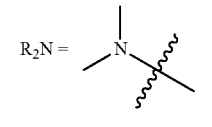 | 606 | 121,000 | 626 | 0.52 |
|  | R$_2$N = 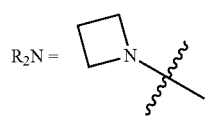 | 608 | 99,000 | 631 | 0.67 |
| 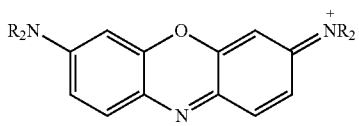 | R$_2$N = 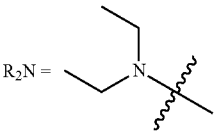 | 655 | 111,000 | 669 | 0.07 |
|  | R$_2$N = 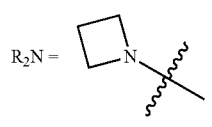 | 647 | 99,000 | 661 | 0.24 |

TABLE 3-continued

Spectroscopic data for embodiments of fluorophore scaffolds having the
N,N-dialkyl (i.e., dimethylamino or diethylamino) moiety(ies) replaced with azetidine rings.

| Parent structure | Substitution | $\lambda_{max}$ (nm) | $\varepsilon$ (M$^{-1}$ cm$^{-1}$) | $\lambda_{em}$ (nm) | $\phi$ |
|---|---|---|---|---|---|
| 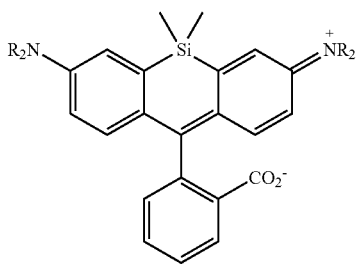 | 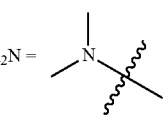 | 643 | 141,000$^a$ | 662 | 0.41 |
| | 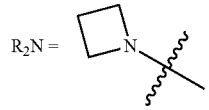 | 646 | 152,000$^a$ | 664 | 0.54 |

All measurements were taken in 10 mM HEPES pH 7.3 unless otherwise noted.
$^a$Extinction coefficient measured in ethanol containing 0.1% v/v trifluoroacetic acid In all cases the azetidine substitution imparted increases in quantum yield without substantial deleterious effects on other spectral properties (Table 3). Coumarin 461 exhibited) $\lambda_{max}/\lambda_{em}$=372 nm/470 nm, $\varepsilon$=1.8×10$^4$ M$^{-1}$cm$^{-1}$, and a modest $\phi$=0.19 in aqueous buffer. The azetidine substituted compound (Example 49) showed a five-fold increase in quantum yield ($\phi$=0.96) along with an 18-nm hypsochromic shift in absorbance maxima ($\lambda_{max}$=354 nm). The emission spectrum and extinction coefficient of the azetidine substituted compound ($\lambda_{max}$=467 nm, $\varepsilon$=1.5×10$^4$ M$^{-1}$cm$^{-1}$) were similar to the parent coumarin dye. 7-(Diethylamino)coumarin-3-carboxylic acid (DEAC) displayed $\lambda_{max}/\lambda_{em}$=410 nm/471 nm, $\varepsilon$=3.5×10$^4$M$^{-1}$cm$^{-1}$, but a low quantum yield ($\phi$=0.03). The azetidine-substituted compound (Example 51) showed a shorter absorption maximum ($\lambda_{max}$=387 nm), a smaller extinction coefficient ($\varepsilon$=2.4×10$^4$M$^{-1}$cm$^{-1}$), and an emission maxima of $\lambda_{em}$=470 nm, where the azetidine substitution increased the quantum yield by almost 30-fold ($\phi$=0.84).

Next, acridine and rhodol fluorophore scaffolds were modified. The classic fluorophore Acridine Orange gave $\phi$=0.21 when measured in aqueous solution, whereas the azetidine-substituted compound (Example 60) was 2.5-fold brighter with $\phi$=0.52. Other spectral properties of the two acridines were similar. The dimethyl rhodol showed $\lambda_{max}/\lambda_{em}$=518 nm/546 nm, $\varepsilon$=6.0×10$^4$M$^{-1}$cm$^{-1}$, and $\phi$=0.21, and its azetidine-substituted counterpart (Example 59) had similar $\lambda_{max}$, $\lambda_{em}$, and $\varepsilon$ values, although replacement of the N,N-dimethylamino group with an azetidine gave a 4-fold increase in quantum yield ($\phi$=0.85).

Next, with respect to longer-wavelength fluorophores, the carbon-containing analog of TMR exhibited $\lambda_{max}/\lambda_{em}$=606 nm/626 nm, $\varepsilon$=1.21×10$^5$ M$^{-1}$cm$^{-1}$, and $\phi$=0.52 in aqueous buffer (Table 3). The azetidinyl-carborhodamine (Example 40) showed similar absorption and emission maxima ($\lambda_{max}/\lambda_{em}$=608 nm/631 nm) and extinction coefficient ($\varepsilon$=9.9×10$^4$ M$^{-1}$cm$^{-1}$), and a quantum yield $\phi$=0.67. The dye Oxazine 1 showed spectral properties in the far red with $\lambda_{max}/\lambda_{em}$=655 nm/669 nm, $\varepsilon$=1.11×10$^5$M$^{-1}$cm$^{-1}$, and a relatively low $\phi$=0.07, and azetidine substitution (Example 61) gave a small hypsochromic shift ($\lambda_{max}/\lambda_{em}$=647 nm/661 nm), a slightly lower extinction coefficient ($\varepsilon$=9.9×10$^4$ M$^{-1}$cm$^{-1}$), and a 3.4-fold improvement in quantum yield ($\phi$=0.24). Finally, the silarhodamine analog of TMR (SiTMR; from Lukinavičius, G.; et al. Nat. Chem. 2013, 5, 132) showed $\lambda_{max}/\lambda_{em}$=643 nm/662 nm and $\phi$=0.41; the azetidine-substituted compound (Example 30) gave similar absorption and emission maxima ($\lambda_{max}/\lambda_{em}$=646 nm/664 nm) and a higher $\phi$=0.54. Since silarhodamines can adopt a colorless form in water, extinction coefficients were measured in acidic ethanol, finding $\varepsilon$=1.41×10$^5$ M$^{-1}$cm$^{-1}$ for SiTMR and $\varepsilon$=1.52× 10$^5$ M$^{-1}$cm$^{-1}$ for the azetidine-substituted compound.

Example 4

This Example describes cellular imaging using an azetidinyl-silarhodamine. Compounds based on SiTMR are efficient labels for the SnapTag, HaloTag, and other proteins inside live cells. The azetidinyl-silarhodamine (Example 30) exhibits superior brightness ($\varepsilon$×$\phi$, Table 3) relative to the non-azetidinyl parent compound SiTMR. The azetidinyl-silarhodamine embodiment described in this Example displays a $\lambda_{max}$=646, and is referred to herein as "JF$_{646}$."

Figure 10:
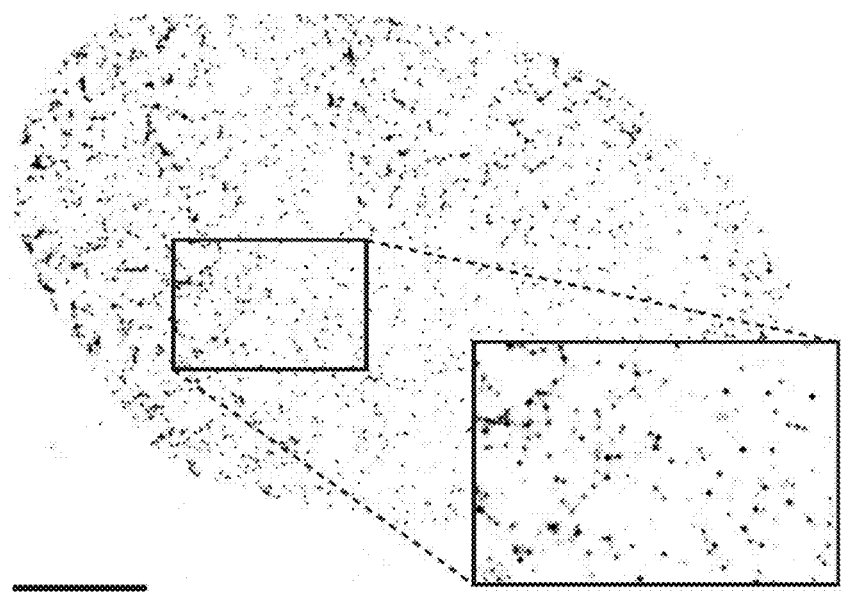
FIG. 10 includes a dSTORM fluorescence microscopy image of a fixed U2OS cell nucleus expressing HaloTag-H2B and labeled with $JF_{646}$-HaloTag ligand. The mean localization error was 11.1 nm, the median localization error was 8.4 nm; scale bar=5 μm.
Figure 11:
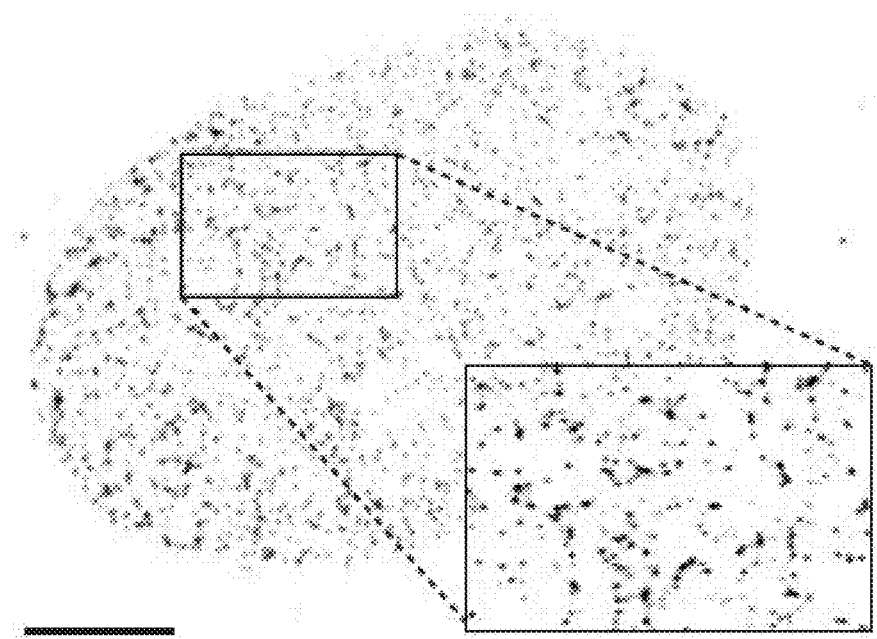
FIG. 11 includes a dSTORM fluorescence microscopy image of a fixed U2OS cell expressing HaloTag-H2B and labeled with SiTMR-HaloTag ligand. The mean localization error was 11.9 nm, the median localization error was 9.0 nm; scale bar=5 μm.
Figure 12:
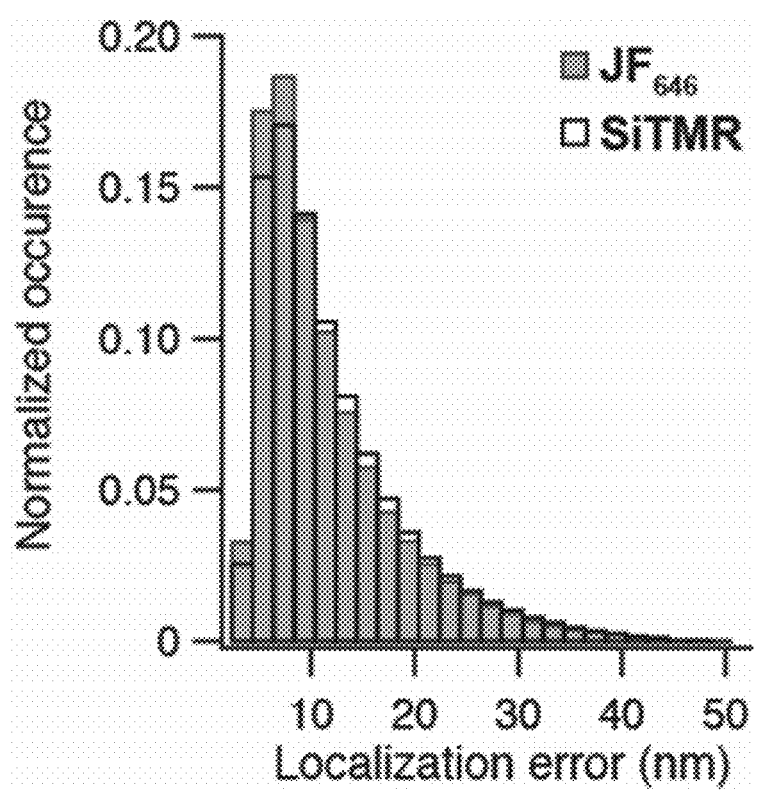
FIG. 12 includes a plot showing normalized distributions of the localization errors for imaging experiments using the $JF_{646}$-HaloTag ligand (FIG. 10) and the SiTMR-HaloTag ligand (FIG. 11).
Figure 13:
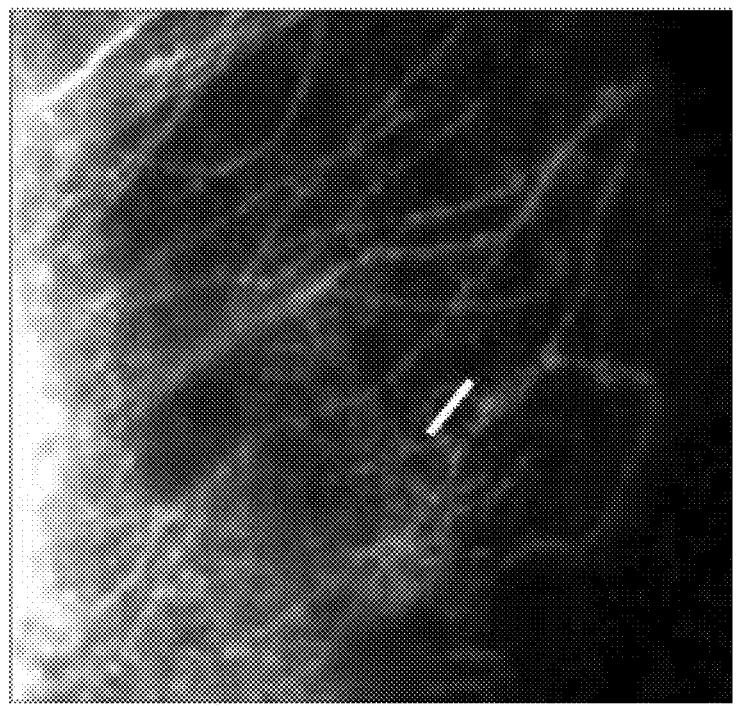
FIG. 13 includes a wide-field fluorescence microscopy image of a live HeLa cell expressing HaloTag-tubulin and labeled with $JF_{646}$-HaloTag ligand.
Figure 14:
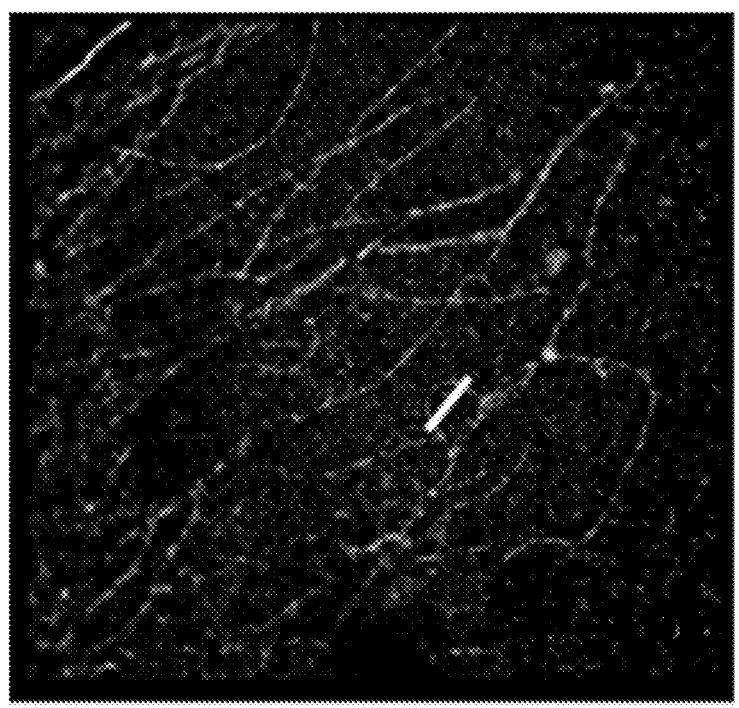
FIG. 14 includes a dSTORM microscopy image of a live HeLa cell expressing HaloTag-tubulin and labeled with $JF_{646}$-HaloTag ligand. The mean localization error was 9.23 nm; the median localization error was 7.14 nm.
Figure 15:
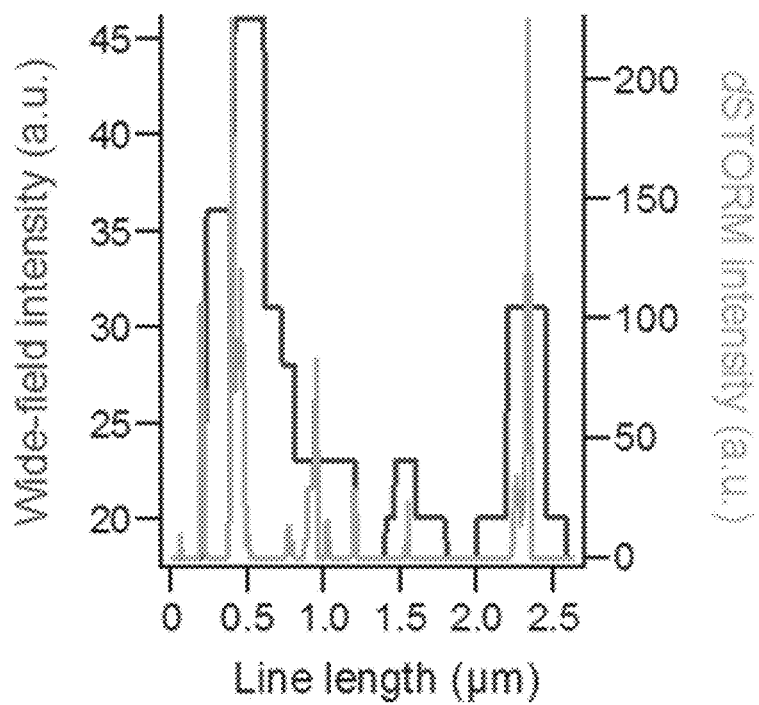
FIG. 15 includes a plot showing line scan intensity in the wide-field image (FIG. 13) and dSTORM image (FIG. 14) as a function of line length.

To compare these two dyes directly in cellular imaging experiments, the HaloTag ligands of the azetidinyl-silarhodamine (JF$_{646}$-HaloTag ligand, Example 35) and SiTMR (Lukinavičius, G.; et al. Nat. Chem. 2013, 5, 132) were synthesized from a novel silafluorescein precursor. Both silarhodamine ligands were excellent labels for super-resolution dSTORM imaging of HaloTag-H2B (FIGS. 10 and 11), showing median localization errors of 8.4 nm and 9.0 nm, respectively (FIG. 12). dSTORM was also performed on live cells expressing HaloTag-tubulin and labeled with JF$_{646}$ ligand. High photon yields and low background were observed with this label, giving a median $\sigma$=7.1 nm (FIGS. 13 to 15).

Figure 16:
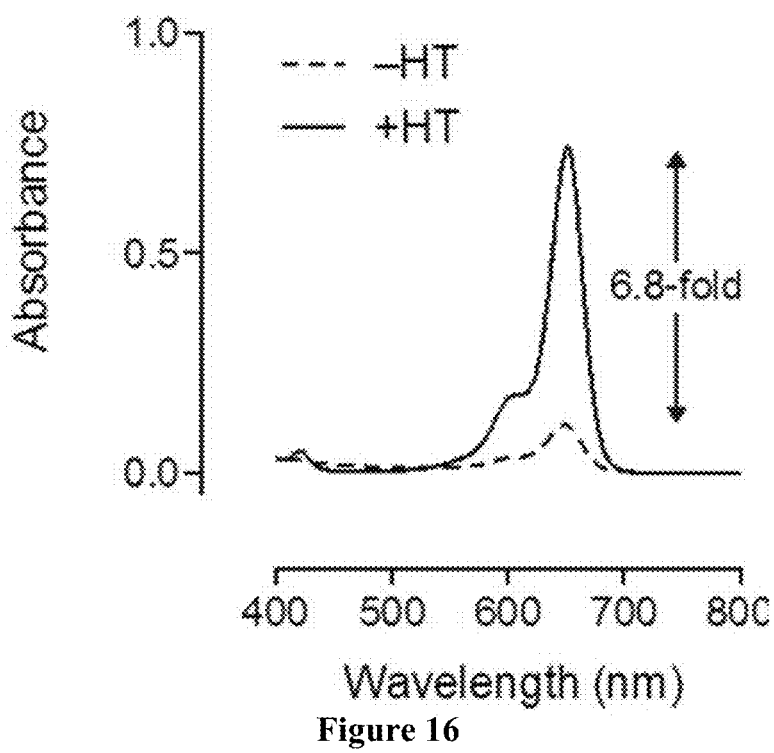
FIG. 16 includes a plot of the absorbance spectrum of SiTMR-HaloTag ligand (5 μM) in the absence (−HT) and presence (+HT) of excess HaloTag protein.
Figure 17:
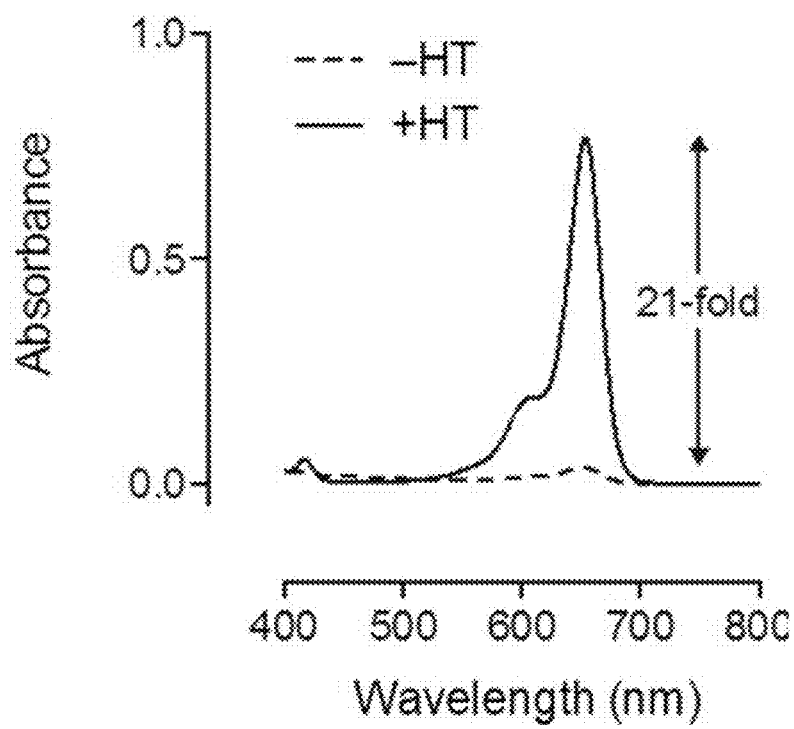
FIG. 17 includes a plot of the absorbance spectrum of $JF_{646}$-HaloTag ligand (5 μM) in the absence (−HT) and presence (+HT) of excess HaloTag protein.

The chromogenicity of the Halotag ligands was compared upon reaction with purified protein and in live-cell imaging experiments. The SiTMR ligand showed an enhancement of 6.8-fold upon reaction with excess HaloTag protein in buffer (FIG. 16). The azetidinyl-silarhodamine HaloTag ligand showed lower background, leading to a larger, 21-fold increase in absorbance under the same conditions (FIG. 17).

Figure 18:
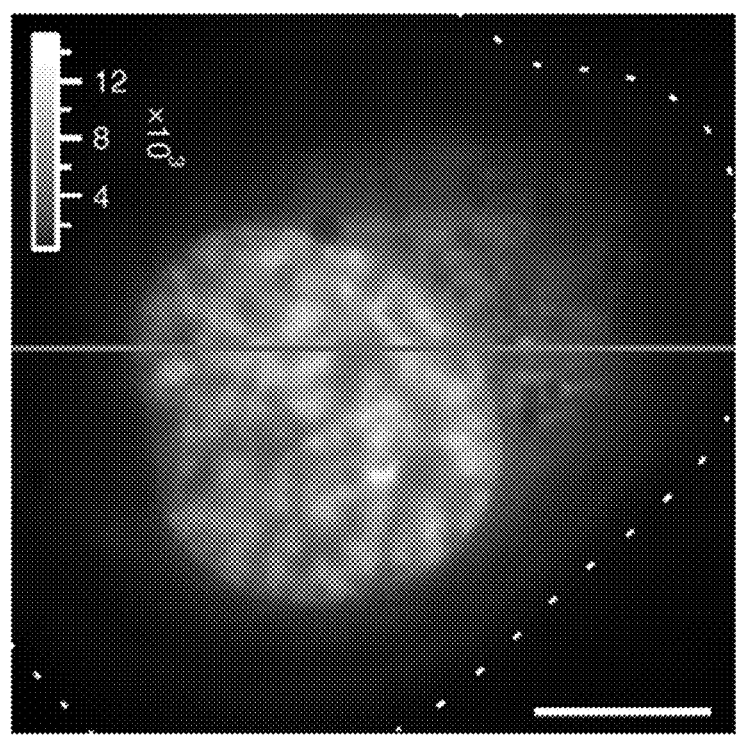
FIG. 18 includes a wide-field fluorescence microscopy image of a live HeLa cell transfected with H2B-HaloTag, incubated with SiTMR-HaloTag ligand (100 nM), and imaged without intermediate washing steps; dashed line indicates cellular boundary; scale bars: 10 μm.
Figure 19:
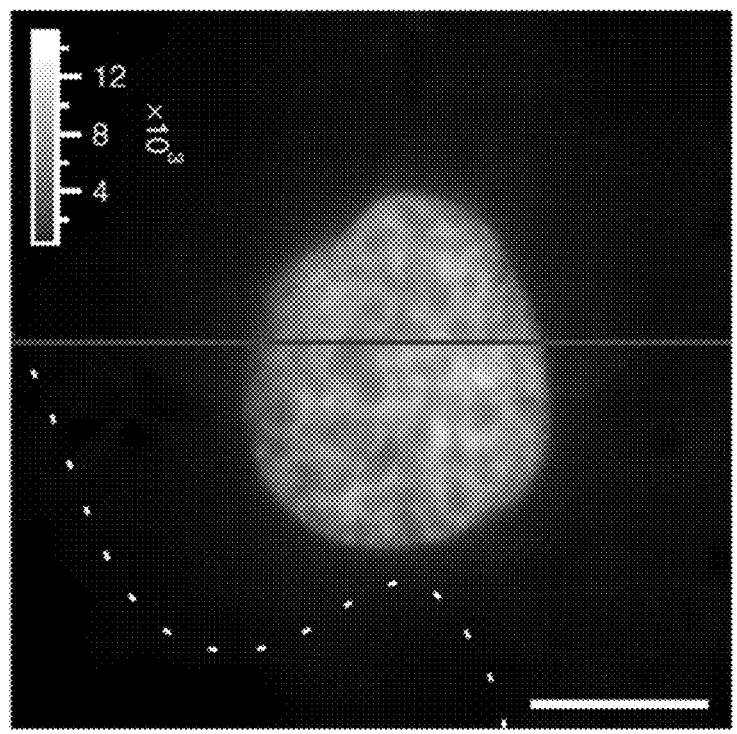
FIG. 19 includes a wide-field fluorescence microscopy image of a live HeLa cell transfected with H2B-HaloTag, incubated with $JF_{646}$-HaloTag ligand (100 nM), and imaged without intermediate washing steps; dashed line indicates cellular boundary; scale bars: 10 μm.
Figure 20:
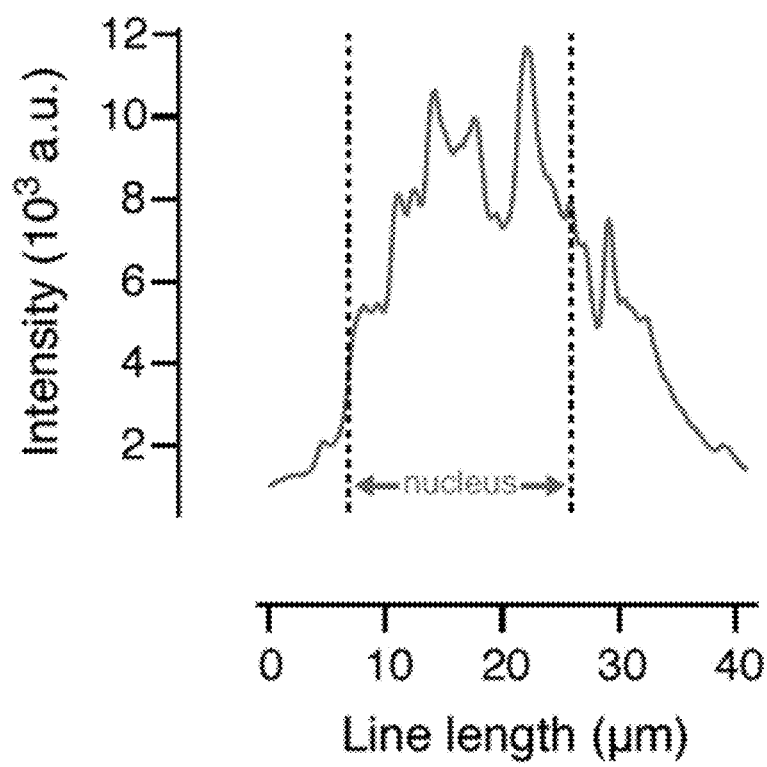
FIG. 20 includes a plot of line scan intensity in FIG. 18 as a function of line length.
Figure 21:
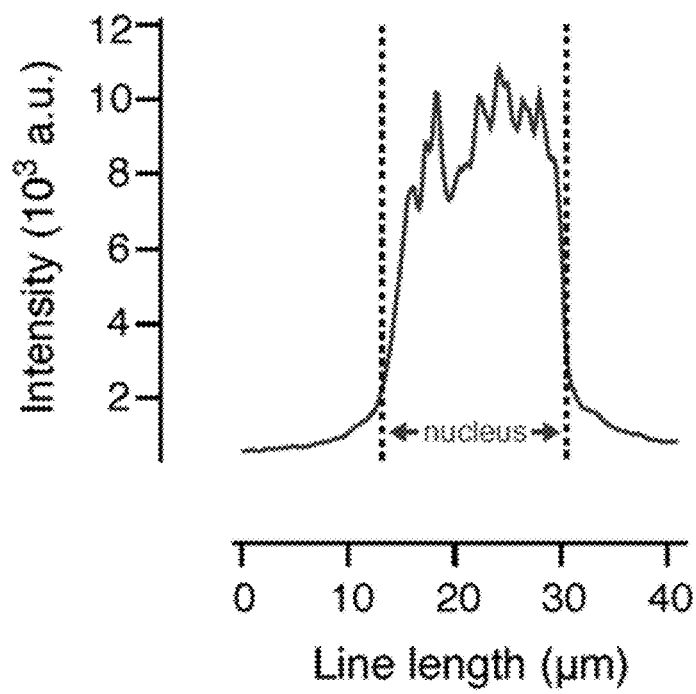
FIG. 21 includes a plot of line scan intensity in FIG. 19 as a function of line length.
Figure 22:
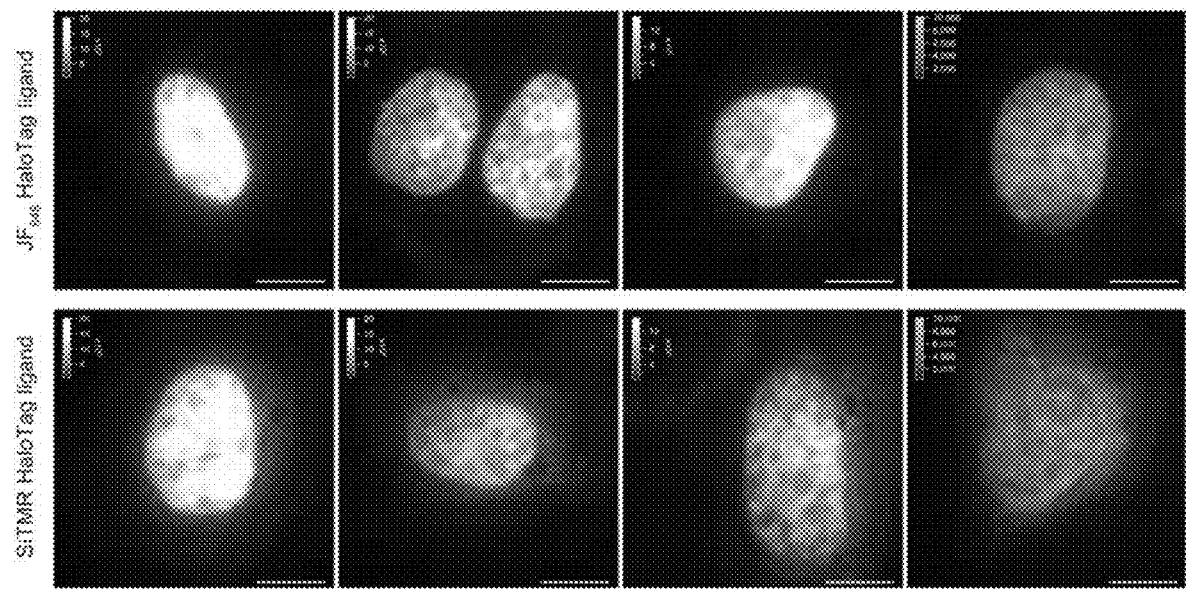
FIG. 22 includes examples of wide-field fluorescence microscopy images of live unwashed HeLa cells expressing HaloTag-H2B and incubated with 100 nM of either $JF_{646}$-HaloTag ligand (top row) or SiTMR-HaloTag ligand (bottom row).

Next, "no wash" imaging experiments were performed using cells expressing the HaloTag-H2B fusion. Incubation with either ligand (100 nM) followed directly by wide-field imaging gave brightly labeled nuclei using both the SiTMR ligand (FIG. 18) and the JF$_{646}$ ligand (FIG. 19). SiTMR showed extranuclear fluorescence (FIG. 20), whereas the JF$_{646}$ ligand exhibited lower nonspecific staining (FIGS. 21 and 22). Overall, these results show the known SiTMR ligand can be replaced with the structurally similar JF$_{646}$ ligand to achieve improved localization error in super-resolution imaging and lower background in conventional fluorescence microscopy.

Example 5

This Example describes a multiplexed single particle tracking and super resolution imaging process performed in the same cell. Given the spectral separation between $JF_{549}$ and $JF_{646}$, two distinct protein species were imaged at the single-molecule level in the same living cell.

Figure 23:
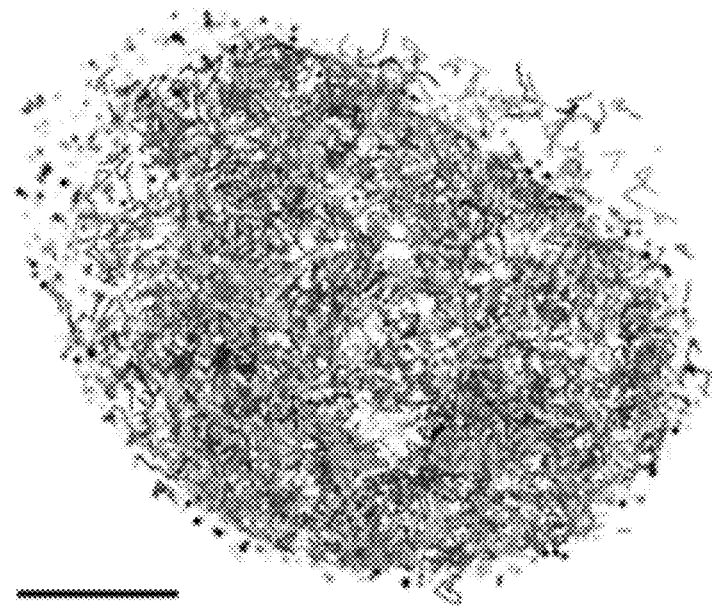
FIG. 23 includes a rendering of single-molecule trajectories of SnapTag-TetR-$JF_{549}$ conjugate from $JF_{549}$-SnapTag ligand overlaid on a dSTORM $H_2B$ image of HaloTag-$H_2B$ labeled with $JF_{646}$-HaloTag ligand in the nucleus of a live U2OS cell; scale bar=5 μm.
Figure 24:
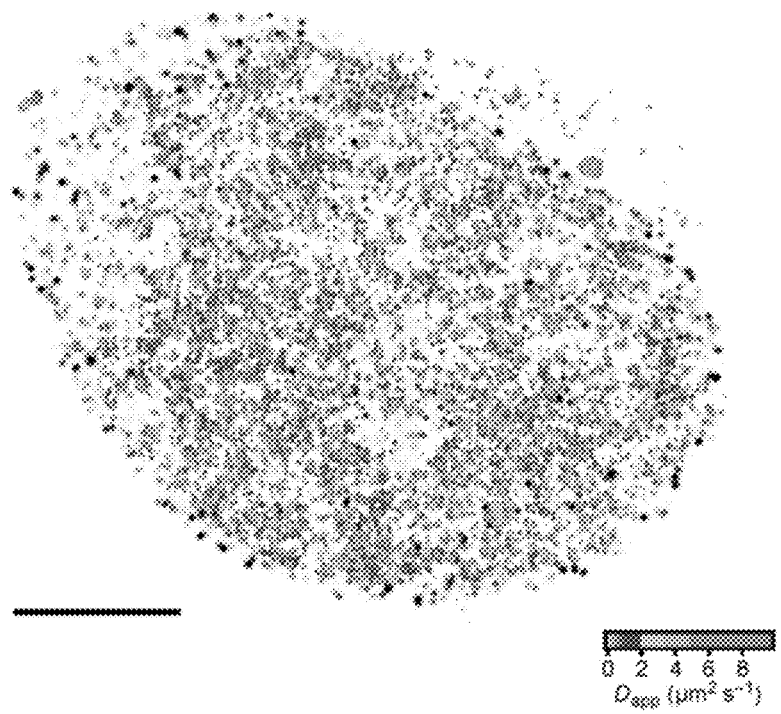
FIG. 24 includes an image showing the overlay of the dSTORM image of H$_2$B and regions of fast TetR diffusivity (2-10 µm$^2$s$^{-1}$; yellow) and slow TetR diffusivity (<2 µm$^2$s$^{-1}$; blue) in a live U2OS cell.
Figure 25:
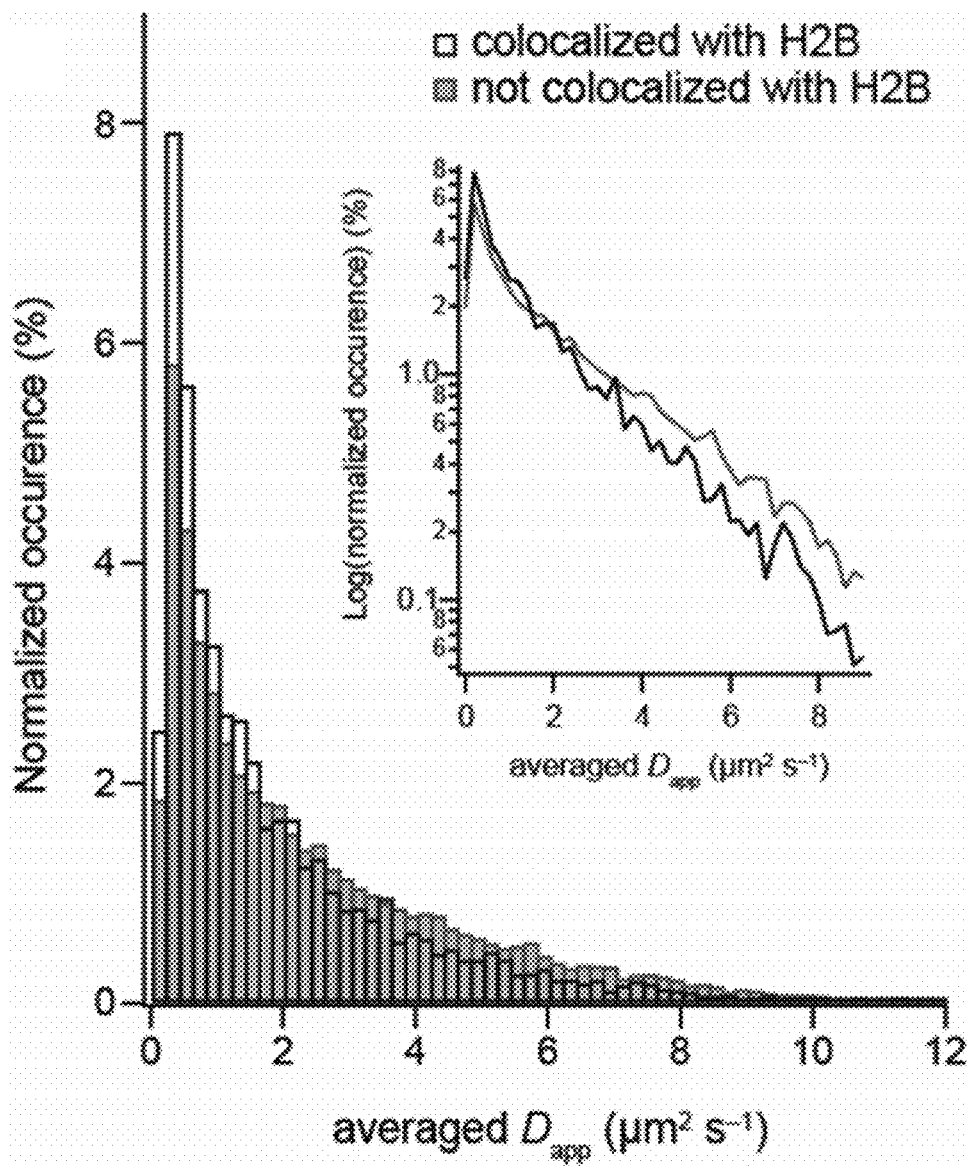
FIG. 25 includes normalized distributions of the apparent diffusion coefficients (D$_{app}$) of SnapTag-TetR that colocalize with HaloTag-H2B (black) or do not colocalize with HaloTag-H2B (gray).

To achieve orthogonal labeling, the SnapTag ligand of $JF_{549}$ was prepared. HaloTag $H_2B$ and a fusion of the SnapTag enzyme and the Tet repressor protein (SnapTag-TetR) were coexpressed and labeled with, respectively, $JF_{646}$-HaloTag ligand (Example 35) and $JF_{549}$-SnapTag ligand (Example 22). The trajectories of individual $JF_{549}$-labeled TetR proteins were imaged, and a rapid live-cell dSTORM experiment of the $JF_{646}H_2B$ conjugate was subsequently performed (FIG. 23). This two-color procedure revealed the respective partitions of fast- and slow-diffusing DNA-binding protein in relation to the chromatin structure of the nucleus (FIG. 24). Histograms of the diffusion coefficient of both the H2B-colocalized and the non-colocalized TetR trajectories were then plotted and showed TetR colocalized with H2B to a greater extent than with non-colocalized positions (FIG. 25).

Thus, the present compounds may be used in multicolor experiments in living cells, where several components involved in a biological process can be tracked and localized with molecular precision within the same cell.

Example 6

Figure 26:
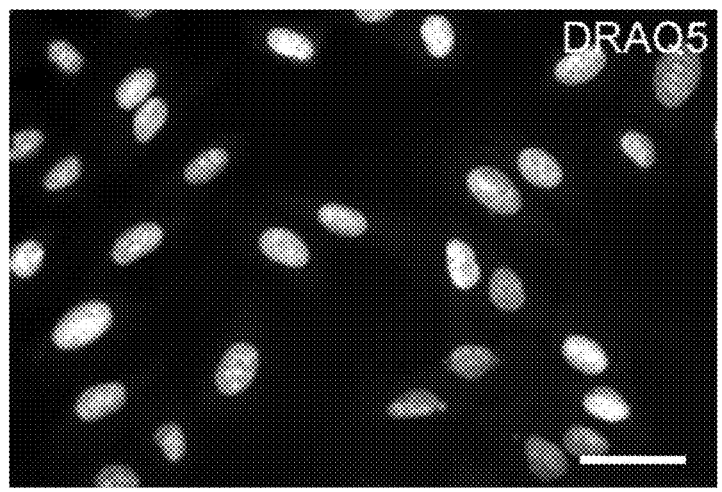
FIG. 26 includes a wide-field fluorescence microscopy image showing fluorescence of DRAQ5 nuclear staining in live HeLa cells expressing SnapTag-H2B and labeled with DRAQ5 and Snap-Cell 430; scale bar=50 µm.
Figure 27:
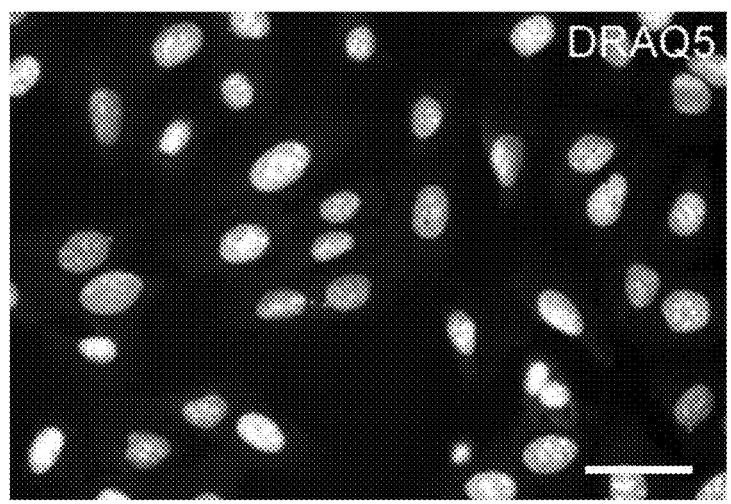
FIG. 27 includes a wide-field fluorescence microscopy image showing fluorescence of DRAQ5 nuclear staining in live HeLa cells expressing SnapTag-H2B and labeled with DRAQ5 and azetidinyl-coumarin-SnapTag ligand; scale bar=50 µm.
Figure 28:
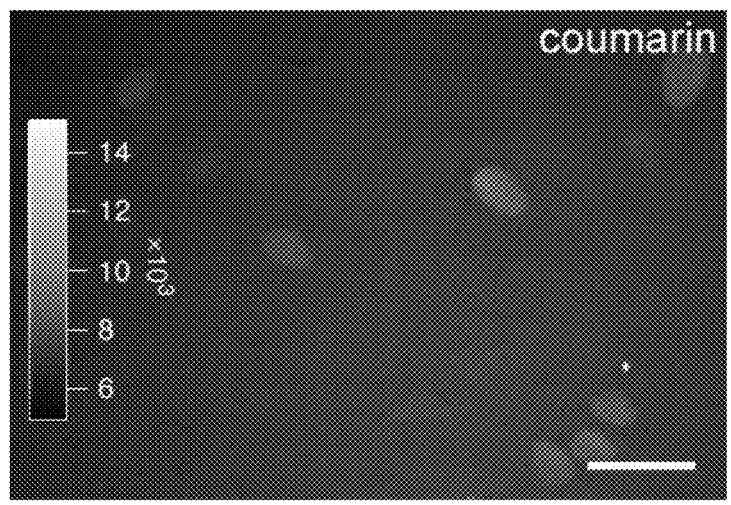
FIG. 28 includes a wide-field fluorescence microscopy image showing fluorescence of Snap-Cell 430-labeled SnapTag-H2B in live HeLa cells expressing SnapTag-H2B and labeled with DRAQ5 and Snap-Cell 430; scale bar=50 µm.
Figure 29:
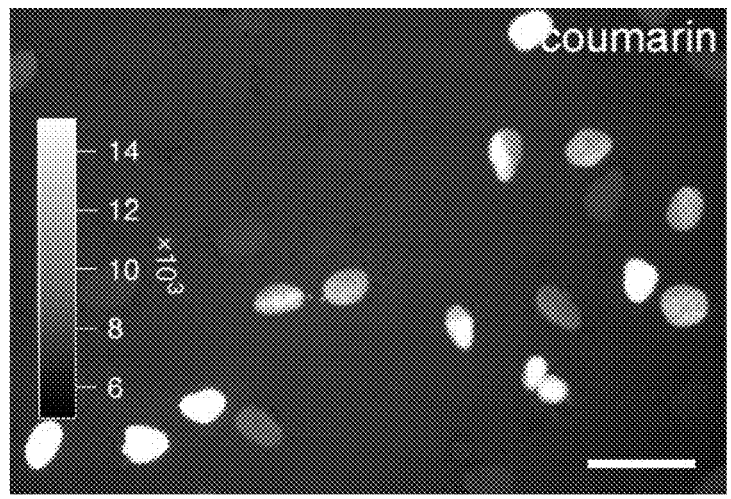
FIG. 29 includes a wide-field fluorescence microscopy image showing fluorescence of azetidinyl-coumarin-labeled SnapTag-H2B in live HeLa cells expressing SnapTag-H2B and labeled with DRAQ5 and azetidinyl-coumarin-SnapTag ligand; scale bar=50 µm.
Figure 30:
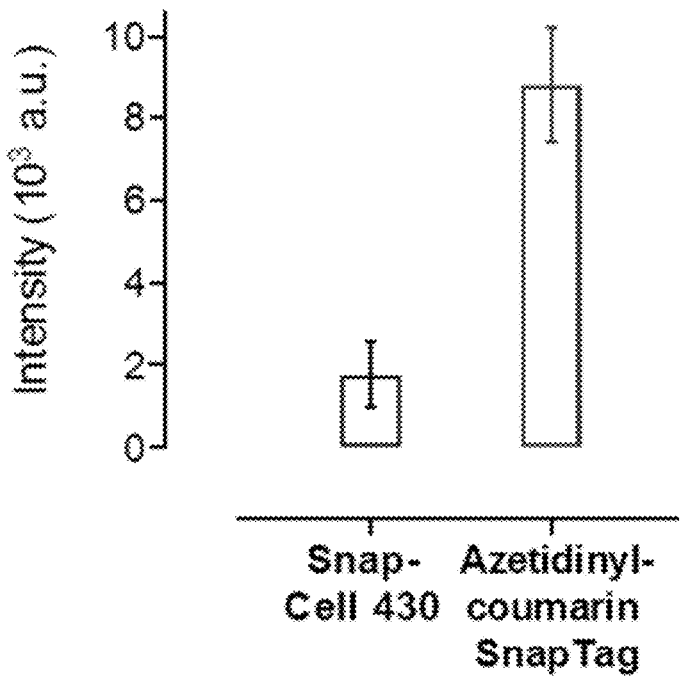
FIG. 30 includes a plot showing the quantification of the median nuclear fluorescence above background coumarin label in cells when labeled with Snap-Cell 430 or azetidinyl-coumarin-SnapTag ligand (n=50, error bars, s.e.m.).

In this Example, an azetidinyl-coumarin label was used for cellular imaging. The performance of a commercial SnapTag ligand (i.e., Snap Cell 430) was compared to a novel azetidinyl derivative (Example 52), which was synthesized from a 7-azetidinyl-coumarin-3-carboxylic acid. Under identical transient transfection, labeling, and imaging conditions, $H_2B$-SnapTag-expressing cells were stained with the red fluorescent nuclear stain DRAQ5 and either Snap Cell 430 or the azetidinyl ligand. Using the DRAQ5 staining as a spatial reference (FIGS. 26 and 27) the intensity of individual nuclei labeled by either SnapTag ligand was measured. Cells incubated with Snap Cell 430 ligand showed low fluorescence intensity (FIG. 28), whereas cells labeled with the azetidinyl-coumarin SnapTag ligand exhibited brighter nuclear labeling (FIG. 29). Quantification of nuclear intensity showed the cells labeled with azetidine had median values that were five-fold higher than cells labeled with the commercial compound (FIG. 30).

Examples 7-61

The following examples describe specific embodiments of the compounds described herein, and illustrates the flexibility of the present azetidine approach for making dyes. We reasoned that we could further tune the physicochemical properties of $JF_{549}$ by exploring different substitution patterns at the 3-position of the azetidine. For instance, the substituted azetidinyl-rhodamines shown in Table 1 had relatively high e values and quantum yield values.

Fluorescent and fluorogenic molecules for spectroscopy were prepared as stock solutions in DMSO and diluted such that the DMSO concentration did not exceed 1% v/v. Phosphate buffered saline (PBS) was at pH 7.4 unless otherwise noted.

Spectroscopy was performed using 1-cm path length, 3.5-mL quartz cuvettes from Starna Cells or 1-cm path length, 1.0-mL quartz microcuvettes from Hellma. All measurements were taken at ambient temperature (22±2° C.) in 10 mM HEPES, pH 7.3 buffer unless otherwise noted. Absorption spectra were recorded on a Cary Model 100 spectrometer (Varian); reported values for extinction coefficients (e) are averages (n=3). Fluorescence spectra were recorded on a Cary Eclipse fluorometer (Varian). Normalized spectra are shown for clarity.

All reported quantum yield values were measured in under identical conditions using a Quantaurus-QY spectrometer (C11374, Hamamatsu). Measurements were carried out using dilute samples (A<0.1) and self-absorption corrections were performed using the instrument software. Reported values are averages (n=3).

Dioxane-$H_2O$ titrations were performed in spectral grade dioxane (SigmaAldrich) and milliQ $H_2O$. The solvent mixtures contained 0.01% v/v triethylamine to ensure the rhodamine dyes were in the zwitterionic form. The absorbance values at $\lambda_{max}$ were measured on 5 μM samples (n=2) using a quartz 96-well microplate (Hellma) and a FlexStation3 microplate reader (Molecular Devices).

For fluorescence lifetime measurements, a pulse picker (Model 350-160, ConOptics) was placed in the laser beam to reduce the pulse frequency from 80 MHz to 20 MHz. Samples (2 μM dye diluted in 50 mM HEPES, pH 7.2, $H_2O$, or $CH_3OH$) were excited at 830 nm laser wavelength and 6 mW laser power. The emitted light was collected by the fast-timing APD and fed to the single-photon counting board (TimeHarp200; PicoQuant). Timing pulses were obtained from a PIN diode (DET01CFC; ThorLabs) monitoring the 20 MHz pulse train. The temporal impulse response of the system was determined by second harmonic generation of laser pulses using a thin nonlinear crystal in place of a dye sample. The lifetime decay data was fit to a single exponential decay function using a custom MATLAB program. Lifetime value of the reference fluorescein dye measured using this system was 4.025±0.015 ns ($R^2$=0.99) compared to a literature value of 4.1±0.1 ns (Magde, D.; Rojas, G. E.; Seybold, P. G. *Photochem. Photobiol.* 1999, 70, 737).

To measure fluorescence of HaloTag ligands upon reaction with HaloTag protein, absorbance measurements were performed in 1 mL quartz cuvettes. HaloTag protein was used as a 100 λsolution in 75 mM NaCl, 50 mM TRIS.HCl, pH 7.4 with 50% v/v glycerol (TBS-glycerol). HaloTag ligands of $JF_{646}$ and SiTMR (5 μM) were dissolved in 10 mM HEPES, pH 7.3 containing 0.1 mg·$mL^{-1}$ CHAPS. An aliquot of HaloTag protein (1.5 equiv) or an equivalent volume of TBS-glycerol blank was added and the resulting mixture was incubated until consistent absorbance signal was observed (~30 min). Additional HaloTag protein did not elicit an increase in absorbance (not shown). Absorbance scans are averages (n=2).

HeLa cells (ATCC) and U2OS cells (ATCC) were cultured in Dulbecco's modified eagle medium (DMEM; Life Technologies) supplemented with 10% v/v fetal bovine serum (FBS; Life Technologies), 1 mM GlutaMax (Life Technologies), and 1 mM sodium pyruvate (Sigma) and maintained at 37° C. in a humidified 5% v/v $CO_2$ environment. These cell lines undergo regular mycoplasma testing by the Janelia Cell Culture Facility. Cells were transfected with HaloTag-H2B, HaloTag-tubulin, SnapTag-TetR, or SnapTag-H2B using an Amaxa Nucleofector (Lonza).

Before the imaging experiments, transfected cells were transferred onto a No. 1 coverslip (Warner Instruments) that was cleaned by Piranha solution (3:1 v/v mixture of concentrated $H_2SO_4$ and 30% v/v hydrogen peroxide). To label live cells with the HaloTag or SnapTag ligands, the ligands were added to the growth medium and the samples incubated for 15 min. Labeling concentrations were typically 100-500 nM for confocal, wide-field, and dSTORM experiments and 5-50 nM for single-molecule tracking experiments. Cells were then washed briefly with PBS (1×) and then incubated in DMEM-FBS for an additional 15 min. Before imaging, the cells were washed briefly with PBS (3×) and placed in fresh DMEM-FBS for imaging. All washes were omitted in the "no wash" experiments. For nuclear staining, cells were incubated in PBS for 5 min (2×), and then incubated in PBS containing 5 μM DRAQ5 (Cell Signaling) for 5 min, followed by brief wash with PBS (1×). During all imaging experiments, cells were maintained at 37° C. in a humidified 5% $CO_2$ v/v environment supplied by a live-cell incubator (TOKAI HIT).

Three separate systems were used to acquire microscopic images. Confocal microscopy was performed using a Zeiss LSM 510 META confocal microscope with a LD C-APOCHROMAT 40×/1.2 W Korr M27 UV-VIS-IR objective. Wide-field microscopy, 2D single-molecule tracking, and super-resolution imaging experiments were conducted on a Nikon Eclipse Ti wide field epifluorescence microscope equipped with a 100×, 1.4NA oil-immersion objective lens (Nikon), a Lumencor light source, a set of lasers (405 nm/100 mW, Coherent Cube; 561 nm/200 mW, Cobolt Jive; 633 nm/140 mW, Vortran Stradus), controlled by an Acousto-Optic Tunable Filter (AA Opto-Electronic), two filter wheels (Lambda 10-3; Sutter Instruments), a perfect focusing system (Nikon), and an EMCCD camera (iXon3, Andor). Emission filters (FF01 593/40 or FF01 676/37; Semrock) were placed in front of the cameras for $JF_{549}$ and $JF_{646}$ emission. A multi-band mirror (405/488/561/633 BrightLine quad-band bandpass filter, Semrock) was used to reflect the excitation laser beams into the objective. The microscope, cameras, and hardware were controlled through the NIS-Elements software (Nikon). Other live-cell single super-resolution imaging experiments were recorded on a custom-built three-camera RAMM frame (ASI) microscope using an 1.4NA PLAPON 60×OSC objective (Olympus), and a 300 mm focal length tube lens (LAO-300.0, Melles Griot), resulting in 100× overall magnification. Stroboscopic 405 nm excitation of the Stradus 405-100 laser (Vortran) was achieved using a NI-DAQ-USB-6363 acquisition board (National Instruments), which also controlled the 637 nm laser emission from a Stradus 637-140 laser (Vortran). A 2 mm-thick quad-band dichroic (ZT 405/488/561/640rpx, Chroma), and a band-pass emission filter (FF01-731/137-25, Semrock) filtered the emitted light. Fluorescence was detected with a back-illuminated EMCCD camera (Andor Technology, Ixon Ultra DU-897U-CS0-EXF, 17 MHz EM amplifier), which was controlled through Micro-Manager (1.4.17).

For live-cell dSTORM imaging the cells were labeled, washed, and imaged directly in DMEM-FBS. For fixed cell preparations, cells were labeled, washed, and fixed in 4% paraformaldehyde (Electron Microscopy Sciences) in PBS buffer (pH=7.5). The cells were imaged in a sealed cell chamber (Life Technologies) containing nitrogen-degassed redox buffer consisting of PBS supplemented with 50 mM mercaptoethylamine (Sigma-Aldrich), 10% w/v glucose, 0.5 mg/mL glucose oxidase (Sigma-Aldrich), and 28400 U/mL catalase (Sigma-Aldrich). Before imaging, $JF_{549}$ could be efficiently "shelved" in a dark state upon illumination with 2 kW·cm$^{-2}$ of excitation light (561 nm), and then activated back to a fluorescent state by blue light (405 nm) with low intensity (~20 W cm$^{-2}$). $JF_{646}$ fluorophores were converted into a predominately dark state using continuous illumination of 637 nm excitation light at 14 kW·cm$^{-2}$, after which individual rapidly blinking molecules of $JF_{646}$ fluorophores were observed. These experiments were conducted on the two wide-field microscope systems described above: the Nikon Eclipse Ti epifluorescence microscope and the custom-built three-camera microscope with an ASI RAMM frame.

The spot localization (x,y) was obtained based on the multiple-target tracing (MTT) algorithm (Serge, A.; Bertaux, N.; Rigneault, H.; Marguet, D. Nature Protocol Exchange 2008, doi:10.1038/nprot.2008.1128; Serge, A.; Bertaux, N.; Rigneault, H.; Marguet, D. Nat. Methods 2008, 5, 687) using a custom MATLAB program. For each frame, the PSF of individual fluorophores was fitted into a two-dimensional Gaussian distribution. Integrated fluorescence intensities were calculated and converted to photon counts using analysis routines written in IGOR Pro version 6.34A. Localization errors were calculated using Equation 6 in Mortensen et al. (Mortensen, K. I.; Churchman, L. S.; Spudich, J. A.; Flyvbjerg, H. Nat. Methods 2010, 7, 377). Super-resolution images were rendered using the software package Localizer by Dedecker et al. (Dedecker, P.; Duwé, S.; Neely, R. K.; Zhang, J. J. Biomed. Opt. 2012, 17, 126008) running from Igor Pro v. 3.34A, which superimposes the position coordinates of detected spots as Gaussian masks using the fitted intensity values as amplitudes and the localization errors as the widths. The dSTORM data for experiments comparing two different fluorophore ligands was recorded on the same day under identical illumination conditions.

The two-color single-molecule experiments were recorded on the Nikon Eclipse Ti wide field epifluorescence microscope. We first performed a 2D single molecule tracking of SnapTag-TetR-$JF_{549}$ using a 561-nm laser of excitation intensity ~1 kW cm$^{-2}$ at a frame rate of 100 Hz. Immediately after the completion of the single-particle tracking experiment, we then imaged HaloTag-H2B-$JF_{646}$ under the dSTORM mode as described above. Transmission images were taken before and after the tracking-dSTORM experiments and a cross-correlation algorithm was employed to calculate the image drift (Guizar-Sicairos, M.; Thurman, S. T.; Fienup, J. R. Opt. Lett. 2008, 33, 156). Tracking analysis of TetR was performed using the commercial tracking software DiaTrack (v. 3.03, Semasopht), which identifies and fits the intensity spots of fluorescent particles with 2D Gaussian functions matched to the experimentally determined point-spread function. The diffusion map was created using tracking routines written in IGOR Pro 6.34A, calculating the local apparent diffusion of TetR mobility evaluated on a 20 nm×20 nm x-y grid from the mean square displacements over a timescale of 10 milliseconds. Whenever two or more separate displacements originating within 80 nm of a given grid node were found, a local apparent diffusion coefficient was calculated and plotted. H2B clusters were then selected as the 500 brightest spots in the super-resolved image. From this analysis, a histogram of apparent diffusion coefficients for all trajectories that dwelled within 320 nm of a H2B cluster for at least 10 milliseconds was generated. Histograms of the diffusion coefficient of both the H2B-colocalized and the non-colocalized TetR trajectories were then plotted.

Example 7.
2-(3,6-Di(azetidin-1-yl)xanthylium-9-yl)benzoate

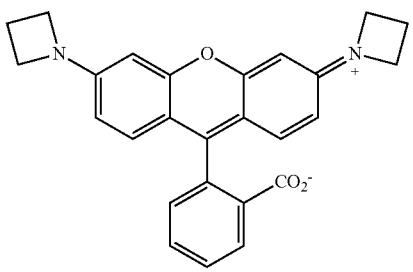

A vial was charged with fluorescein ditriflate (75 mg, 126 µmol; from Grimm, J. B.; Lavis, L. D. Org. Lett. 2011, 13, 6354), $Pd_2dba_3$ (11.5 mg, 12.6 µmol, 0.1 eq), XPhos (18.0 mg, 37.7 µmol, 0.3 eq), and $Cs_2CO_3$ (115 mg, 352 µmol, 2.8 eq). The vial was sealed and evacuated/backfilled with nitrogen (3×). Dioxane (1 mL) was added, and the reaction was flushed again with nitrogen (3×). Following the addition of azetidine (20.3 µL, 302 µmol, 2.4 eq), the reaction was stirred at 100° C. for 18 h. It was then cooled to room temperature, diluted with MeOH, deposited onto Celite, and concentrated to dryness. Purification by silica gel chromatography (0-10% MeOH (2 M $NH_3$)/$CH_2Cl_2$, linear gradient; dry load with Celite) afforded the title compound (49 mg, 95%) as a purple solid. $^1$H NMR ($CDCl_3$, 400 MHz) δ 8.03-7.96 (m, 1H), 7.63 (td, J=7.4, 1.3 Hz, 1H), 7.58 (td, J=7.4, 1.1 Hz, 1H), 7.20-7.13 (m, 1H), 6.56 (d, J=8.6 Hz, 2H), 6.20 (d, J=2.3 Hz, 2H), 6.09 (dd, J=8.6, 2.3 Hz, 2H), 3.91 (t, J=7.3 Hz, 8H), 2.37 (p, J=7.2 Hz, 4H); $^{13}$C NMR ($CDCl_3$, 101 MHz) δ 169.9 (C), 153.7 (C), 153.1 (C), 152.9 (C), 134.6 (CH), 129.4 (CH), 129.0 (CH), 127.8 (C), 125.0 (CH), 124.3 (CH), 107.9 (C), 107.8 (CH), 97.7 (CH), 52.2 ($CH_2$), 16.8 ($CH_2$); Analytical HPLC: >99% purity (4.6 mm×150 mm 5 µm C18 column; 5 µL injection; 10-95% $CH_3CN/H_2O$, linear gradient, with constant 0.1% v/v TFA additive; 20 min run; 1 mL/min flow; ESI; positive ion mode; detection at 550 nm); HRMS (ESI) calcd for $C_{26}H_{23}N_2O_3[M+H]^+$ 411.1703, found 411.1714.

Example 8. 2-(3,6-Bis(3,3-dimethylazetidin-1-yl)xanthylium-9-yl)benzoate

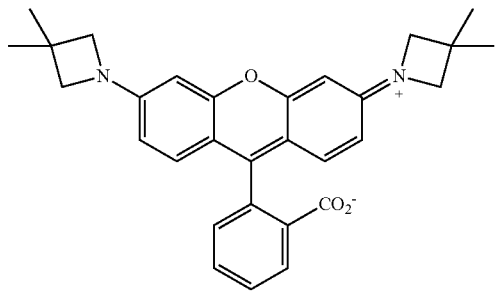

The procedure described for Example 7 was used to prepare the title compound from fluorescein ditriflate and 3,3-dimethylazetidine hydrochloride (86%, purple solid). $^1$H NMR (MeOD, 400 MHz) δ 8.11-8.06 (m, 1H), 7.67-7.57 (m, 2H), 7.23-7.20 (m, 1H), 7.19 (d, J=9.2 Hz, 2H), 6.56 (dd, J=9.1, 2.2 Hz, 2H), 6.49 (d, J=2.2 Hz, 2H), 3.92 (s, 8H), 1.39 (s, 12H); $^{13}$C NMR (MeOD, 101 MHz) δ 173.1 (C), 160.2 (C), 158.7 (C), 158.2 (C), 140.8 (C), 134.9 (C), 132.9 (CH), 130.82 (CH), 130.77 (CH), 130.74 (CH), 130.2 (CH), 115.0 (C), 113.1 (CH), 95.5 (CH), 64.4 ($CH_2$), 33.0 (C), 27.1 ($CH_3$); Analytical HPLC: >99% purity (4.6 mm×150 mm 5 µm C18 column; 5 µL injection; 10-95% $CH_3CN/H_2O$, linear gradient, with constant 0.1% v/v TFA additive; 20 min run; 1 mL/min flow; ESI; positive ion mode; detection at 550 nm); HRMS (ESI) calcd for $C_{30}H_{31}N_2O_3$ $[M+H]^+$ 467.2329, found 467.2341.

Example 9. 2-(3,6-Bis(3,3-difluoroazetidin-1-yl)xanthylium-9-yl)benzoate

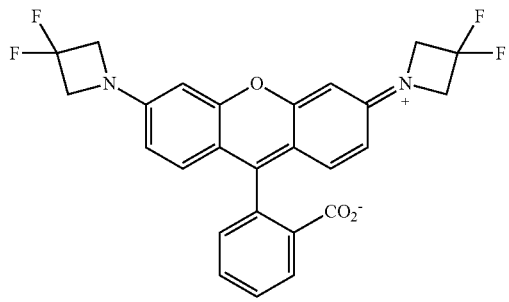

The procedure described for Example 7 was used to prepare the title compound from fluorescein ditriflate and 3,3-difluoroazetidine hydrochloride (91%, pink solid). $^1$H NMR ($CDCl_3$, 400 MHz) δ 8.03-7.99 (m, 1H), 7.66 (td, J=7.4, 1.3 Hz, 1H), 7.60 (td, J=7.4, 1.1 Hz, 1H), 7.17-7.14 (m, 1H), 6.64 (d, J=8.6 Hz, 2H), 6.30 (d, J=2.4 Hz, 2H), 6.17 (dd, J=8.6, 2.4 Hz, 2H), 4.25 (t, $^3J_{HF}$=11.7 Hz, 8H); $^{19}$F NMR ($CDCl_3$, 376 MHz) δ-100.05 (p, $^3J_{FH}$=11.8 Hz); $^{13}$C NMR ($CDCl_3$, 101 MHz) δ 169.6 (C), 153.3 (C), 152.6 (C), 151.3 (t, $^4J_{CF}$=2.9 Hz, C), 135.0 (CH), 129.7 (CH), 129.3 (CH), 127.2 (C), 125.1 (CH), 124.0 (CH), 115.8 (t, $^1J_{CF}$=274.6 Hz, $CF_2$), 109.7 (C), 108.8 (CH), 99.4 (CH), 83.9 (C), 63.4 (t, $^2J_{CF}$=26.3 Hz, $CH_2$); Analytical HPLC: >99% purity (4.6 mm×150 mm 5 µm C18 column; 5 µL injection; 10-95% $CH_3CN/H_2O$, linear gradient, with constant 0.1% v/v TFA additive; 20 min run; 1 mL/min flow; ESI; positive ion mode; detection at 525 nm); HRMS (ESI) calcd for $C_{26}H_{19}F_4N_2O_3$ $[M+H]^+$ 483.1326, found 483.1336.

Example 10. 2-(3,6-Bis(3-fluoroazetidin-1-yl)xanthylium-9-yl)benzoate

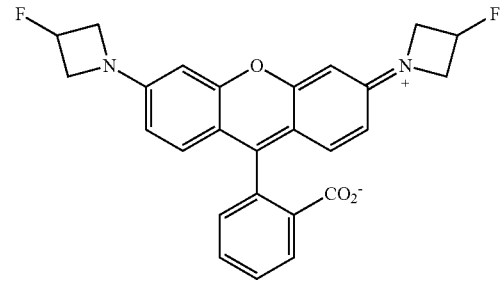

The procedure described for Example 7 was used to prepare the title compound from fluorescein ditriflate and 3-fluoroazetidine hydrochloride (89%, pink solid). $^1$H NMR (DMSO-d$_6$, 400 MHz) δ 8.01-7.95 (m, 1H), 7.78 (td, J=7.5, 1.2 Hz, 1H), 7.71 (td, J=7.5, 0.9 Hz, 1H), 7.25-7.20 (m, 1H), 6.52 (d, J=8.6 Hz, 2H), 6.33 (d, J=2.3 Hz, 2H), 6.24 (dd, J=8.6, 2.3 Hz, 2H), 5.49 (dtt, $^2J_{HF}$=57.6 Hz, J=6.0, 3.1 Hz, 2H), 4.26-4.13 (m, 4H), 4.00-3.88 (m, 4H); $^{19}$F NMR (DMSO-d$_6$, 376 MHz) δ-178.95 (dtt, J$_{FH}$=57.4, 24.2, 20.9 Hz); $^{13}$C NMR (DMSO-d$_6$, 101 MHz) δ 168.7 (C), 152.54 (d, $^4J_{CF}$=1.3 Hz, C), 152.47 (C), 151.8 (C), 135.4 (CH), 129.9 (CH), 128.6 (CH), 126.4 (C), 124.5 (CH), 123.9 (CH), 108.6 (CH), 107.8 (C), 98.0 (CH), 83.8 (C), 83.3 (d, $^1J_{CF}$=200.3 Hz, CFH), 59.2 (d, $^2J_{CF}$=23.7 Hz, CH$_2$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 550 nm); HRMS (ESI) calcd for C$_{26}$H$_{21}$F$_2$N$_2$O$_3$ [M+H]$^+$ 447.1515, found 447.1525.

Example 11. 2-(3,6-Bis(3-methoxyazetidin-1-yl)xanthylium-9-yl)benzoate

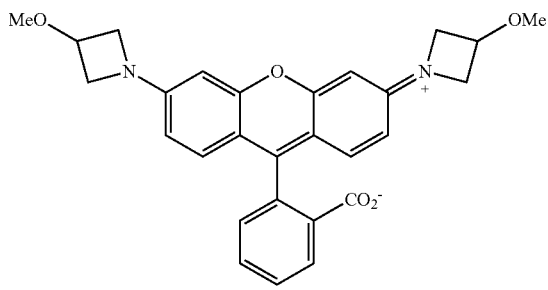

The procedure described for Example 7 was used to prepare the title compound from fluorescein ditriflate and 3-methoxyazetidine hydrochloride (83%, purple solid). $^1$H NMR (DMSO-d$_6$, 400 MHz) δ 8.00-7.94 (m, 1H), 7.77 (td, J=7.5, 1.2 Hz, 1H), 7.70 (td, J=7.5, 0.9 Hz, 1H), 7.25-7.20 (m, 1H), 6.48 (d, J=8.6 Hz, 2H), 6.26 (d, J=2.3 Hz, 2H), 6.19 (dd, J=8.6, 2.3 Hz, 2H), 4.32 (tt, J=6.2, 4.2 Hz, 2H), 4.07 (dd, J=8.0, 6.6 Hz, 4H), 3.66 (dd, J=8.4, 4.1 Hz, 4H), 3.24 (s, 6H); $^{13}$C NMR (DMSO-d$_6$, 101 MHz) δ 168.7 (C), 152.8 (C), 152.5 (C), 151.9 (C), 135.4 (CH), 129.9 (CH), 128.5 (CH), 126.5 (C), 124.5 (CH), 123.9 (CH), 108.2 (CH), 107.2 (C), 97.5 (CH), 84.1 (C), 69.2 (CH), 58.3 (CH$_2$), 55.4 (CH$_3$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 550 nm); HRMS (ESI) calcd for C$_{28}$H$_{27}$N$_2$O$_5$ [M+H]$^+$ 471.1914, found 471.1926.

Example 12. 2-(3,6-Bis(3-cyanoazetidin-1-yl)xanthylium-9-yl)benzoate

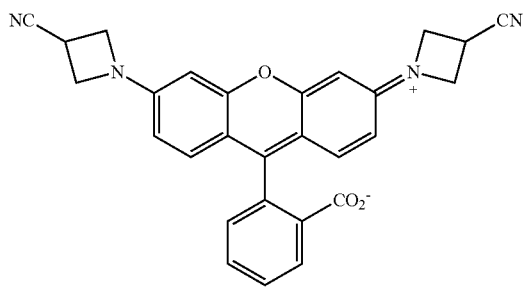

The procedure described for Example 7 was used to prepare the title compound from fluorescein ditriflate and 3-azetidinecarbonitrile hydrochloride (85%, magenta solid). $^1$H NMR (CDCl$_3$, 400 MHz) δ 8.03-7.98 (m, 1H), 7.66 (td, J=7.4, 1.3 Hz, 1H), 7.60 (td, J=7.4, 1.1 Hz, 1H), 7.17-7.13 (m, 1H), 6.62 (d, J=8.6 Hz, 2H), 6.25 (d, J=2.3 Hz, 2H), 6.12 (dd, J=8.6, 2.4 Hz, 2H), 4.25-4.18 (m, 4H), 4.15-4.08 (m, 4H), 3.60 (tt, J=8.5, 6.2 Hz, 2H); NMR (CDCl$_3$, 101 MHz) δ 169.6 (C), 153.2 (C), 152.5 (C), 151.9 (C), 135.0 (CH), 129.7 (CH), 129.3 (CH), 127.1 (C), 125.1 (CH), 124.0 (CH), 119.7 (C), 109.7 (C), 108.1 (CH), 98.7 (CH), 83.9 (C), 55.2 (CH$_2$), 18.4 (CH); Analytical HPLC: >99% purity (4.6 mm×150 mm 5 μm C18 column; 5 μL injection; 10-95% CH3CN/H$_2$O, linear gradient, with constant 0.1% v/v TFA additive; 20 min run; 1 mL/min flow; ESI; positive ion mode; detection at 550 nm); HRMS (ESI) calcd for C$_{28}$H$_{21}$N$_4$O$_3$ [M+H]$^+$ 461.1608, found 461.1628.

Example 13

2-(3,6-Bis(3-(dimethylamino)azetidin-1-yl)xanthylium-9-yl)benzoate

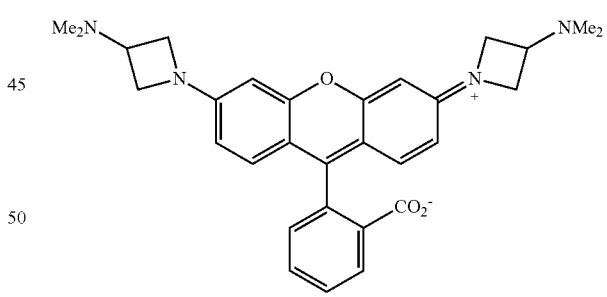

The procedure described for Example 7 was used to prepare the title compound from fluorescein ditriflate and 3-(dimethylamino)azetidine dihydrochloride (80%, purple solid). $^1$H NMR (MeOD, 400 MHz) δ 8.10-8.05 (m, 1H), 7.69-7.60 (m, 2H), 7.24-7.19 (m, 1H), 7.12 (d, J=9.0 Hz, 2H), 6.56 (dd, J=9.0, 2.2 Hz, 2H), 6.53 (d, J=2.2 Hz, 2H), 4.31-4.22 (m, 4H), 4.01 (dd, J=10.5, 5.1 Hz, 4H), 3.39 (tt, J=7.0, 5.1 Hz, 2H), 2.27 (s, 12H); $^{13}$C NMR (MeOD, 101 MHz) δ 172.8 (C), 157.9 (C), 157.1 (C), 147.7 (C), 138.7 (C), 138.4 (C), 132.5 (CH), 131.8 (CH), 130.8 (CH), 129.9 (CH), 129.3 (CH), 114.1 (C), 112.4 (CH), 96.3 (CH), 57.0 (CH), 56.6 (CH$_2$), 42.0 (CH$_3$); Analytical HPLC: >99% purity (4.6 mm×150 mm 5 μm C18 column; 5 μL injection;

10-95% CH₃CN/H₂O, linear gradient, with constant 0.1% v/v TFA additive; 20 min run; 1 mL/min flow; ESI; positive ion mode; detection at 550 nm); HRMS (ESI) calcd for C₃₀H₃₃N₄O₃ [M+H]⁺ 497.2547, found 497.2561.

Example 14. 2-(3,6-Bis(3-(methoxycarbonyl)azetidin-1-yl)xanthylium-9-yl)benzoate

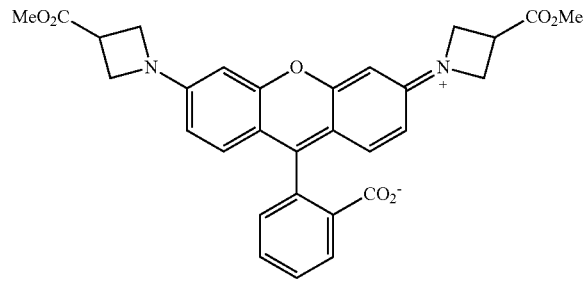

The procedure described for Example 7 was used to prepare the title compound from fluorescein ditriflate and methyl azetidine-3-carboxylate hydrochloride (79%, purple solid). ¹H NMR (MeOD, 400 MHz) δ 8.09-8.03 (m, 1H), 7.69-7.62 (m, 2H), 7.24-7.17 (m, 1H), 7.02 (d, J=8.9 Hz, 2H), 6.48 (dd, J=8.9, 2.2 Hz, 2H), 6.45 (d, J=2.1 Hz, 2H), 4.34 (t, J=9.0 Hz, 4H), 4.25 (dd, J=9.0, 5.9 Hz, 4H), 3.77 (s, 6H), 3.71 (tt, J=8.9, 5.9 Hz, 2H); ¹³C NMR (MeOD, 101 MHz) δ 174.4 (C), 172.6 (C), 157.0 (C), 156.5 (C), 141.6 (C), 136.7 (C), 135.8 (C), 132.7 (CH), 131.9 (CH), 130.9 (CH), 129.0 (CH), 128.5 (CH), 113.3 (C), 111.7 (CH), 96.8 (CH), 55.2 (CH₂), 52.9 (CH₃), 34.0 (CH); HRMS (ESI) calcd for C₃₀H₂₇N₂O₇ [M+H]⁺ 527.1813, found 527.1823.

Example 15. 2-(3,6-Bis(3-(2-methoxy-2-oxoethyl)azetidin-1-yl)xanthylium-9-yl)benzoate

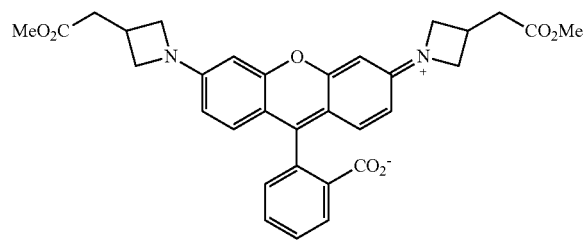

The procedure described for Example 7 was used to prepare the title compound from fluorescein ditriflate and methyl 3-azetidineacetate trifluoroacetate (67%, purple solid). ¹H NMR (MeOD, 400 MHz) δ 8.10-8.05 (m, 1H), 7.67-7.57 (m, 2H), 7.21-7.18 (m, 1H), 7.16 (d, J=9.1 Hz, 2H), 6.54 (dd, J=9.1, 2.2 Hz, 2H), 6.48 (d, J=2.2 Hz, 2H), 4.41-4.32 (m, 4H), 3.97-3.88 (m, 4H), 3.69 (s, 6H), 3.26-3.13 (m, 2H), 2.80 (d, J=7.7 Hz, 4H); ¹³C NMR (MeOD, 101 MHz) δ 173.7 (C), 173.0 (C), 158.3 (C), 157.5 (C), 154.9 (C), 140.1 (C), 136.3 (C), 132.7 (CH), 131.1 (CH), 130.8 (CH), 130.4 (CH), 129.8 (CH), 114.5 (C), 112.7 (CH), 95.7 (CH), 57.5 (CH₂), 52.2 (CH₃), 38.5 (CH₂), 27.3 (CH); HRMS (ESI) calcd for C₃₂H₃₁N₂O₇[M+H]⁺ 555.2126, found 555.2132.

Example 16. 2-(3,6-Bis(3-carboxyazetidin-1-yl)xanthylium-9-yl)benzoate

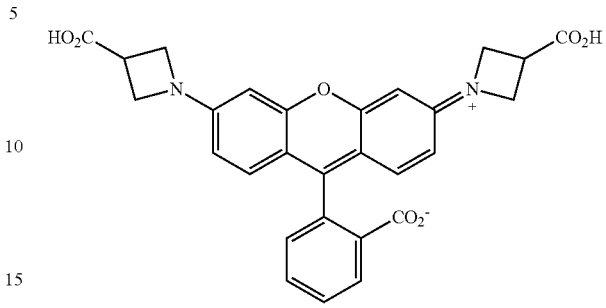

2-(3,6-Bis(3-(methoxycarbonyl)azetidin-1-yl)xanthylium-9-yl)benzoate (Example 14; 40 mg, 76.0 μmol) was dissolved in MeOH (2.5 mL), and 1 M NaOH (304 μL, 304 μmol, 4 eq) was added. After stirring the reaction at room temperature for 18 h, it was acidified with 1 M HCl (350 μL) and directly purified by reverse phase HPLC (10-50% MeCN/H₂O, linear gradient, with constant 0.1% v/v TFA additive) to provide 28 mg (60%, TFA salt) of the title compound as a red-purple solid. ¹H NMR (MeOD, 400 MHz) δ 8.36-8.30 (m, 1H), 7.84 (td, J=7.5, 1.6 Hz, 1H), 7.79 (td, J=7.6, 1.5 Hz, 1H), 7.40-7.36 (m, 1H), 7.12 (d, J=9.2 Hz, 2H), 6.66 (dd, J=9.2, 2.2 Hz, 2H), 6.61 (d, J=2.2 Hz, 2H), 4.48 (t, J=9.6 Hz, 4H), 4.39 (dd, J=9.9, 5.9 Hz, 4H), 3.72 (tt, J=9.0, 5.8 Hz, 2H); ¹³C NMR (MeOD, 101 MHz) δ 175.2 (C), 168.0 (C), 162.4 (C), 158.9 (C), 157.9 (C), 135.3 (C), 133.9 (CH), 132.6 (CH), 132.5 (CH), 131.5 (CH), 131.4 (CH), 115.4 (C), 113.8 (CH), 95.6 (CH), 55.3 (CH₂), 33.9 (CH); Analytical HPLC: >99% purity (4.6 mm×150 mm 5 μm C18 column; 5 μL injection; 10-75% CH₃CN/H₂O, linear gradient, with constant 0.1% v/v TFA additive; 20 min run; 1 mL/min flow; ESI; positive ion mode; detection at 550 nm); HRMS (ESI) calcd for C₂₈H₂₃N₂O₇ [M+H]⁺ 499.1500, found 499.1507.

Example 17. 2-(3,6-Bis(3-(carboxymethyl)azetidin-1-yl)xanthylium-9-yl)benzoate

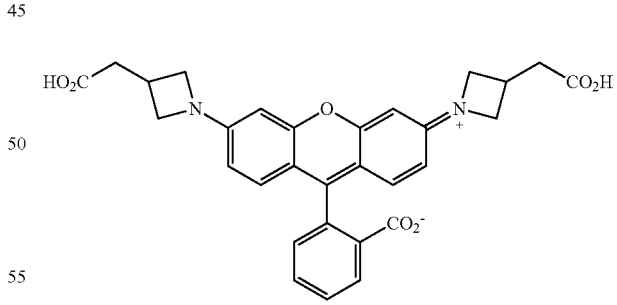

The procedure described for Example 16 was used to prepare the title compound from Example 15 (80%, red-purple solid, TFA salt). ¹H NMR (MeOD, 400 MHz) δ 8.35-8.30 (m, 1H), 7.83 (td, J=7.5, 1.5 Hz, 1H), 7.78 (td, J=7.6, 1.5 Hz, 1H), 7.40-7.35 (m, 1H), 7.07 (d, J=9.2 Hz, 2H), 6.62 (dd, J=9.2, 2.2 Hz, 2H), 6.56 (d, J=2.2 Hz, 2H), 4.43 (t, J=9.6 Hz, 4H), 4.05-3.96 (m, 4H), 3.28-3.16 (m, 2H), 2.78 (d, J=7.7 Hz, 4H); ¹³C NMR (MeOD, 101 MHz) δ 175.1 (C), 167.9 (C), 161.7 (C), 158.8 (C), 158.0 (C), 135.4 (C), 133.8 (CH), 132.5 (CH), 132.3 (CH), 131.41

(CH), 131.40 (CH), 115.1 (C), 113.7 (CH), 95.3 (CH), 57.6 (CH$_2$), 38.5 (CH$_2$), 27.3 (CH); Analytical HPLC: >99% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; detection at 550 nm); HRMS (ESI) calcd for C$_{30}$H$_{27}$N$_2$O$_7$ [M+H]$^+$ 527.1813, found 527.1815.

Example 18. 4-(tert-Butoxycarbonyl)-2-(3,6-di(azetidin-1-yl)xanthylium-9-yl)benzoate

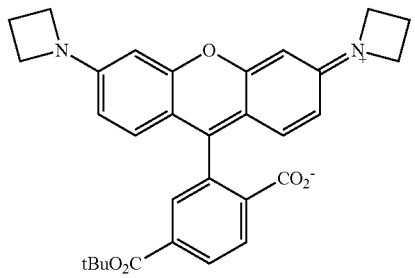

Step 1: A suspension of 6-carboxyfluorescein diacetate (1.39 g, 3.02 mmol) in toluene (6 mL) was heated to 80° C., and N,N-dimethylformamide di-tert-butyl acetal (4.34 mL, 18.1 mmol, 6 eq) was added dropwise over 5 min. The reaction was stirred at 80° C. for 15 min. After cooling the mixture to room temperature, it was diluted with saturated NaHCO$_3$ and extracted with CH$_2$Cl$_2$ (2×). The combined organic extracts were dried (MgSO$_4$), filtered, and evaporated. Flash chromatography (0-20% EtOAc/hexanes, linear gradient, with constant 40% v/v CH2Cl$_2$) provided 6-(tert-butoxycarbonyl)-3-oxo-3H-spiro[isobenzofuran-1,9'-xanthene]-3',6'-diyl diacetate as a colorless solid (971 mg, 62%). $^1$H NMR (CDCl$_3$, 400 MHz) δ 8.26 (dd, J=8.0, 1.3 Hz, 1H), 8.07 (dd, J=8.0, 0.7 Hz, 1H), 7.73 (dd, J=1.2, 0.8 Hz, 1H), 7.12 (dd, J=2.1, 0.4 Hz, 2H), 6.84 (dd, J=8.7, 2.1 Hz, 2H), 6.80 (dd, J=8.7, 0.5 Hz, 2H), 2.32 (s, 6H), 1.56 (s, 9H); $^{13}$C NMR (CDCl$_3$, 101 MHz) δ 168.9 (C), 168.3 (C), 164.0 (C), 152.8 (C), 152.3 (C), 151.7 (C), 138.8 (C), 131.4 (CH), 129.4 (C), 129.1 (CH), 125.2 (CH), 125.1 (CH), 118.0 (CH), 116.0 (C), 110.6 (CH), 83.0 (C), 82.1 (C), 28.2 (CH$_3$), 21.3 (CH$_3$); HRMS (ESI) calcd for C$_{29}$H$_{25}$O$_9$ [M+H]$^+$ 517.1493, found 517.1495.

Step 2: To a solution of the intermediate from Step 1 (910 mg, 1.76 mmol) in 1:1 THF/MeOH (20 mL) was added 1 M NaOH (4.23 mL, 4.23 mmol, 2.4 eq). The reaction was stirred at room temperature for 1 h. The resulting red-orange solution was acidified with 1 N HCl (5 mL), diluted with water, and extracted with EtOAc (2×). The organics were washed with brine, dried (MgSO$_4$), filtered, and concentrated in vacuo to provide a red solid. The crude solid was suspended in CH$_2$Cl$_2$ (15 mL) and cooled to 0° C. Pyridine (1.14 mL, 14.1 mmol, 8 eq) and trifluoromethanesulfonic anhydride (1.19 mL, 7.05 mmol, 4 eq) were added, and the ice bath was removed. The reaction was stirred at room temperature for 1 h. It was subsequently diluted with water and extracted with CH$_2$Cl$_2$ (2×). The combined organic extracts were dried (MgSO$_4$), filtered, and evaporated. Silica gel chromatography (0-25% EtOAc/hexanes, linear gradient) yielded 841 mg (69%) of tert-butyl 3-oxo-3',6'-bis(((trifluoromethyl)sulfonyl)oxy)-3H-spiro[isobenzofuran-1,9'-xanthene]-6-carboxylate as a colorless solid. $^1$H NMR (CDCl$_3$, 400 MHz) δ 8.28 (dd, J=8.0, 1.3 Hz, 1H), 8.11 (dd, J=8.0, 0.7 Hz, 1H), 7.75 (dd, J=1.2, 0.7 Hz, 1H), 7.32 (d, J=2.4 Hz, 2H), 7.04 (dd, J=8.8, 2.5 Hz, 2H), 6.94 (d, J=8.8 Hz, 2H), 1.57 (s, 9H); $^{19}$F NMR (CDCl$_3$, 376 MHz) δ -73.12 (s); $^{13}$C NMR (CDCl$_3$, 101 MHz) δ 167.7 (C), 163.8 (C), 152.2 (C), 151.5 (C), 150.5 (C), 139.3 (C), 131.9 (CH), 130.1 (CH), 128.8 (C), 125.8 (CH), 124.9 (CH), 118.9 (C), 118.8 (q, $^1J_{CF}$=320.9 Hz, CF$_3$), 118.0 (CH), 111.0 (CH), 83.3 (C), 80.5 (C), 28.2 (CH$_3$); HRMS (ESI) calcd for C$_{27}$H$_{19}$F$_6$O$_{11}$S$_2$ [M+H]$^+$ 697.0267, found 697.0255.

Step 3: The procedure described for Example 7 was used to prepare the title compound 4-(tert-butoxycarbonyl)-2-(3,6-di(azetidin-1-yl)xanthylium-9-yl)benzoate from the ditriflate synthesized in Step 2 (86%, dark purple solid). $^1$H NMR (CDCl$_3$, 400 MHz) δ 8.19 (dd, J=8.0, 1.4 Hz, 1H), 8.02 (dd, J=8.0, 0.7 Hz, 1H), 7.73 (dd, J=1.3, 0.7 Hz, 1H), 6.55 (d, J=8.6 Hz, 2H), 6.21 (d, J=2.3 Hz, 2H), 6.09 (dd, J=8.6, 2.3 Hz, 2H), 3.92 (t, J=7.3 Hz, 8H), 2.38 (p, J=7.2 Hz, 4H), 1.54 (s, 9H); $^{13}$C NMR (CDCl$_3$, 101 MHz) δ 169.1 (C), 164.5 (C), 153.8 (C), 153.0 (C), 152.6 (C), 137.9 (C), 131.1 (C), 130.6 (CH), 129.0 (CH), 125.4 (CH), 125.0 (CH), 107.9 (CH), 107.4 (C), 97.6 (CH), 82.4 (C), 52.2 (CH$_2$), 28.2 (CH$_3$), 16.8 (CH$_2$); HRMS (ESI) calcd for C$_{31}$H$_{13}$N$_2$O$_5$ [M+H]$^+$ 511.2227, found 511.2253.

Example 19. 4-Carboxy-2-(3,6-di(azetidin-1-yl)xanthylium-9-yl)benzoate

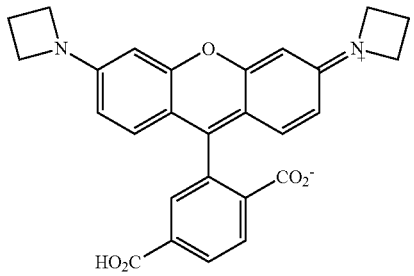

4-(tert-Butoxycarbonyl)-2-(3,6-di(azetidin-1-yl)xanthylium-9-yl)benzoate (Example 18; 70 mg, 0.137 mmol) was taken up in CH$_2$Cl$_2$ (2.5 mL), and trifluoroacetic acid (0.5 mL) was added. The reaction was stirred at room temperature for 6 h. Toluene (3 mL) was added; the reaction mixture was concentrated to dryness and then azeotroped with MeOH three times to provide the title compound as a dark red powder (77 mg, 99%, TFA salt). Analytical HPLC and NMR indicated that the material was >95% pure and did not require further purification prior to amide coupling. $^1$H NMR (MeOD, 400 MHz) δ 8.40 (dd, J=8.2, 0.6 Hz, 1H), 8.37 (dd, J=8.2, 1.5 Hz, 1H), 7.94 (dd, J=1.5, 0.6 Hz, 1H), 7.06 (d, J=9.2 Hz, 2H), 6.61 (dd, J=9.2, 2.2 Hz, 2H), 6.55 (d, J=2.2 Hz, 2H), 4.31 (t, J=7.6 Hz, 8H), 2.56 (p, J=7.6 Hz, 4H); $^{19}$F NMR (MeOD, 376 MHz) δ -75.32 (s); $^{13}$C NMR (MeOD, 101 MHz) δ 167.7 (C), 167.5 (C), 160.1 (C), 158.7 (C), 158.0 (C), 136.2 (C), 135.9 (C), 135.4 (C), 132.8 (CH), 132.25 (CH), 132.24 (CH), 132.19 (CH), 114.8 (C), 113.6 (CH), 95.2 (CH), 52.9 (CH$_2$), 16.8 (CH$_2$); Analytical HPLC: >99% purity (4.6 mm×150 mm 5 µm C$_{18}$ column; 5 µL injection; 10-95% CH$_3$CN/H$_2$O, linear gradient, with constant 0.1% v/v TFA additive; 20 min run; 1 mL/min flow; ESI; positive ion mode; detection at 550 nm); HRMS (ESI) calcd for C$_{27}$H$_{23}$N$_2$O$_5$ [M+H]$^+$ 455.1601, found 455.1610.

Example 20. 2-(3,6-Di(azetidin-1-yl)xanthylium-9-yl)-4-4(2,5-dioxopyrrolidin-1-yl)oxy)carbonyl)benzoate

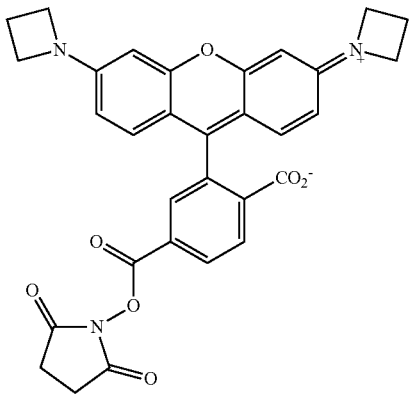

4-Carboxy-2-(3,6-di(azetidin-1-yl)xanthylium-9-yl)benzoate (Example 19; 20 mg, 35.2 µmol) was combined with DSC (19.8 mg, 77.4 µmol, 2.2 eq) in DMF (1.5 mL). After adding Et$_3$N (14.7 µL, 106 µmol, 3 eq) and DMAP (0.4 mg, 3.52 µmol, 0.1 eq), the reaction was stirred at room temperature for 2 h. Purification of the crude reaction mixture by reverse phase HPLC (10-95% MeCN/H$_2$O, linear gradient, with constant 0.1% v/v TFA additive) afforded 18.3 mg (78%, TFA salt) of the title compound as a dark purple solid. $^1$H NMR (DMSO-d$_6$, 400 MHz) δ 8.47 (dd, J=8.2, 1.8 Hz, 1H), 8.42 (d, J=8.2 Hz, 1H), 8.11 (d, J=1.6 Hz, 1H), 7.06 (d, J=9.1 Hz, 2H), 6.60 (d, J=9.1 Hz, 2H), 6.58-6.53 (m, 2H), 4.26 (t, J=7.4 Hz, 8H), 2.91 (s, 4H), 2.44 (p, J=7.7 Hz, 4H); Analytical HPLC: 97.4% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; UV detection at 550 nm); MS (ESI) calcd for C$_{31}$H$_{26}$N$_3$O$_7$ [M+H]$^+$ 552.2, found 552.0.

Example 21. 4-((2-(2-((6-Chlorohexyl)oxy)ethoxy)ethyl)carbamoyl)-2-(3,6-di(azetidin-1-yl)xanthylium-9-yl)benzoate

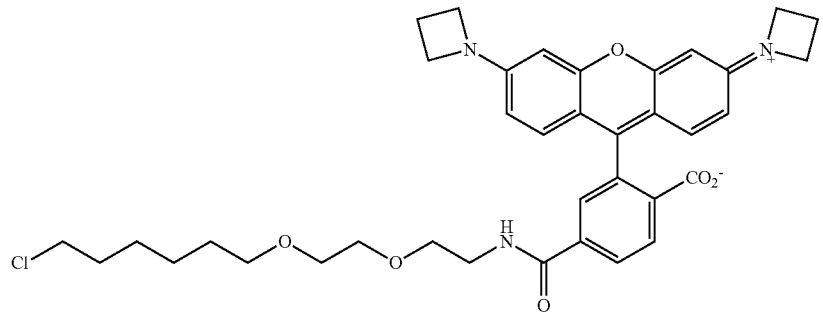

4-Carboxy-2-(3,6-di(azetidin-1-yl)xanthylium-9-yl)benzoate (Example 19; 10 mg, 17.6 µmol) was combined with DSC (9.9 mg, 38.7 µmol, 2.2 eq) in DMF (1 mL). After adding Et$_3$N (14.7 µL, 106 µmol, 6 eq) and DMAP (0.2 mg, 1.76 µmol, 0.1 eq), the reaction was stirred at room temperature for 1 h while shielded from light. A solution of 2-(2-((6-chlorohexyl)oxy)ethoxy)ethanamine ("HaloTag (O2)amine," 9.8 mg, 44.0 µmol, 2.5 eq) in DMF (100 µL) was then added. The reaction was stirred an additional 4 h at room temperature. It was subsequently diluted with saturated NaHCO$_3$ and extracted with CH$_2$Cl$_2$ (2×). The combined organic extracts were dried (MgSO$_4$), filtered, deposited onto Celite, and concentrated in vacuo. Silica gel chromatography (0-10% MeOH/CH$_2$Cl$_2$, linear gradient, with constant 1% v/v AcOH additive; dry load with Celite) followed by reverse phase HPLC (10-95% MeCN/H$_2$O, linear gradient, with constant 0.1% v/v TFA additive) afforded 8.5 mg (62%, TFA salt) of the title compound as a dark red solid. $^1$H NMR (MeOD, 400 MHz) δ 8.79 (t, J=5.4 Hz, 1H), 8.39 (d, J=8.2 Hz, 1H), 8.20 (dd, J=8.2, 1.8 Hz, 1H), 7.80 (d, J=1.6 Hz, 1H), 7.07 (d, J=9.2 Hz, 2H), 6.61 (dd, J=9.2, 2.2 Hz, 2H), 6.56 (d, J=2.2 Hz, 2H), 4.31 (t, J=7.6 Hz, 8H), 3.68-3.55 (m, 8H), 3.53 (t, J=6.6 Hz, 2H), 3.43 (t, J=6.5 Hz, 2H), 2.56 (p, J=7.6 Hz, 4H), 1.77-1.66 (m, 2H), 1.56-1.27 (m, 6H); $^{19}$F NMR (MeOD, 376 MHz) δ-75.33 (s); Analytical HPLC: >99% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; detection at 550 nm); HRMS (ESI) calcd for C$_{37}$H$_{43}$ClN$_3$O$_6$ [M+H]$^+$ 660.2835, found 660.2844.

Example 22. 4-((4-(((2-Amino-9H-purin-6-yl)oxy)methyl)benzyl)carbamoyl)-2-(3,6-di(azetidin-1-yl)xanthylium-9-yl)benzoate

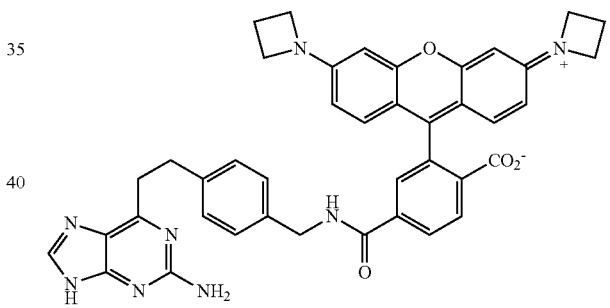

4-Carboxy-2-(3,6-di(azetidin-1-yl)xanthylium-9-yl)benzoate (Example 19; 10 mg, 17.6 µmol) was combined with DSC (9.9 mg, 38.7 µmol, 2.2 eq) in DMF (1 mL). After adding Et$_3$N (14.7 µL, 106 µmol, 6 eq) and DMAP (0.2 mg, 1.76 µmol, 0.1 eq), the reaction was stirred at room temperature for 1 h while shielded from light. 6-((4-(Aminomethyl)benzyl)oxy)-9H-purin-2-amine ("BG—NH$_2$," 11.9 mg, 44.0 µmol, 2.5 eq) was then added. The reaction was stirred an additional 2 h at room temperature. Purification of the crude reaction mixture by reverse phase HPLC (10-95% MeCN/H$_2$O, linear gradient, with constant 0.1% v/v TFA additive) afforded 11.5 mg (80%, TFA salt) of the title compound as a dark red solid. $^1$H NMR (MeOD, 400 MHz) δ 9.28 (t, J=5.8 Hz, 1H), 8.39 (d, J=8.3 Hz, 1H), 8.20 (dd, J=8.2, 1.8 Hz, 1H), 8.17 (s, 1H), 7.81 (d, J=1.7 Hz, 1H), 7.50 (d, J=8.1 Hz, 2H), 7.40 (d, J=8.2 Hz, 2H), 7.04 (d, J=9.2 Hz, 2H), 6.58 (dd, J=9.1, 2.2 Hz, 2H), 6.54 (d, J=2.1 Hz, 2H), 5.60 (s, 2H), 4.63-4.55 (m, 2H), 4.30 (t, J=7.6 Hz, 8H), 2.56 (p, J=7.7 Hz, 4H); $^{19}$F NMR (MeOD, 376 MHz) δ-75.44 (s); Analytical HPLC: 98.3% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; UV detection at 550 nm); HRMS (ESI) calcd for C$_{40}$H$_{35}$N$_8$O$_5$ [M+H]$^+$ 707.2725, found 707.2723.

Example 23. 2-(3,6-Bis(3,3-difluoroazetidin-1-yl)xanthylium-9-yl)-4-(tert-butoxycarbonyl)benzoate

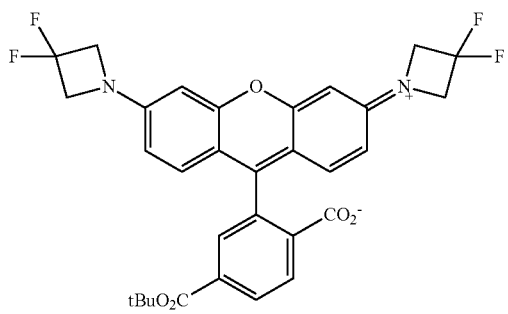

The procedure described for Example 7 was used to prepare the title compound from tert-butyl 3-oxo-3',6'-bis(((trifluoromethyl)sulfonyl)oxy)-3H-spiro[isobenzofuran-1,9'-xanthene]-6-carboxylate (Example 18, Step 2) and 3,3-difluoroazetidine hydrochloride (84%, pink solid). $^1$H NMR (CDCl$_3$, 400 MHz) δ 8.21 (dd, J=8.0, 1.3 Hz, 1H), 8.04 (dd, J=8.0, 0.8 Hz, 1H), 7.73 (dd, J=1.2, 0.8 Hz, 1H), 6.61 (d, J=8.6 Hz, 2H), 6.30 (d, J=2.4 Hz, 2H), 6.17 (dd, J=8.6, 2.4 Hz, 2H), 4.25 (t, $^3$J$_{HF}$=11.7 Hz, 8H), 1.55 (s, 9H); $^{19}$F NMR (CDCl$_3$, 376 MHz) δ-100.06 (p, $^3$J$_{FH}$=11.7 Hz); $^{13}$C NMR (CDCl$_3$, 101 MHz) δ 168.8 (C), 164.3 (C), 153.3 (C), 152.6 (C), 151.4 (t, $^4$J$_{CF}$=2.9 Hz, C), 138.4 (C), 130.9 (CH), 130.2 (C), 129.3 (CH), 125.1 (CH), 125.0 (CH), 115.7 (t, $^1$J$_{CF}$=274.5 Hz, CF$_2$), 109.1 (C), 108.9 (CH), 99.4 (CH), 84.3 (C), 82.7 (C), 63.4 (t, $^2$J$_{CF}$=26.3 Hz, CH$_2$), 28.2 (CH$_3$); Analytical HPLC: >99% purity (4.6 mm×150 mm 5 µm C18 column; 5 µL injection; 30-95% CH$_3$CN/H$_2$O, linear gradient, with constant 0.1% v/v TFA additive; 20 min run; 1 mL/min flow; ESI; positive ion mode; detection at 550 nm); MS (ESI) calcd for C$_{31}$H$_{27}$F$_4$N$_2$O$_5$ [M+H]$^+$ 583.2, found 583.1.

Example 24. 2-(3,6-Bis(3,3-difluoroazetidin-1-yl)xanthylium-9-yl)-4-carboxybenzoate

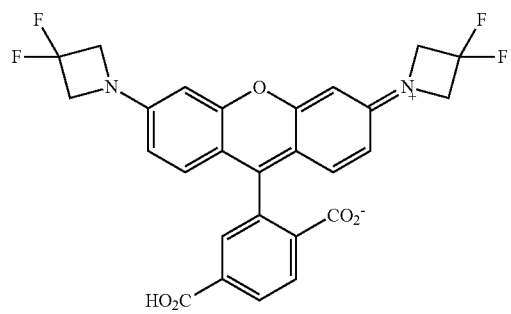

The procedure described for Example 19 was used to prepare the title compound from Example 23 (93%, dark pink solid, TFA salt). $^1$H NMR (MeOD, 400 MHz) δ 8.44 (d, J=8.3 Hz, 1H), 8.40 (dd, J=8.2, 1.6 Hz, 1H), 7.99-7.96 (m, 1H), 7.23 (d, J=9.1 Hz, 2H), 6.83 (d, J=2.2 Hz, 2H), 6.79 (dd, J=9.1, 2.3 Hz, 2H), 4.70 (t, $^3$J$_{HF}$=11.6 Hz, 8H); $^{19}$F NMR (MeOD, 376 MHz) δ-75.59 (s, 3F), -100.90 (p, $^3$J$_{FH}$=11.6 Hz, 4F); $^{13}$C NMR (MeOD, 101 MHz) δ 167.6 (C), 167.3 (C), 159.1 (C), 157.7 (t, $^4$J$_{CF}$=3.9 Hz, C), 136.1 (C), 135.8 (C), 135.4 (C), 132.9 (CH), 132.7 (CH), 132.6 (CH), 132.1 (CH), 119.2 (C), 116.5 (t, $^1$J$_{CF}$=271.9 Hz, CF$_2$), 116.1 (C), 115.2 (CH), 97.4 (CH), 64.2 (t, $^2$J$_{CF}$=29.1 Hz, CH$_2$); Analytical HPLC: >99% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; detection at 550 nm); MS (ESI) calcd for C$_{27}$H$_{19}$F$_4$N$_2$O$_5$ [M+H]$^+$ 527.1, found 527.0.

Example 25. 2-(3,6-Bis(3,3-difluoroazetidin-1-yl)xanthylium-9-yl)-4-((2-(2-((6-chlorohexyl)oxy)ethoxy)ethyl)carbamoyl)benzoate

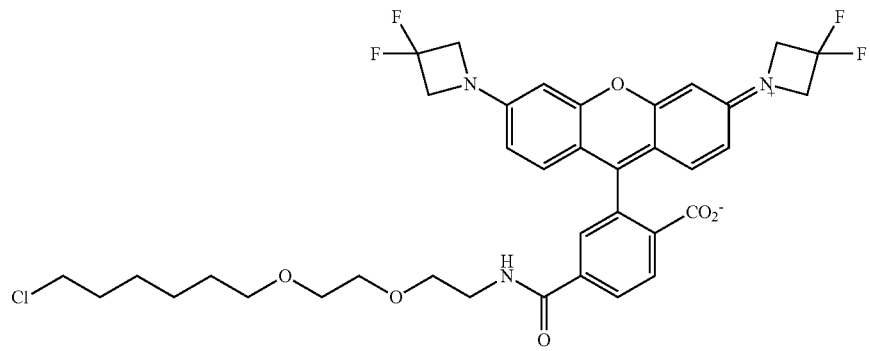

The procedure described for Example 21 was used to prepare the title compound from Example 24 (62%, pink solid). ¹H NMR (CDCl₃, 400 MHz) δ 8.05 (dd, J=8.0, 0.8 Hz, 1H), 7.98 (dd, J=8.0, 1.4 Hz, 1H), 7.55 (dd, J=1.5, 0.8 Hz, 1H), 6.72 (s, 1H), 6.62 (d, J=8.6 Hz, 2H), 6.31 (d, J=2.4 Hz, 2H), 6.17 (dd, J=8.6, 2.4 Hz, 2H), 4.26 (t, ³J$_{HF}$=11.7 Hz, 8H), 3.69-3.57 (m, 6H), 3.56-3.48 (m, 4H), 3.40 (t, J=6.6 Hz, 2H), 1.79-1.70 (m, 2H), 1.54-1.48 (m, 2H), 1.46-1.38 (m, 2H), 1.37-1.29 (m, 2H); ¹⁹F NMR (CDCl₃, 376 MHz) δ-100.04 (p, ³J$_{FH}$=11.8 Hz, 4F); Analytical HPLC: >99% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; detection at 550 nm); MS (ESI) calcd for C₃₇H₃₉ClF₄N₃O₆ [M+H]⁺ 732.2, found 732.1.

Example 26. 2-(3,6-Di(azetidin-1-yl)xanthylium-9-yl)-4-(methoxycarbonyl)benzoate

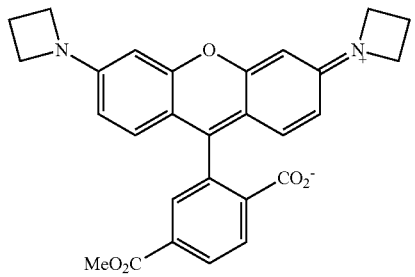

Step 1: 3',6'-Dibromo-3-oxo-3H-spirolisobenzofuran-1,9'-xanthene1-6-carboxylic acid (1.50 g, 2.99 mmol; Woodroofe, C. C.; Lim, M. H.; Bu, W.; Lippard, S. J. *Tetrahedron* 2005, 61, 3097) was suspended in MeOH (50 mL), and H₂SO₄ (293 mg, 2.99 mmol, 1 eq) was added. The reaction was stirred at reflux for 72 h. It was subsequently concentrated in vacuo, and the resulting residue was diluted with saturated NaHCO₃ and extracted with 15% i-PrOH/CHCl₃ (2×). The combined organic extracts were dried (MgSO₄), filtered, and evaporated. Silica gel chromatography (0-10% EtOAc/hexanes, linear gradient, with constant 40% v/v CH₂Cl₂) yielded 1.49 g (97%) of methyl 3',6'-dibromo-3-oxo-3H-spirolisobenzofuran-1,9'-xanthene1-6-carboxylate as a white solid. ¹H NMR (CDCl₃, 400 MHz) δ 8.31 (dd, J=8.0, 1.3 Hz, 1H), 8.10 (dd, J=8.0, 0.7 Hz, 1H), 7.76 (dd, J=1.2, 0.8 Hz, 1H), 7.52 (d, J=1.9 Hz, 2H), 7.20 (dd, J=8.5, 1.9 Hz, 2H), 6.68 (d, J=8.5 Hz, 2H), 3.89 (s, 3H); ¹³C NMR (CDCl₃, 101 MHz) δ 168.1 (C), 165.3 (C), 153.1 (C), 151.2 (C), 137.0 (C), 131.6 (CH), 129.24 (C), 129.21 (CH), 127.8 (CH), 125.7 (CH), 125.1 (CH), 124.6 (C), 120.7 (CH), 117.4 (C), 81.5 (C), 53.0 (CH₃); MS (ESI) calcd for C₂₂H₁₃Br₂O₅ [M+H]⁺ 514.9, found 515.1.

Step 2: The procedure described for Example 7 was used to prepare the title compound 2-(3,6-di(azetidin-1-yl)xanthylium-9-yl)-4-(methoxycarbonyl)benzoate from the bromide synthesized in Step 1 (86%, red solid). ¹H NMR (MeOD, 400 MHz) δ 8.24 (dd, J=8.1, 1.7 Hz, 1H), 8.12 (dd, J=8.1, 0.4 Hz, 1H), 7.83-7.80 (m, 1H), 7.16 (d, J=9.2 Hz, 2H), 6.56 (dd, J=9.2, 2.2 Hz, 2H), 6.48 (d, J=2.2 Hz, 2H), 4.32-4.22 (m, 8H), 3.90 (s, 3H), 2.54 (p, J=7.6 Hz, 4H); MS (ESI) calcd for C₂₈H₂₅N₂O₅ [M+H]⁺ 469.2, found 469.2.

Example 27. Methyl 3',6'-di(azetidin-1-yl)-2-diazo-3-oxo-2,3-dihydrospiro[indene-1,9'-xanthene]-6-carboxylate

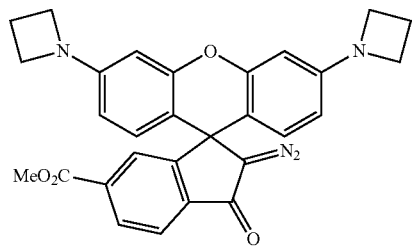

To a solution of 2-(3,6-di(azetidin-1-yl)xanthylium-9-yl)-4-(methoxycarbonyl)benzoate (Example 26; 135 mg, 0.288 mmol) in CH₂Cl₂ (9 mL) was added oxalyl chloride (98 μL, 1.15 mmol, 4 eq). After stirring the reaction at room temperature for 2 h, it was concentrated to dryness. The residue was redissolved in CH₂Cl₂ (9 mL); Et₃N (50 μL, 0.360 mmol, 1.25 eq) and (trimethylsilyl)diazomethane (2.0 M in Et₂O, 252 μL, 0.504 mmol, 1.75 eq) were then added in succession. The reaction was stirred at room temperature for 90 min, concentrated in vacuo, and purified twice by flash chromatography on silica gel (0-50% EtOAc/hexanes, linear gradient; then, 0-25% EtOAc/toluene, linear gradient) to afford 40 mg (28%) of the title compound as a yellow solid. ¹H NMR (CDCl₃, 400 MHz) δ 8.07 (dd, J=8.0, 1.4 Hz, 1H), 7.87 (dd, J=8.0, 0.6 Hz, 1H), 7.68 (dd, J=1.4, 0.6 Hz, 1H), 6.66 (d, J=8.5 Hz, 2H), 6.18 (d, J=2.3 Hz, 2H), 6.07 (dd, J=8.5, 2.4 Hz, 2H), 3.96-3.84 (m, 8H), 3.82 (s, 3H), 2.37 (p, J=7.2 Hz, 4H); MS (ESI) calcd for C₂₉H₂₅N₄O₄ [M+H]⁺ 493.2, found 493.3.

Example 28. 2,5-Dioxopyrrolidin-1-yl 3',6'-di(azetidin-1-yl)-2-diazo-3-oxo-2,3-dihydrospiro[indene-1,9'-xanthene]-6-carboxylate

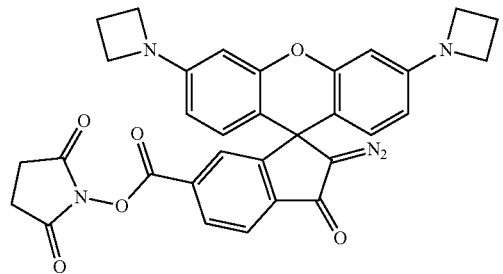

Step 1: To a solution of methyl 3',6'-di(azetidin-1-yl)-2-diazo-3-oxo-2,3-dihydrospiro[indene-1,9'-xanthene]-6-carboxylate (Example 27; 40 mg, 81.2 μmol) in 2:1 MeOH/THF (6 mL) under nitrogen was added 1 M NaOH (203 μL, 0.203 mmol, 2.5 eq). After stirring the solution at room temperature for 2 h, additional 1 M NaOH (203 μL, 0.203 mmol, 2.5 eq) was added. The reaction was stirred at room temperature for 24 h. It was subsequently acidified with 1 M HCl (420 μL), diluted with water, and extracted with CH₂Cl₂ (2×). The organic extracts were dried (MgSO₄), filtered, and concentrated in vacuo to provide 3',6'-di(azetidin-1-yl)-2-diazo-3-oxo-2,3-dihydrospiro[indene-1,9'-xanthene]-6-carboxylic acid (37 mg, 95%) as a yellow solid. MS (ESI) calcd for $C_{28}H_{23}N_4O_4$ [M]$^+$ 479.2, found 479.3.

Step 2: The acid from Step 1 (37 mg, 77.3 µmol) was combined with TSTU (35 mg, 0.116 mmol, 1.5 eq) in DMF (2 mL), and DIEA (40 µL, 0.232 mmol, 3 eq) was added. After stirring the reaction at room temperature for 1 h, it was concentrated to dryness and deposited onto Celite. Flash chromatography on silica gel (10-100% EtOAc/hexanes, linear gradient; dry load with Celite) afforded the title compound 2,5-dioxopyrrolidin-1-yl 3',6'-di(azetidin-1-yl)-2-diazo-3-oxo-2,3-dihydrospiro[indene-1,9'-xanthene]-6-carboxylate as a yellow-orange solid (30 mg, 68%). $^1$H NMR (CDCl$_3$, 400 MHz) δ 8.16 (dd, J=8.0, 1.5 Hz, 1H), 7.93 (dd, J=8.0, 0.6 Hz, 1H), 7.75 (dd, J=1.4, 0.6 Hz, 1H), 6.66 (d, J=8.5 Hz, 2H), 6.16 (d, J=2.3 Hz, 2H), 6.09 (dd, J=8.5, 2.4 Hz, 2H), 3.90 (t, J=7.3 Hz, 8H), 2.86 (s, 4H), 2.37 (p, J=7.2 Hz, 4H); MS (ESI) calcd for $C_{32}H_{26}N_5O_6$ [M+H]$^+$ 576.2, found 576.3.

Example 29. 3',6'-Di(azetidin-1-yl)-N-(2-(2-((6-chlorohexyl)oxy)ethoxy)ethyl)-2-diazo-3-oxo-2,3-dihydrospiro[indene-1,9'-xanthene]-6-carboxamide

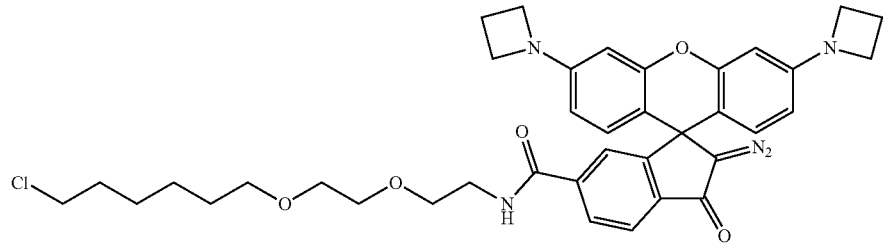

2,5-Dioxopyrrolidin-1-yl 3',6'-di(azetidin-1-yl)-2-diazo-3-oxo-2,3-dihydrospiro[indene-1,9'-xanthene]-6-carboxylate (Example 28; 15 mg, 26.1 µmol) was dissolved in DMF (1 mL). A solution of 2-(2-((6-chlorohexyl)oxy)ethoxy) ethanamine ("HaloTag(O2)amine," 11.7 mg, 52.2 µmol, 2 eq) in DMF (250 µL) was added, followed by DIEA (22.7 µL, 0.131 mmol, 5 eq). After stirring the reaction at room temperature for 2 h, it was concentrated to dryness and purified by silica gel chromatography (0-100% EtOAc/toluene, linear gradient) to provide the title compound as a yellow foam (15.9 mg, 89%). $^1$H NMR (CDCl$_3$, 400 MHz) δ 7.86 (dd, J=7.9, 0.6 Hz, 1H), 7.79 (dd, J=8.0, 1.5 Hz, 1H), 7.43 (dd, J=1.4, 0.6 Hz, 1H), 6.66 (d, J=8.5 Hz, 2H), 6.59 (t, J=5.1 Hz, 1H), 6.16 (d, J=2.3 Hz, 2H), 6.07 (dd, J=8.5, 2.4 Hz, 2H), 3.95-3.83 (m, 8H), 3.64-3.48 (m, 10H), 3.39 (t, J=6.6 Hz, 2H), 2.37 (p, J=7.2 Hz, 4H), 1.78-1.69 (m, 2H), 1.55-1.48 (m, 2H), 1.46-1.36 (m, 2H), 1.36-1.27 (m, 2H); MS (ESI) calcd for $C_{38}H_{43}ClN_5O_5$ [M+H]$^+$ 684.3, found 684.4.

Example 30. 2-(3,7-Di(azetidin-1-yl)-5,5-dimethyldibenzo[b,e]silin-10-ylium-10(5H)-yl)benzoate

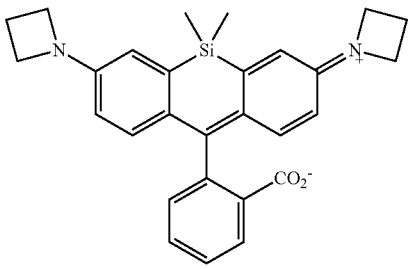

Step 1: A vial was charged with tert-butyl 2-bromobenzoate (309 mg, 1.20 mmol, 1.5 eq), sealed, and flushed with nitrogen. After dissolving the bromide in THF (2 mL) and cooling the reaction to −15° C., iPrMgCl.LiCl (1.3 M in THF, 924 µL, 1.20 mmol, 1.5 eq) was added. The reaction was warmed to −5° C. and stirred for 5 h. A solution of 3,7-bis((tert-butyldimethylsilyl)oxy)-5,5-dimethyldibenzo[b,e]silin-10(5H)-one (400 mg, 0.802 mmol; from Egawa, T.; Koide, Y.; Hanaoka, K.; Komatsu, T.; Terai, T.; Nagano, T. Chem. Commun., 2011, 47, 4162) in THF (2 mL) was then added dropwise. After stirring for 10 min at −5° C., the reaction mixture was warmed to room temperature and stirred for 30 min. It was subsequently quenched with saturated NH$_4$Cl, diluted with water, and extracted with EtOAc (2×). The combined organics were washed with brine, dried (MgSO$_4$), filtered, and evaporated. Silica gel chromatography (0-20% Et$_2$O/hexanes, linear gradient) provided 271 mg (56%) of 3,7-bis((tert-butyldimethylsilyl)oxy)-5,5-dimethyl-3'H,5H-spiro[dibenzo[b,e]siline-10,1'-isobenzofuran]-3'-one as a colorless gum. $^1$H NMR (CDCl$_3$, 400 MHz) δ 7.97 (dt, J=7.5, 0.9 Hz, 1H), 7.66 (td, J=7.5, 1.2 Hz, 1H), 7.56 (td, J=7.5, 0.9 Hz, 1H), 7.35-7.29 (m, 1H), 7.12 (d, J=2.7 Hz, 2H), 6.85 (d, J=8.7 Hz, 2H), 6.67 (dd, J=8.7, 2.7 Hz, 2H), 0.97 (s, 18H), 0.62 (s, 3H), 0.60 (s, 3H), 0.19 (s, 12H); $^{13}$C NMR (CDCl$_3$, 101 MHz) δ 170.5 (C), 155.3 (C), 154.0 (C), 137.8 (C), 137.2 (C), 134.0 (CH), 129.1 (CH), 128.6 (CH), 126.6 (C), 126.1 (CH), 125.1 (CH), 124.7 (CH), 121.2 (CH), 90.8 (C), 25.8 (CH$_3$), 18.4 (C), 0.2 (CH$_3$), −1.5 (CH$_3$), −4.21 (CH$_3$), −4.23 (CH$_3$); HRMS (ESI) calcd for $C_{34}H_{47}O_4Si_3$ [M+H]$^+$ 603.2777, found 603.2771.

Step 2: To a solution of the product from Step 1 (194 mg, 0.322 mmol) in THF (5 mL) at 0° C. was added TBAF (1.0 M in THF, 965 µL, 0.965 mmol, 3 eq). The reaction was stirred at 0° C. for 10 min. It was subsequently diluted at 0° C. with saturated NH$_4$Cl and extracted with EtOAc (2×). The organic extracts were dried (MgSO$_4$), filtered, evaporated, and deposited onto silica gel. Flash chromatography (20-100% EtOAc/hexanes, linear gradient, with constant 1% v/v AcOH additive; dry load with silica gel) yielded 3,7-dihydroxy-5,5-dimethyl-3'H,5H-spiro[dibenzo[b,e]siline-10,1'-isobenzofuran]-3'-one (120 mg, 99%) as an off-white solid. $^1$H NMR (MeOD, 400 MHz) δ 7.95 (d, J=7.7 Hz, 1H), 7.77 (td, J=7.6, 1.1 Hz, 1H), 7.65 (td, J=7.6, 0.7 Hz, 1H), 7.32 (d, J=7.7 Hz, 1H), 7.13 (d, J=2.7 Hz, 2H), 6.74 (d, J=8.7 Hz, 2H), 6.65 (dd, J=8.7, 2.7 Hz, 2H), 0.61 (s, 3H), 0.55 (s, 3H); $^{13}$C NMR (MeOD, 101 MHz) δ 172.6 (C), 158.3 (C), 155.8 (C), 138.8 (C), 136.3 (C), 135.6 (CH), 130.4 (CH), 129.6 (CH), 127.4 (C), 126.6 (CH), 125.8 (CH), 121.1 (CH), 117.7 (CH), 92.9 (C), 0.2 (CH$_3$), −1.6 (CH$_3$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; UV detection at 254 nm); HRMS (ESI) calcd for C$_{22}$H$_{19}$O$_4$Si [M+H]$^+$ 375.1047, found 375.1047.

Step 3: The intermediate from Step 2 (120 mg, 0.320 mmol) was taken up in CH$_2$Cl$_2$ (5 mL) and cooled to 0° C. Pyridine (207 μL, 2.56 mmol, 8.0 eq) and trifluoromethanesulfonic anhydride (216 μL, 1.28 mmol, 4.0 eq) were added, and the ice bath was removed. The reaction was stirred at room temperature for 2 h. It was subsequently diluted with water and extracted with CH$_2$Cl$_2$ (2×). The combined organic extracts were washed with brine, dried (MgSO$_4$), filtered, and concentrated in vacuo. Flash chromatography on silica gel (0-30% EtOAc/hexanes, linear gradient) afforded 172 mg (84%) of 5,5-dimethyl-3'-oxo-3'H,5H-spiro[dibenzo[b,e]siline-10,1'-isobenzofuran]-3,7-diyl bis(trifluoromethanesulfonate) as a colorless foam. $^1$H NMR (CDCl$_3$, 400 MHz) δ 8.04 (dt, J=7.7, 0.9 Hz, 1H), 7.77 (td, J=7.5, 1.2 Hz, 1H), 7.66 (td, J=7.5, 0.8 Hz, 1H), 7.57 (dd, J=2.4, 0.5 Hz, 2H), 7.38 (dt, J=7.6, 0.7 Hz, 1H), 7.185 (AB of ABX, ☐$_A$=2878.9, J$_{AX}$=0.3, ☐$_B$=2871.0, J$_{BX}$=2.8, J$_{AB}$=8.9 Hz, 4H), 0.75 (s, 3H), 0.72 (s, 3H); $^{19}$F NMR (CDCl$_3$, 376 MHz) δ-73.30; $^{13}$C NMR (CDCl$_3$, 101 MHz) δ 169.2 (C), 151.8 (C), 149.5 (C), 144.3 (C), 139.3 (C), 134.8 (CH), 130.3 (CH), 129.2 (CH), 127.0 (CH), 126.5 (CH), 126.0 (C), 124.6 (CH), 122.8 (CH), 118.9 (CF$_3$, $^1$J$_{CF}$=320.8 Hz), 88.7 (C), 0.1 (CH$_3$), −1.7 (CH$_3$); HRMS (ESI) calcd for C$_{24}$H$_{17}$F$_6$O$_8$S$_2$Si [M+H]$^+$ 639.0033, found 639.0030.

Step 4: The procedure described for Example 7 was used to prepare the title compound 2-(3,7-di(azetidin-1-yl)-5,5-dimethyldibenzo[b,e]silin-10-ylium-10(5H)-yl)benzoate from the ditriflate synthesized in Step 3 (92%, off-white solid). $^1$H NMR (CDCl$_3$, 400 MHz) δ 7.98-7.93 (m, 1H), 7.63 (td, J=7.5, 1.2 Hz, 1H), 7.53 (td, J=7.5, 0.9 Hz, 1H), 7.32-7.28 (m, 1H), 6.75 (d, J=8.7 Hz, 2H), 6.66 (d, J=2.6 Hz, 2H), 6.25 (dd, J=8.7, 2.7 Hz, 2H), 3.89 (t, J=7.2 Hz, 8H), 2.36 (p, J=7.2 Hz, 4H), 0.60 (s, 3H), 0.58 (s, 3H); $^{13}$C NMR (CDCl$_3$, 101 MHz) δ 170.7 (C), 154.3 (C), 151.0 (C), 137.1 (C), 133.7 (CH), 132.9 (C), 128.8 (CH), 128.0 (CH), 127.2 (C), 125.8 (CH), 124.8 (CH), 115.7 (CH), 112.3 (CH), 92.1 (C), 52.4 (CH$_2$), 17.1 (CH$_2$), 0.5 (CH$_3$), −1.5 (CH$_3$); Analytical HPLC: 98.7% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 650 nm); HRMS (ESI) calcd for C$_{28}$H$_{29}$N$_2$O$_2$Si [M+H]$^+$ 453.1993, found 453.1998.

Example 31. 2-(3,7-Bis(3-fluoroazetidin-1-yl)-5,5-dimethyldibenzo[b,e]silin-10-ylium-10(5H)-yl)benzoate

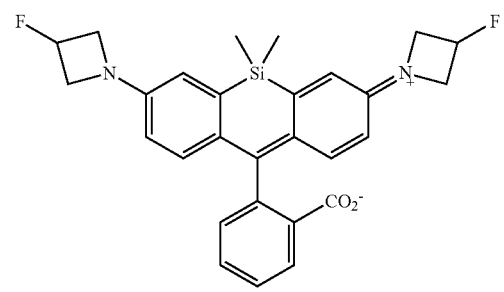

The procedure described for Example 7 was used to prepare the title compound from 5,5-dimethyl-3'-oxo-3'H,5H-spiro[dibenzo[b,e]siline-10,1'-isobenzofuran]-3,7-diyl bis(trifluoromethanesulfonate) (Example 30, Step 3) and 3-fluoroazetidine hydrochloride (78%, off-white solid). $^1$H NMR (CDCl$_3$, 400 MHz) δ 7.97 (dt, J=7.6, 0.9 Hz, 1H), 7.65 (td, J=7.5, 1.2 Hz, 1H), 7.55 (td, J=7.5, 0.9 Hz, 1H), 7.29 (dt, J=7.7, 0.8 Hz, 1H), 6.80 (d, J=8.7 Hz, 2H), 6.70 (d, J=2.6 Hz, 2H), 6.30 (dd, J=8.7, 2.7 Hz, 2H), 5.41 (dtt, $^2$J$_{HF}$=57.0 Hz, J=5.9, 3.7 Hz, 2H), 4.25-4.14 (m, 4H), 4.04-3.91 (m, 4H), 0.62 (s, 3H), 0.60 (s, 3H); $^{19}$F NMR (CDCl$_3$, 376 MHz) δ-180.48 (dtt, J$_{FH}$=57.0, 23.9, 18.2 Hz); $^{13}$C NMR (CDCl$_3$, 101 MHz) δ 170.6 (C), 154.1 (C), 150.0 (d, $^4$J$_{CF}$=1.0 Hz, C), 137.2 (C), 133.93 (C), 133.86 (CH), 129.0 (CH), 128.1 (CH), 127.0 (C), 126.0 (CH), 124.7 (CH), 116.3 (CH), 112.9 (CH), 91.6 (C), 82.8 (d, $^1$J$_{CF}$=204.8 Hz, CFH), 59.6 (d, $^2$J$_{CF}$=23.8 Hz, CH$_2$), 0.5 (CH$_3$), −1.4 (CH$_3$); Analytical HPLC: 98.7% purity (4.6 mm×150 mm 5 μm C18 column; 5 μL injection; 30-95% CH$_3$CN/H$_2$O, linear gradient, with constant 0.1% v/v TFA additive; 20 min run; 1 mL/min flow; ESI; positive ion mode; detection at 650 nm); MS (ESI) calcd for C$_{28}$H$_{27}$F$_2$N$_2$O$_2$Si [M+H]$^+$ 489.2, found 489.1.

Example 32. 4-(tert-Butoxycarbonyl)-2-(3,7-di(azetidin-1-yl)-5,5-dimethyldibenzo[b,e]silin-10-ylium-10(5H)-yl)benzoate

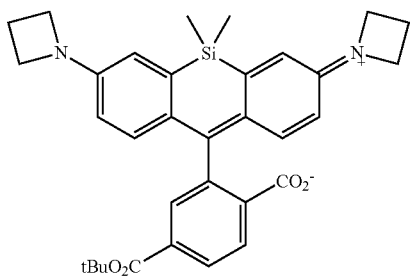

Step 1: A suspension of 2-bromoterephthalic acid (2.50 g, 10.2 mmol) in toluene (25 mL) was heated to 80° C., and N,N-dimethylformamide di-tert-butyl acetal (24.5 mL, 102 mmol, 10 eq) was added dropwise over 15 min. The reaction was stirred at 80° C. for 30 min. After cooling the mixture to room temperature, it was diluted with saturated NaHCO$_3$ and extracted with EtOAc (2×). The combined organic extracts were washed with water and brine, dried (MgSO$_4$), filtered, and evaporated. Flash chromatography (0-10% Et$_2$O/hexanes, linear gradient) provided di-tert-butyl 2-bromoterephthalate as a colorless gum (3.29 g, 90%). $^1$H NMR (CDCl$_3$, 400 MHz) δ 8.19 (d, J=1.4 Hz, 1H), 7.92 (dd, J=8.0, 1.6 Hz, 1H), 7.67 (d, J=8.0 Hz, 1H), 1.62 (s, 9H), 1.60 (s, 9H); $^{13}$C NMR (CDCl$_3$, 101 MHz) δ 165.4 (C), 163.8 (C), 138.0 (C), 135.1 (C), 134.9 (CH), 130.4 (CH), 128.1 (CH), 120.7 (C), 83.3 (C), 82.3 (C), 28.26 (CH$_3$), 28.25 (CH$_3$); HRMS (ESI) calcd for C$_{16}$H$_{21}$BrO$_4$Na [M+Na]$^+$ 379.0515, found 379.0531.

Step 2: A vial was charged with the product of Step 1 (537 mg, 1.50 mmol, 1.5 eq), sealed, and flushed with nitrogen. After dissolving the bromide in THF (2.5 mL) and cooling the reaction to −50° C., iPrMgCl.LiCl (1.3 M in THF, 1.16 mL, 1.50 mmol, 1.5 eq) was added. The reaction was warmed to −40° C. and stirred for 2 h. A solution of 3,7-bis((tert-butyldimethylsilyl)oxy)-5,5-dimethyldibenzo[b,e]silin-10(5H)-one (500 mg, 1.00 mmol; from Egawa, T.; Koide, Y.; Hanaoka, K.; Komatsu, T.; Terai, T.; Nagano, T. Chem. Commun., 2011, 47, 4162) in THF (2.5 mL) was then added dropwise. The reaction mixture was warmed to room temperature and stirred for 2 h. It was subsequently quenched with saturated NH$_4$Cl, diluted with water, and extracted with EtOAc (2×). The combined organics were washed with brine, dried (MgSO$_4$), filtered, and evaporated. Silica gel chromatography (0-10% Et$_2$O/hexanes, linear gradient) provided 213 mg (30%) of tert-butyl 3,7-bis((tert-butyldimethylsilyl)oxy)-5,5-dimethyl-3'-oxo-3'H,5H-spiro[dibenzo[b,e]siline-10,1'-isobenzofuran]-6'-carboxylate as a colorless solid. $^1$H NMR (CDCl$_3$, 400 MHz) δ 8.13 (dd, J=8.0, 1.3 Hz, 1H), 7.98 (dd, J=8.0, 0.7 Hz, 1H), 7.84 (dd, J=1.2, 0.8 Hz, 1H), 7.13 (d, J=2.7 Hz, 2H), 6.93 (d, J=8.7 Hz, 2H), 6.72 (dd, J=8.7, 2.7 Hz, 2H), 1.56 (s, 9H), 0.98 (s, 18H), 0.67 (s, 3H), 0.59 (s, 3H), 0.196 (s, 6H), 0.194 (s, 6H); NMR (CDCl$_3$, 101 MHz) δ 170.1 (C), 164.3 (C), 155.4 (C), 155.0 (C), 137.5 (C), 136.9 (C), 136.8 (C), 130.2 (CH), 128.7 (C), 128.3 (CH), 125.9 (CH), 125.2 (CH), 125.1 (CH), 121.6 (CH), 90.6 (C), 82.5 (C), 28.2 (CH$_3$), 25.8 (CH$_3$), 18.4 (C), −0.1 (CH$_3$), −0.7 (CH$_3$), −4.21 (CH$_3$), −4.23 (CH$_3$); HRMS (ESI) calcd for C$_{39}$H$_{55}$O$_6$Si$_3$ [M+H]$^+$ 703.3301, found 703.3311.

Step 3: To a solution of the product from Step 2 (205 mg, 0.292 mmol) in THF (5 mL) at 0° C. was added TBAF (1.0 M in THF, 1.17 □L, 1.17 mmol, 4 eq). The reaction was stirred at 0° C. for 10 min. It was subsequently diluted with saturated NH$_4$Cl and extracted with EtOAc (2×). The organic extracts were washed with brine, dried (MgSO$_4$), filtered, and evaporated to provide an orange residue. The crude intermediate was taken up in CH$_2$Cl$_2$ (5 mL) and cooled to 0° C. Pyridine (189 μL, 2.33 mmol, 8 eq) and trifluoromethanesulfonic anhydride (196 μL, 1.17 mmol, 4 eq) were added, and the ice bath was removed. The reaction was stirred at room temperature for 2 h. It was then diluted with water and extracted with CH$_2$Cl$_2$ (2×). The combined organics were washed with brine, dried (MgSO$_4$), filtered, and concentrated in vacuo. Flash chromatography on silica gel (0-20% EtOAc/hexanes, linear gradient) afforded 209 mg (97%) of tert-butyl 5,5-dimethyl-3'-oxo-3,7-bis(((trifluoromethyl)sulfonyl)oxy)-3'H,5H-spiro[dibenzo[b,e]siline-10,1'-isobenzofuran]-6'-carboxylate as a colorless solid. $^1$H NMR (CDCl$_3$, 400 MHz) δ 8.21 (dd, J=8.0, 1.3 Hz, 1H), 8.05 (dd, J=8.0, 0.7 Hz, 1H), 7.93-7.90 (m, 1H), 7.58 (d, J=2.6 Hz, 2H), 7.28 (d, J=8.9 Hz, 2H), 7.22 (dd, J=8.9, 2.7 Hz, 2H), 1.58 (s, 9H), 0.81 (s, 3H), 0.71 (s, 3H); $^{19}$F NMR (CDCl$_3$, 376 MHz) δ-73.28 (s); $^{13}$C NMR (CDCl$_3$, 101 MHz) δ 168.9 (C), 163.8 (C), 152.8 (C), 149.5 (C), 144.1 (C), 138.3 (C), 138.2 (C), 131.2 (CH), 128.8 (CH), 128.0 (C), 126.8 (CH), 126.6 (CH), 124.8 (CH), 123.2 (CH), 118.9 (q, $^1J_{CF}$=320.8 Hz, CF$_3$), 88.6 (C), 83.1 (C), 28.2 (CH$_3$), −0.1 (CH$_3$), −0.9 (CH$_3$); HRMS (ESI) calcd for C$_{29}$H$_{25}$F$_6$O$_{10}$S$_2$Si [M+H]$^+$ 739.0557, found 739.0555.

Step 4: The procedure described for Example 7 was used to prepare the title compound 4-(tert-butoxycarbonyl)-2-(3,7-di(azetidin-1-yl)-5,5-dimethyldibenzo[b,e]silin-10-ylium-10(5H)-yl)benzoate from the ditriflate synthesized in Step 3 (91%, off-white foam). $^1$H NMR (CDCl$_3$, 400 MHz) δ 8.11 (dd, J=8.0, 1.3 Hz, 1H), 7.95 (dd, J=8.0, 0.7 Hz, 1H), 7.82 (dd, J=1.2, 0.8 Hz, 1H), 6.82 (d, J=8.7 Hz, 2H), 6.66 (d, J=2.6 Hz, 2H), 6.29 (dd, J=8.7, 2.7 Hz, 2H), 3.90 (t, J=7.3 Hz, 8H), 2.36 (p, J=7.2 Hz, 4H), 1.54 (s, 9H), 0.64 (s, 3H), 0.58 (s, 3H); $^{13}$C NMR (CDCl$_3$, 101 MHz) δ 170.3 (C), 164.5 (C), 155.4 (C), 151.0 (C), 137.2 (C), 136.2 (C), 132.4 (C), 129.9 (CH), 129.2 (C), 127.7 (CH), 125.6 (CH), 125.2 (CH), 115.6 (CH), 112.6 (CH), 91.9 (C), 82.3 (C), 52.3 (CH$_2$), 28.2 (CH$_3$), 17.0 (CH$_2$), 0.2 (CH$_3$), −0.7 (CH$_3$); HRMS (ESI) calcd for C$_{33}$H$_{37}$N$_2$O$_4$Si [M+H]$^+$ 553.2517, found 553.2529.

Example 33. 4-Carboxy-2-(3,7-di(azetidin-1-yl)-5,5-dimethyldibenzo[b,e]silin-10-ylium-10(5H)-yl)benzoate

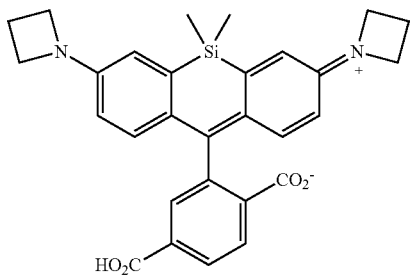

The procedure described for Example 19 was used to prepare the title compound from Example 32 (99%, dark blue-green solid, TFA salt). $^1$H NMR (MeOD, 400 MHz) δ 8.30-8.23 (m, 2H), 7.82-7.78 (m, 1H), 6.90 (d, J=2.5 Hz, 2H), 6.86 (d, J=9.2 Hz, 2H), 6.33 (dd, J=9.2, 2.5 Hz, 2H), 4.27 (t, J=7.4 Hz, 8H), 2.51 (p, J=7.6 Hz, 4H), 0.60 (s, 3H), 0.53 (s, 3H); $^{19}$F NMR (MeOD, 376 MHz) δ-75.45 (s); Analytical HPLC: 98.7% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 650 nm); HRMS (ESI) calcd for C$_{29}$H$_{29}$N$_2$O$_4$Si [M+H]$^+$ 497.1891, found 497.1890.

Example 34. 2-(3,7-Di(azetidin-1-yl)-5,5-dimethyl-dibenzo[b,e]silin-10-ylium-10(5H)-yl)-4-4(2,5-dioxopyrrolidin-1-yl)oxy)carbonyl)benzoate

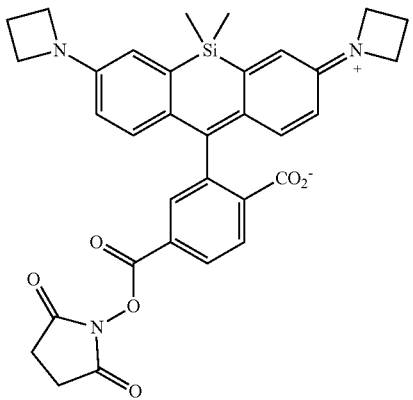

4-Carboxy-2-(3,7-di(azetidin-1-yl)-5,5-dimethyldibenzo[b,e]silin-10-ylium-10(5H)-yl)benzoate (Example 33; 40 mg, 65.5 μmol) was combined with DSC (37 mg, 144 μmol, 2.2 eq) in DMF (2.5 mL). After adding Et₃N (55 μL, 393 μmol, 6 eq) and DMAP (0.8 mg, 6.55 μmol, 0.1 eq), the reaction was stirred at room temperature for 3 h. It was subsequently diluted with 10% w/v citric acid and extracted with EtOAc (2×). The combined organic extracts were washed with brine, dried (MgSO₄), filtered, and concentrated in vacuo. Flash chromatography (0-50% EtOAc/toluene, linear gradient) yielded 31 mg (80%) of the title compound as a yellow-green solid. ¹H NMR (CDCl₃, 400 MHz) δ 8.27 (dd, J=8.0, 1.4 Hz, 1H), 8.07 (dd, J=8.0, 0.7 Hz, 1H), 8.00 (dd, J=1.3, 0.7 Hz, 1H), 6.74 (d, J=8.7 Hz, 2H), 6.66 (d, J=2.6 Hz, 2H), 6.30 (dd, J=8.7, 2.7 Hz, 2H), 3.91 (t, J=7.3 Hz, 8H), 2.89 (s, 4H), 2.37 (p, J=7.2 Hz, 4H), 0.62 (s, 3H), 0.56 (s, 3H); ¹³C NMR (CDCl₃, 101 MHz) δ 169.4 (C), 169.0 (C), 161.1 (C), 155.5 (C), 151.2 (C), 136.5 (C), 131.7 (C), 131.6 (C), 130.7 (CH), 130.1 (C), 127.8 (CH), 126.8 (CH), 126.3 (CH), 115.8 (CH), 112.7 (CH), 92.4 (C), 52.3 (CH₂), 25.8 (CH₂), 17.0 (CH₂), 0.3 (CH₃), −1.1 (CH₃); HRMS (ESI) calcd for $C_{33}H_{32}N_3O_6Si$ [M+H]⁺ 594.2055, found 594.2069.

Example 35. 4-((2-(2-((6-Chlorohexyl)oxy)ethoxy)ethyl)carbamoyl)-2-(3,7-di(azetidin-1-yl)-5,5-dimethyldibenzo[b,e]silin-10-ylium-10(5H)-yl)benzoate

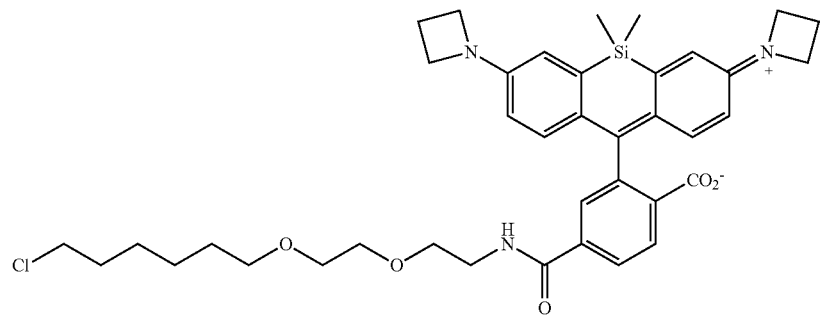

4-Carboxy-2-(3,7-di(azetidin-1-yl)-5,5-dimethyldibenzo[b,e]silin-10-ylium-10(5H)-yl)benzoate (Example 33; 30 mg, 49.1 μmol) was combined with DSC (28 mg, 108 μmol, 2.2 eq) in DMF (2 mL). After adding Et₃N (41 μL, 295 μmol, 6 eq) and DMAP (0.6 mg, 4.91 μmol, 0.1 eq), the reaction was stirred at room temperature for 1 h while shielded from light. A solution of 2-(2-((6-chlorohexyl)oxy)ethoxy)ethanamine ("HaloTag(O2)amine," 27 mg, 123 μmol, 2.5 eq) in DMF (250 μL) was then added. The reaction was stirred an additional 2 h at room temperature. It was subsequently diluted with saturated NaHCO₃ and extracted with EtOAc (2×). The combined organic extracts were washed with water and brine, dried (MgSO₄), filtered, and concentrated in vacuo. Silica gel chromatography (10-100% EtOAc/toluene, linear gradient) afforded 25 mg (73%) of the title compound as a blue foam. ¹H NMR (CDCl₃, 400 MHz) δ 7.98 (dd, J=8.0, 0.7 Hz, 1H), 7.90 (dd, J=8.0, 1.4 Hz, 1H), 7.68 (dd, J=1.2, 0.7 Hz, 1H), 6.75 (d, J=8.7 Hz, 2H), 6.74-6.68 (m, 1H), 6.66 (d, J=2.6 Hz, 2H), 6.26 (dd, J=8.7, 2.7 Hz, 2H), 3.89 (t, J=7.3 Hz, 8H), 3.67-3.60 (m, 6H), 3.56-3.53 (m, 2H), 3.50 (t, J=6.7 Hz, 2H), 3.39 (t, J=6.7 Hz, 2H), 2.36 (p, J=7.2 Hz, 4H), 1.78-1.68 (m, 2H), 1.56-1.47 (m, 2H), 1.44-1.35 (m, 2H), 1.35-1.25 (m, 2H), 0.63 (s, 3H), 0.57 (s, 3H); Analytical HPLC: >99% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; UV detection at 650 nm); HRMS (ESI) calcd for $C_{39}H_{49}ClN_3O_5Si$ [M+H]⁺ 702.3125, found 702.3137.

Example 36. 4-((4-(((2-Amino-9H-purin-6-yl)oxy)methyl)benzyl)carbamoyl)-2-(3,7-di(azetidin-1-yl)-5,5-dimethyldibenzo[b,e]silin-10-ylium-10(5H)-yl)benzoate

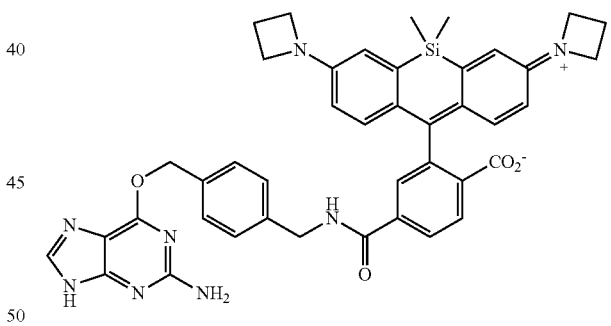

4-Carboxy-2-(3,7-di(azetidin-1-yl)-5,5-dimethyldibenzo[b,e]silin-10-ylium-10(5H)-yl)benzoate (Example 33; 25 mg, 40.9 µmol) was combined with DSC (23.1 mg, 90.1 µmol, 2.2 eq) in DMF (2 mL). After adding Et₃N (34 µL, 246 µmol, 6 eq) and DMAP (0.5 mg, 4.09 µmol, 0.1 eq), the reaction was stirred at room temperature for 1 h while shielded from light. 6-((4-(Aminomethyl)benzyl)oxy)-9H-purin-2-amine ("BG—NH₂," 28 mg, 102 µmol, 2.5 eq) was then added. The reaction was stirred an additional 2 h at room temperature. It was subsequently diluted with saturated NaHCO₃ and extracted with CH₂Cl₂ (2×). The combined organic extracts were dried (MgSO₄), filtered, and concentrated in vacuo. Silica gel chromatography (0-10% MeOH/EtOAc, linear gradient) afforded 24.7 mg (80%) of the title compound as a blue solid. ¹H NMR (MeOD, 400 MHz) δ 8.02 (dd, J=8.0, 1.3 Hz, 1H), 7.99 (dd, J=8.0, 0.7 Hz, 1H), 7.82 (s, 1H), 7.67-7.64 (m, 1H), 7.46 (d, J=8.1 Hz, 2H), 7.32 (d, J=8.2 Hz, 2H), 6.73 (d, J=2.6 Hz, 2H), 6.70 (d, J=8.7 Hz, 2H), 6.32 (dd, J=8.7, 2.6 Hz, 2H), 5.51 (s, 2H), 4.52 (s, 2H), 3.87 (t, J=7.3 Hz, 8H), 2.35 (p, J=7.1 Hz, 4H), 0.58 (s, 3H), 0.51 (s, 3H); Analytical HPLC: >99% purity (4.6 mm×150 mm 5 µm C18 column; 5 µL injection; 10-95% CH₃CN/H₂O, linear gradient, with constant 0.1% v/v TFA additive; 20 min run; 1 mL/min flow; ESI; positive ion mode; UV detection at 650 nm); HRMS (ESI) calcd for C₄₂H₄₁N₈O₄Si [M+H]⁺ 749.3015, found 749.2971.

Example 37. 2-(3,7-Bis(3-fluoroazetidin-1-yl)-5,5-dimethyldibenzo[b,e]silin-10-ylium-10(5H)-yl)-4-(tert-butoxycarbonyl)benzoate

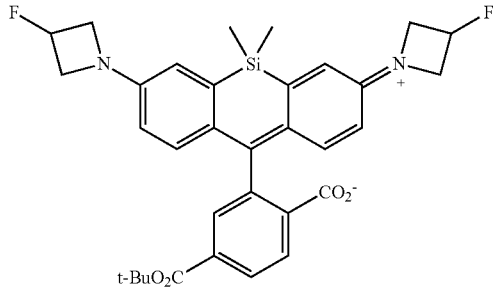

The procedure described for Example 7 was used to prepare the title compound from tert-butyl 5,5-dimethyl-3'-oxo-3,7-bis(((trifluoromethyl)sulfonyl)oxy)-3'H,5H-spiro[dibenzo[b,e]siline-10,1'-isobenzofuran]-6'-carboxylate (Example 32, Step 3) and 3-fluoroazetidine hydrochloride (85%, off-white solid). ¹H NMR (CDCl₃, 400 MHz) δ 8.12 (dd, J=8.0, 1.3 Hz, 1H), 7.97 (dd, J=7.9, 0.8 Hz, 1H), 7.82 (dd, J=1.3, 0.8 Hz, 1H), 6.88 (d, J=8.7 Hz, 2H), 6.70 (d, J=2.6 Hz, 2H), 6.35 (dd, J=8.7, 2.7 Hz, 2H), 5.41 (dtt, ²J$_{HF}$=57.0, 5.9, 3.7 Hz, 2H), 4.26-4.15 (m, 4H), 4.05-3.93 (m, 4H), 1.55 (s, 9H), 0.67 (s, 3H), 0.60 (s, 3H); ¹⁹F NMR (CDCl₃, 376 MHz) δ −180.48 (dtt, J$_{FH}$=57.0, 23.9, 18.2 Hz); ¹³C NMR (CDCl₃, 101 MHz) δ 170.2 (C), 164.4 (C), 155.1 (C), 150.0 (d, J$_{CF}$=1.2 Hz, C), 137.4 (C), 136.3 (C), 133.5 (C), 130.1 (CH), 129.0 (C), 127.8 (CH), 125.8 (CH), 125.1 (CH), 116.3 (CH), 113.3 (CH), 91.4 (C), 82.8 (d, ¹J$_{CF}$=204.8, CFH), 82.5 (C), 59.6 (d, ²J$_{CF}$=23.8 Hz, CH₂), 28.2 (CH₃), 0.17 (CH₃), −0.68 (CH₃); Analytical HPLC: >99% purity (4.6 mm×150 mm 5 µm C18 column; 5 µL injection; 50-95% CH₃CN/H₂O, linear gradient, with constant 0.1% v/v TFA additive; 20 min run; 1 mL/min flow; ESI; positive ion mode; detection at 633 nm); MS (ESI) calcd for C₃₃H₃₅F₂N₂O₄Si [M+H]⁺589.2, found 589.2.

Example 38. 2-(3,7-Bis(3-fluoroazetidin-1-yl)-5,5-dimethyldibenzo[b,e]silin-10-ylium-10(5H)-yl)-4-carboxybenzoate

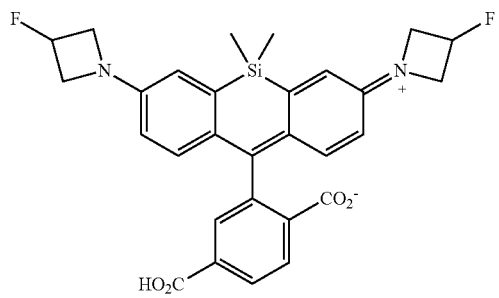

The procedure described for Example 19 was used to prepare the title compound from Example 37 (80%, dark blue solid, TFA salt). ¹H NMR (MeOD, 400 MHz) δ 8.25 (dd, J=8.0, 1.4 Hz, 1H), 8.11 (d, J=8.1 Hz, 1H), 7.84 (dd, J=1.4, 0.7 Hz, 1H), 6.87 (d, J=2.6 Hz, 2H), 6.83 (d, J=8.8 Hz, 2H), 6.39 (dd, J=8.9, 2.6 Hz, 2H), 5.43 (dtt, ²J$_{HF}$=57.3, 6.1, 3.3 Hz, 2H), 4.41-4.20 (m, 4H), 4.16-4.01 (m, 4H), 0.65 (s, 3H), 0.56 (s, 3H); Analytical HPLC: 88.1% purity (4.6 mm×150 mm 5 µm C18 column; 5 µL injection; 10-95% CH₃CN/H₂O, linear gradient, with constant 0.1% v/v TFA additive; 20 min run; 1 mL/min flow; ESI; positive ion mode; detection at 633 nm); MS (ESI) calcd for C₂₉H₂₇F₂N₂O₄Si [M+H]⁺ 533.2, found 533.0.

Example 39. 2-(3,7-Bis(3-fluoroazetidin-1-yl)-5,5-dimethyldibenzo[b,e]silin-10-ylium-10(5H)-yl)-4-((2-(2-(6-chlorohexyl)oxy)ethoxy)ethyl)carbamoyl)benzoate

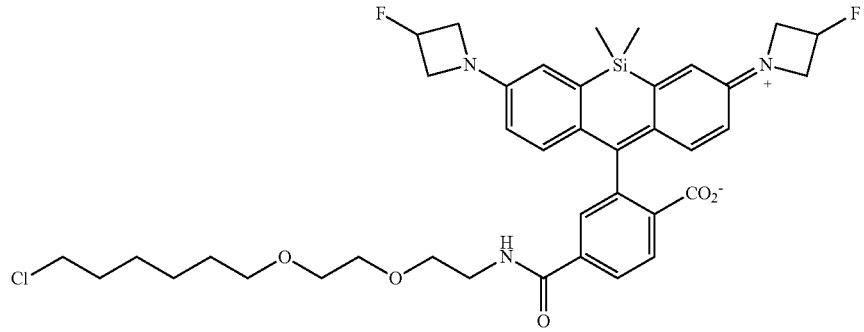

The procedure described for Example 35 was used to prepare the title compound from Example 38 (61%, blue-green solid). ¹H NMR (CDCl₃, 400 MHz) δ 7.99 (dd, J=7.9, 0.7 Hz, 1H), 7.89 (dd, J=8.0, 1.4 Hz, 1H), 7.69 (dd, J=1.4, 0.8 Hz, 1H), 6.81 (d, J=8.7 Hz, 2H), 6.78 (s, 1H), 6.69 (d, J=2.6 Hz, 2H), 6.36-6.26 (m, 2H), 5.41 (dtt, ²$J_{HF}$=56.9, 5.9, 3.7 Hz, 2H), 4.29-4.13 (m, 4H), 4.06-3.91 (m, 4H), 3.67-3.60 (m, 6H), 3.58-3.53 (m, 2H), 3.50 (t, J=6.6 Hz, 2H), 3.40 (t, J=6.7 Hz, 2H), 1.79-1.67 (m, 2H), 1.54-1.47 (m, 2H), 1.45-1.35 (m, 2H), 1.35-1.24 (m, 2H), 0.66 (s, 3H), 0.59 (s, 3H); ¹⁹F NMR (CDCl₃, 376 MHz) δ-180.49 (dtt, $J_{FH}$=56.9, 23.9, 18.2 Hz); Analytical HPLC: 98.7% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; detection at 633 nm); MS (ESI) calcd for C₃₉H₄₇ClF₂N₃O₅Si [M+H]⁺ 738.3, found 738.2.

Example 40. 2-(3,6-Di(azetidin-1-yl)-10,10-dimethylanthracen-9-ylium-9(10H)-yl)benzoate

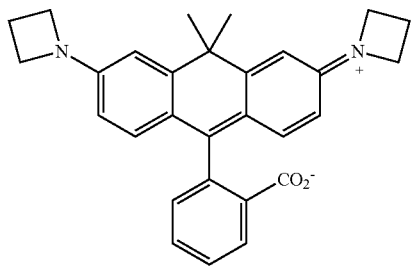

The procedure described for Example 7 was used to prepare the title compound (88%, pale blue solid) from carbofluorescein ditriflate (Grimm, J. B.; Sung, A. J.; Legant, W. R.; Hulamm, P.; Matlosz, S. M.; Betzig, E.; Lavis, L. D. ACS Chem. Biol. 2013, 8, 1303). ¹H NMR (CDCl₃, 400 MHz) δ 8.00-7.95 (m, 1H), 7.58 (td, J=7.4, 1.4 Hz, 1H), 7.53 (td, J=7.4, 1.2 Hz, 1H), 7.08-7.03 (m, 1H), 6.58 (d, J=2.4 Hz, 2H), 6.55 (d, J=8.5 Hz, 2H), 6.20 (dd, J=8.6, 2.4 Hz, 2H), 3.90 (t, J=7.2 Hz, 8H), 2.37 (p, J=7.2 Hz, 4H), 1.82 (s, 3H), 1.72 (s, 3H); ¹³C NMR (CDCl₃, 101 MHz) δ 170.9 (C), 155.6 (C), 152.4 (C), 146.9 (C), 134.5 (CH), 128.94 (CH), 128.89 (CH), 127.4 (C), 125.0 (CH), 124.1 (CH), 120.6 (C), 110.4 (CH), 107.9 (CH), 88.4 (C), 52.4 (CH₂), 38.6 (C), 35.7 (CH₃), 32.3 (CH₃), 17.0 (CH₂); Analytical HPLC: >99% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; detection at 600 nm); HRMS (ESI) calcd for C₂₉H₂₉N₂O₂ [M+H]⁺ 437.2224, found 437.2236.

Example 41. 2-(3,6-Bis(3,3-difluoroazetidin-1-yl)-10,10-dimethylanthracen-9-ylium-9(10H)-yl)benzoate

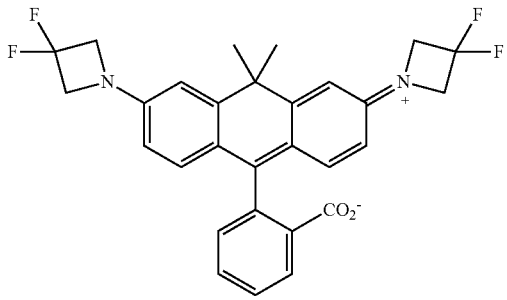

The procedure described for Example 7 was used to prepare the title compound from carbofluorescein ditriflate (Grimm, J. B.; Sung, A. J.; Legant, W. R.; Hulamm, P.; Matlosz, S. M.; Betzig, E.; Lavis, L. D. ACS Chem. Biol. 2013, 8, 1303) and 3,3-difluoroazetidine hydrochloride (95%, off-white solid). ¹H NMR (CDCl₃, 400 MHz) δ 8.04-7.98 (m, 1H), 7.60 (td, J=7.3, 1.5 Hz, 1H), 7.56 (td, J=7.3, 1.3 Hz, 1H), 7.04 (s, 1H), 6.64 (d, J=2.8 Hz, 2H), 6.63 (d, J=8.7 Hz, 2H), 6.28 (dd, J=8.6, 2.5 Hz, 2H), 4.25 (t, ³$J_{HF}$=11.8 Hz, 8H), 1.84 (s, 3H), 1.74 (s, 3H); ¹⁹F NMR (CDCl₃, 376 MHz) δ-99.95 (p, ³$J_{FH}$=11.8 Hz); ¹³C NMR (CDCl₃, 101 MHz) δ 170.6 (C), 155.2 (C), 150.1 (t, ⁴$J_{CF}$=2.7 Hz, C), 146.9 (C), 134.8 (CH), 129.3 (CH), 129.2 (CH), 127.0 (C), 125.2 (CH), 123.9 (CH), 122.4 (C), 115.9 (t, ¹$J_{CF}$=274.6 Hz, CF₂), 111.6 (CH), 109.2 (CH), 87.2 (C), 63.4 (t, ²$J_{CF}$=25.9 Hz, CH₂), 38.6 (C), 35.6 (CH₃), 32.5 (CH₃); Analytical HPLC: >99% purity (4.6 mm×150 mm 5 μm C18 column; 5 μL injection; 30-95% CH₃CN/H₂O, linear gradient, with constant 0.1% v/v TFA additive; 20 min run; 1 mL/min flow; ESI; positive ion mode; detection at 600 nm); MS (ESI) calcd for C₂₉H₂₅F₄N₂O₂ [M+H]⁺ 509.2, found 509.1.

Example 42. 4-(tert-Butoxycarbonyl)-2-(3,6-di(azetidin-1-yl)-10,10-dimethylanthracen-9-ylium-9(10H)-yl)benzoate

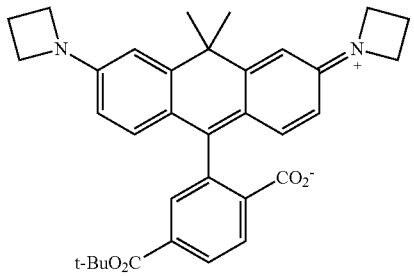

Step 1: A vial was charged with di-tert-butyl 2-bromoterephthalate (Example 32, Step 1; 1.48 g, 4.14 mmol, 2 eq), sealed, and flushed with nitrogen. After dissolving the bromide in THF (7 mL) and cooling the reaction to −15° C., iPrMgCl.LiCl (1.3 M in THF, 3.19 mL, 4.14 mmol, 2 eq) was added. The reaction was warmed to −10° C. and stirred for 4 h. A solution of 3,6-bis((tert-butyldimethylsilyl)oxy)-10,10-dimethylanthracen-9(10H)-one (1.00 g, 2.07 mmol; from Grimm, J. B.; Sung, A. J.; Legant, W. R.; Hulamm, P.; Matlosz, S. M.; Betzig, E.; Lavis, L. D. ACS Chem. Biol. 2013, 8, 1303) in THF (4 mL) was then added dropwise. The reaction mixture was warmed to room temperature and stirred for 2 h. It was subsequently quenched with saturated $NH_4Cl$, diluted with water, and extracted with EtOAc (2×). The combined organics were washed with brine, dried ($MgSO_4$), filtered, and evaporated. Silica gel chromatography (0-10% $Et_2O$/hexanes, linear gradient) provided 245 mg (17%) of tert-butyl 3,6-bis((tert-butyldimethylsilyl)oxy)-10,10-dimethyl-3'-oxo-3'H,10H-spiro[anthracene-9,1'-isobenzofuran]-6'-carboxylate as a colorless solid. $^1$H NMR ($CDCl_3$, 400 MHz) δ 8.16 (dd, J=8.0, 1.3 Hz, 1H), 8.02 (dd, J=8.0, 0.6 Hz, 1H), 7.63-7.59 (m, 1H), 7.09-7.05 (m, 2H), 6.64-6.57 (m, 4H), 1.81 (s, 3H), 1.72 (s, 3H), 1.54 (s, 9H), 0.99 (s, 18H), 0.22 (s, 12H); $^{13}$C NMR ($CDCl_3$, 101 MHz) δ 169.9 (C), 164.4 (C), 156.5 (C), 155.5 (C), 147.0 (C), 138.1 (C), 130.3 (CH), 129.7 (C), 129.3 (CH), 125.1 (CH), 125.0 (CH), 124.0 (C), 119.2 (CH), 117.8 (CH), 87.0 (C), 82.5 (C), 38.2 (C), 35.0 ($CH_3$), 33.2 ($CH_3$), 28.2 ($CH_3$), 25.8 ($CH_3$), 18.4 (C), −4.17 ($CH_3$), −4.19 ($CH_3$); HRMS (ESI) calcd for $C_{40}H_{55}O_6Si_2$ [M+H]$^+$ 687.3537, found 687.3533.

Step 2: To a solution of the product from Step 1 (170 mg, 0.247 mmol) in THF (5 mL) was added TBAF (1.0 M in THF, 990 µL, 0.990 mmol, 4 eq). The reaction was stirred at room temperature for 10 min. It was subsequently diluted with saturated $NH_4Cl$ and extracted with EtOAc (2×). The organic extracts were washed with brine, dried ($MgSO_4$), filtered, and evaporated to provide an orange residue. The crude intermediate was taken up in $CH_2Cl_2$ (5 mL) and cooled to 0° C. Pyridine (160 µL, 1.98 mmol, 8 eq) and trifluoromethanesulfonic anhydride (167 µL, 0.990 mmol, 4 eq) were added, and the ice bath was removed. The reaction was stirred at room temperature for 2 h. It was then diluted with water and extracted with $CH_2Cl_2$ (2×). The combined organics were washed with brine, dried ($MgSO_4$), filtered, and concentrated in vacuo. Flash chromatography on silica gel (0-20% EtOAc/hexanes, linear gradient) afforded 159 mg (89%) of tert-butyl 10,10-dimethyl-3'-oxo-3,6-bis(((trifluoromethyl)sulfonyl)oxy)-3'H,10H-spiro[anthracene-9,1'-isobenzofuran]-6'-carboxylate as a colorless solid. $^1$H NMR ($CDCl_3$, 400 MHz) δ 8.24 (dd, J=8.0, 1.3 Hz, 1H), 8.11 (dd, J=8.0, 0.6 Hz, 1H), 7.63-7.60 (m, 1H), 7.56 (d, J=2.5 Hz, 2H), 7.10 (dd, J=8.8, 2.5 Hz, 2H), 6.88 (d, J=8.8 Hz, 2H), 1.91 (s, 3H), 1.81 (s, 3H), 1.56 (s, 9H); $^{19}$F NMR ($CDCl_3$, 376 MHz) δ-73.20 (s); $^{13}$C NMR ($CDCl_3$, 101 MHz) δ 168.8 (C), 163.9 (C), 153.9 (C), 150.4 (C), 147.2 (C), 138.9 (C), 131.4 (CH), 131.1 (C), 130.3 (CH), 128.8 (C), 125.9 (CH), 124.7 (CH), 120.6 (CH), 119.8 (CH), 118.9 (q, $^1J_{CF}$=320.9 Hz, $CF_3$), 84.3 (C), 83.1 (C), 39.0 (C), 34.8 ($CH_3$), 33.2 ($CH_3$), 28.2 ($CH_3$); HRMS (ESI) calcd for $C_{30}H_{25}F_6O_{10}S_2$ [M+H]$^+$ 723.0793, found 723.0797.

Step 3: The procedure described for Example 7 was used to prepare the title compound 4-(tert-butoxycarbonyl)-2-(3,6-di(azetidin-1-yl)-10,10-dimethylanthracen-9-ylium-9(10H)-yl)benzoate from the ditriflate synthesized in Step 2 (84%, blue solid). $^1$H NMR ($CDCl_3$, 400 MHz) δ 8.14 (dd, J=8.0, 1.3 Hz, 1H), 8.00 (dd, J=8.0, 0.7 Hz, 1H), 7.61 (dd, J=1.3, 0.8 Hz, 1H), 6.58 (d, J=2.3 Hz, 2H), 6.54 (d, J=8.6 Hz, 2H), 6.21 (dd, J=8.6, 2.4 Hz, 2H), 3.91 (t, J=7.2 Hz, 8H), 2.38 (p, J=7.2 Hz, 4H), 1.83 (s, 3H), 1.73 (s, 3H), 1.53 (s, 9H); $^{13}$C NMR ($CDCl_3$, 101 MHz) δ 170.1 (C), 164.6 (C), 155.6 (C), 152.4 (C), 146.8 (C), 137.8 (C), 130.3 (C), 130.1 (CH), 128.9 (CH), 125.1 (CH), 124.8 (CH), 119.9 (C), 110.5 (CH), 108.0 (CH), 88.8 (C), 82.3 (C), 52.3 ($CH_2$), 38.5 (C), 35.5 ($CH_3$), 32.8 ($CH_3$), 28.2 ($CH_3$), 17.0 ($CH_2$); HRMS (ESI) calcd for $C_{34}H_{37}N_2O_4$ [M+H]$^+$ 537.2753, found 537.2768.

Example 43. 4-Carboxy-2-(3,6-di(azetidin-1-yl)-10,10-dimethylanthracen-9-ylium-9(10H)-yl)benzoate

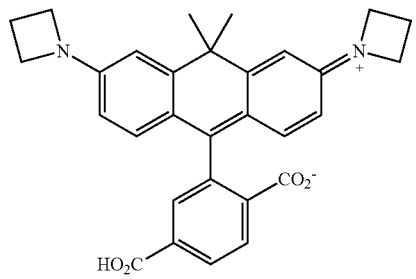

The procedure described for Example 19 was used to prepare the title compound from Example 42 (98%, dark blue solid, TFA salt). $^1$H NMR (MeOD, 400 MHz) δ 8.34 (dd, J=8.2, 0.5 Hz, 1H), 8.31 (dd, J=8.2, 1.5 Hz, 1H), 7.84 (dd, J=1.5, 0.5 Hz, 1H), 6.93 (d, J=9.1 Hz, 2H), 6.82 (d, J=2.2 Hz, 2H), 6.39 (dd, J=9.1, 2.3 Hz, 2H), 4.33 (t, J=7.6 Hz, 8H), 2.55 (p, J=7.6 Hz, 4H), 1.82 (s, 3H), 1.70 (s, 3H); $^{19}$F NMR (MeOD, 376 MHz) δ-75.24 (s); $^{13}$C NMR (MeOD, 101 MHz) δ 167.9 (C), 167.5 (C), 165.4 (C), 158.0 (C), 156.8 (C), 139.3 (C), 137.6 (CH), 136.2 (C), 135.5 (C), 132.5 (CH), 132.4 (CH), 131.5 (CH), 121.8 (C), 111.9 (CH), 109.7 (CH), 52.9 ($CH_2$), 42.8 (C), 35.6 ($CH_3$), 32.0 ($CH_3$), 16.8 ($CH_2$); Analytical HPLC: >99% purity (4.6 mm×150 mm 5 µm C18 column; 5 µL injection; 10-95% $CH_3CN$/$H_2O$, linear gradient, with constant 0.1% v/v TFA additive; 20 min run; 1 mL/min flow; ESI; positive ion mode; detection at 600 nm); HRMS (ESI) calcd for $C_{30}H_{29}N_2O_4$ [M+H]$^+$ 481.2127, found 481.2120.

Example 44. 4-((2-(2-((6-Chlorohexyl)oxy)ethoxy)ethyl)carbamoyl)-2-(3,6-di(azetidin-1-yl)-10,10-dimethylanthracen-9-ylium-9(10H)-yl)benzoate

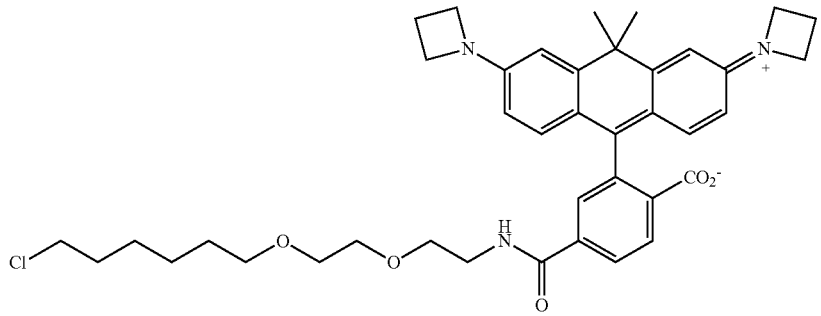

The procedure described for Example 35 was used to prepare the title compound from Example 43 (72%, dark blue solid). $^1$H NMR (CDCl$_3$, 400 MHz) δ 8.02 (dd, J=8.0, 0.6 Hz, 1H), 7.94 (dd, J=8.0, 1.4 Hz, 1H), 7.42-7.40 (m, 1H), 6.68-6.62 (m, 1H), 6.57 (d, J=2.3 Hz, 2H), 6.52 (d, J=8.6 Hz, 2H), 6.20 (dd, J=8.6, 2.4 Hz, 2H), 3.91 (t, J=7.4 Hz, 8H), 3.64-3.56 (m, 6H), 3.55-3.48 (m, 4H), 3.38 (t, J=6.6 Hz, 2H), 2.37 (p, J=7.2 Hz, 4H), 1.83 (s, 3H), 1.77-1.68 (m, 2H), 1.72 (s, 3H), 1.56-1.47 (m, 2H), 1.46-1.36 (m, 2H), 1.36-1.28 (m, 2H); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; UV detection at 600 nm); HRMS (ESI) calcd for C$_{40}$H$_{49}$ClN$_3$O$_5$ [M+H]$^+$ 686.3361, found 686.3375.

Example 45. 2-(3,6-Bis(3,3-difluoroazetidin-1-yl)-10,10-dimethylanthracen-9-ylium-9(10H)-yl)-4-(tert-butoxycarbonyl)benzoate

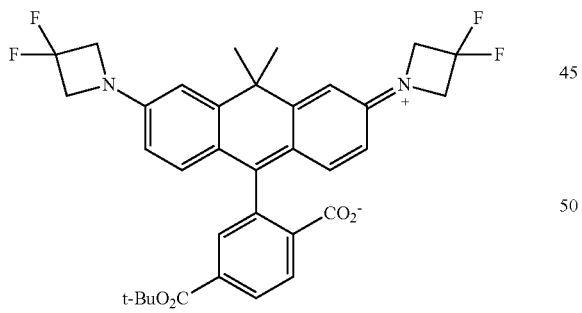

The procedure described for Example 1 was used to prepare the title compound from tert-butyl 10,10-dimethyl-3'-oxo-3,6-bis(((trifluoromethyl)sulfonyl)oxy)-3'H,10H-spiro[anthracene-9,1'-isobenzofuran]-6'-carboxylate (Example 42, Step 2) and 3,3-difluoroazetidine hydrochloride (93%, off-white solid). $^1$H NMR (CDCl$_3$, 400 MHz) δ 8.16 (dd, J=8.0, 1.3 Hz, 1H), 8.02 (dd, J=8.0, 0.7 Hz, 1H), 7.60 (dd, J=1.2, 0.8 Hz, 1H), 6.65 (d, J=2.4 Hz, 2H), 6.62 (d, J=8.6 Hz, 2H), 6.29 (dd, J=8.6, 2.5 Hz, 2H), 4.26 (t, $^3$J$_{HF}$=11.7 Hz, 8H), 1.85 (s, 3H), 1.75 (s, 3H), 1.53 (s, 9H); $^{19}$F NMR (CDCl$_3$, 376 MHz) δ-99.96 (p, $^3$J$_{FH}$=11.8 Hz); $^{13}$C NMR (CDCl$_3$, 101 MHz) δ 169.2 (C), 164.4 (C), 155.3 (C), 150.1 (t, $^4$J$_{CF}$=2.7 Hz, C), 146.8 (C), 138.1 (C), 130.3 (CH), 129.9 (C), 129.2 (CH), 125.1 (CH), 124.9 (CH), 121.7 (C), 115.9 (t, $^1$J$_{CF}$=274.6 Hz, CF$_2$), 111.8 (CH), 109.3 (CH), 87.5 (C), 82.5 (C), 63.4 (t, $^2$J$_{CF}$=26.0 Hz, CH$_2$), 38.5 (C), 35.4 (CH$_3$), 33.0 (CH$_3$), 28.2 (CH$_3$); MS (ESI) calcd for C$_{34}$H$_{33}$F$_4$N$_2$O$_4$ [M+H]$^+$ 609.2, found 609.3.

Example 46. 2-(3,6-Bis(3,3-difluoroazetidin-1-yl)-10,10-dimethylanthracen-9-ylium-9(10H)-yl)-4-carboxybenzoate

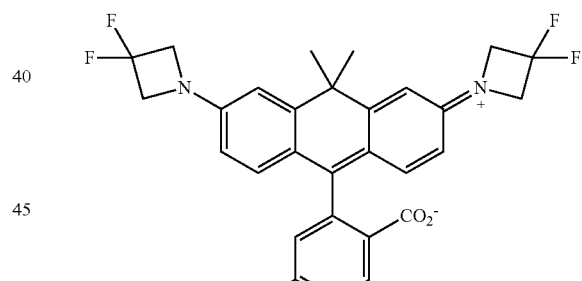

The procedure described for Example 19 was used to prepare the title compound from Example 45 (99%, dark blue-purple solid, TFA salt). $^1$F NMR (MeOD, 400 MHz) δ 8.30 (dd, J=8.1, 1.4 Hz, 1H), 8.23-8.15 (m, 1H), 7.69 (s, 1H), 6.92 (d, J=2.1 Hz, 2H), 6.79 (d, J=7.6 Hz, 2H), 6.47 (dd, J=8.8, 2.3 Hz, 2H), 4.45 (t, $^3$J$_{HF}$=11.0 Hz, 8H), 1.88 (s, 3H), 1.76 (s, 3H); $^{19}$F NMR (MeOD, 376 MHz) δ-75.81 (s, 3F), −100.32 (m, 4F); Analytical HPLC: >99% purity (4.6 mm×150 mm 5 μm C18 column; 5 μL injection; 30-95% CH$_3$CN/H$_2$O, linear gradient, with constant 0.1% v/v TFA additive; 20 min run; 1 mL/min flow; ESI; positive ion mode; detection at 600 nm); MS (ESI) calcd for C$_{30}$H$_{25}$F$_4$N$_2$O$_4$ [M+H]+553.2, found 553.1.

Example 47. 2-(3,6-Bis(3,3-difluoroazetidin-1-yl)-10,10-dimethylanthracen-9-ylium-9(10H)-yl)-4-4(2,5-dioxopyrrolidin-1-yl)oxy)carbonyl)benzoate

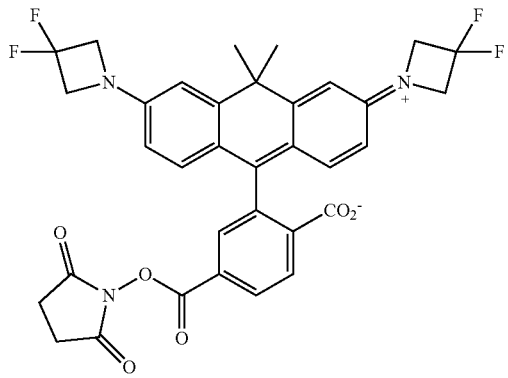

The procedure described for Example 34 was used to prepare the title compound from Example 46 (93%, yellow solid). $^1$H NMR (CDCl$_3$, 400 MHz) δ 8.32 (dd, J=8.0, 1.4 Hz, 1H), 8.14 (dd, J=8.0, 0.7 Hz, 1H), 7.74 (dd, J=1.3, 0.8 Hz, 1H), 6.65 (d, J=2.4 Hz, 2H), 6.58 (d, J=8.6 Hz, 2H), 6.31 (dd, J=8.6, 2.5 Hz, 2H), 4.26 (t, $^3J_{HF}$=11.7 Hz, 8H), 2.88 (s, 4H), 1.84 (s, 3H), 1.73 (s, 3H); $^{19}$F NMR (CDCl$_3$, 376 MHz) δ-99.97 (p, J$_{FH}$=11.7 Hz); $^{13}$C NMR (CDCl$_3$, 101 MHz) δ 169.1 (C), 168.9 (C), 160.9 (C), 155.6 (C), 150.3 (t, $^4J_{CF}$=2.5 Hz, C), 146.9 (C), 132.0 (C), 131.3 (CH), 131.0 (C), 129.3 (CH), 126.2 (CH), 125.8 (CH), 120.9 (C), 115.9 (t, $^1J_{CF}$=274.5 Hz, CF$_2$), 112.0 (CH), 109.4 (CH), 87.9 (C), 63.4 (t, $^2J_{CF}$=26.0 Hz, CH$_2$), 38.5 (C), 35.5 (CH$_3$), 32.8 (CH$_3$), 25.8 (CH$_2$); Analytical HPLC: >99% purity (4.6 mm×150 mm 5 μm C18 column; 5 μL injection; 30-95% CH$_3$CN/H$_2$O, linear gradient, with constant 0.1% v/v TFA additive; 20 min run; 1 mL/min flow; ESI; positive ion mode; detection at 600 nm); MS (ESI) calcd for C$_{34}$H$_{28}$F$_4$N$_3$O$_6$ [M+H]$^+$ $^{650.2}$, found 650.1.

Example 48. 2-(3,6-Bis(3,3-difluoroazetidin-1-yl)-10,10-dimethylanthracen-9-ylium-9(10H)-yl)-4-((2-(2-((6-chlorohexyl)oxy)ethoxy)ethyl)carbamoyl)benzoate

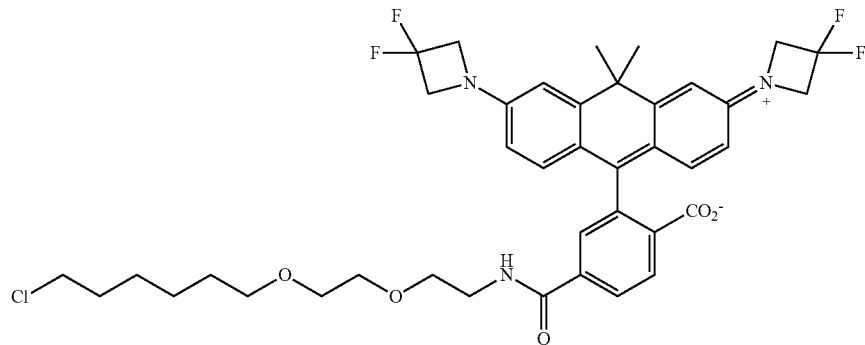

The procedure described for Example 35 was used to prepare the title compound from Example 46 (54%, off-white/bluish solid). $^1$H NMR (CDCl$_3$, 400 MHz) δ 8.04 (dd, J=8.0, 0.5 Hz, 1H), 7.93 (dd, J=8.0, 1.4 Hz, 1H), 7.44-7.40 (m, 1H), 6.70-6.65 (m, 1H), 6.64 (d, J=2.4 Hz, 2H), 6.60 (d, J=8.6 Hz, 2H), 6.28 (dd, J=8.6, 2.4 Hz, 2H), 4.25 (t, $^3J_{HF}$=11.7 Hz, 8H), 3.66-3.57 (m, 6H), 3.56-3.48 (m, 4H), 3.39 (t, J=6.6 Hz, 2H), 1.85 (s, 3H), 1.79-1.70 (m, 5H), 1.57-1.48 (m, 2H), 1.46-1.37 (m, 2H), 1.37-1.26 (m, 2H); $^{19}$F NMR (CDCl$_3$, 376 MHz) δ-99.94 (p, $^3J_{FH}$=11.8 Hz); Analytical HPLC: >99% purity (4.6 mm×150 mm 5 μm C18 column; 5 μL injection; 30-95% CH$_3$CN/H$_2$O, linear gradient, with constant 0.1% v/v TFA additive; 20 min run; 1 mL/min flow; ESI; positive ion mode; detection at 600 nm); MS (ESI) calcd for C$_{40}$H$_{45}$ClF$_4$N$_3$O$_5$ [M+H]$^+$ 758.3, found 758.2.

Example 49. 7-(Azetidin-1-yl)-4-methyl-2H-chromen-2-one

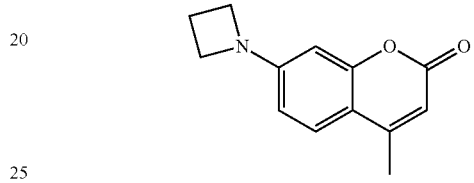

A vial was charged with 4-methylumbelliferone triflate (300 mg, 0.973 mmol; from Kövér, J.; Antus, S. Z. Naturforsch., B: J. Chem. Sci. 2005, 60, 792), RuPhos-G3-palladacycle (41 mg, 0.049 mmol, 0.05 eq), RuPhos (23 mg, 0.049 mmol, 0.05 eq), and K$_2$CO$_3$ (188 mg, 1.36 mmol, 1.4 eq). The vial was sealed and evacuated/backfilled with nitrogen (3×). Dioxane (8 mL) was added, and the reaction was flushed again with nitrogen (3×). Following the addition of azetidine (72 μL, 1.07 mmol, 1.1 eq), the reaction was stirred at 80° C. for 6.5 h. It was then cooled to room temperature, deposited onto Celite, and concentrated to dryness. Purification by silica gel chromatography (0-30% EtOAc/hexanes, linear gradient; dry load with Celite) afforded the title compound (190 mg, 91%) as a yellow solid. $^1$H NMR (CDCl$_3$, 400 MHz) δ 7.38 (d, J=8.6 Hz, 1H), 6.30 (dd, J=8.6, 2.3 Hz, 1H), 6.22 (d, J=2.3 Hz, 1H), 5.97 (q, J=1.1 Hz, 1H), 4.03-3.95 (m, 4H), 2.44 (p, J=7.3 Hz, 2H), 2.34 (d, J=1.1 Hz, 3H); $^{13}$C NMR (CDCl$_3$, 101 MHz) δ 162.0 (C), 155.7 (C), 154.0 (C), 153.1 (C), 125.5 (CH), 110.4 (C), 109.5 (CH), 107.8 (CH), 97.2 (CH), 51.9 (CH$_2$), 18.7 (CH$_3$), 16.6 (CH$_2$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 350 nm); HRMS (ESI) calcd for $C_{13}H_{14}NO_2$ [M+H]$^+$ 216.1019, found 216.1014.

Example 50. Ethyl 7-(azetidin-1-yl)-2-oxo-2H-chromene-3-carboxylate

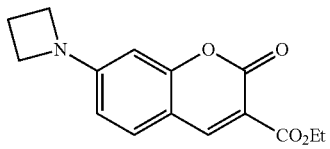 [SMILES: CCOC(=O)c1cc2ccc(N3CCC3)cc2oc1=O]

Step 1: A flask was charged with Pd(OAc)$_2$ (130 mg, 0.578 mmol, 0.05 eq), sealed, and evacuated/backfilled with nitrogen (3×). Toluene (40 mL) was added; separate solutions of 3-bromophenol (2.00 g, 11.6 mmol) in toluene (8 mL), 2,8,9-triisobutyl-2,5,8,9-tetraaza-1-phosphabicyclo[3.3.3]undecane ("Verkade base," 396 mg, 1.16 mmol, 0.1 eq) in toluene (8 mL), and LiHMDS (1.0 M in THF, 26.6 mL, 26.6 mmol, 2.3 eq) were then added sequentially. Following the addition of azetidine (935 µL, 13.9 mmol, 1.2 eq), the reaction was stirred at 80° C. for 18 h. It was then cooled to room temperature, deposited onto Celite, and concentrated to dryness. Purification by silica gel chromatography (0-35% EtOAc/hexanes, linear gradient; dry load with Celite) afforded 3-(azetidin-1-yl)phenol (1.44 g, 84%) as an off-white solid. $^1$H NMR (CDCl$_3$, 400 MHz) δ 7.05 (t, J=8.0 Hz, 1H), 6.19 (ddd, J=8.0, 2.4, 0.8 Hz, 1H), 6.04 (ddd, J=8.1, 2.1, 0.8 Hz, 1H), 5.92 (t, J=2.3 Hz, 1H), 4.77 (s, 1H), 3.89-3.81 (m, 4H), 2.34 (p, J=7.2 Hz, 2H); $^{13}$C NMR (CDCl$_3$, 101 MHz) δ 156.7 (C), 153.9 (C), 130.1 (CH), 105.1 (CH), 104.5 (CH), 99.0 (CH), 52.7 (CH$_2$), 17.0 (CH$_2$); HRMS (ESI) calcd for $C_9H_{12}NO$ [M+H]$^+$ 150.0913, found 150.0915.

Step 2: DMF (2 mL) was cooled to 0° C. under nitrogen, and POCl$_3$ (500 µL, 5.36 mmol, 2 eq) was added dropwise. The ice bath was then removed, and the reaction was stirred at room temperature for 1 h. The phenol from Step 1 (400 mg, 2.68 mmol) in DMF (4 mL) was then added. After stirring the reaction at room temperature for 1 h, it was carefully diluted with saturated NaHCO$_3$ (~20 mL) and EtOAc (~20 mL) and vigorously stirred for 10 min. The mixture was diluted with additional water and extracted with EtOAc (2×). The combined organic extracts were washed with water and brine, dried (MgSO$_4$), filtered, and concentrated in vacuo. The residue was purified by flash chromatography on silica gel (0-40% EtOAc/hexanes, linear gradient) to yield 230 mg (48%) of 4-(azetidin-1-yl)-2-hydroxybenzaldehyde as a white solid. $^1$F NMR (CDCl$_3$, 400 MHz) δ 11.69 (s, 1H), 9.50 (s, 1H), 7.25 (d, J=8.5 Hz, 1H), 5.94 (dd, J=8.5, 2.1 Hz, 1H), 5.75 (d, J=2.1 Hz, 1H), 4.08-3.98 (m, 4H), 2.43 (p, J=7.4 Hz, 2H); $^{13}$C NMR (CDCl$_3$, 101 MHz) δ 192.6 (CH), 164.4 (C), 156.6 (C), 135.5 (CH), 112.2 (C), 103.2 (CH), 95.6 (CH), 51.2 (CH$_2$), 16.3 (CH$_2$); HRMS (ESI) calcd for $C_{10}H_{12}NO_2$ [M+H]$^+$ 178.0863, found 178.0866.

Step 3: The aldehyde from Step 2 (175 mg, 0.988 mmol) was suspended in EtOH (10 mL). Diethyl malonate (301 µL, 1.98 mmol, 2 eq) and piperidine (29 µL, 0.296 mmol, 0.3 eq) were added, and the reaction was stirred at reflux for 12 h. It was then cooled to room temperature and allowed to stand for 12 h, during which time a yellow solid crystallized out of the solution. The mixture were filtered; the filter cake was washed with EtOH and dried to afford 232 mg (86%) of the title compound ethyl 7-(azetidin-1-yl)-2-oxo-2H-chromene-3-carboxylate as a bright yellow crystalline solid. $^1$H NMR (CDCl$_3$, 400 MHz) δ 8.39 (s, 1H), 7.31 (d, J=8.6 Hz, 1H), 6.26 (dd, J=8.6, 2.2 Hz, 1H), 6.09 (d, J=2.1 Hz, 1H), 4.37 (q, J=7.1 Hz, 2H), 4.10-4.02 (m, 4H), 2.48 (p, J=7.4 Hz, 2H), 1.38 (t, J=7.1 Hz, 3H); $^{13}$C NMR (CDCl$_3$, 101 MHz) δ 164.2 (C), 158.13 (C), 158.12 (C), 155.2 (C), 149.5 (CH), 131.0 (CH), 109.4 (C), 108.39 (C), 108.36 (CH), 95.4 (CH), 61.2 (CH$_2$), 51.4 (CH$_2$), 16.3 (CH$_2$), 14.5 (CH$_3$); HRMS (ESI) calcd for $C_{15}H_{15}NO_4Na$ [M+Na]$^+$ 296.0893, found 296.0900.

Example 51. 7-(Azetidin-1-yl)-2-oxo-2H-chromene-3-carboxylic acid

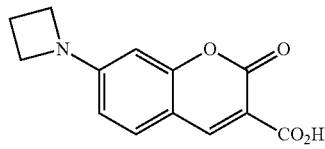 [SMILES: O=C(O)c1cc2ccc(N3CCC3)cc2oc1=O]

Ethyl 7-(azetidin-1-yl)-2-oxo-2H-chromene-3-carboxylate (Example 50; 65 mg, 0.238 mmol) was taken up in 1:1 THF/MeOH (8 mL), and 1 M NaOH (476 µL, 0.476 mmol, 2 eq) was added. The reaction was stirred at room temperature for 3 h. It was then acidified with 1 M HCl (500 µL), and the resulting yellow suspension was filtered. The filter cake was washed (water, EtOAc) and dried to provide the title compound (47 mg, 81%) as a bright yellow solid. $^1$H NMR (DMSO-d$_6$, 400 MHz) δ 12.52 (s, 1H), 8.59 (s, 1H), 7.64 (d, J=8.7 Hz, 1H), 6.42 (dd, J=8.7, 2.2 Hz, 1H), 6.23 (d, J=1.9 Hz, 1H), 4.10-4.01 (m, 4H), 2.39 (p, J=7.4 Hz, 2H); $^{13}$C NMR (DMSO-d$_6$, 101 MHz) δ 164.4 (C), 159.1 (C), 157.4 (C), 155.1 (C), 149.7 (CH), 131.7 (CH), 108.7 (CH), 108.0 (C), 107.6 (C), 94.7 (CH), 51.2 (CH$_2$), 15.6 (CH$_2$); Analytical HPLC: >99% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; detection at 400 nm); HRMS (ESI) calcd for $C_{13}H_{12}NO_4$ [M+H]$^+$ 246.0761, found 246.0770.

Example 52. N-(4-(((2-Amino-9H-purin-6-yl)oxy)methyl)benzyl)-7-(azetidin-1-yl)-2-oxo-2H-chromene-3-carboxamide

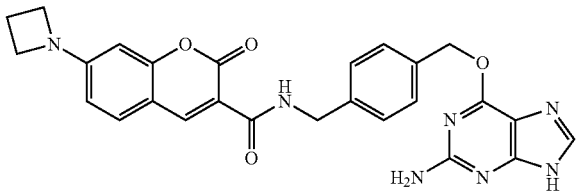 [SMILES: Nc1nc(OCc2ccc(CNC(=O)c3cc4ccc(N5CCC5)cc4oc3=O)cc2)c2nc[nH]c2n1]

7-(Azetidin-1-yl)-2-oxo-2H-chromene-3-carboxylic acid (Example 51; 6.0 mg, 24.5 µmol) was combined with TSTU (11.0 mg, 36.7 µmol, 1.5 eq) in DMF (1 mL). After adding DIEA (21.3 µL, 122 µmol, 5 eq), the reaction was stirred at room temperature for 1 h while shielded from light. 6-((4-(Aminomethyl)benzyl)oxy)-9H-purin-2-amine ("BG—NH$_2$," 9.9 mg, 36.7 µmol, 1.5 eq) was then added. The reaction was stirred an additional 2 h at room temperature. Purification of the crude reaction mixture by reverse phase HPLC (10-75% MeCN/H$_2$O, linear gradient, with constant 0.1% v/v TFA additive) afforded 11.5 mg (77%, TFA salt) of the title compound as a yellow solid. $^1$H NMR (MeOD, 400 MHz) δ 8.65 (s, 1H), 8.31 (s, 1H), 7.57-7.50 (m, 3H), 7.41 (d, J=8.1 Hz, 2H), 6.45 (dd, J=8.7, 2.1 Hz, 1H), 6.22 (d, J=2.0 Hz, 1H), 5.64 (s, 2H), 4.62 (s, 2H), 4.15-4.06 (m, 4H), 2.48 (p, J=7.4 Hz, 2H); $^{19}$F NMR (MeOD, 376 MHz) δ-75.44 (s); Analytical HPLC: >99% purity (4.6 mm×150 mm 5 µm C18 column; 5 µL injection; 10-95% CH$_3$CN/H$_2$O, linear gradient, with constant 0.1% v/v TFA additive; 20 min run; 1 mL/min flow; ESI; positive ion mode; detection at 400 nm); HRMS (ESI) calcd for C$_{26}$H$_{24}$N$_7$O$_4$ [M+H]$^+$ 498.1884, found 498.1891.

Example 53. Methyl 2-(7-(azetidin-1-yl)-4-methyl-2-oxo-2H-chromen-3-yl)acetate

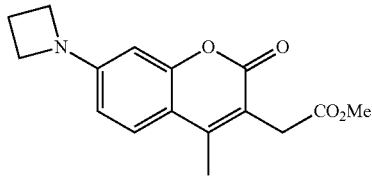 [SMILES: COC(=O)Cc1c(C)c2ccc(N3CCC3)cc2oc1=O]

Step 1: Methyl 7-hydroxy-4-methylcoumarin-3-acetate (1.00 g, 4.03 mmol; from Franzini, R. M.; Kool, E. T. *Chembiochem* 2008, 9, 2981), N-phenyl-bis(trifluoromethanesulfonimide) (1.58 g, 4.43 mmol, 1.1 eq), and DIEA (912 µL, 5.24 mmol, 1.3 eq) were combined in MeCN (20 mL) and stirred at room temperature for 18 h. The reaction mixture was concentrated to dryness, and the resulting residue was purified by flash chromatography on silica gel (0-50% EtOAc/hexanes, linear gradient) to afford methyl 2-(4-methyl-2-oxo-7-(((trifluoromethyl)sulfonyl)oxy)-2H-chromen-3-yl)acetate (1.41 g, 92%) as an off-white solid. $^1$H NMR (CDCl$_3$, 400 MHz) δ 7.73 (d, J=8.8 Hz, 1H), 7.29 (d, J=2.4 Hz, 1H), 7.26 (dd, J=8.8, 2.5 Hz, 1H), 3.76 (s, 2H), 3.73 (s, 3H), 2.44 (s, 3H); $^{19}$F NMR (CDCl$_3$, 376 MHz) δ-73.08 (s); $^{13}$C NMR (CDCl$_3$, 101 MHz) δ 170.2 (C), 160.4 (C), 153.0 (C), 150.5 (C), 147.9 (C), 126.7 (CH), 121.0 (C), 120.5 (C), 118.8 (q, $^1J_{CF}$=321.0 Hz, CF$_3$), 117.6 (CH), 110.5 (CH), 52.6 (CH$_3$), 33.0 (CH$_2$), 15.7 (CH$_3$); HRMS (ESI) calcd for C$_{14}$H$_{11}$F$_3$O$_7$SNa [M+Na]$^+$ 403.0070, found 403.0081.

Step 2: A vial was charged with the triflate from Step 1 (300 mg, 0.789 mmol), RuPhos-G3-palladacycle (33 mg, 0.039 mmol, 0.05 eq), RuPhos (18 mg, 0.039 mmol, 0.05 eq), and K$_2$CO$_3$ (153 mg, 1.10 mmol, 1.4 eq). The vial was sealed and evacuated/backfilled with nitrogen (3×). Dioxane (5 mL) was added, and the reaction was flushed again with nitrogen (3×). Following the addition of azetidine (58 µL, 0.868 mmol, 1.1 eq), the reaction was stirred at 80° C. for 4 h. It was then cooled to room temperature, diluted with CH$_2$Cl$_2$, deposited onto Celite, and concentrated to dryness. Purification by silica gel chromatography (0-50% EtOAc/hexanes, linear gradient, with constant 40% v/v CH$_2$Cl$_2$; dry load with Celite) afforded the title compound methyl 2-(7-(azetidin-1-yl)-4-methyl-2-oxo-2H-chromen-3-yl)acetate (210 mg, 93%) as a pale yellow solid. $^1$H NMR (CDCl$_3$, 400 MHz) δ 7.42 (d, J=8.7 Hz, 1H), 6.32 (dd, J=8.7, 2.3 Hz, 1H), 6.22 (d, J=2.3 Hz, 1H), 4.03-3.94 (m, 4H), 3.70 (s, 3H), 3.69 (s, 2H), 2.43 (p, J=7.3 Hz, 2H), 2.33 (s, 3H); $^{13}$C NMR (CDCl$_3$, 101 MHz) δ 171.4 (C), 162.4 (C), 154.6 (C), 153.7 (C), 149.8 (C), 125.7 (CH), 113.7 (C), 110.7 (C), 108.0 (CH), 97.0 (CH), 52.2 (CH$_3$), 51.9 (CH$_2$), 32.8 (CH$_2$), 16.6 (CH$_2$), 15.3 (CH$_3$); HRMS (ESI) calcd for C$_{16}$H$_{17}$NO$_4$Na [M+Na]$^+$ 310.1050, found 310.1068.

Example 54. Methyl 2-(7-(3,3-difluoroazetidin-1-yl)-4-methyl-2-oxo-2H-chromen-3-yl)acetate

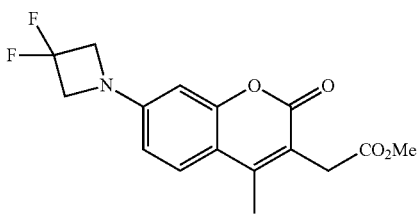 [SMILES: COC(=O)Cc1c(C)c2ccc(N3CC(F)(F)C3)cc2oc1=O]

A vial was charged with methyl 2-(4-methyl-2-oxo-7-(((trifluoromethyl)sulfonyl)oxy)-2H-chromen-3-yl)acetate (Example 53, Step 1; 240 mg, 0.631 mmol), RuPhos-G3-palladacycle (26 mg, 0.032 mmol, 0.05 eq), RuPhos (15 mg, 0.032 mmol, 0.05 eq), K$_2$CO$_3$ (218 mg, 1.58 mmol, 2.5 eq), and 3,3-difluoroazetidine hydrochloride (84 mg, 0.694 mmol, 1.1 eq). The vial was sealed and evacuated/backfilled with nitrogen (3×). Dioxane (4 mL) was added, and the reaction was flushed again with nitrogen (3×). The mixture was then stirred at 80° C. for 24 h. It was subsequently cooled to room temperature, diluted with CH$_2$Cl$_2$, deposited onto Celite, and concentrated to dryness. Purification by silica gel chromatography (0-40% EtOAc/hexanes, linear gradient, with constant 40% v/v CH$_2$Cl$_2$; dry load with Celite) afforded the title compound as an off-white solid (158 mg, 77%). $^1$H NMR (CDCl$_3$, 400 MHz) δ 7.50 (d, J=8.7 Hz, 1H), 6.41 (dd, J=8.7, 2.4 Hz, 1H), 6.34 (d, J=2.4 Hz, 1H), 4.32 (t, $^3J_{HF}$=11.7 Hz, 4H), 3.71 (s, 3H), 3.71 (s, 2H), 2.36 (s, 3H); $^{19}$F NMR (CDCl$_3$, 376 MHz) δ-100.14 (p, $^3J_{FH}$=11.6 Hz); $^{13}$C NMR (CDCl$_3$, 101 MHz) δ 171.1 (C), 161.9 (C), 154.3 (C), 151.5 (t, $^4J_{CF}$=3.2 Hz, C), 149.4 (C), 126.1 (CH), 115.5 (t, $^1J_{CF}$=274.6 Hz, CF$_2$), 115.4 (C), 112.3 (C), 109.0 (CH), 98.9 (CH), 63.3 (t, $^2J_{CF}$=26.8 Hz, CH$_2$), 52.3 (CH$_3$), 32.8 (CH$_2$), 15.4 (CH$_3$); HRMS (ESI) calcd for C$_{16}$H$_{15}$F$_2$NO$_4$Na [M+Na]$^+$ 346.0861, found 346.0872.

Example 55. 2-(7-(Azetidin-1-yl)-4-methyl-2-oxo-2H-chromen-3-yl)acetic acid

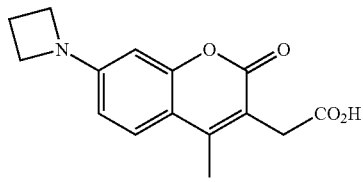 [SMILES: Cc1c(CC(=O)O)c(=O)oc2cc(N3CCC3)ccc12]

Methyl 2-(7-(azetidin-1-yl)-4-methyl-2-oxo-2H-chromen-3-yl)acetate (Example 53; 190 mg, 0.661 mmol) was dissolved in 1:1 THF/MeOH (8 mL), and 1 M NaOH (1.32 mL, 1.32 mmol, 2 eq) was added. After stirring the reaction at room temperature for 24 h, it was acidified with 1 M HCl (1.40 mL), diluted with water, and extracted with EtOAc (2×). The combined organic extracts were washed with brine, dried (MgSO$_4$), filtered, and concentrated in vacuo. The resulting residue was triturated with CH₂Cl₂/hexanes, filtered, and dried to provide 164 mg (91%) of the title compound as a pale yellow solid. ¹H NMR (DMSO-d₆, 400 MHz) δ 12.33 (s, 1H), 7.58 (d, J=8.8 Hz, 1H), 6.40 (dd, J=8.7, 2.3 Hz, 1H), 6.25 (d, J=2.3 Hz, 1H), 3.94 (t, J=7.3 Hz, 4H), 3.52 (s, 2H), 2.36 (p, J=7.3 Hz, 2H), 2.30 (s, 3H); ¹³C NMR (DMSO-d₆, 101 MHz) δ 171.8 (C), 161.2 (C), 153.7 (C), 153.4 (C), 149.5 (C), 126.2 (CH), 113.6 (C), 109.7 (C), 108.0 (CH), 96.1 (CH), 51.5 (CH₂), 32.5 (CH₂), 16.0 (CH₂), 14.9 (CH₃); Analytical HPLC: >99% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; detection at 350 nm); HRMS (ESI) calcd for C₁₅H₁₅NO₄Na [M+Na]⁺ 296.0893, found 296.0909.

Example 56. 2-(7-(3,3-Difluoroazetidin-1-yl)-4-methyl-2-oxo-2H-chromen-3-yl)acetic acid

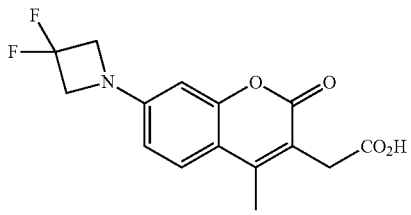 [SMILES: Cc1c(CC(=O)O)c(=O)oc2cc(N3CC(F)(F)C3)ccc12]

The procedure described for Example 55 was used to prepare the title compound from Example 54 (93%, white solid). ¹H NMR (DMSO-d₆, 400 MHz) δ 12.37 (s, 1H), 7.67 (d, J=8.7 Hz, 1H), 6.58 (dd, J=8.7, 2.4 Hz, 1H), 6.51 (d, J=2.3 Hz, 1H), 4.42 (t, ³J_HF=12.3 Hz, 4H), 3.55 (s, 2H), 2.33 (s, 3H); ¹⁹F NMR (DMSO-d₆, 376 MHz) δ-98.45 (p, ³J_HF=12.4 Hz); ¹³C NMR (DMSO-d₆, 101 MHz) δ 171.7 (C), 161.0 (C), 153.3 (C), 151.7 (t, ⁴J_CF=3.2 Hz, C), 149.3 (C), 126.4 (CH), 116.4 (t, ¹J_CF=272.9 Hz, CF₂), 115.1 (C), 111.3 (C), 109.6 (CH), 98.6 (CH), 62.8 (t, ²J_CF=26.1 Hz, CH₂), 32.6 (CH₂), 14.9 (CH₃); Analytical HPLC: >99% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; detection at 350 nm); HRMS (ESI) calcd for C₁₅H₁₃F₂NO₄Na [M+Na]⁺ 332.0705, found 332.0714.

Example 57. 2,5-Dioxopyrrolidin-1-yl 2-(7-(azetidin-1-yl)-4-methyl-2-oxo-2H-chromen-3-yl)acetate

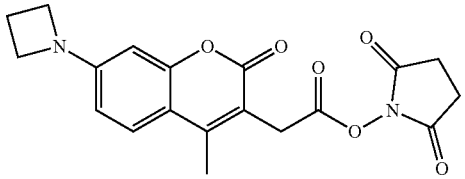 [SMILES: Cc1c(CC(=O)ON2C(=O)CCC2=O)c(=O)oc2cc(N3CCC3)ccc12]

To a solution of 2-(7-(azetidin-1-yl)-4-methyl-2-oxo-2H-chromen-3-yl)acetic acid (Example 55; 75 mg, 0.274 mmol) and TSTU (124 mg, 0.412 mmol, 1.5 eq) in DMF (4 mL) was added DIEA (96 μL, 0.549 mmol, 2 eq). The reaction was stirred at room temperature for 4 h. It was subsequently diluted with 10% w/v citric acid and extracted with EtOAc (2Δ). The combined organic extracts were washed with water and brine, dried (MgSO₄), filtered, and concentrated in vacuo. Silica gel chromatography (0-50% EtOAc/CH₂Cl₂, linear gradient) yielded 84 mg (83%) of the title compound as a pale yellow solid. ¹H NMR (CDCl₃, 400 MHz) δ 7.43 (d, J=8.7 Hz, 1H), 6.31 (dd, J=8.7, 2.3 Hz, 1H), 6.21 (d, J=2.3 Hz, 1H), 4.02 (s, 2H), 4.02-3.96 (m, 4H), 2.81 (s, 4H), 2.44 (p, J=7.3 Hz, 2H), 2.38 (s, 3H); ¹³C NMR (CDCl₃, 101 MHz) δ 169.0 (C), 166.4 (C), 162.0 (C), 154.7 (C), 154.0 (C), 151.3 (C), 125.9 (CH), 111.2 (C), 110.3 (C), 108.1 (CH), 96.9 (CH), 51.8 (CH₂), 29.8 (CH₂), 25.7 (CH₂), 16.6 (CH₂), 15.5 (CH₃); HRMS (ESI) calcd for C₁₉H₁₈N₂O₆Na [M+Na]⁺ 393.1057, found 393.1065.

Example 58. 2,5-Dioxopyrrolidin-1-yl 2-(7-(3,3-difluoroazetidin-1-yl)-4-methyl-2-oxo-2H-chromen-3-yl)acetate

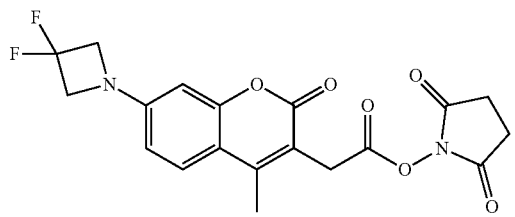 [SMILES: Cc1c(CC(=O)ON2C(=O)CCC2=O)c(=O)oc2cc(N3CC(F)(F)C3)ccc12]

The procedure described for Example 57 was used to prepare the title compound from Example 56 (82%, white solid). ¹H NMR (DMSO-d₆, 400 MHz) δ 7.71 (d, J=8.8 Hz, 1H), 6.59 (dd, J=8.7, 2.4 Hz, 1H), 6.53 (d, J=2.3 Hz, 1H), 4.43 (t, ³J_HF=12.3 Hz, 4H), 4.03 (s, 2H), 2.79 (s, 4H), 2.40 (s, 3H); ¹⁹F NMR (DMSO-d₆, 376 MHz) δ-98.49 (p, ³J_FH=12.3 Hz); ¹³C NMR (DMSO-d₆, 101 MHz) δ 170.0 (C), 166.5 (C), 160.6 (C), 153.5 (C), 152.1 (t, ⁴J_CF=3.2 Hz, C), 151.2 (C), 126.7 (CH), 116.4 (t, ¹J_CF=272.8 Hz, CF₂), 112.1 (C), 110.9 (C), 109.8 (CH), 98.5 (CH), 62.8 (t, ²J_CF=26.2 Hz, CH₂), 29.5 (CH₂), 25.4 (CH₂), 15.1 (CH₃); HRMS (ESI) calcd for C₁₉H₁₆F₂N₂O₆Na [M+Na]⁺ 429.0869, found 429.0876.

Example 59. 2-(6-(Azetidin-1-yl)-3-oxo-3H-xanthen-9-yl)benzoic acid

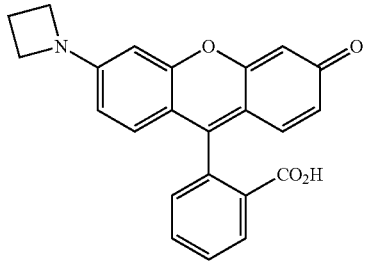 [SMILES: O=C(O)c1ccccc1-c1c2ccc(=O)cc-2oc2cc(N3CCC3)ccc12]

Step 1: A vial was charged with fluorescein ditriflate (500 mg, 0.838 mmol), Pd₂dba₃ (38 mg, 0.042 mmol, 0.05 eq), XPhos (60 mg, 0.126 mmol, 0.15 eq), and Cs₂CO₃ (382 mg, 1.17 mmol, 1.4 eq). The vial was sealed and evacuated/backfilled with nitrogen (3Δ). Dioxane (4 mL) was added, and the reaction was flushed again with nitrogen (3×). Following the addition of azetidine (57 μL, 0.838 mmol, 1 eq), the reaction was stirred at 80° C. for 2 h. It was then cooled to room temperature, deposited onto Celite, and concentrated to dryness. Purification by silica gel chromatography (0-35% EtOAc/hexanes, linear gradient; dry load with Celite) afforded 3'-(azetidin-1-yl)-3-oxo-3H-spiro[isobenzofuran-1,9'-xanthen]-6'-yltrifluoromethanesulfonate (125 mg, 30%) as an off-white solid. MS (ESI) calcd for $C_{24}H_{17}F_3NO_6S$ [M+H]$^+$ 504.1, found 504.2.

Step 2: The product of Step 1 (72 mg, 0.143 mmol) was taken up in 1:1 THF/MeOH (5 mL), and 1 M NaOH (286 μL, 0.286 mmol, 2 eq) was added. After stirring the reaction at room temperature for 6 h, the reaction was concentrated to dryness. The residue was purified by reverse phase HPLC (10-95% MeCN/H$_2$O, linear gradient, with constant 0.1% v/v TFA additive) to yield 40 mg (58%) of the title compound 2-(6-(azetidin-1-yl)-3-oxo-3H-xanthen-9-yl)benzoic acid as a bright orange solid. $^1$H NMR (MeOD, 400 MHz) δ 8.36-8.30 (m, 1H), 7.85 (td, J=7.5, 1.5 Hz, 1H), 7.81 (td, J=7.6, 1.5 Hz, 1H), 7.43-7.38 (m, 1H), 7.16 (d, J=9.3 Hz, 1H), 7.15 (d, J=9.0 Hz, 1H), 7.08 (d, J=2.3 Hz, 1H), 6.93 (dd, J=9.0, 2.3 Hz, 1H), 6.74 (dd, J=9.3, 2.2 Hz, 1H), 6.64 (d, J=2.2 Hz, 1H), 4.44-4.35 (m, 4H), 2.58 (p, J=7.7 Hz, 2H); $^{13}$C NMR (MeOD, 101 MHz) δ 168.4 (C), 168.0 (C), 161.0 (C), 159.9 (C), 159.1 (C), 157.9 (C), 135.7 (C), 134.0 (CH), 133.1 (CH), 132.42 (CH), 132.40 (CH), 132.1 (C), 131.7 (CH), 131.2 (CH), 118.0 (CH), 117.1 (C), 116.4 (C), 115.9 (CH), 103.3 (CH), 95.1 (CH), 53.4 (CH$_2$), 16.7 (CH$_2$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 500 nm); HRMS (ESI) calcd for $C_{23}H_{18}NO_4$ [M+H]$^+$ 372.1230, found 372.1230.

Example 60. 3,6-Di(azetidin-1-yl)acridine

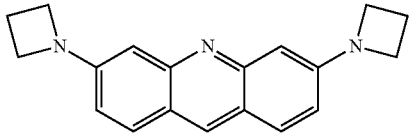 [SMILES: c1cc2cc3ccc(N4CCC4)cc3nc2cc1N1CCC1]

Step 1: Proflavine hydrochloride (250 mg, 1.02 mmol) was suspended in water (1 mL) in a microwave vial, and concentrated H$_2$SO$_4$ (450 μL) was added. The sealed mixture was heated in a microwave at 195° C. for 8 h. The brown suspension was diluted with water and filtered; the resulting filter cake was washed with water and dried to provide crude 3,6-dihydroxyacridine as a red-brown solid (260 mg). The 3,6-dihydroxyacridine (260 mg, 1.23 mmol) was then suspended in CH$_2$Cl$_2$ (5 mL). Pyridine (796 μL, 9.85 mmol, 8 eq) and trifluoromethanesulfonic anhydride (828 μL, 4.92 mmol, 4 eq) were added, and the reaction was stirred at room temperature for 2 h. It was subsequently diluted with water and extracted with CH$_2$Cl$_2$ (2×). The combined organic extracts were dried (MgSO$_4$), filtered, and concentrated in vacuo. Purification by flash chromatography on silica gel (0-30% EtOAc/hexanes, linear gradient) afforded 303 mg (63%, 2 steps) of acridine-3,6-diyl bis(trifluoromethanesulfonate) as an off-white solid. $^1$H NMR (CDCl$_3$, 400 MHz) δ 8.93 (s, 1H), 8.19-8.13 (m, 4H), 7.54 (dd, J=9.2, 2.4 Hz, 2H); $^{19}$F NMR (CDCl$_3$, 376 MHz) δ-73.10 (s); $^{13}$C NMR (CDCl$_3$, 101 MHz) δ 151.1 (C), 149.5 (C), 137.0 (CH), 131.2 (CH), 125.7 (C), 121.4 (CH), 120.8 (CH), 119.0 (q, $^1J_{CF}$=321.0 Hz, CF$_3$); HRMS (ESI) calcd for $C_{15}H_8F_6NO_6S_2$ [M+H]$^+$ 475.9692, found 475.9689.

Step 2: A vial was charged with the ditriflate from Step 1 (200 mg, 0.421 mmol), Pd(OAc)$_2$ (19 mg, 0.084 mmol, 0.2 eq), BINAP (79 mg, 0.126 mmol, 0.3 eq), and Cs$_2$CO$_3$ (384 mg, 1.18 mmol, 2.8 eq). The vial was sealed and evacuated/backfilled with nitrogen (3Δ). Toluene (2.5 mL) was added, and the reaction was flushed again with nitrogen (3Δ). Following the addition of azetidine (68 μL, 1.01 mmol, 2.4 eq), the reaction was stirred at 100° C. for 18 h. It was then cooled to room temperature, diluted with MeOH, deposited onto Celite, and concentrated to dryness. Purification by silica gel chromatography (0-10% MeOH (2 M NH$_3$)/CH$_2$Cl$_2$, linear gradient; dry load with Celite) afforded the title compound 3,6-di(azetidin-1-yl)acridine (89 mg, 73%) as a red-orange solid. $^1$H NMR (MeOD, 400 MHz) δ 8.44 (s, 1H), 7.74 (d, J=9.0 Hz, 2H), 6.78 (dd, J=9.0, 2.2 Hz, 2H), 6.57 (d, J=2.0 Hz, 2H), 4.08 (t, J=7.3 Hz, 8H), 2.47 (p, J=7.3 Hz, 4H); $^{13}$C NMR (MeOD, 101 MHz) δ 156.0 (C), 144.2 (CH), 143.1 (C), 132.6 (CH), 118.1 (C), 114.1 (CH), 91.4 (CH), 52.3 (CH$_2$), 17.0 (CH$_2$); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; detection at 500 nm); HRMS (ESI) calcd for $C_{19}H_{20}N_3$ [M+H]$^+$ 290.1652, found 290.1650.

Example 61. 3,7-Di(azetidin-1-yl)phenoxazin-5-ium trifluoroacetate

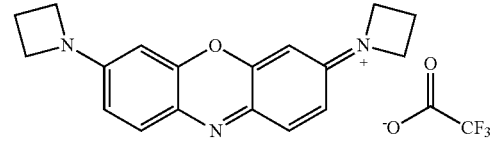

Step 1: Amplex Red (449 mg, 1.75 mmol) was taken up in CH$_2$Cl$_2$ (45 mL) and cooled to 0° C. Pyridine (1.14 mL, 14.0 mmol, 8.0 eq) and trifluoromethanesulfonic anhydride (1.17 mL, 6.98 mmol, 4.0 eq) were added, and the ice bath was removed. The reaction was stirred at room temperature for 3 h. It was subsequently diluted with water and extracted with CH$_2$Cl$_2$ (2×). The combined organic extracts were washed with brine, dried (MgSO$_4$), filtered, and concentrated in vacuo. Flash chromatography on silica gel (0-35% EtOAc/hexanes, linear gradient) afforded 836 mg (92%) of 10-acetyl-10H-phenoxazine-3,7-diyl bis(trifluoromethanesulfonate) as an off-white solid. $^1$H NMR (CDCl$_3$, 400 MHz) δ 7.58-7.54 (m, 2H), 7.14-7.09 (m, 4H), 2.35 (s, 3H); $^{19}$F NMR (CDCl$_3$, 376 MHz) δ-73.15 (s); $^{13}$C NMR (CDCl$_3$, 101 MHz) δ 168.9 (C), 151.0 (C), 147.4 (C), 129.1 (C), 126.3 (CH), 118.8 (q, $^1J_{CF}$=320.9 Hz, CF$_3$), 117.2 (CH), 111.1 (CH), 23.0 (CH$_3$); HRMS (ESI) calcd for $C_{16}H_{10}F_6NO_8S_2$ [M+H]$^+$ 521.9747, found 521.9748.

Step 2: A vial was charged with the ditriflate from Step 1 (150 mg, 0.288 mmol), Pd$_2$dba$_3$ (26 mg, 0.029 mmol, 0.1 eq), XPhos (41 mg, 0.086 mmol, 0.3 eq), and Cs$_2$CO$_3$ (262 mg, 0.806 mmol, 2.8 eq). The vial was sealed and evacuated/backfilled with nitrogen (3×). Dioxane (4 mL) was added, and the reaction was flushed again with nitrogen (3×). Following the addition of azetidine (47 μL, 0.691 mmol, 2.4 eq), the reaction was stirred at 80° C. for 4 h. It was then cooled to room temperature, deposited onto Celite, and concentrated to dryness. Purification by silica gel chromatography (5-50% EtOAc/hexanes, linear gradient; dry load with Celite) afforded 1-(3,7-di(azetidin-1-yl)-10H-phenoxazin-10-yl)ethanone (91 mg, 94%) as a colorless solid. MS (ESI) calcd for $C_{20}H_{22}N_3O_2$ $[M+H]^+$ 336.2, found 336.2.

Step 3: The intermediate from Step 2 (63 mg, 0.189 mmol) was taken up in a mixture of $CH_2Cl_2$ (11.7 mL) and water (1.3 mL) and cooled to 0° C. DDQ (47 mg, 0.207 mmol, 1.1 eq) was added, and the reaction was stirred at room temperature for 2.5 h. A second portion of DDQ (21 mg, 0.094 mmol, 0.5 eq) was added, and the reaction was stirred for an additional 30 min. The mixture was evaporated, redissolved in MeCN, deposited onto Celite, and concentrated to dryness. Silica gel chromatography (0-15% MeOH/$CH_2Cl_2$, linear gradient, with constant 1% v/v AcOH additive; dry load with Celite) followed by reverse phase HPLC (10-95% MeCN/$H_2O$, linear gradient, with constant 0.1% v/v TFA additive) afforded 38 mg (50%) of the title compound 3,7-di(azetidin-1-yl)phenoxazin-5-ium trifluoroacetate as a deep blue solid. $^1$H NMR (MeOD, 400 MHz) δ 7.72 (d, J=9.3 Hz, 2H), 6.92 (dd, J=9.3, 2.4 Hz, 2H), 6.50 (d, J=2.4 Hz, 2H), 4.43 (t, J=7.7 Hz, 8H), 2.60 (p, J=7.7 Hz, 4H); $^{19}$F NMR (MeOD, 376 MHz) δ-75.45 (s); $^{13}$C NMR (MeOD, 101 MHz) δ 158.0 (C), 150.3 (C), 135.4 (CH), 135.3 (C), 116.4 (CH), 95.1 (CH), 53.7 ($CH_2$), 16.6 ($CH_2$); Analytical HPLC: >99% purity (4.6 mm×150 mm 5 μm C18 column; 5 μL injection; 10-95% $CH_3CN/H_2O$, linear gradient, with constant 0.1% v/v TFA additive; 20 min run; 1 mL/min flow; ESI; positive ion mode; detection at 650 nm); HRMS (ESI) calcd for $C_{18}H_{18}N_3O$ $[M]^+$ 292.1444, found 292.1439.

Throughout this document, various references are mentioned. All such references are incorporated herein by reference, including the references set forth in the following list:

REFERENCES

1 Kremers, G.-J., Gilbert, S. G., Cranfill, P. J., Davidson, M. W. & Piston, D. W. Fluorescent proteins at a glance. *J. Cell Sci.* 124, 157-160, (2011).
2 Xia, T., Li, N. & Fang, X. Single-molecule fluorescence imaging in living cells. *Ann. Review Phys. Chem.* 64, 459-480, (2013).
3 Gautier, A. et al. An engineered protein tag for multiprotein labeling in living cells. *Chem. Biol.* 15, 128-136, (2008).
4 Los, G. V. et al. HaloTag: A novel protein labeling technology for cell imaging and protein analysis. *ACS Chem. Biol.* 3, 373-382, (2008).
5 Encell, L. P. et al. Development of a dehalogenase-based protein fusion tag capable of rapid, selective and covalent attachment to customizable ligands. *Curr. Chem. Genomics* 6, (Suppl 1-M7) 55-71, (2012).
6 Wombacher, R. et al. Live-cell super-resolution imaging with trimethoprim conjugates. *Nat. Methods* 7, 717-719, (2010).
7 Zhao, Z. W. et al. Spatial organization of RNA polymerase II inside a mammalian cell nucleus revealed by reflected light-sheet super-resolution microscopy. *Proc. Natl. Acad. Sci. U.S.A.* 111, 681-686, (2014).
8 Abrahamsson, S. et al. Fast multicolor 3D imaging using aberration-corrected multifocus microscopy. *Nat. Methods* 10, 60-63, (2013).
9 Chen, J. et al. Single-molecule dynamics of enhanceosome assembly in embryonic stem cells. *Cell* 156, 1274-1285, (2014).
10 Beija, M., Afonso, C. A. M. & Martinho, J. M. G. Synthesis and applications of rhodamine derivatives as fluorescent probes. *Chem. Soc. Rev.* 38, 2410-2433, (2009).
11 Lavis, L. D. & Raines, R. T. Bright building blocks for chemical biology. *ACS Chem. Biol.* 9, 855-866 (2014).
12 Grimm, J. B. et al. Carbofluoresceins and carborhodamines as scaffolds for high-contrast fluorogenic probes. *ACS Chem. Biol.* 8, 1303-1310, (2013).
13 Arden-Jacob, J., Frantzeskos, J., Kemnitzer, N. U., Zilles, A. & Drexhage, K. H. New fluorescent markers for the red region. *Spectrochim. Acta, Part A* 57, 2271-2283, (2001).
14 Koide, Y., Urano, Y., Hanaoka, K., Terai, T. & Nagano, T. Evolution of Group 14 rhodamines as platforms for near-infrared fluorescence probes utilizing photoinduced electron transfer. *ACS Chem. Biol.* 6, 600-608, (2011).
15 Lukinavičius, G. et al. A near-infrared fluorophore for live-cell super-resolution microscopy of cellular proteins. *Nature Chem.* 5, 132-139, (2013).
16 Watkins, R. W., Lavis, L. D., Kung, V. M., Los, G. V. & Raines, R. T. Fluorogenic affinity label for the facile, rapid imaging of proteins in live cells. *Org. Biomol. Chem.* 7, 3969-3975, (2009).
17 Panchuk-Voloshina, N. et al. Alexa Dyes, a series of new fluorescent dyes that yield exceptionally bright, photostable conjugates. *J. Histochem. Cytochem.* 47, 1179-1188, (1999).
18 Kolmakov, K. et al. Polar red-emitting rhodamine dyes with reactive groups: Synthesis, photophysical Properties, and two-color STED nanoscopy applications. *Chem. Eur. J.* 20, 146-157, (2013).
19 Grimm, J. B. & Lavis, L. D. Synthesis of rhodamines from fluoresceins using Pd-catalyzed C—N cross-coupling. *Org. Lett.* 13, 6354-6357, (2011).
20 Grabowski, Z. R., Rotkiewicz, K. & Rettig, W. Structural changes accompanying intramolecular electron transfer: Focus on twisted intramolecular charge-transfer states and structures. *Chem. Rev.* 103, 3899-4032, (2003).
21 Vogel, M., Rettig, W., Sens, R. & Drexhage, K. H. Structural relaxation of rhodamine dyes with different N-substitution patterns—study of fluorescence decay times and quantum yields. *Chem. Phys. Lett.* 147, 452-460, (1988).
22 Song, X., Johnson, A. & Foley, J. 7-Azabicyclo[2.2.1] heptane as a unique and effective dialkylamino auxochrome moiety: Demonstration in a fluorescent rhodamine dye. *J. Am. Chem. Soc* 130, 17652-17653, (2008).
23 Rozeboom, M. D., Houk, K., Searles, S. & Seyedrezai, S. E. Photoelectron spectroscopy of N-aryl cyclic amines. Variable conformations and relationships to gas- and solution-phase basicities. *J. Am. Chem. Soc.* 104, 3448-3453, (1982).
24 Karstens, T. & Kobs, K. Rhodamine B and rhodamine 101 as reference substances for fluorescence quantum yield measurements. *J. Phys. Chem.* 84, 1871-1872, (1980).
25 Cavallo, L., Moore, M. H., Corrie, J. E. T. & Fraternali, F. Quantum mechanics calculations on rhodamine dyes require inclusion of solvent water for accurate representation of the structure. *J. Phys. Chem. A* 108, 7744-7751, (2004).
26 Pearson, W. H., Lian, B. W. & Bergmeier, S. C. in *Comprehensive Heterocyclic Chemistry II* Vol. 1A (eds A. R. Katritzky, C. W. Rees, & E. F. V. Scriven) 1 (Elsevier, 1996).
27 Smith, S. A., Hand, K. E., Love, M. L., Hill, G. & Magers, D. H. Conventional strain energies of azetidine 27 and phosphetane: Can density functional theory yield reliable results? *J. Comp. Chem.* 34, 558-565, (2013).

28 Mütze, J. et al. Excitation spectra and brightness optimization of two-photon excited probes. *Biophys. J.* 102, 934-944, (2012).

29 Neklesa, T. K. et al. Small-molecule hydrophobic tagging-induced degradation of HaloTag fusion proteins. *Nat. Chem. Biol.* 7,538-543, (2011).

30 Zhang, Z., Revyakin, A., Grimm, J. B., Lavis, L. D. & Tjian, R. Single-molecule tracking of the transcription cycle by sub-second RNA detection. *eLife* 3, e01775, (2014).

31 Wu, B., Chao, J. A. & Singer, R. H. Fluorescence fluctuation spectroscopy enables quantitative imaging of single mRNAs in living cells. *Biophys. J.* 102, 2936-2944, (2012).

32 Mchedlov-Petrossyan, N., Vodolazkaya, N. & Doroshenko, A. Ionic equilibria of fluorophores in organized solutions: The influence of micellar microenvironment on protolytic and photophysical properties of rhodamine B. *J. Fluoresc.* 13, 235-248, (2003).

33 Bancaud, A. et al. Molecular crowding affects diffusion and binding of nuclear proteins in heterochromatin and reveals the fractal organization of chromatin. *EMBO J.* 28, 3785-3798, (2009).

34 Bancaud, A., Lavelle, C., Huet, S. & Ellenberg, J. A fractal model for nuclear organization: Current evidence and biological implications. *Nucleic Acids Res.* 40, 8783-8792, (2012).

35 Altman, R. B. et al. Cyanine fluorophore derivatives with enhanced photostability. *Nat. Methods* 9, 68-71, (2012).

36 Egawa, T.; Koide, Y.; Hanaoka, K.; Komatsu, T.; Terai, T.; Nagano, T. *Chem. Commun.* 2011, 47, 4162-4164.

37 Suzuki, K.; Kobayashi, A.; Kaneko, S.; Takehira, K.; Yoshihara, T.; Ishida, H.; Shiina, Y.; Oishi, S.; Tobita, S. *Phys. Chem. Chem. Phys.* 2009, 11, 9850-9860.

38 Akerboom, J.; Chen, T.-W.; Wardill, T. J.; Tian, L.; Marvin, J. S.; Mutlu, S.; Calderón, N. C.; Esposti, F.; Borghuis, B. G.; Sun, X. R. *J. Neurosci.* 2012, 32, 13819-13840.

39 Magde, D., Rojas, G. E. & Seybold, P. G. Solvent dependence of the fluorescence lifetimes of xanthene dyes. *Photochem. Photobiol.* 70, 737-744 (1999).

40 Lavis, L. D., Rutkoski, T. J. & Raines, R. T. Tuning the $pK_a$ of fluorescein to optimize binding assays. *Anal. Chem.* 79, 6775-6782 (2007).

41 Revyakin, A.; Zhang, Z.; Coleman, R. A.; Li, Y.; Inouye, C.; Lucas, J. K.; Park, S.-R.; Chu, S.; Tjian, R. *Genes Dev.* 2012, 26, 1691-1702.

42 Arnauld, S.; Nicolas, B.; Hervé, R.; Didier, M. *Nature Protocol Exchange* 2008, doi:10.1038/nprot.2008.128.

43 Griffin, B. A., Adams, S. R. & Tsien, R. Y. Specific covalent labeling of recombinant protein molecules inside live cells. *Science* 281, 269-272 (1998).

44 Keppler, A. et al. A general method for the covalent labeling of fusion proteins with small molecules in vivo. *Nat. Biotechnol.* 21, 86-89 (2002).

45 Hori, Y., Ueno, H., Mizukami, S. & Kikuchi, K. Photoactive yellow protein-based protein labeling system with turn-on fluorescence intensity. *J. Am. Chem. Soc.* 131, 16610-16611 (2009).

46 Uttamapinant, C. et al. A fluorophore ligase for site-specific protein labeling inside living cells. *Proc. Natl. Acad. Sci. U.S.A.* 107, 10914-10919 (2010).

47 Testa, I. et al. Multicolor fluorescence nanoscopy in fixed and living cells by exciting conventional fluorophores with a single wavelength. *Biophys. J.* 99, 2686-2694 (2010).

48 Mujumdar, R. B., Ernst, L. A., Mujumdar, S. R., Lewis, C. J. & Waggoner, A. S. Cyanine dye labeling reagents: Sulfoindocyanine succinimidyl esters. *Bioconjugate Chem.* 4, 105-111 (1993).

49 Haugland, R. P., Spence, M. T. Z., Johnson, I. D. & Basey, A. *The Handbook: A Guide to Fluorescent Probes and Labeling Technologies*, 10th ed., (Molecular Probes, 2005).

50 Bosch, P. J. et al. Evaluation of fluorophores to label SNAP-tag fused proteins for multicolor single-molecule tracking microscopy in live cells. *Biophys. J.* 107, 803-814 (2014).

51 Heilemann, M. et al. Subdiffraction-resolution fluorescence imaging with conventional fluorescent probes. *Angew. Chem. Int. Ed.* 47, 6172-6176 (2008).

52 Dempsey, G. T., Vaughan, J. C., Chen, K. H., Bates, M. & Zhuang, X. Evaluation of fluorophores for optimal performance in localization-based super-resolution imaging. *Nat. Methods* 8, 1027-1036 (2011).

53 Ha, T. & Tinnefeld, P. Photophysics of fluorescence probes for single molecule biophysics and super-resolution imaging. *Annu. Rev. Phys. Chem.* 63, 595-617 (2012).

54 Lukinavičius, G. et al. Fluorogenic probes for live-cell imaging of the cytoskeleton. *Nat. Methods* 11, 731-733 (2014).

55 Kubota, Y. & Steiner, R. F. Fluorescence decay and quantum yield characteristics of acridine orange and proflavine bound to DNA. *Biophys. Chem.* 6, 279-289 (1977).

56 Lee, L. G., Berry, G. M. & Chen, C.-H. Vita Blue: A new 633-nm excitable fluorescent dye for cell analysis. *Cytometry* 10, 151-164 (1989).

57 Speight, L. C. et al. Efficient synthesis and in vivo incorporation of acridon-2-ylalanine, a fluorescent amino acid for lifetime and Forster resonance energy transfer/luminescence resonance energy transfer studies. *J. Am. Chem. Soc.* 135, 18806-18814 (2013).

58 Mitronova, G. Y. et al. New fluorinated rhodamines for optical microscopy and nanoscopy. *Chem. Eur. J.* 16, 4477-4488 (2010).

59 Critchfield, F. E., Gibson Jr, J. A. & Hall, J. L. Dielectric constant for the dioxane-water system from 20 to 35°. *J. Am. Chem. Soc.* 75, 1991-1992 (1953).

60 Mütze, J. et al. Excitation spectra and brightness optimization of two-photon excited probes. *Biophys. J.* 102, 934-944 (2012).

61 Lavis, L. D. & Raines, R. T. Bright ideas for chemical biology. *ACS Chem. Biol.* 3, 142-155 (2008).

62 Köver, J. & Antus, S. Facile deoxygenation of hydroxylated flavonoids by palladium-catalysed reduction of its triflate derivatives. *Z. Naturforsch., B: J Chem. Sci.* 60, 792-796 (2005).

63 Urgaonkar, S. & Verkade, J. G. Palladium/proazaphosphatrane-catalyzed amination of aryl halides possessing a phenol, alcohol, acetanilide, amide or an enolizable ketone functional group: efficacy of lithium bis(trimethylsilyl)amide as the base. *Adv. Synth. Catal.* 346, 611-616 (2004).

64 Whitaker, J. E. et al. Fluorescent rhodol derivatives: Versatile, photostable labels and tracers. *Anal. Biochem.* 207, 267-279 (1992).

65 Sauers, R. R., Husain, S. N., Piechowski, A. P. & Bird, G. R. Shaping the absorption and fluorescence bands of a class of efficient, photoactive chromophores: synthesis and properties of some new 3H-xanthen-3-ones. *Dyes Pigments* 8, 35-53 (1987).

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound of the formula:

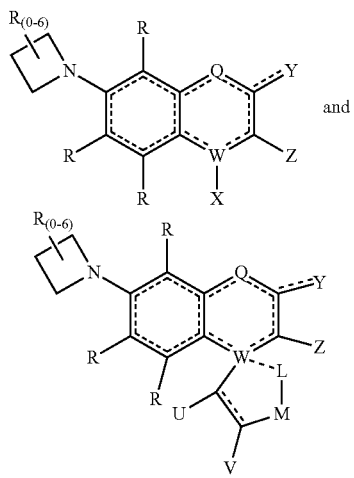

and wherein:
each R is independently selected from halogen, H, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, $SO_3H$, and alkyl, excluding $CH_3$, alkyl being optionally substituted with halogen, =O, OH, O(alkyl), O(aryl), SH, S(alkyl), S(aryl), $NH_2$, NHR, $NR_2$, $NO_2$, CHO, COO, COOH, C(O)$NR_2$, COO(alkyl), COO(aryl), $PO_3H_2$, and/or $SO_3H$;

Q is selected from $CR_2$, NR', O, $SiR_2$, and Se;
R' is independently selected from halogen, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, $SO_3H$, and alkyl, alkyl being optionally substituted with halogen, =O, OH, O(alkyl), O(aryl), SH, S(alkyl), S(aryl), $NH_2$, NHR, $NR_2$, $NO_2$, CHO, COO, COOH, C(O)$NR_2$, COO(alkyl), COO(aryl), $PO_3H_2$, and/or $SO_3H$;

W is selected from C and N;
X is selected from a lone pair of electrons, H, alkyl, aryl, halogen, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, and $SO_3H$, X being optionally substituted with halogen, =O, OH, O(alkyl), O(aryl), SH, S(alkyl), S(aryl), $NH_2$ NHR, $NR_2$, $NO_2$, CHO, COO, COOH, C(O)$NR_2$, COO(alkyl), COO (aryl), C(O)$NR_2$, $PO_3H_2$, and/or $SO_3H$;

M is selected from $CR_2$, C(O), $SO_2$, and $PO_2$;
L is selected from =O and OH, or wherein L is selected from O, S, NR, and C=$N_2$ when L and W are taken together with the atoms to which they are bonded to form form a substituted or unsubstituted 5-7 membered ring;
U and V are independently selected from H, alkyl, halogen, CN, OH, O(alkyl), O(aryl), SH, S(alkyl), S(aryl), amine, $NO_2$, CHO, COOH, C(O)$NR_2$, COO(alkyl), COO(aryl), $PO_3H_2$, and $SO_3H$, alkyl being optionally substituted with halogen, =O, OH, O(alkyl), O(aryl), SH, S(alkyl), S(aryl), $NH_2$, NHR, $NR_2$, $NO_2$, CHO, COO, COOH, C(O)$NR_2$, COO(alkyl), COO(aryl), $PO_3H_2$, and/or $SO_3H$, or wherein U and V, taken together with the atoms to which they are bonded, can form a substituted or unsubstituted 5-7 membered ring;
Y is selected from $CR_2$, C(O)$NR_2$, NR, O, and S; and
Z is selected from H, halogen, CN, OH, O(alkyl), O(aryl), SH, S(alkyl), S(aryl), amine, $NO_2$, CHO, COOH, C(O) $NR_2$, COO(alkyl), COO(aryl), $PO_3H_2$, $SO_3H$, aryl, and alkyl, alkyl and aryl being optionally substituted with halogen, OH, O(alkyl), O(aryl), SH, S(alkyl), S(aryl), $NH_2$, NHR, $NR_2$, $NO_2$, CHO, COOH, C(O)$NR_2$, COO (alkyl), COO(aryl), $PO_3H_2$, and $SO_3H$, or wherein Z and Y, taken together with the atoms to which they are bonded, can form a substituted or unsubstituted 5-7 membered ring.

2. The compound of claim 1, wherein Y and Z, taken together with the atoms to which they are bonded, form the 5-7 membered ring substituted with one or more substituents selected from halogen, CN, =O, OH, O(alkyl), O(aryl), SH, S(alkyl), S(aryl), $NH_2$, NHR, $NR_2$, $NO_2$, CHO, COOH, C(O)$NR_2$, COO(alkyl), COO(aryl), $PO_3H_2$, $SO_3H$, and alkyl.

3. The compound of claim 2, wherein Y and Z, taken together with the atoms to which they are bonded, form the 5-7 membered ring substituted with an unsubstituted or substituted azetidine group.

4. The compound of claim 1, of the following formula:

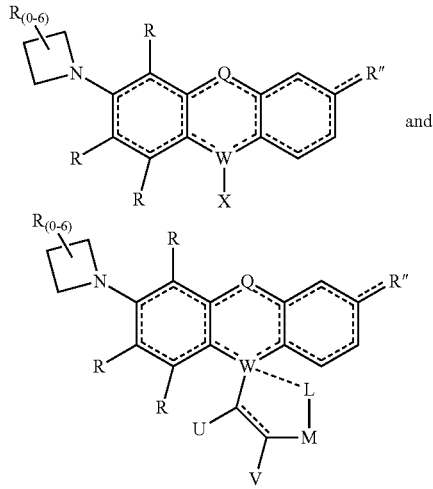

and wherein R" is selected from halogen, H, CN, OH, O(alkyl), O(aryl), SH, S(alkyl), S(aryl), $NH_2$, NHR, $NR_2$, $NO_2$, CHO, COOH, C(O)$NR_2$, COO(alkyl), COO (aryl), $PO_3H_2$, $SO_3H$, and alkyl, alkyl being optionally substituted with halogen, =O, OH, O(alkyl), O(aryl), SH, S(alkyl), S(aryl), —$NH_2$, NHR, $NR_2$, $NO_2$, CHO, COO, COOH, COO(alkyl), COO(aryl), $PO_3H_2$, and/or $SO_3H$.

5. The compound of claim 1, of the following formula:

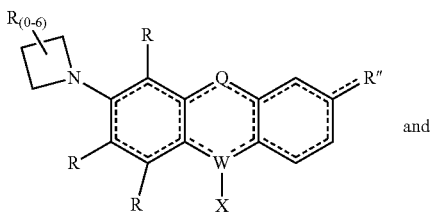

and

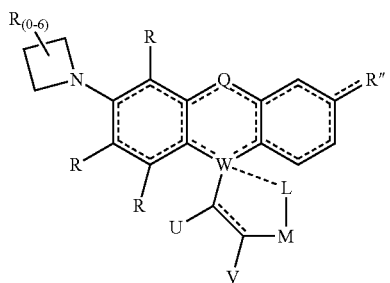

wherein R" is selected from an azetidine group that is unsubstituted or substituted with one or more of halogen, H, CN, OH, O(alkyl), O(aryl), SH, S(alkyl), S(aryl), amine, $NO_2$, CHO, COOH, $C(O)NR_2$, COO(alkyl), COO(aryl), $PO_3H_2$, $SO_3H$, and alkyl.

6. The compound of claim 1, of the formula:

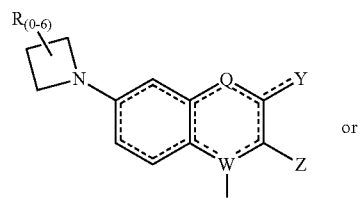

or

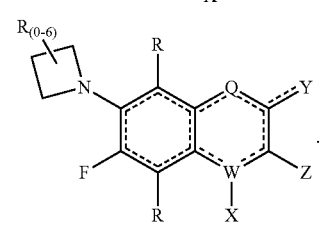

7. The compound of claim 1, of a formula selected from the group consisting of:

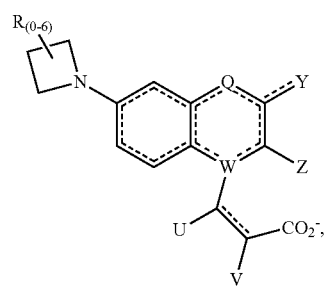

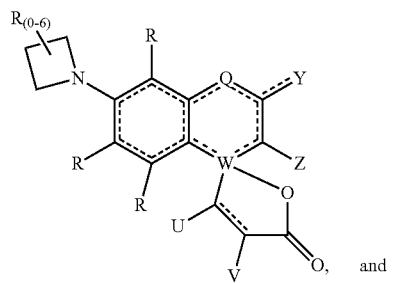

and

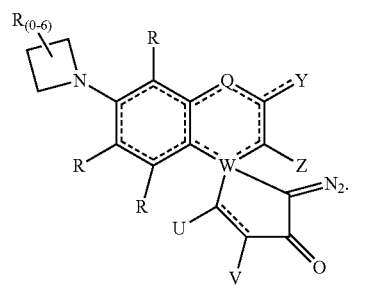

8. The compound of claim 1, wherein U and V, taken together with the atoms to which they are bonded, include a substituted aryl.

9. The compound of claim 1, according to a formula selected from the group consisting of:

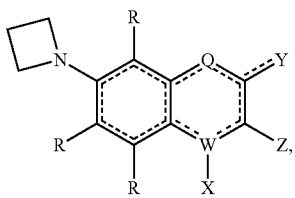

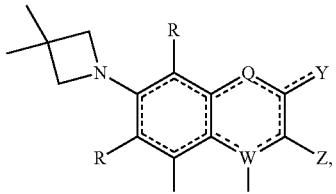

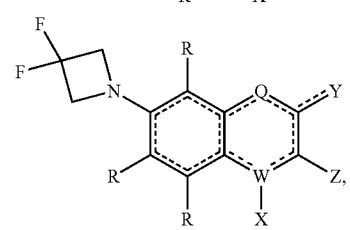

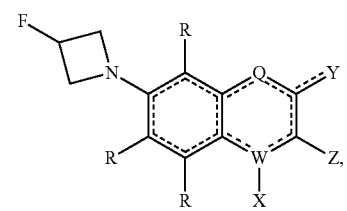

-continued
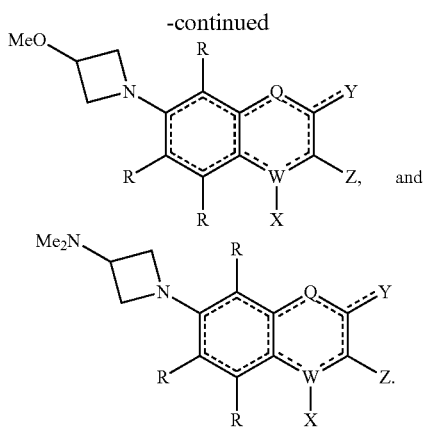
10. The compound of claim 1, wherein X is a substituted aryl.
11. The compound of claim 1, wherein X is selected from:
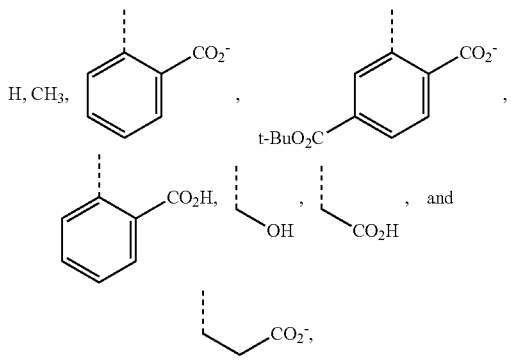
H, and a lone pair of electrons.
12. A compound according to a formula selected from:
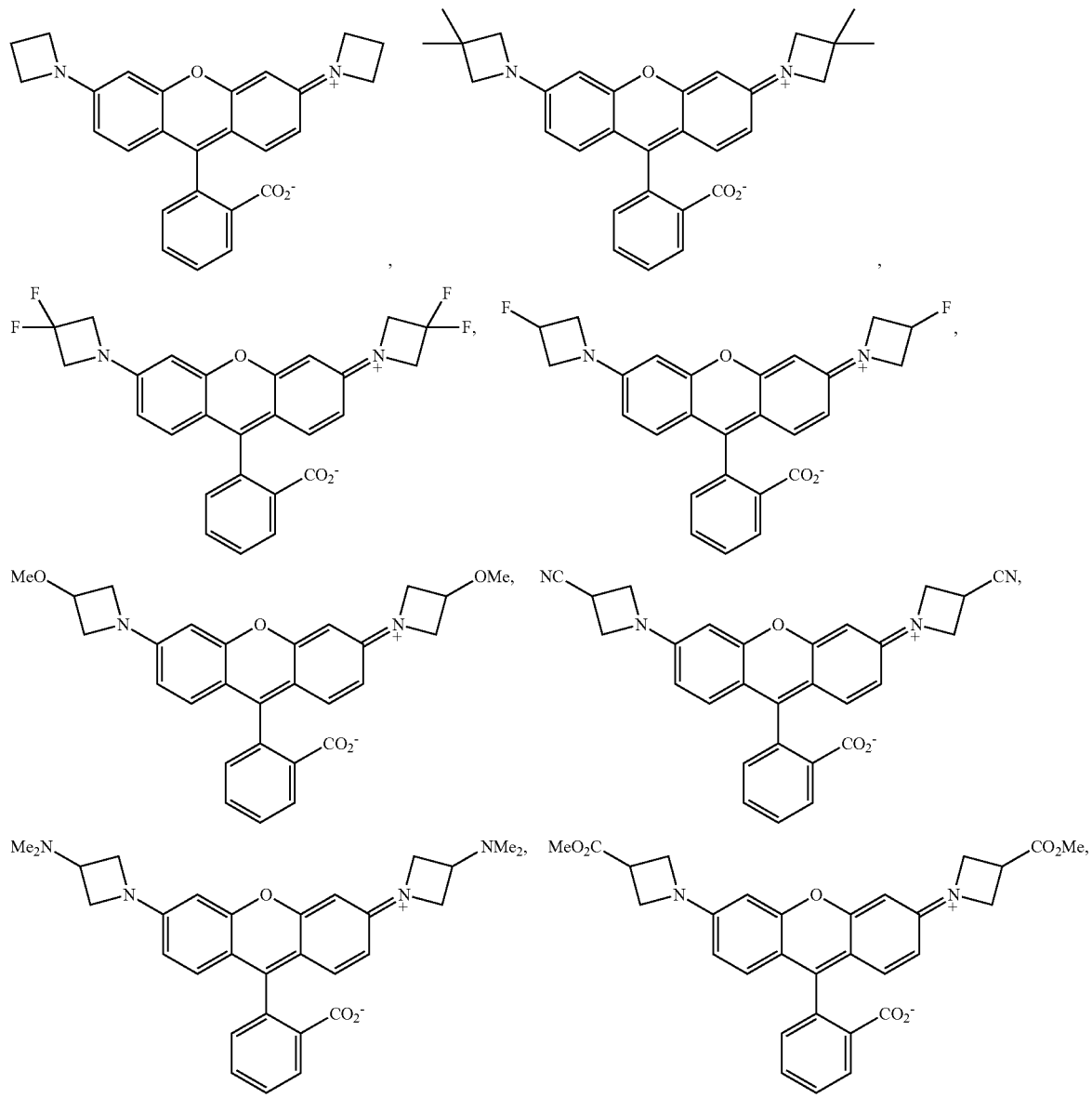

-continued
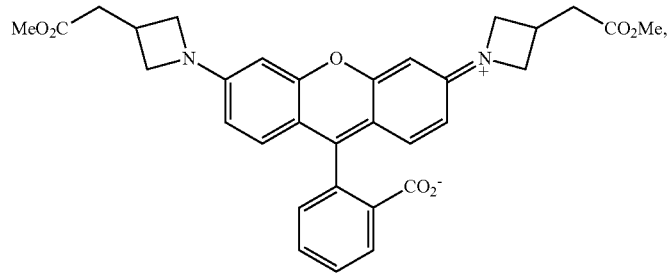
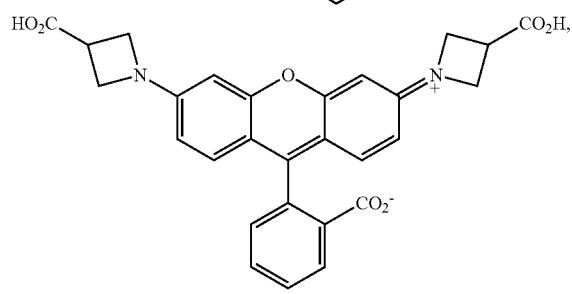
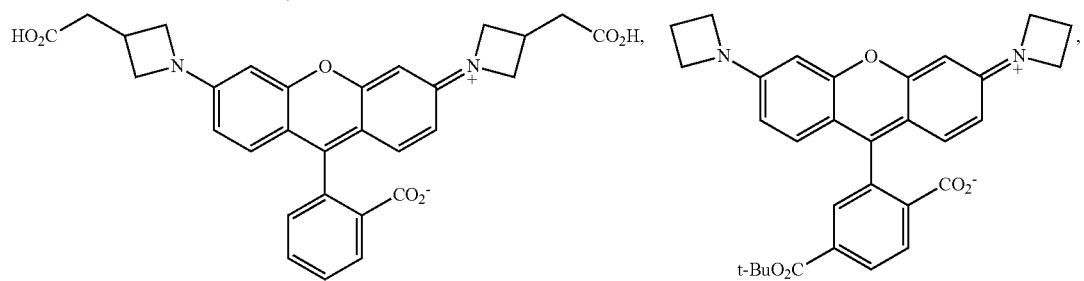
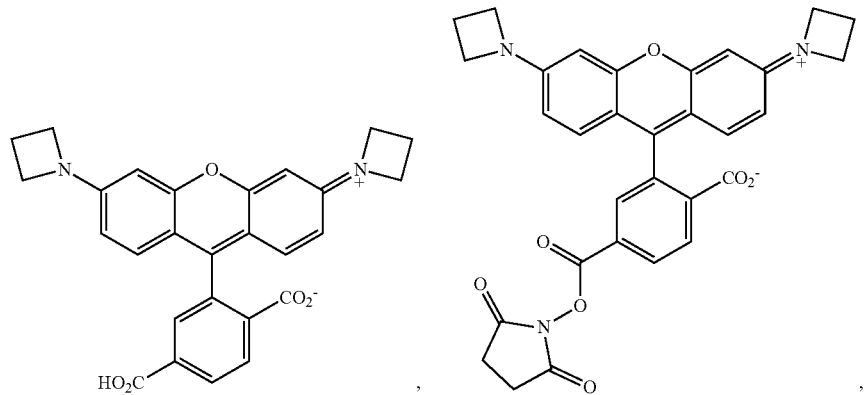
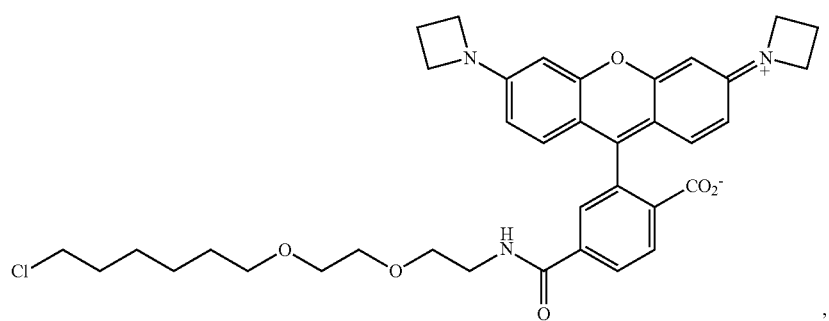

-continued
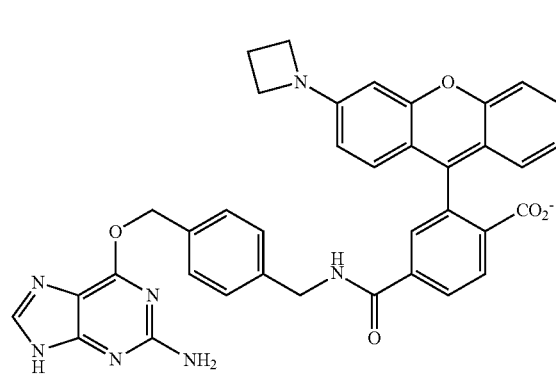
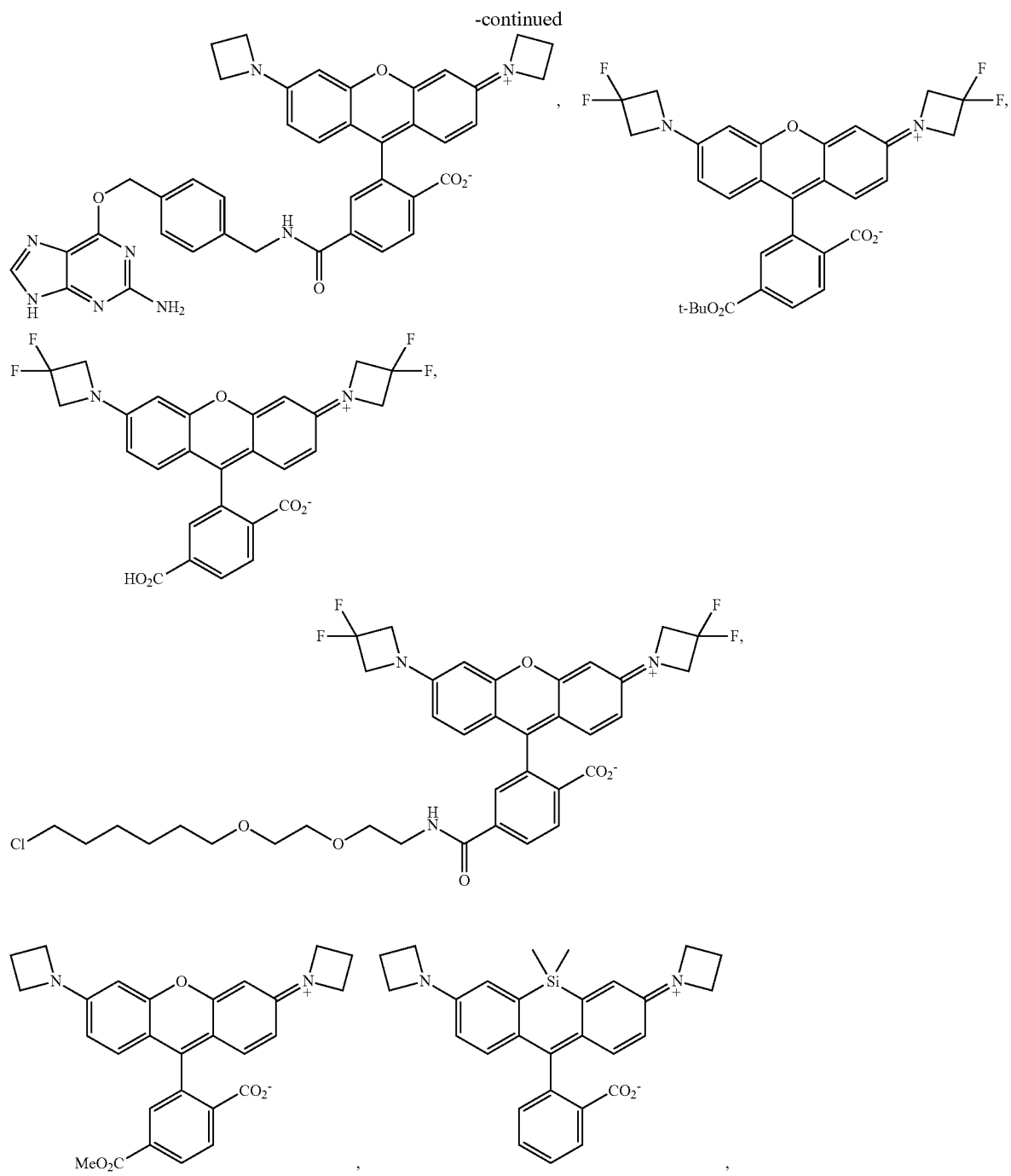
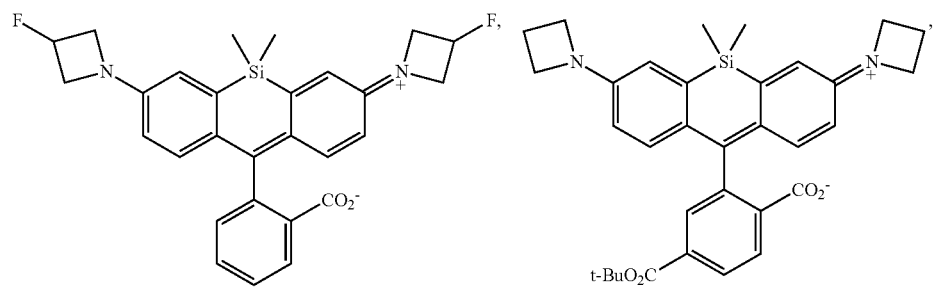

-continued
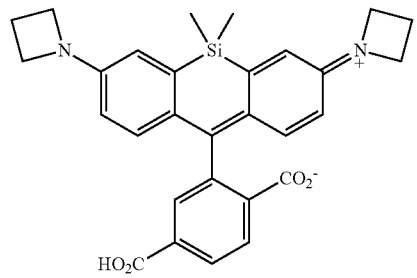
,
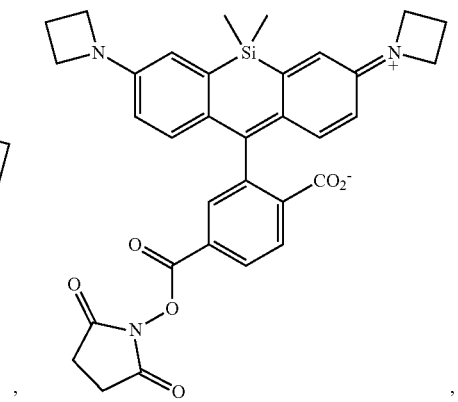
,
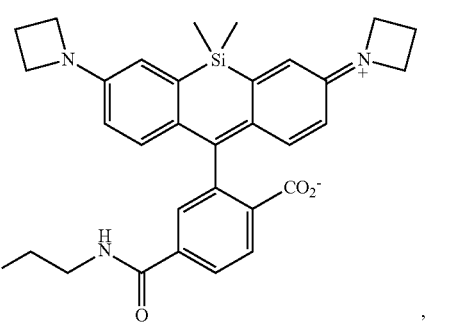
,
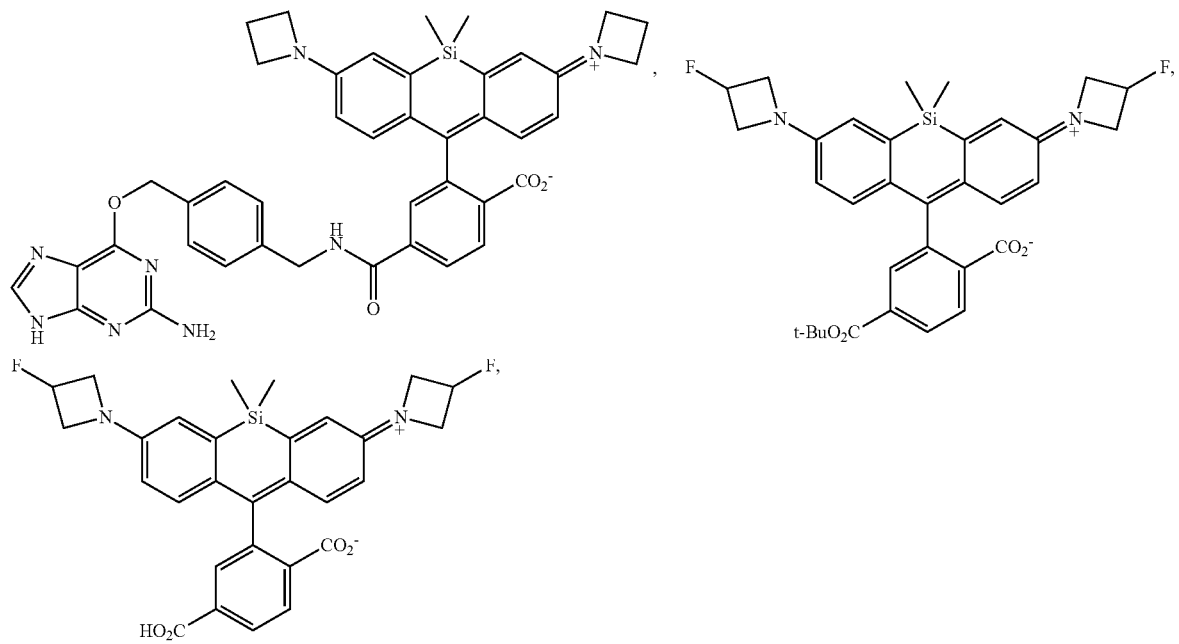
,
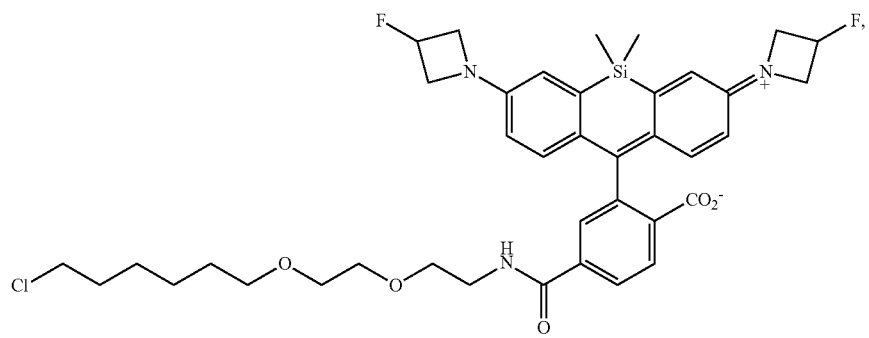

-continued
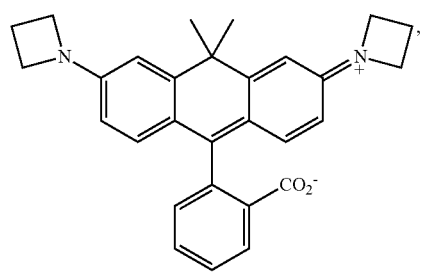
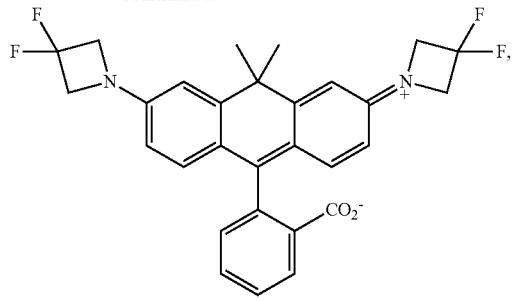
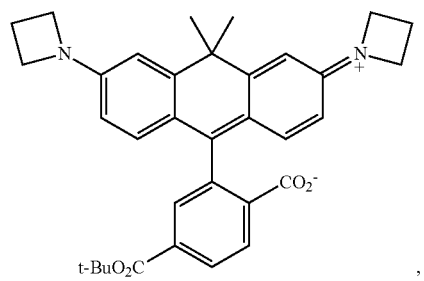
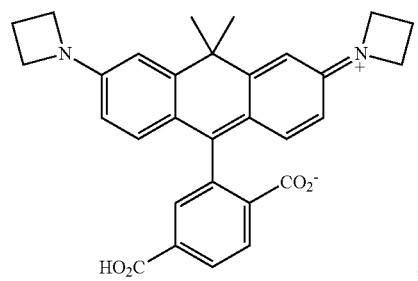
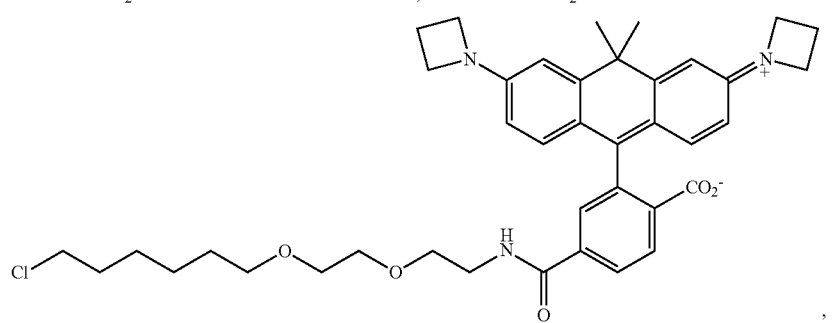
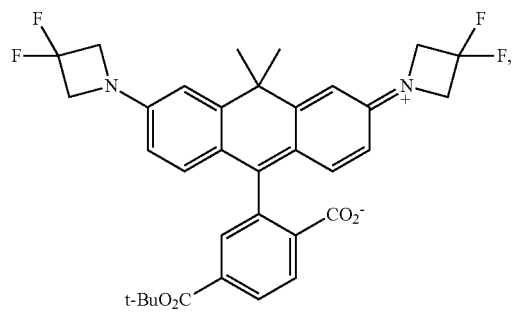
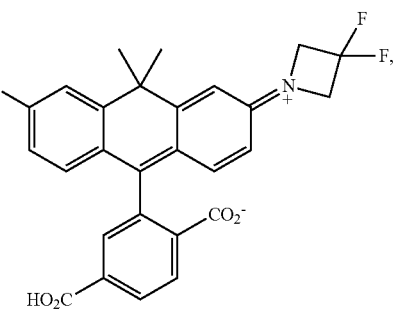
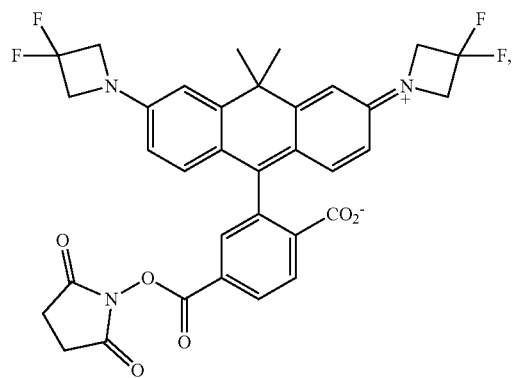

-continued
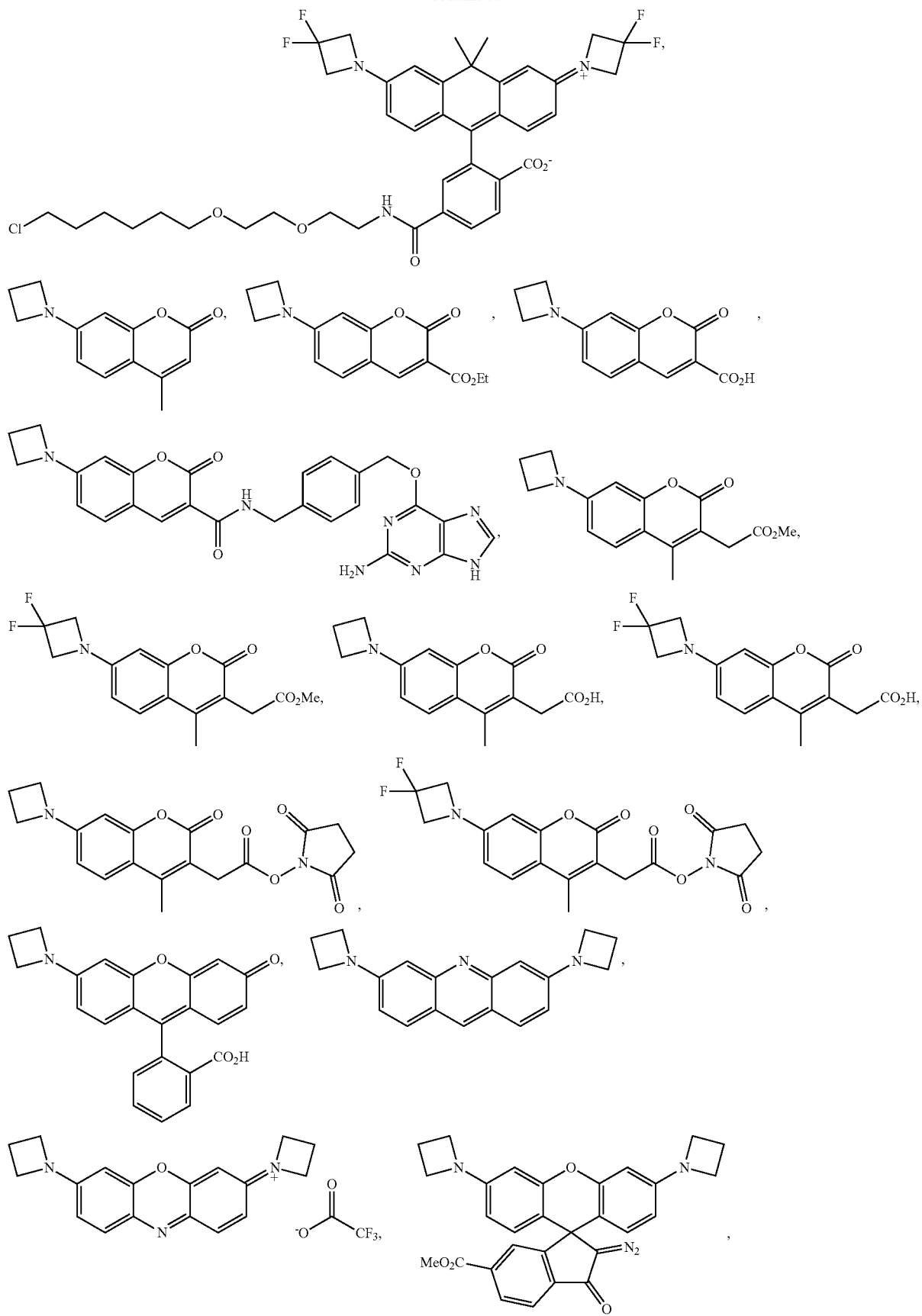

-continued
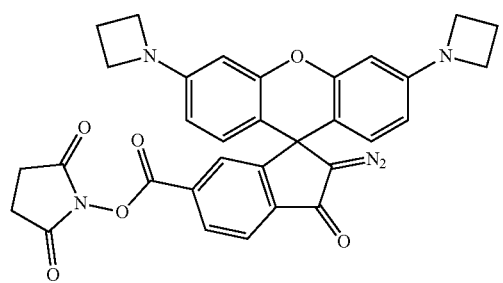
,
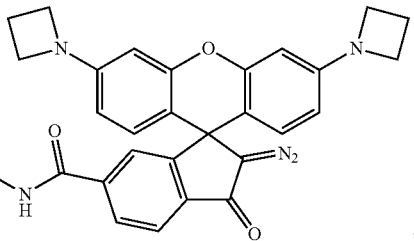
,
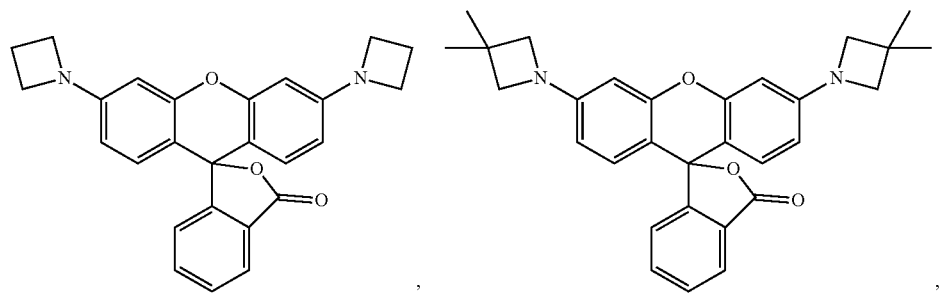
,
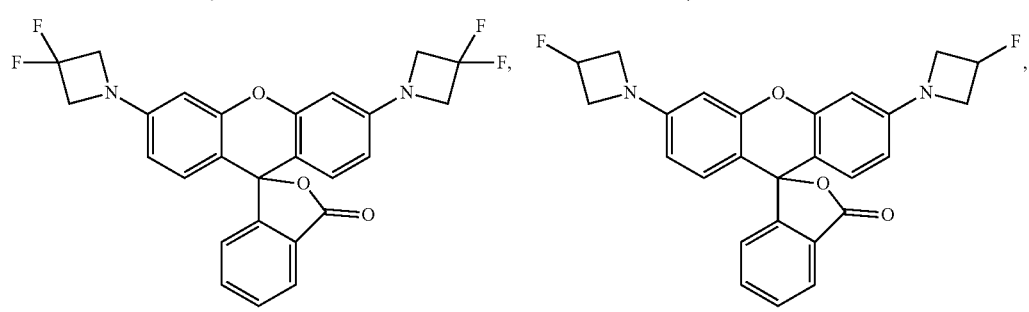
,
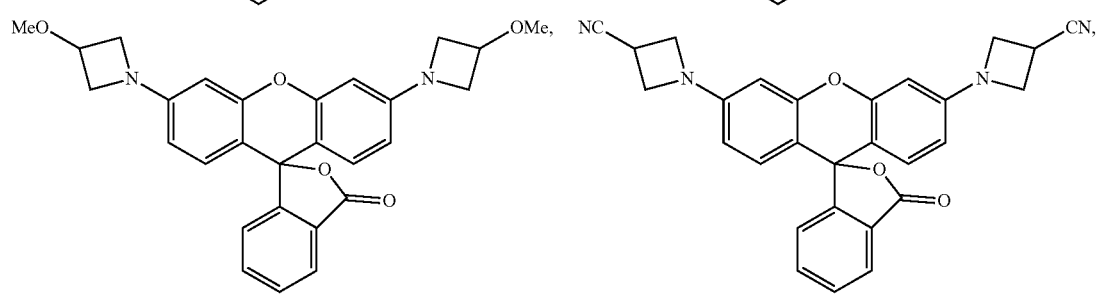
,
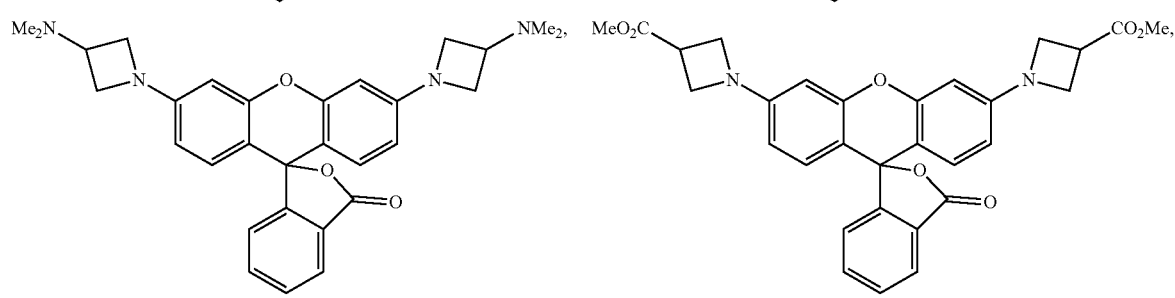
, -continued
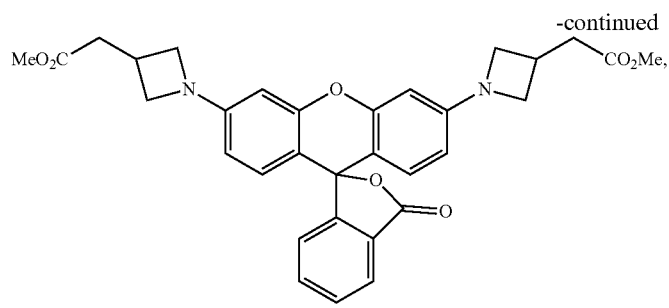
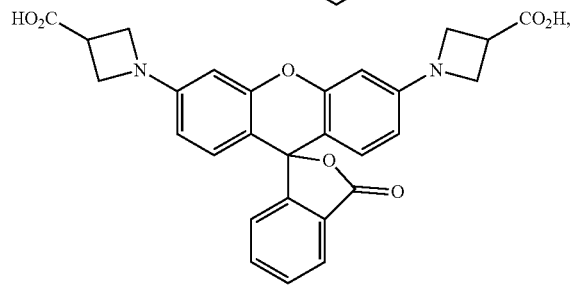
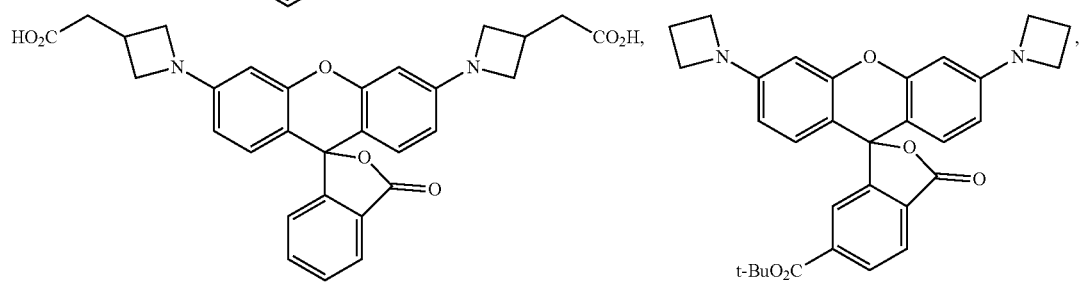
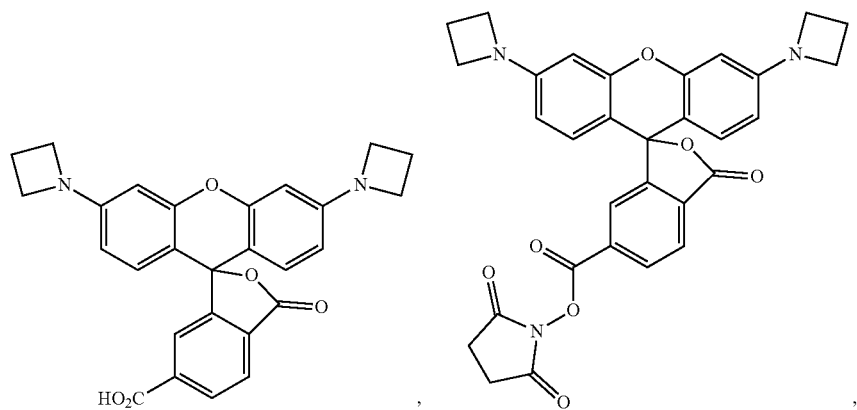
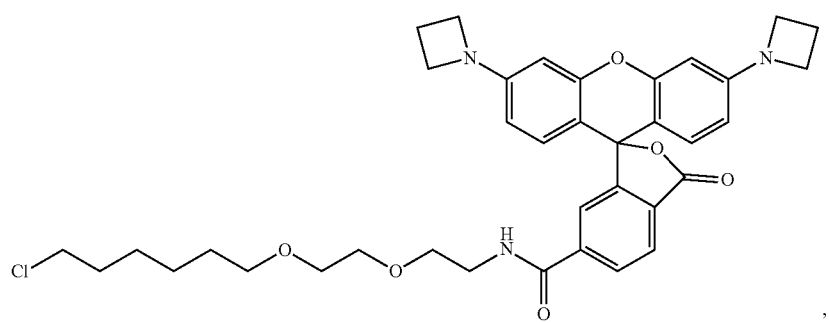

-continued
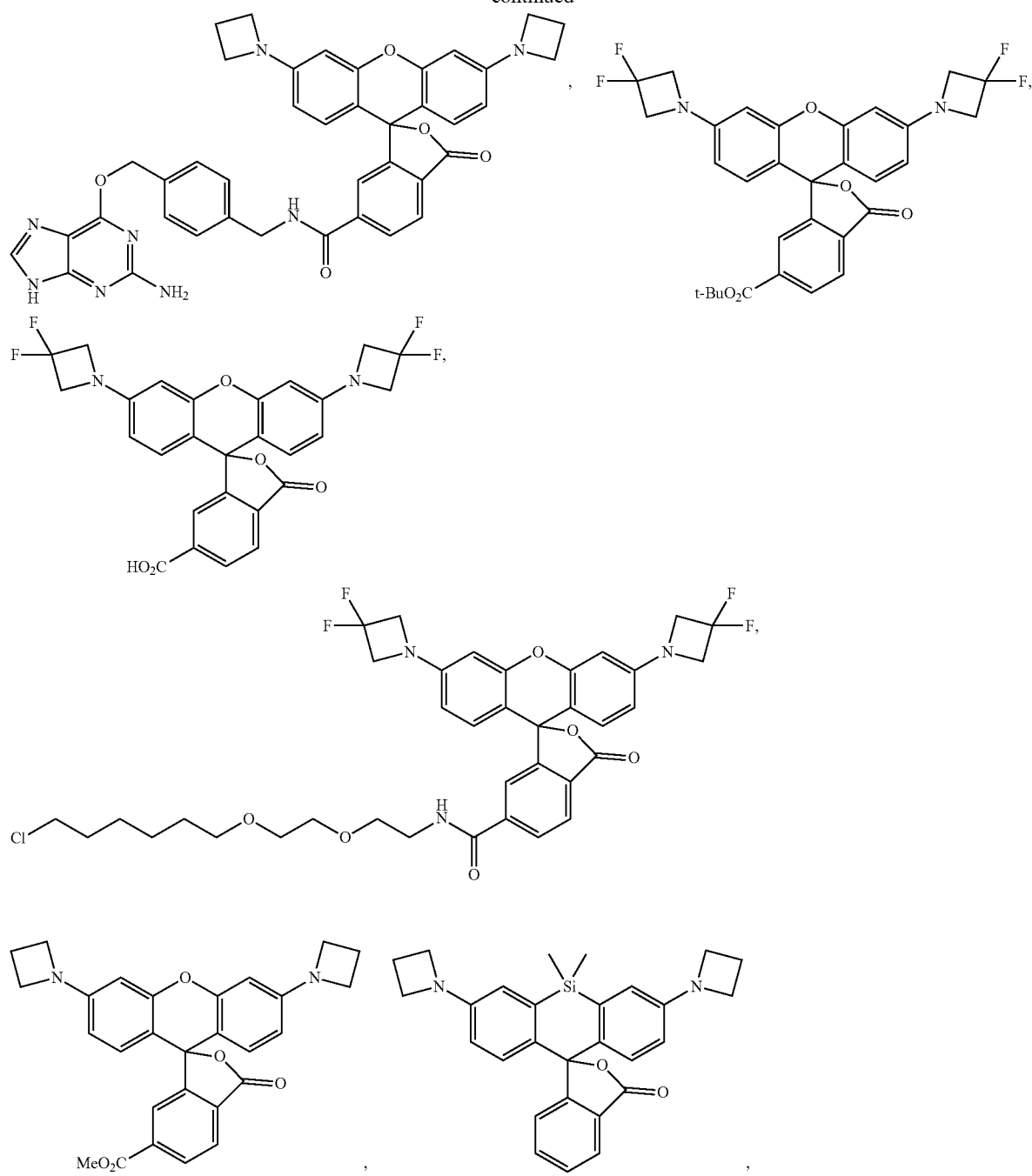
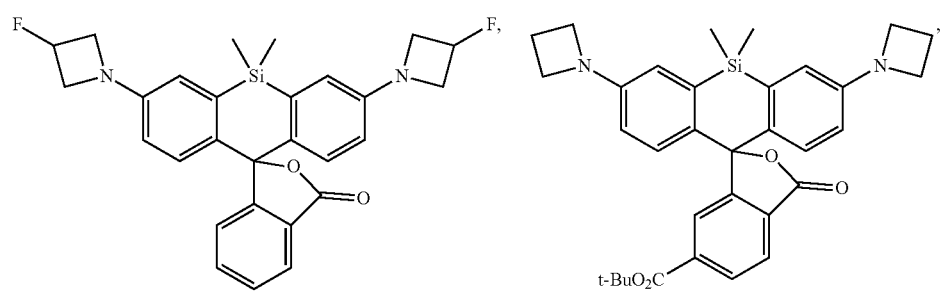

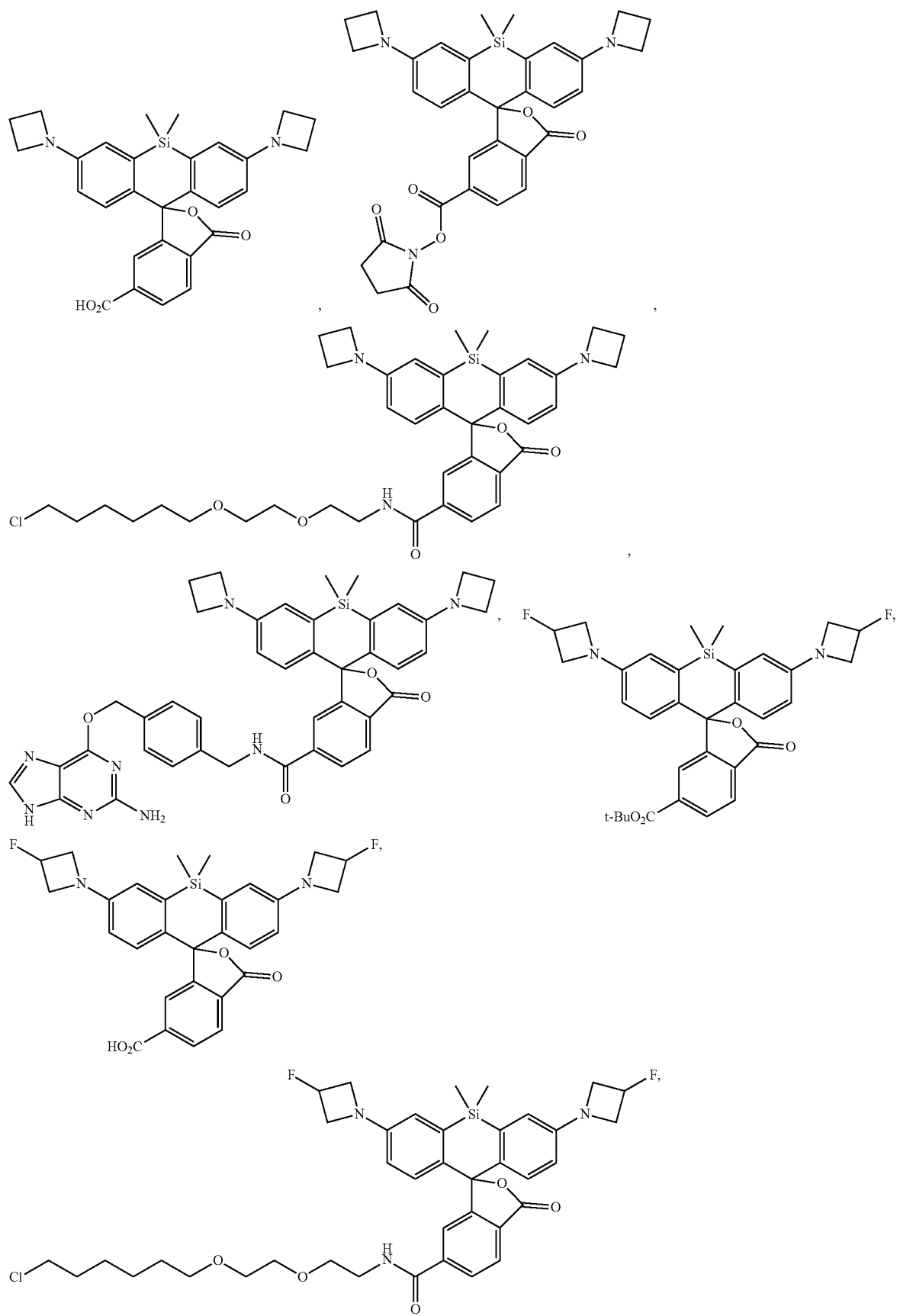

-continued
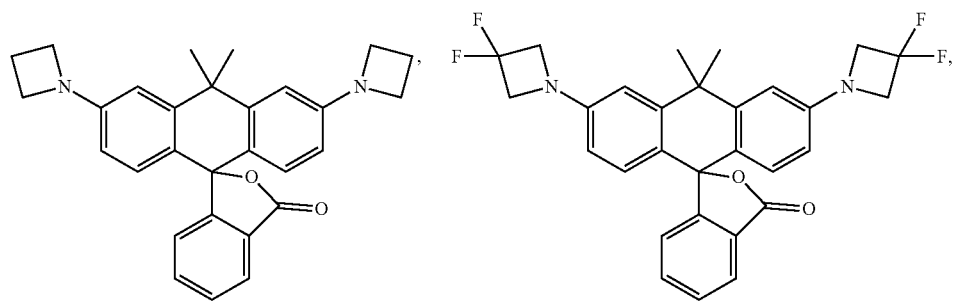
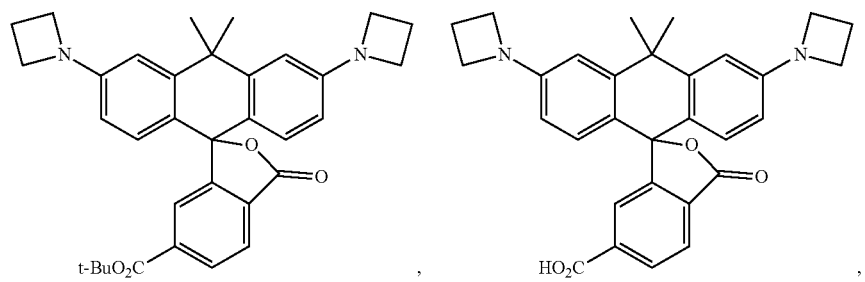
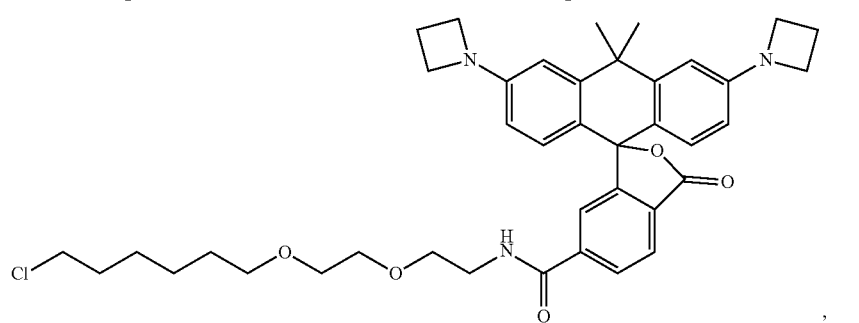
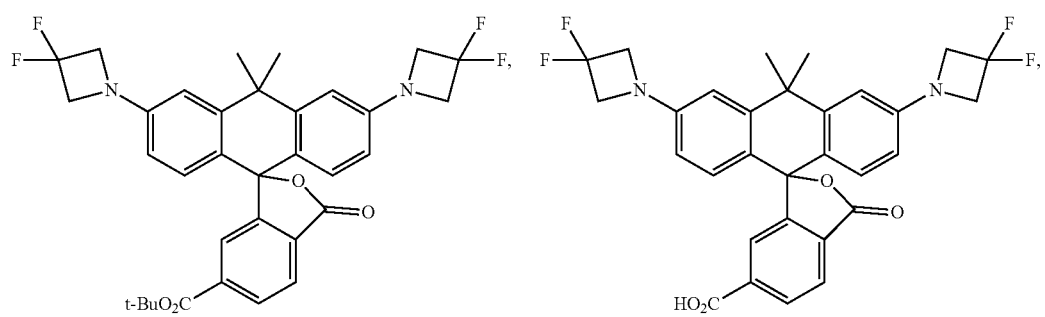
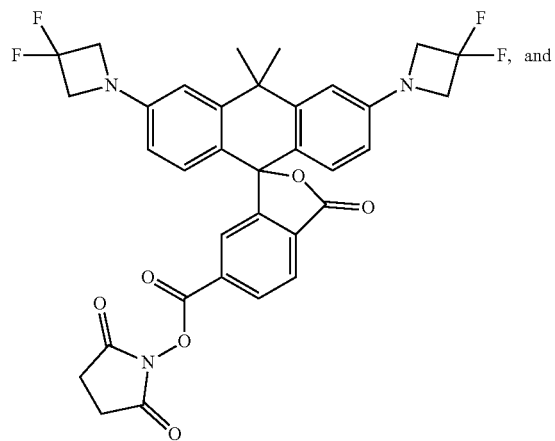

-continued

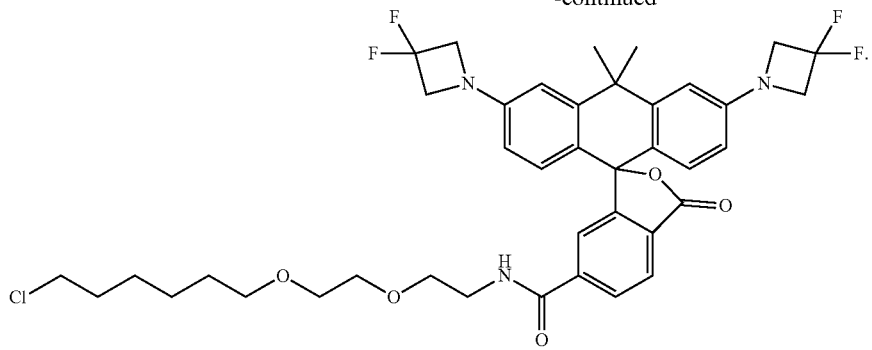

13. A method for detecting a target substance, comprising: contacting a sample with the compound of claim 12; and detecting an emission light from the compound, the emission light indicating the presence of the target substance.

14. The method of claim 13, wherein the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a liprotein, and a combination thereof.

15. The method of claim 13, wherein the detecting step is performed with a microscope.

16. The method of claim 13, further comprising a step of exposing the compound to an absorption light that includes a wavelength of about 100 nm to about 1000 nm.

17. The method of claim 13, wherein the contact step and the detecting step are performed in a live cell.

18. The method of claim 13, wherein:
the compound includes a first compound and a second compound;
the first compound being selective for a first target substance and capable of emitting a first emission light;
the second compound being selective for a second target substance and capable of emitting a second emission light, and
the detecting step includes detecting the first emission light that indicates the presence of the first target substance and the second emission light that indicates the presence of the second target substance.

19. A method for detecting a target substance, comprising: contacting a sample with the compound of claim 1; and detecting an emission light from the compound, the emission light indicating the presence of the target substance.

20. The method of claim 19, wherein the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a liprotein, and a combination thereof.

21. The method of claim 19, wherein the detecting step is performed with a microscope.

22. The method of claim 19, further comprising a step of exposing the compound to an absorption light that includes a wavelength of about 100 nm to about 1000 nm.

23. The method of claim 19, wherein the contact step and the detecting step are performed in a live cell.

24. The method of claim 19, wherein:
the compound includes a first compound and a second compound;
the first compound being selective for a first target substance and capable of emitting a first emission light;
the second compound being selective for a second target substance and capable of emitting a second emission light, and
the detecting step includes detecting the first emission light that indicates the presence of the first target substance and the second emission light that indicates the presence of the second target substance.

* * * * *